United States Patent [19]

Shiozaki et al.

[11] Patent Number: 5,792,840

[45] Date of Patent: Aug. 11, 1998

[54] LIPID A ANALOGS HAVING IMMUNOACTIVATING AND ANTI-TUMOR ACTIVITY

[75] Inventors: Masao Shiozaki; Noboru Ishida; Masami Arai; Tetsuo Hiraoka; Tomowo Kobayashi; Yuzuru Akamatsu, all of Tokyo; Masahiro Nishijima, Kawasaki, all of Japan

[73] Assignee: Sankyo Company, Limited. Tokyo, Japan

[21] Appl. No.: 280,298

[22] Filed: Jul. 26, 1994

Related U.S. Application Data

[63] Continuation of Ser. No. 539,605, Jun. 18, 1990, abandoned.

[30] Foreign Application Priority Data

Dec. 11, 1989 [JP] Japan ................................. 1-321153
Feb. 20, 1990 [JP] Japan ................................. 2-37339

[51] Int. Cl.$^6$ .................... C07H 5/02; C07H 11/04; C07H 13/02; C07H 13/06
[52] U.S. Cl. ................ 536/1.11; 536/18.4; 536/117; 536/119; 536/122
[58] Field of Search .................... 536/1.11, 4.1, 536/18.4, 117, 119, 122

[56] References Cited

U.S. PATENT DOCUMENTS

| | | |
|---|---|---|
| 4,746,742 | 5/1988 | Hasegawa et al. ............... 536/117 |
| 4,912,094 | 3/1990 | Myers et al. .................... 536/117 |

FOREIGN PATENT DOCUMENTS

| | | |
|---|---|---|
| WO-87/00174 | 1/1987 | European Pat. Off. . |
| A-0224260 | 6/1987 | European Pat. Off. . |
| A-0309411 | 3/1989 | European Pat. Off. . |
| A-3834377 | 5/1990 | Germany . |
| 2 211 503 | 7/1989 | United Kingdom . |
| 84/04526 | 11/1984 | WIPO . |

OTHER PUBLICATIONS

Imoto et al., *Tetrahedron Lett.*, 26, 1545–1548 (1985).
Kiso et al., *Carbohydrate Research*, 162, 127–140 (1987).
Kiso et al., *J. Carbohydrate Chem.*, 6 (4), 625–638 (1987).
Tetrahedron Letters, vol. 25, 1984, Pergamon Press Ltd, (GB), Imoto et al: "Chemical Synthesis of Phosphorylated, Tetraacyl Disaccharide corresponding to a Biosynthetic Precursor of Lipid A", pp. 2667–2670.

Chemical Abstracts, vol. 103, No. 3, 22 Jul. 1985, (Columbus, Ohio, US) Kasai et al.: "In Vitro Antigenic Reactivity of Synthetic Lipid A Analogs as determined by Monoclonal and Conventional Antibodies", p. 436, abstract 20888u. Biochem. Biophys. Res. Comman.

Chemical Abstracts, vol. 97, No. 23, 6 Dec. 1982, (Columbus, Ohio, U.S.), Verret et al.: "Fatty Acyl Amidases from Dictyostelium Discoideum that Act on Lipopolysaccharide and Derivatives. II. Aspects of Substrate Specificity." p. 271, abstract 195017u. J. Biol. Chem. 1982, 157 (17), 10228–34.

Internal Medicine, 4th Edition, Editor-in-Chief Jay Stein, Chapters 71–72, pp. 699–715.

*Primary Examiner*—John Kight
*Assistant Examiner*—Everett White
*Attorney, Agent, or Firm*—Frishauf, Holtz, Goodman, Langer & Chick, P.C.

[57] ABSTRACT

Compounds of formula (I):

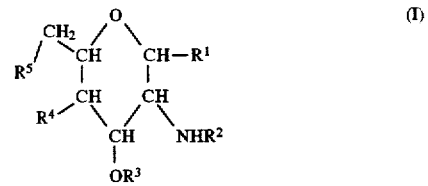

in which: $R^1$ is hydroxy, protected hydroxy, fluorine, or —OP(O)(OH)$_2$; $R^2$ and $R^3$ are independently optionally substituted $C_6$–$C_{20}$ aliphatic acyl; $R^4$ is hydroxy, protected hydroxy, or —OP(O)(OH)$_2$, where at least one of $R^1$ and $R^4$ is —OP(O)(OH)$_2$; and $R^5$ is hydroxy, protected hydroxy, or fluorine; provided that, except where at least one of $R^1$ and $R^5$ is fluorine, then at least one of $R^2$ and $R^3$ is a substituted $C_6$–$C_{20}$ aliphatic acyl having (i) at least one halogen substituent and (ii) at least one substituent selected from the group consisting of halogen, hydroxy and $C_6$–$C_{20}$ aliphatic acyloxy or at least one of $R^2$ and $R^3$ is a substituted $C_6$–$C_{20}$ aliphatic acyl which is substituted by at least one halogen-substituted $C_6$–$C_{20}$ aliphatic carboxylic acyloxy; have Lipid A-like activity and may be used for the treatment, prophylaxis, diagnosis and support of an animal suffering a disease or disorder arising from a deficiency in the immune system or from a tumor. They may be prepared by phosphorylation of corresponding compounds lacking a phosphoryl group.

60 Claims, No Drawings

LIPID A ANALOGS HAVING IMMUNOACTIVATING AND ANTI-TUMOR ACTIVITY

This application is a continuation of application Ser. No. 07/539,605, filed Jun. 18, 1990, now abandoned.

BACKGROUND TO THE INVENTION

The present invention provides a series of novel monosaccharide compounds which are analogs of the known lipid A, and which have been found to have immunoactivating and anti-tumor activities. The invention also provides processes for preparing these novel compounds as well as methods and compositions using them for the treatment, prophylaxis, diagnosis and support of patients suffering from immunodeficiency diseases and disorders and for inhibiting the growth of tumors.

The outermost layer of the cell wall of a gram negative bacterium obtained from species of enteric bacteria, such as *Escherichia coli*, contains a toxic component (an endotoxin) which is not secreted out of the bacterium. This endotoxin exhibits various biological activities, in addition to its endotoxic activities: for example, it is an immunoadjuvant, activates macrophages, induces mitogenesis, causes pyrogenesis and may cause tumor necrosis; it also enhances the production of antibodies and induces the production of TNF (tumor necrosis factor), both of which have important functions in the immune systems of animals, including human beings. It is, therefore, of considerable interest as a possible precursor of drugs which may be of value in the treatment, prophylaxis, support or diagnosis of diseases and disorders which arise from or result in deficiencies of the immune system in humans and other animals.

It has previously been found that the endotoxin comprises a lipopolysaccharide and that the center of activity of this endotoxicity lies in the moiety now known as "lipid A". It has also been found that the monosaccharides known as "lipid X" and "lipid Y", which are lipid A biosynthesis precursors, may be separated from an *E. coli* mutant, and that these exhibit similar activities to those of lipid A, although weakly.

Consequently, various derivatives of lipid A monosaccharide, lipid X, lipid Y and the non-reducing sugar part of lipid A have been synthesized and their activities examined [see for example Imoto et al., Tetrahedron Lett., 26, 1545 (1985) or Kiso et al., Carbohydrate Research, 162, 127 (1987)].

However, since these derivatives are the bacterial endotoxins per se, their use as drugs can still give rise to problems, including the induction of lethal toxicity, exothermic activity, leukopenia and autoimmune diseases. There is, therefore, a need for a compound of this type, which, whilst retaining their desirable activities, lacks the toxicity problems of the naturally occurring compounds.

Several attempts have been made to provide compounds which fulfil these requirements. For example, Lipid X is disclosed in WO 84/04526 as having immunostimulating activity, and a number of saccharide derivatives are disclosed in British Patent No. 2 211 503 and are said to be useful as modulators of antimicrobial resistance, for enhancing immune response, for the prevention of endotoxic shock and for the treatment of malignant tumors and inflammation. However, of the compounds known to date, the most active is thought to be that known as GLA-60, which is disclosed, for example, in J. Carbohydrate Chem., 6(4), 625–638 (1987) and Carbohydrate Research, 162, 127–140 (1987).

We have now discovered a series of saccharide derivatives, which are lipid A monosaccharide analogs and which have activities of the type discussed above which are, at worst, comparable with those of GLA-60, and which are, in some cases, very substantially better than those of GLA-60, and are therefore probably the most active compounds of this type currently known. The compounds of the present invention are distinguished from the prior art compounds by the presence of at least one halogen, and preferably fluorine, atom at one or more of certain specific selected sites in the molecule.

BRIEF SUMMARY OF INVENTION

It is, therefore, an object of the present invention to provide a series of novel compounds having activity of the lipid A type.

It is a further object of the invention to provide methods and compositions for the treatment, prophylaxis, diagnosis and support of patients suffering from diseases and disorders arising from tumors or from deficiencies in the immune system and employing the compounds of the invention.

In accordance with the invention, these objects are achieved by the provision of the new compounds of formula (I):

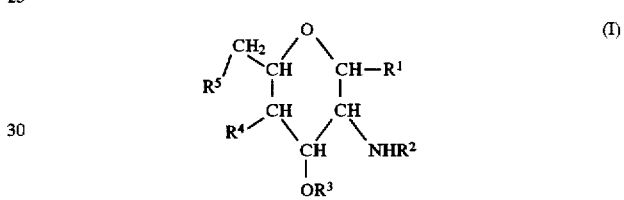

in which:

$R^1$ represents a hydroxy group, a protected hydroxy group as defined below, a fluorine atom, or a group of formula —OP(O)(OH)$_2$;

$R^2$ and $R^3$ are independently selected from the group consisting of aliphatic carboxylic acyl groups having from 6 to 20 carbon atoms, said acyl groups being unsubstituted or having at least one substituent selected from the group consisting of substituents (a), defined below;

$R^4$ represents a hydroxy group, a protected hydroxy group as defined below, or a group of formula —OP(O)(OH)$_2$, where at least one of $R^1$ and $R^4$ represents a group of formula —OP(O)(OH)$_2$;

$R^5$ represents a hydroxy group, a protected hydroxy group as defined below, or a fluorine atom;

provided that, except where at least one of $R^1$ and $R^5$ represents a fluorine atom, either:

at least one of $R^2$ and $R^3$ represents a substituted aliphatic carboxylic acyl group having from 6 to 20 carbon atoms and having (i) at least one halogen substituent and (ii) at least one substituent selected from the group consisting of halogen atoms, hydroxy groups and aliphatic carboxylic acyloxy groups having from 6 to 20 carbon atoms or at least one of $R^2$ and $R^3$ represents a substituted aliphatic acyl group having from 6 to 20 carbon atoms and which is substituted by at least one halogen-substituted aliphatic carboxylic acyloxy group having from 6 to 20 carbon atoms;

said protected hydroxy groups are selected from the group consisting of: aliphatic carboxylic acyloxy groups having from 1 to 20 carbon atoms; halogenated carboxylic acyloxy groups having from 2 to 6 carbon atoms; alkoxy-substituted carboxylic acyloxy groups in which the alkoxy part has from 1 to 6 carbon atoms and the acyl part has from 2 to 6 carbon atoms; carbocyclic aromatic carboxylic acyloxy groups in which the aromatic part has from 6 to 14 ring carbon atoms and is unsubstituted or has at least one substituent selected from the group consisting of substituents (b), defined below; groups of formula Het—O— where Het represents a heterocyclic group having 5 or 6 ring atoms of which from 1 to 3 are hetero-atoms selected from the group consisting of nitrogen, oxygen and sulfur atoms, said heterocyclic group being unsubstituted or having at least one substituent selected from the group consisting of substituents (c), defined below; groups of formula $R^aR^bR^cSi$—O—, where $R^a$, $R^b$ and $R^c$ are independently selected from the group consisting of alkyl groups having from 1 to 6 carbon atoms and carbocyclic aryl groups having from 6 to 10 carbon atoms said aryl groups being unsubstituted or having at least one substituent selected from the group consisting of substituents (b), defined below; alkoxyalkoxy groups, in which the two alkoxy parts are the same or different and each has from 1 to 6 carbon atoms; aralkyloxy groups in which an alkyl group having from 1 to 6 carbon atoms is substituted with from 1 to 3 aryl groups, said aryl groups being unsubstituted or having at least one substituent selected from the group consisting of substituents (b), defined below; alkoxycarbonyloxy groups, in which the alkoxy part has from 1 to 6 carbon atoms; substituted alkoxycarbonyloxy groups, in which the alkoxy part has from 1 to 6 carbon atoms and the substituent is selected from the group consisting of substituents (d), defined below; alkenyloxycarbonyloxy groups, in which the alkenyl part has from 2 to 6 carbon atoms; alkenyloxy groups having from 2 to 6 carbon atoms; carboxy-substituted aliphatic carboxylic acyloxy groups in which the acyl part has from 1 to 6 carbon atoms, in which the acyl part is otherwise unsubstituted or has at least one hydroxy substituent; acyloxymethoxycarbonyloxy groups in which the acyl group is a carboxylic acyl group having from 1 to 6 carbon atoms; (arylselenyl)ethoxy groups in which the aryl part has from 6 to 14 ring carbon atoms and is unsubstituted or has at least one substituent selected from the group consisting of substituents (b), defined below; alkoxyalkoxymethoxy groups, in which each alkoxy part has from 1 to 6 carbon atoms; methoxy groups substituted by one, two or three haloalkoxy substituents, in which the alkoxy part has from 1 to 6 carbon atoms and is substituted by at least one halogen atom; haloethoxy groups in which the ethyl part is substituted by at least one halogen atom; and aralkyloxycarbonyloxy groups, in which the aralkyl part comprises an alkyl group having from 1 to 6 carbon atoms which is substituted with from 1 to 3 aryl groups, said aryl groups being unsubstituted or having at least one substituent selected from the group consisting of substituents (b), defined below;

substituents (a)

halogen atoms; aryl groups having from 6 to 14 carbon atoms and being unsubstituted or having at least one substituent selected from the group consisting of substituents (b), defined below; aralkyl groups, in which an alkyl group having from 1 to 6 carbon atoms is substituted with from 1 to 3 aryl groups, said aryl groups being unsubstituted or having at least one substituent selected from the group consisting of substituents (b), defined below; hydroxy groups; aliphatic carboxylic acyloxy groups having from 6 to 20 carbon atoms; and halogen-substituted aliphatic carboxylic acyloxy groups having from 6 to 20 carbon atoms;

substituents (b)

halogen atoms; alkyl groups having from 1 to 6 carbon atoms; halogen-substituted alkyl groups having from 1 to 6 carbon atoms; alkoxy groups having from 1 to 6 carbon atoms; nitro groups, alkoxycarbonyl groups, in which the alkoxy part has from 1 to 6 carbon atoms; aryl groups having from 6 to 14 ring carbon atoms and being unsubstituted or having at least one substituent selected from the group consisting of substituents (b), defined here other than the aryl groups; cyano groups; alkylenedioxy groups having from 1 to 4 carbon atoms; divalent aliphatic hydrocarbon groups having from 1 to 4 carbon atoms; groups of formula —$NR^dR^e$, where $R^d$ and $R^e$ are independently selected from the group consisting of hydrogen atoms and alkyl groups having from 1 to 6 carbon atoms; haloalkoxycarbonyl groups, in which the alkoxy part has from 1 to 6 carbon atoms; aralkyloxycarbonyl groups, in which the aralkyl part comprises an alkyl group having from 1 to 6 carbon atoms which is substituted with from 1 to 3 aryl groups, said aryl groups being unsubstituted or having at least one substituent selected from the group consisting of substituents (b), defined above; groups of formula —CO—$NR^dR^e$, where $R^d$ and $R^e$ are as defined above; and aliphatic acyl groups having from 1 to 20 carbon atoms;

substituents (c)

halogen atoms; alkyl groups having from 1 to 6 carbon atoms; halogen-substituted alkyl groups having from 1 to 6 carbon atoms; alkoxy groups having from 1 to 6 carbon atoms; aryl groups having from 6 to 14 ring carbon atoms and being unsubstituted or having at least one substituent selected from the group consisting of substituents (b), defined here other than the aryl groups; and oxygen atoms;

substituents (d)

halogen atoms; groups of formula $R^aR^bR^cSi$—O—, where $R^a$, $R^b$ and $R^c$ are as defined above; and alkanoyloxy groups, where the alkanoyl group has from 1 to 6 carbon atoms;

and salts thereof and, where the compound of formula (I) includes a carboxy group, esters thereof.

The invention also provides a composition for the treatment, prophylaxis, diagnosis and support of patients suffering diseases and disorders arising from or resulting in tumors or from deficiencies in the immune system, said composition comprising an effective amount of at least one compound of formula (I) or a pharmaceutically acceptable salt thereof in admixture with a pharmaceutically acceptable carrier, diluent or excipient.

The invention still further provides a method for the treatment, prophylaxis, diagnosis and support of an animal suffering from a disease or disorder arising from or resulting in a deficiency in the immune system or from a tumor, said method comprising administering to said animal, which is preferably a mammal and may be human or non-human, an effective amount of at least one compound of formula (I) or a pharmaceutically acceptable salt thereof.

DETAILED DESCRIPTION OF INVENTION

In the following description, where reference is made to a group being "substituted", and the number of substituents is not otherwise qualified, then the number is limited only by the number of substitutable positions, and possibly by steric constraints. In that case, although it is not limiting, we would normally prefer (subject to the number of substitutable positions) from 1 to 5, and more preferably from 1 to 3, of the substituents.

In the compounds of the present invention, where $R^1$, $R^4$ or $R^5$ represents a protected hydroxy group, the protecting group is selected from the group consisting of:

aliphatic carboxylic acyl groups having from 1 to 20 carbon atoms, which may be straight or branched chain groups, and are more preferably groups having from 2 to 20 carbon atoms, most preferably groups having from 6 to 20 carbon atoms, for example: the alkylcarbonyl groups, such as the formyl, acetyl, propionyl, butyryl, isobutyryl, pivaloyl, valeryl, isovaleryl, octanoyl, lauroyl, tridecanoyl, tetradecanoyl, palmitoyl and stearoyl groups; the alkenylcarbonyl groups, such as the acryloyl, methacryloyl and 2-methyl-2-butenoyl groups [especially the (E)-2-methyl-2-butenoyl isomer]; and the alkynylcarbonyl groups, such as the propiolyl group; in the case of the unsaturated groups, the minimum number of carbon atoms is 3;

halogenated aliphatic carboxylic acyl groups having from 2 to 6 carbon atoms, in which the aliphatic acyl part may be any of those acyl groups exemplified above which has from 2 to 6 carbon atoms and which is substituted by at least one halogen (e.g. chlorine, bromine, fluorine or iodine) atom, and preferably from 1 to 3 halogen atoms; examples of such groups include the chloroacetyl, dichloroacetyl, trichloroacetyl and trifluoroacetyl groups;

alkoxy-substituted carboxylic acyl groups in which the alkoxy part or parts has or have from 1 to 6 carbon atoms and the acyl part has from 2 to 6 carbon atoms; there may be two or more such alkoxy substituents, but a single such substituent is preferred; examples of such alkoxy groups include the methoxy, ethoxy, propoxy, isopropoxy, butoxy, isobutoxy, sec-butoxy, t-butoxy, pentyloxy and hexyloxy groups and examples of the acyl groups include the acetyl, propionyl, butyryl, isobutyryl, valeryl, isovaleryl, pivaloyl and hexanoyl groups; examples of the alkoxy-substituted acyl groups include the methoxyacetyl, ethoxyacetyl, propoxyacetyl, 3-methoxypropionyl, 4-methoxybutyryl, 5-methoxyvaleryl, 6-methoxyhexanoyl, 3-ethoxypropionyl, 4-ethoxybutyryl, 5-ethoxyvaleryl, 6-ethoxyhexanoyl and 6-hexyloxyhexanoyl groups;

carbocyclic aromatic carboxylic acyl groups in which the aromatic part has from 6 to 14 ring carbon atoms and is unsubstituted or has at least one substituent, preferably from 1 to 4 and more preferably from 1 to 3 substituents, selected from the group consisting of substituents (b), defined above and exemplified below; examples of such acyl groups include: the unsubstituted groups, such as the benzoyl, α-naphthoyl and β-naphthoyl groups; halogen-substituted groups, such as the 2-bromobenzoyl and 4-chlorobenzoyl groups; alkyl-substituted groups, such as the 2,4,6-trimethylbenzoyl and 4-toluoyl groups; alkoxy-substituted groups, such as the 4-anisoyl group; nitro-substituted groups, such as the 4-nitrobenzoyl and 2-nitrobenzoyl groups; alkoxycarbonyl-substituted groups, such as the 2-(methoxycarbonyl)benzoyl group; and aryl-substituted groups, such as the 4-phenylbenzoyl group;

groups of formula Het- where Het represents a heterocyclic group having 5 or 6 ring atoms of which from 1 to 3 are hetero-atoms selected from the group consisting of nitrogen, oxygen and sulfur atoms, said heterocyclic group being unsubstituted or having at least one substituent, and preferably only one substituent, selected from the group consisting of substituents (c), defined above and exemplified below; examples of such unsubstituted groups include the pyranyl, furyl, pyridyl, piperazinyl, piperidyl, tetrahydropyranyl (e.g. tetrahydropyran-2-yl), tetrahydrothiopyranyl (e.g. tetrahydrothiopyran-2-yl), tetrahydrofuranyl (e.g. tetrahydrofuran-2-yl) and tetrahydrothienyl (e.g. tetrahydrothien-2-yl) groups; and examples of such substituted groups include the 3-bromotetrahydropyran-2-yl, 4-methoxytetrahydropyran-4-yl and 4-methoxytetrahydrothien-4-yl groups; of these, the tetrahydropyranyl, tetrahydrothiopyranyl, tetrahydrofuryl and tetrahydrothienyl groups and substituted equivalents are preferred;

groups of formula $R^aR^bR^cSi-$, where $R^a$, $R^b$ and $R^c$ are independently selected from the group consisting of alkyl groups having from 1 to 6 carbon atoms (e.g. the methyl, ethyl, propyl, isopropyl, butyl, isobutyl, sec-butyl, pentyl, isopentyl, 2-methylbutyl, hexyl, isohexyl and 2-methylpentyl groups) and carbocyclic aryl groups having from 6 to 10 carbon atoms (preferably the phenyl group), said aryl groups being unsubstituted or having at least one substituent selected from the group consisting of substituents (b), defined above and exemplified below (e.g. those aryl groups exemplified above); examples of the substituted silyl groups include the trialkylsilyl groups (such as the trimethylsilyl, triethylsilyl, isopropyldimethylsilyl, t-butyldimethylsilyl, methyldiisopropylsilyl, methyldi-t-butylsilyl and triisopropylsilyl groups), and a tri-substituted silyl group substituted with 1 or 2 aryl groups and correspondingly 2 or 1 alkyl groups (such as the diphenylmethylsilyl, diphenyl-t-butylsilyl, diphenylisopropylsilyl and phenyldiisopropylsilyl groups);

alkoxyalkyl groups, in which each of the alkoxy and the alkyl parts has from 1 to 6 carbon atoms, preferably from 1 to 4 carbon atoms; examples of the alkyl groups are as given above and examples of the alkoxy groups are the alkoxy groups exemplified in relation to the alkoxy-substituted acyl groups; for example: the alkoxymethyl groups, such as the methoxymethyl, ethoxymethyl, propoxymethyl, isopropoxymethyl, butoxymethyl, isobutoxymethyl, sec-butoxymethyl, pentyloxymethyl, isopentyloxymethyl, 2-methylbutoxymethyl, hexyloxymethyl, isohexyloxymethyl and 2-methylpentyloxymethyl groups); alkoxyethyl groups, such as the 1- and 2-methoxyethyl, 1- and 2-ethoxyethyl, 1- and 2-propoxyethyl, 1- and 2-isopropoxyethyl, 1- and 2-butoxyethyl, 1- and 2-isobutoxyethyl, 1- and 2-sec-butoxyethyl, 1- and 2-pentyloxyethyl, 1- and 2-isopentyloxyethyl, 1- and 2-2-methylbutoxyethyl, 1- and 2-hexyloxyethyl, 1- and 2-isohexyloxyethyl and 1- and 2-(2-methylpentyloxy)ethyl groups); and alkoxypropyl groups, such as the 1,1-dimethyl-1-methoxymethyl, methoxypropyl and 1-methyl-1-methoxyethyl groups;

aralkyl groups in which an alkyl group having from 1 to 6 carbon atoms is substituted with from 1 to 3 aryl groups, said aryl groups being unsubstituted or having at least one substituent selected from the group consisting of substituents (b), defined above and exemplified below; where the aryl group is substituted, it preferably has from 1 to 4, more preferably from 1 to 3, substituents; for example the benzyl, phenethyl, 1-phenylethyl, 3-phenylpropyl, α-naphthylmethyl, β-naphthylmethyl, diphenylmethyl, triphenylmethyl, α-naphthyldiphenylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanophenyldiphenylmethyl, bis(2-nitrophenyl)methyl and piperonyl groups;

alkoxycarbonyl groups, in which the alkoxy part has from 1 to 6, preferably from 1 to 4, carbon atoms, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, 2-methylbutoxycarbonyl, hexyloxycarbonyl, isohexyloxycarbonyl and 2-methylpentyloxycarbonyl groups;

substituted alkoxycarbonyl groups, in which the alkoxy part has from 1 to 6, preferably from 1 to 4, carbon atoms and the substituent is selected from the group consisting of substituents (d), defined above and exemplified below, preferably a halogen atom or a silyl group; there is, in principle, no restriction on the number of substituents, except such as may be dictated by the number of substitutable positions; however, in general, from 1 to 3 substituents are preferred; the alkoxycarbonyl part may be any of the unsubstituted alkoxycarbonyl groups exemplified above, and examples of the substituted groups include the 2,2,2-trichloroethoxycarbonyl and 2-trimethylsilylethoxycarbonyl groups;

alkenyloxycarbonyl groups, in which the alkenyl part has from 2 to 6, preferably from 2 to 4 and more preferably 2 or 3, carbon atoms; examples include the vinyloxycarbonyl and allyloxycarbonyl groups;

alkenyl groups having from 2 to 6, especially from 2 to 4, carbon atoms, such as the vinyl and allyl groups;

carboxy-substituted aliphatic carboxylic acyl groups in which the acyl part has from 1 to 6 carbon atoms (from 3 to 6 carbon atoms if unsaturated) and is substituted only by the carboxy group or has, in addition, at least one hydroxy substituent; examples of the acyl groups include those acyl groups having from 1 to 6 carbon atoms and exemplified below; specific examples of the substituted groups include the 3-carboxypropionyl, 3-carboxy-3-hydroxypropionyl and 3-carboxyacryloyl groups;

acyloxymethoxycarbonyl groups in which the acyl group is a carboxylic acyl group having from 1 to 6 carbon atoms; the acyl part may be any of those acyl groups exemplified below which have from 1 to 6 carbon atoms; and a specific example of the groups is the pivaloyloxymethoxycarbonyl group;

aralkyloxycarbonyl groups, in which the aralkyl part comprises an alkyl group having from 1 to 6 carbon atoms which is substituted with from 1 to 3 aryl groups, said aryl groups being unsubstituted or having at least one substituent selected from the group consisting of substituents (b), defined above and exemplified below, preferably 1 or 2 lower alkoxy or nitro substituents; the aralkyl parts of such groups may be as exemplified above, and examples of such aralkyloxycarbonyl groups include the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

alkoxyalkoxymethyl groups in which each of the alkoxy parts has from 1 to 6, preferably from 1 to 4, carbon atoms, and may be the same or different although it is preferred that the total number of carbon atoms in the two alkoxy parts does not exceed 7, and more preferably does not exceed 4; examples of such alkoxy groups have been given above, and examples of the alkoxyalkoxymethyl groups include the 2-methoxyethoxymethyl and 2-ethoxyethoxymethyl groups;

methyl groups substituted by one, two or three, preferably one or two, haloalkoxy substituents, in which the alkoxy part has from 1 to 6 carbon atoms and is substituted by at least one halogen atom (e.g. a chlorine, fluorine, bromine or iodine atom, preferably a chlorine atom); there is no restriction on the number of halogen substituents, except that dictated by the number of substitutable positions, but, in general, we prefer to have from 1 to 3 halogen substituents on each alkoxy group; examples of such groups include the 2,2,2-trichloroethoxymethyl and bis (2-chloroethoxy)methyl groups;

haloethyl groups, in which the ethyl part is substituted by at least one halogen atom (e.g. a chlorine, fluorine, bromine or iodine atom, preferably a chlorine or bromine atom); there is no restriction on the number of halogen substituents, except that dictated by the number of substitutable positions, but, in general, we prefer to have from 1 to 3 halogen substituents; an example of such a group is the 2,2,2-trichloroethyl group;

arylselenylethyl groups, in which the aryl group is a carbocyclic aryl group having from 6 to 14 carbon atoms, said aryl group being unsubstituted or having at least one substituent selected from the group consisting of substituents (b), defined above and exemplified below (e.g. those aryl groups exemplified above, preferably a phenyl group which may be substituted but is preferably unsubstituted); an example of a preferred such group is the 2-(phenylselenyl)ethyl group.

Where $R^2$ or $R^3$ represents an aliphatic carboxylic acyl group having from 6 to 20 carbon atoms, the acyl group may be unsubstituted or may have at least one substituent selected from the group consisting of substituents (a), defined above and exemplified in more detail below; the acyl group may be a straight or branched chain group, and examples of the unsubstituted groups include the hexanoyl, heptanoyl, octanoyl, nonanoyl, decanoyl, undecanoyl, 4-methyldecanoyl, 9-methyldecanoyl, 4-ethylnonanoyl, 4,8-dimethylnonanoyl, dodecanoyl (lauroyl), tridecanoyl, tetradecanoyl (myristoyl), pentadecanoyl, hexadecanoyl (palmitoyl), heptadecanoyl, 2-methylhexadecanoyl, 15-methylhexadecanoyl, 14,14-dimethylpentadecanoyl, octadecanoyl (stearoyl), 16-methylheptadecanoyl, nonadecanoyl, 2-methyloctadecanoyl and icosanoyl groups. Of these, we prefer the straight or branched chain aliphatic acyl groups having from 10 to 16 carbon atoms, and more preferably those in this range having an even number of carbon atoms, i.e. 10, 12, 14 or 16. The saturated groups are preferred.

Where substituent (a) is an aliphatic carboxylic acyloxy group having from 6 to 20 carbon atoms or a halogen-substituted aliphatic carboxylic acyloxy group having from 6 to 20 carbon atoms, the acyloxy group may be the acyloxy equivalent to any of the acyl groups exemplified above in relation to $R^2$ and $R^3$. In the case of the halogen-substituted groups, the halogen substituent may be a fluorine, chlorine, bromine or iodine atom, but the preferred halogen substituent is a fluorine atom.

Where substituent (a) is a halogen atom, it may be a fluorine, chlorine, bromine or iodine atom, and is preferably a fluorine or chlorine atom, and more preferably a fluorine atom.

Where substituent (a) is an aryl group, this has from 6 to 14 ring carbon atoms and is a carbocyclic group, which may be unsubstituted or may have at least one of substituents (b), defined above and exemplified below. Where the group is substituted, there is no particular restriction on the number of substituents, other than that imposed by the number of substitutable positions (e.g. 5 in the case of phenyl groups and 7 in the case of naphthyl groups); however, from 1 to 4 substituents are normally preferred. Examples of such unsubstituted groups include the phenyl, α-naphthyl and β-naphthyl groups. Examples of the substituted groups include: the halogen-substituted aryl groups, such as the 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 3,5-difluorophenyl, 2,5-difluorophenyl, 2,6-difluorophenyl, 2,4-difluorophenyl, 3,5-dibromophenyl, 2,5-dibromophenyl, 2,6-dichlorophenyl, 2,4-dichlorophenyl, 2,3,6-trifluorophenyl, 2,3,4-trifluorophenyl, 3,4,5-trifluorophenyl, 2,5,6-trifluorophenyl, 2,4,6-trifluorophenyl, 2,3,6-tribromophenyl, 2,3,4-tribromophenyl, 3,4,5-tribromophenyl, 2,5,6-trichlorophenyl, 2,4,6-trichlorophenyl, 1-fluoro-β-naphthyl, 2-fluoro-α-naphthyl, 3-fluoro-α-naphthyl, 1-chloro-β-naphthyl, 2-chloro-α-naphthyl, 3-bromo-α-naphthyl, 3,8-difluoro-α-naphthyl, 2,3-difluoro-α-naphthyl, 7,8-difluoro-α-naphthyl, 5,6-difluoro-α-naphthyl, 3,8-dichloro-α-naphthyl, 2,3-dichloro-α-naphthyl, 4,8-dibromo-α-naphthyl, 5,6-dibromo-α-naphthyl, 2,3,6-trifluoro-α-naphthyl, 2,3,4-trifluoro-α-naphthyl, 3,4,5-trifluoro-α-naphthyl, 4,5,6-trifluoro-α-naphthyl and 2,4,8-trifluoro-α-naphthyl groups; aryl groups substituted with at least one haloalkyl group, such as the 2-trifluoromethylphenyl, 3-trifluoromethylphenyl, 4-trifluoromethylphenyl, 2-trichloromethylphenyl, 3-dichloromethylphenyl, 4-trichloromethylphenyl, 2-tribromomethylphenyl, 3-dibromomethylphenyl, 4-dibromomethylphenyl, 3,5-bis(trifluoromethyl)phenyl, 2,5-bis(trifluoromethyl)phenyl, 2,6-bis(trifluoromethyl)phenyl, 2,4-bis(trifluoromethyl)phenyl, 3,5-bis(tribromomethyl)phenyl, 2,5-bis(dibromomethyl)phenyl, 2,6-bis(dichloromethyl)phenyl, 2,4-bis(dichloromethyl)phenyl, 2,3,6-tris(trifluoromethyl)phenyl, 2,3,4-tris(trifluoromethyl)phenyl, 3,4,5-tris(trifluoromethyl)phenyl, 2,5,6-tris(trifluoromethyl)phenyl, 2,4,6-tris(trifluoromethyl)phenyl, 2,3,6-tris(tribromomethyl)phenyl, 2,3,4-tris(dibromomethyl)phenyl, 3,4,5-tris(tribromomethyl)phenyl, 2,5,6-tris(dichloromethyl)phenyl, 2,4,6-tris(dichloromethyl)phenyl, 1-trifluoromethyl-β-naphthyl, 2-trifluoromethyl-α-naphthyl, 3-trifluoromethyl-α-naphthyl, 1-trichloromethyl-β-naphthyl, 2-dichloromethyl-α-naphthyl, 3-tribromomethyl-α-naphthyl, 3,8-bis(trifluoromethyl)-α-naphthyl, 2,3-bis(trifluoromethyl)-α-naphthyl, 4,8-bis(trifluoromethyl)-α-naphthyl, 5,6-bis(trifluoromethyl)-α-naphthyl, 3,8-bis(trichloromethyl)-α-naphthyl, 2,3-bis(dichloromethyl)-α-naphthyl, 4,8-bis(dibromomethyl)-α-naphthyl, 5,6-bis(tribromomethyl)-α-naphthyl, 2,3,6-tris(trifluoromethyl)-α-naphthyl, 2,3,4-tris(trifluoromethyl)-α-naphthyl, 3,4,5-tris(trifluoromethyl)-α-naphthyl, 4,5,6-tris(trifluoromethyl)-α-naphthyl and 2,4,8-tris(trifluoromethyl)-α-naphthyl groups; aryl groups substituted with at least one alkyl group, such as the 2-methylphenyl, 3-methylphenyl, 4-methylphenyl, 2-ethylphenyl, 3-propylphenyl, 4-ethylphenyl, 2-butylphenyl, 3-pentylphenyl, 4-pentylphenyl, 3,5-dimethylphenyl, 2,5-dimethylphenyl, 2,6-dimethylphenyl, 2,4-dimethylphenyl, 3,5-dibutylphenyl, 2,5-dipentylphenyl, 2,6-dipropylmethylphenyl, 2,4-dipropylphenyl, 2,3,6-trimethylphenyl, 2,3,4-trimethylphenyl, 3,4,5-trimethylphenyl, 2,5,6-trimethylphenyl, 2,4,6-trimethylphenyl, 2,3,6-tributylphenyl, 2,3,4-tripentylphenyl, 3,4,5-tributylphenyl, 2,5,6-tripropylmethylphenyl, 2,4,6-tripropylphenyl, 1-methyl-β-naphthyl, 2-methyl-α-naphthyl, 3-methyl-α-naphthyl, 1-ethyl-β-naphthyl, 2-propyl-α-naphthyl, 3-butyl-α-naphthyl, 3,8-dimethyl-α-naphthyl, 2,3-dimethyl-α-naphthyl, 4,8-dimethyl-α-naphthyl, 5,6-dimethyl-α-naphthyl, 3,8-diethyl-α-naphthyl, 2,3-dipropyl-α-naphthyl, 4,8-dipentyl-α-naphthyl, 5,6-dibutyl-α-naphthyl, 2,3,6-trimethyl-α-naphthyl, 2,3,4-trimethyl-α-naphthyl, 3,4,5-trimethyl-α-naphthyl, 4,5,6-trimethyl-α-naphthyl and 2,4,8-trimethyl-α-naphthyl groups; aryl groups substituted with at least one amino group, such as the 2-aminophenyl, 3-aminophenyl, 4-aminophenyl, 3,5-diaminophenyl, 2,5-diaminophenyl, 2,6-diaminophenyl, 2,4-diaminophenyl, 2,3,6-triaminophenyl, 2,3,4-triaminophenyl, 3,4,5-triaminophenyl, 2,5,6-triaminophenyl, 2,4,6-triaminophenyl, 1-amino-β-naphthyl, 2-amino-α-naphthyl, 3-amino-α-naphthyl, 3,8-diamino-α-naphthyl, 2,3-diamino-α-naphthyl, 4,8-diamino-α-naphthyl, 5,6-diamino-α-naphthyl, 2,3,6-triamino-α-naphthyl, 2,3,4-triamino-α-naphthyl, 3,4,5-triamino-α-naphthyl, 4,5,6-triamino-α-naphthyl and 2,4,8-triamino-α-naphthyl groups; aryl groups substituted with at least one nitro group, such as the 2-nitrophenyl, 3-nitrophenyl, 4-nitrophenyl, 3,5-dinitrophenyl, 2,5-dinitrophenyl, 2,6-dinitrophenyl, 2,4-dinitrophenyl, 2,3,6-trinitrophenyl, 2,3,4-trinitrophenyl, 3,4,5-trinitrophenyl, 2,5,6-trinitrophenyl, 2,4,6-trinitrophenyl, 1-nitro-β-naphthyl, 2-nitro-α-naphthyl, 3-nitro-α-naphthyl, 3,8-dinitro-α-naphthyl, 2,3-dinitro-α-naphthyl, 4,8-dinitro-α-naphthyl, 5,6-dinitro-α-naphthyl, 2,3,6-trinitro-α-naphthyl, 2,3,4-trinitro-α-naphthyl, 3,4,5-trinitro-α-naphthyl, 4,5,6-trinitro-α-naphthyl and 2,4,8-trinitro-α-naphthyl groups; aryl groups substituted with at least one cyano group, such as the 2-cyanophenyl, 3-cyanophenyl, 4-cyanophenyl, 3,5-dicyanophenyl, 2,5-dicyanophenyl, 2,6-dicyanophenyl, 2,4-dicyanophenyl, 2,3,6-tricyanophenyl, 2,3,4-tricyanophenyl, 3,4,5-tricyanophenyl, 2,5,6-tricyanophenyl, 2,4,6-tricyanophenyl, 1-cyano-β-naphthyl, 2-cyano-α-naphthyl, 3-cyano-α-naphthyl, 3,8-dicyano-α-naphthyl, 2,3-dicyano-α-naphthyl, 4,8-dicyano-α-naphthyl, 5,6-dicyano-α-naphthyl, 2,3,6-tricyano-α-naphthyl, 2,3,4-tricyano-α-naphthyl, 3,4,5-tricyano-α-naphthyl, 4,5,6-tricyano-α-naphthyl and 2,4,8-tricyano-α-naphthyl groups; aryl groups substituted with at least one aliphatic acyl group, such as the 2-acetylphenyl, 3-acetylphenyl, 4-acetylphenyl, 3,5-diacetylphenyl, 2,5-diacetylphenyl, 2,6-diacetylphenyl, 2,4-diacetylphenyl, 2,3,6-tripropionylphenyl, 2,3,4-tripropionylphenyl, 3,4,5-tripropionylphenyl, 2,5,6-tributyrylphenyl, 2,4,6-tributyrylphenyl, 1-acetyl-β-naphthyl, 2-acetyl-α-naphthyl, 3-acetyl-α-naphthyl, 3,8-diacetyl-α-naphthyl, 2,3-dipropionyl-α-naphthyl, 4,8-dibutyryl-α-naphthyl, 5,6-dibutyryl-α-naphthyl, 2,3,6-triacetyl-α-naphthyl, 2,3,4-triacetyl-α-naphthyl, 3,4,5-tripropionyl-α-naphthyl, 4,5,6-tributyryl-α-naphthyl and 2,4,8-tributyryl-α-naphthyl groups; aryl groups substituted with at least one carboxy group, such as the 2-carboxyphenyl, 3-carboxyphenyl, 4-carboxyphenyl, 3,5-dicarboxyphenyl, 2,5-dicarboxyphenyl, 2,6-dicarboxyphenyl and 2,4-dicarboxyphenyl groups; aryl groups substituted with at least one carbamoyl group, such as the 2-carbamoylphenyl, 3-carbamoylphenyl, 4-carbamoylphenyl, 3,5-dicarbamoylphenyl, 2,5-dicarbamoylphenyl, 2,6-dicarbamoylphenyl and 2,4-dicarbamoylphenyl groups; and aryl groups substituted with an alkylenedioxy group, such as the 3,4-methylenedioxyphenyl group.

Where substituent (a) Is an aralkyl group, the alkyl part has from 1 to 6, more preferably from 1 to 4 and still more preferably from 1 to 3, carbon atoms and is substituted by from 1 to 3, more preferably 1, aryl group. Where there is more than one aryl group, these may be the same or different. Preferred aryl groups are those listed in the previous paragraph and preferred alkyl groups are as exemplified previously, more preferably the methyl, ethyl and propyl groups and most preferably the methyl and ethyl groups. Specific examples of such aralkyl groups include: the unsubstituted groups, such as the α-naphthylmethyl, β-naphthylmethyl, diphenylmethyl, triphenylmethyl, α-naphthyldiphenylmethyl, 9-anthrylmethyl, 1-phenylethyl, 2-phenylethyl (phenethyl), 2-(α-naphthyl)ethyl, 2-(β-naphthyl)ethyl, 1-phenylpropyl, 2-phenylpropyl, 3-phenylpropyl, 1-(α- or β-naphthyl)propyl, 2-(α- or β-naphthyl)propyl, 3-(α- or β-naphthyl)propyl, 1-phenylbutyl, 2-phenylbutyl, 3-phenylbutyl, 4-phenylbutyl, 1-(α- or β-naphthyl)butyl, 2-(α- or β-naphthyl)butyl, 3-(α- or β-naphthyl)butyl, 4-(α- or β-naphthyl)butyl, 1-phenylpentyl, 2-phenylpentyl, 3-phenylpentyl, 4-phenylpentyl, 5-phenylpentyl, 1-(α- or β-naphthyl)pentyl, 2-(α- or β-naphthyl)pentyl, 3-(α- or β-naphthyl)pentyl, 4-(α- or β-naphthyl)pentyl, 5-(α- or β-naphthyl)pentyl, 1-phenylhexyl, 2-phenylhexyl, 3-phenylhexyl, 4-phenylhexyl, 5-phenylhexyl, 6-phenylhexyl, 1-(α- or β-naphthyl)hexyl, 2-(α- or β-naphthyl)hexyl, 3-(α- or β-naphthyl)hexyl, 4-(α- or β-naphthyl)hexyl, 5-(α- or β-naphthyl)hexyl and 6-(α- or β-naphthyl)hexyl groups; groups substituted with at least one halogen atom, such as the 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3,5-difluorobenzyl, 2,5-difluorophenethyl, 2,6-difluorobenzyl, 2,4-difluorophenethyl, 3,5-dibromobenzyl, 2,5-dibromophenethyl, 2,6-dichlorobenzyl, 2,4-dichlorophenethyl, 2,3,6-trifluorobenzyl, 2,3,4-trifluorophenethyl, 3,4,5-trifluorobenzyl, 2,5,6-trifluorophenethyl, 2,4,6-trifluorobenzyl, 2,3,6-tribromophenethyl, 2,3,4-tribromobenzyl, 3,4,5-tribromophenethyl, 2,5,6-trichlorobenzyl, 2,4,6-trichlorophenethyl, (1-fluoro-β-naphthyl)methyl, 2-(2-fluoro-α-naphthyl)ethyl, (3-fluoro-α- or β-naphthyl)methyl, 2-(1-chloro-β-naphthyl)ethyl, (2-chloro-α-naphthyl)methyl, 2-(3-bromo-α- or β-naphthyl)ethyl, (3,8-difluoro-α- or β-naphthyl)methyl, 2-(2,3-difluoro-α-naphthyl)ethyl, (4,8-difluoro-α- or β-naphthyl)methyl, 2-(5,6-difluoro-α- or β-naphthyl)ethyl, (3,8-dichloro-α- or β-naphthyl)methyl, 2-(2,3-dichloro-α-naphthyl)ethyl, (4,8-dibromo-α- or β-naphthyl)methyl, 2-(5,6-dibromo-α-or β-naphthyl)ethyl, (2,3,6-trifluoro-α-naphthyl)methyl, 2-(2,3,4-trifluoro-α- or β-naphthyl)ethyl, (3,4,5-trifluoro-α- or β-naphthyl)methyl, 2-(4,5,6-trifluoro-α- or β-naphthyl)ethyl, (2,4,8-trifluoro-α- or β-naphthyl)methyl, bis(2-fluorophenyl)methyl, α-(3-fluorophenyl)benzyl, bis(4-fluorophenyl)methyl, α-(4-fluorophenyl)benzyl, bis(2-chlorophenyl)methyl, bis(3-chlorophenyl)methyl, bis(4-chlorophenyl)methyl, α-(4-chlorophenyl)benzyl, α-(2-bromophenyl)benzyl, α-(3-bromophenyl)benzyl, bis(4-bromophenyl)methyl, bis(3,5-difluorophenyl)methyl, bis(2,5-difluorophenyl)methyl, bis (2,6-difluorophenyl)methyl, 2,4-difluorophenyl)benzyl, bis (3,5-dibromophenyl)methyl, α-(2,5-dibromophenyl)benzyl, 2,6-dichlorophenyl)benzyl, bis(2,4-dichlorophenyl)methyl and bis(2,3,6-trifluorophenyl)methyl groups; aralkyl groups substituted with at least one haloalkyl group, such as the 2-trifluoromethylbenzyl, 3-trifluoromethylphenethyl, 4-trifluoromethylbenzyl, 2-trichloromethylphenethyl, 3-dichloromethylbenzyl, 4-trichloromethylphenethyl, 2-tribromomethylbenzyl, 3-dibromomethylphenethyl, 4-dibromomethylbenzyl, 3,5-bis(trifluoromethyl)phenethyl, 2,5-bis(trifluoromethyl)benzyl, 2,6-bis(trifluoromethyl) phenethyl, 2,4-bis (trifluoromethyl)benzyl, 3,5-bis (tribromomethyl)phenethyl, 2,5bis(dibromomethyl)benzyl, 2,6-bis(dichloromethyl)phenethyl, 2,4-bis(dichloromethyl) benzyl, 2,3,6-tris(trifluoromethyl)phenethyl, 2,3,4-tris (trifluoromethyl)benzyl, 3,4,5-tris(trifluoromethyl) phenethyl, 2,5,6-tris(trifluoromethyl)benzyl, 2,4,6-tris (trifluoromethyl)phenethyl, 2,3,6-tris(tribromomethyl) benzyl, 2,3,4-tris(dibromomethyl)phenethyl, 3,4,5-tris (tribromomethyl)benzyl, 2,5,6-tris(dichloromethyl) phenethyl, 2,4,6-tris(dichloromethyl)benzyl, 2-(1-trifluoromethyl-β-naphthyl)ethyl, (2-trifluoromethyl-α-naphthyl)methyl, 2-(3-trifluoromethyl-α- or β-naphthyl) ethyl, (1-trichloromethyl-α- or β-naphthyl)methyl, 2-(2-dichloromethyl-α-naphthyl)ethyl, (3-tribromomethyl-α- or β-naphthyl)methyl, 2-[3,8-bis(trifluoromethyl)-α- or β-naphthyl]ethyl, [2,3-bis(trifluoromethyl)α-naphthyl ]methyl, 2-(4,8-bis(trifluoromethyl)-α- or β-naphthyl]ethyl, [5,6-bis(trifluoromethyl)-α- or β-naphthyl]methyl, 2-[3,8-bis(trichloromethyl)-α- or β-naphthyl]ethyl, [2,3-bis (dichloromethyl)-α-naphthyl ]methyl, 2-[4,8-bis (dibromomethyl)-α- or β-naphthyl)ethyl, [5,6-bis (tribromomethyl)-α- or β-naphthyl)methyl, 2-[2,3,6-tris (trifluoromethyl)-α- or β-naphthyl]ethyl, [2,3,4-tris (trifluoromethyl)-α-naphthyl]methyl, 2-[3,4,5-tris (trifluoromethyl)-α- or β-naphthyl]ethyl, [4,5,6-tris (trifluoromethyl)-α- or β-naphthyl]methyl, [2,4,8-tris (trifluoromethyl)-α-naphthyl)methyl, bis(4-trifluoromethylphenyl)methyl, α-(4-trifluoromethylphenyl) benzyl, bis(2-trichloromethylphenyl)methyl, bis(3-trichloromethylphenyl)methyl, bis(4-trichloromethylphenyl)methyl, α-(2-tribromomethylphenyl) benzyl, α-(3-tribromomethylphenyl)benzyl, bis(4-tribromomethylphenyl)methyl, bis[3,5-bis(trifluoromethyl) phenyl]methyl, bis[2,5-bis(trifluoromethyl)phenyl]methyl, bis[2,6-bis(trifluoromethyl)phenyl]methyl, α[2,4-bis (trifluoromethyl)phenyl]benzyl, bis 3,5-bis(tribromomethyl) phenyl]methyl, α-[2,5-bis(tribromomethyl)phenyl]benzyl, α-(2,6-bis(trichloromethyl)phenyl]benzyl, bis [2,4-bis (trichloromethyl)phenyl]methyl and bis[2,3,6-tris (trifluoromethyl)phenyl) methyl groups; aralkyl groups substituted with at least one alkyl group, such as the 2-methylbenzyl, 3-methylbenzyl, 4-methylbenzyl, 2-methylphenethyl, 4-methylphenethyl, 2-ethylbenzyl, 3-propylphenethyl, 4-ethylbenzyl, 2-butylphenethyl, 3-pentylbenzyl, 4-pentylphenethyl, 3,5-dimethylbenzyl, 2,5-dimethylphenethyl, 2,6-dimethylbenzyl, 2,4-dimethylphenethyl, 3,5-dibutylbenzyl, 2,5-dipentylphenethyl, 2,6-dipropylbenzyl, 2,4-dipropylphenethyl, 2,3,6-trimethylbenzyl, 2,3,4-trimethylphenethyl, 3,4,5-trimethylbenzyl, 2,4,6-trimethylbenzyl, 2,5,6-trimethylphenethyl, 2,3,6-tributylphenethyl, 2,3,4-tripentylbenzyl, 3,4,5-tributylphenethyl, 2,5,6-tripropylbenzyl, 2,4,6-tripropylphenethyl, (1-methyl-β-naphthyl)methyl, 2-(2-methyl-α-naphthyl)ethyl, (3-methyl-α- or β-naphthyl) methyl, 2-(1-ethyl-β-naphthyl)ethyl, (2-propyl-α-naphthyl) methyl, 2-(3-butyl-α- or β-naphthyl)ethyl, (3,8-dimethyl-α- or β-naphthyl)methyl, 2-(2,3-dimethyl-α-naphthyl)ethyl, (4,8-dimethyl-1-α- or β-naphthyl)methyl, 2-(5,6-dimethyl-α- or β-naphthyl)ethyl, (3,8-diethyl-α- or β-naphthyl) methyl, (2,3-dipropyl-α-naphthyl)methyl, 2-(4,8-dipentyl-α- or β-naphthyl)ethyl, (5,6-dibutyl-α- or β-naphthyl) methyl, (2,3,6-trimethyl-α- or β-naphthyl)methyl, 2-(2,3,4-trimethyl-α- or β-naphthyl)ethyl, (3,4,5-trimethyl-1-(α- or β-naphthyl)methyl, (4,5,6-trimethyl-α- or β-naphthyl) methyl, (2,4,8-trimethyl-1-(α- or β-naphthyl)methyl, bis(2-methylphenyl)methyl, α-(3-methylphenyl)benzyl, bis(4-methylphenyl)methyl, α-(4-methylphenyl)benzyl, bis(2-ethylphenyl)methyl, bis (3-ethylphenyl)methyl, bis(4-ethylphenyl)methyl, 2-propylphenyl)benzyl, 3-propylphenyl)benzyl bis(4-propylphenyl)methyl, bis(3,5-dimethylphenyl)methyl, bis(2,5-dimethylphenyl)methyl, bis (2,6-dimethylphenyl)methyl, α-(2,4-dimethylphenyl) benzyl, bis(3,5-dipropylphenyl) methyl, α-(2,5-dipropylphenyl)benzyl, α-(2,6-diethylphenyl)benzyl, bis(2,4-diethylphenyl)methyl and bis(2,3,6-trimethylphenyl) methyl groups; aralkyl groups substituted with at least one amino group, such as the 2-aminophenethyl, 3-aminobenzyl, 4-aminophenethyl, 3,5-diaminobenzyl, 2,5-diaminophenethyl, 2,6-diaminobenzyl, 2,4-diaminophenethyl, 2,3,6-triaminobenzyl, 2,3,4-triaminophenethyl, 3,4,5-triaminobenzyl, 2,5,6-triaminophenethyl, 2,4,6-triaminobenzyl, (1-amino-β-naphthyl)methyl, 2-(2-amino-α-naphthyl)ethyl, (3-amino-α- or β-naphthyl)methyl, (3,8-diamino-α- or β-naphthyl) methyl, 2-(2,3-diamino-1-(α- or β-naphthyl)ethyl, (4,8-diamino-α- or β-naphthyl)methyl, (5,6-diamino-1-(α- or β-naphthyl)methyl, 2-(2,3,6-triamino-α-naphthyl)ethyl, (2,3,4-triamino-α-naphthyl)methyl, (3,4,5-triamino-α- or β-naphthyl)methyl, 2-(4,5,6-triamino-α- or β-naphthyl) ethyl, (2,4,8-triamino-α-naphthyl)methyl, bis(2-aminophenyl)methyl, α-(3-aminophenyl)benzyl, bis(4-aminophenyl)methyl, α-(4-methylphenyl)benzyl, bis(3,5-diaminophenyl)methyl, bis(2,5-diaminophenyl)methyl, bis (2,6-diaminophenyl)methyl, α-(2,4-diaminophenyl)benzyl and bis(2,3,6-triaminophenyl)methyl groups; aralkyl groups substituted with at least one nitro group, such as the 2-nitrophenethyl, 3-nitrobenzyl, 4-nitrobenzyl, 4-nitrophenethyl, 3,5-dinitrobenzyl, 2,5-dinitrophenethyl, 2,6-dinitrobenzyl, 2,4-dinitrophenethyl, 2,3,6-trinitrobenzyl, 2,3,4-trinitrophenethyl, 3,4,5-trinitrobenzyl, 2,5,6-trinitrophenethyl, 2,4,6-trinitrobenzyl, (1-nitro-β-naphthyl)methyl, (2-nitro-α-naphthyl)ethyl, (3-nitro-α- or β-naphthyl)methyl, (3,8-dinitro-α- or α-naphthyl)methyl, 2-(2,3-dinitro-α-naphthyl)ethyl, (4,8-dinitro-α- or β-naphthyl) methyl, (5,6-dinitro-α- or β-naphthyl)methyl, 2-(2,3,6-trinitro-α- or β-naphthyl)ethyl, (2,3,4-trinitro-α-naphthyl)methyl, (3,4,5-trinitro-α- or β-naphthyl)methyl, 2-(4,5,6-trinitro-α- or β-naphthyl)ethyl, (2,4,8-trinitro-α-naphthyl)methyl, bis (2-nitrophenyl)methyl, α-(3-nitrophenyl)benzyl, bis(4-nitrophenyl)methyl, α-(4-nitrophenyl)benzyl, bis(3,5-dinitrophenyl)methyl, bis(2,5-dinitrophenyl)methyl, bis(2,6-dinitrophenyl)methyl, α-(2,4-dinitrophenyl)benzyl and bis(2,3,6-trinitrophenyl)methyl groups; aralkyl groups substituted with at least one cyano group, such as the 2-cyanophenethyl, 3-cyanobenzyl, 4-cyanobenzyl, 4-cyanophenyldiphenylmethyl, 4-cyanophenethyl, 3,5-dicyanobenzyl, 2,5-dicyanophenethyl, 2,6-dicyanobenzyl, 2,4-dicyanophenethyl, 2,3,6-tricyanobenzyl, 2,3,4-tricyanophenethyl, 3,4,5-tricyanobenzyl, 2,5,6-tricyanophenethyl, 2,4,6-tricyanobenzyl, (1-cyano-β-naphthyl)methyl, (3-cyano-α- or β-naphthyl)methyl, (3,8-dicyano-α- or β-naphthyl)methyl, 2-(2,3-dicyano-α-naphthyl)ethyl, (4,8-dicyano-α- or β-naphthyl)methyl, (5,6-dicyano-α- or β-naphthyl)methyl, 2-(2,3,6-tricyano-α-naphthyl)ethyl, (2,3,4-tricyano-α-naphthyl)methyl, (3,4,5-tricyano-α- or β-naphthyl)methyl, 2-(4,5,6-tricyano-α- or β-naphthyl)ethyl, (2,4,8-tricyano-α-naphthyl)methyl, bis(2-cyanophenyl)methyl, α-(3-cyanophenyl)benzyl, bis(4-cyanophenyl)methyl, α-(4-cyanophenyl)benzyl, bis(3,5-dicyanophenyl)methyl, bis(2,5-dicyanophenyl)methyl, bis (2,6-dicyanophenyl)methyl, α-(2,4-dicyanophenyl)benzyl and bis(2,3,6-tricyanophenyl)methyl groups; aralkyl groups substituted with at least one aliphatic acyl group, such as the 2-acetylphenethyl, 3-acetylbenzyl, 4-acetylphenethyl, 3,5-diacetylbenzyl, 2,5-diacetylphenethyl, 2,6-diacetylbenzyl, 2,4-diacetylphenethyl, 2,3,6-tripropionylbenzyl, 2,3,4-tripropionylphenethyl, 3,4,5-tripropionylbenzyl, 2,5,6-tributyrylphenethyl, 2,4,6-tributyrylbenzyl, (1-acetyl-β-naphthyl)methyl, 2-(2-acetyl-α-naphthyl)ethyl, (3-acetyl-α- or β-naphthyl)methyl, (3,8-diacetyl-1-(α- or β-naphthyl) methyl, 2-(2,3-dipropionyl-α-naphthyl)ethyl, (4,8-dibutyryl-α- or β-naphthyl)methyl, (5,6-dibutyryl-α- or β-naphthyl)methyl, 2-(2,3,6-triacetyl -α- or β-naphthyl) ethyl, (2,3,4-triacetyl-α- or β-naphthyl)methyl, (3,4,5-tripropionyl-α- or β-naphthyl)methyl, 2-(4,5,6-tributyryl-1-(α- or -β-naphthyl)ethyl, (2,4,8-tributyryl-α-naphthyl) methyl, bis(2-acetylphenyl)methyl, α-(3-acetylphenyl) benzyl, bis(4-acetylphenyl)methyl, α-(4-acetylphenyl) benzyl, bis(2-propionylphenyl)methyl, bis(3-propionylphenyl)methyl, bis(4-propionylphenyl)methyl, α-(2-butyrylphenyl)benzyl, α-(3-butyrylphenyl)benzyl, bis (4-butyrylphenyl)methyl, bis(3,5-diacetylphenyl)methyl, bis(2,5-diacetylphenyl)methyl, bis(2,6-diacetylphenyl) methyl, α-(2,4-diacetylphenyl)benzyl, bis(3,5-dibutyrylphenyl)methyl, α-(2,5-dibutylphenyl)benzyl, α-(2,6-dipropionylphenyl)benzyl, bis(2,4-dipropionylphenyl) methyl and bis(2,3,6-triacetylphenyl)methyl groups; aralkyl groups substituted with at least one carboxy group, such as the 2-carboxyphenethyl, 3-carboxybenzyl, 4-carboxyphenethyl, 3,5-dicarboxybenzyl, 2,5-dicarboxyphenethyl, 2,6-dicarboxybenzyl, 2,4-dicarboxyphenethyl, bis(2-carboxyphenyl)methyl, 3-carboxyphenyl)benzyl, bis(4-carboxyphenyl)methyl, 4-methyl, 4-carboxyphenyl)benzyl, bis(3,5-dicarboxyphenyl)methyl, bis(2,5-dicarboxyphenyl)methyl, bis(2,6-dicarboxyphenyl)methyl, 2,4-dicarboxyphenyl) benzyl and bis(2,3,6-tricarboxyphenyl)methyl groups; aralkyl groups substituted with at least one carbamoyl group, such as the 2-carbamoylbenzyl, 3-carbamoylphenethyl, 4-carbamoylbenzyl, 3,5-dicarbamoylphenethyl, 2,5-dicarbamoylbenzyl, 2,6-dicarbamoylphenethyl, 2,4-dicarbamoylbenzyl, bis(2-carbamoylphenyl)methyl, 3-carbamoylphenyl)benzyl, bis (4-carbamoylphenyl)methyl, 4-carbamoylphenyl)benzyl, bis(3,5-dicarbamoylphenyl)methyl, bis(2,5-dicarbamoylphenyl)methyl, bis(2,6-dicarbamoylphenyl) methyl, 2,4-dicarbamoylphenyl)benzyl and bis (2,3,6-tricarbamoylphenyl)methyl groups; and aralkyl groups substituted with an alkylenedioxy group, such as the 3,4-methylenedioxybenzyl (piperonyl), 3,4-methylenedioxyphenethyl, bis (3,4-methylenedioxyphenyl) methyl and 3,4-methylenedioxyphenyl)benzyl groups. Of these, we prefer the unsubstituted aralkyl groups and alkoxy-substituted aralkyl groups, more preferably the benzyl group and alkoxy-substituted benzyl groups and most preferably the benzyl and 4-methoxybenzyl groups.

Examples of the groups and atoms included within substituents (b) include:

halogen atoms, such as the chlorine, fluorine, bromine and iodine atoms, preferably fluorine or chlorine atoms;

alkyl groups having from 1 to 6 carbon atoms, such as the methyl, ethyl, propyl, isopropyl, butyl, isobutyl, sec-butyl, t-butyl, pentyl, isopentyl, 2-methylbutyl, neopentyl, hexyl, isohexyl, 2-methylpentyl, 4-methylpentyl, 3-methylpentyl, 3,3-dimethylbutyl, 2,2-dimethylbutyl, 1,1-dimethylbutyl, 1,2-dimethylbutyl, 1,3-dimethylbutyl and 2,3-dimethylbutyl groups;

halogen-substituted alkyl groups having from 1 to 6 carbon atoms, in which the alkyl group may be any of those exemplified above and the alkyl group may have from 1 to 5 halogen substituents (provided that there are enough substitutable positions), such as the trifluoromethyl, trichloromethyl, difluoromethyl, dichloromethyl, dibromomethyl, fluoromethyl, 2,2,2-trichloroethyl, 2,2,2- trifluoroethyl, 2-bromoethyl, 2-chloroethyl, 2-fluoroethyl and 2,2-dibromoethyl groups;

alkoxy groups having from 1 to 6 carbon atoms, such as the methoxy, ethoxy, propoxy, isopropoxy, butoxy, isobutoxy, sec-butoxy, t-butoxy, pentyloxy, isopentyloxy, 2-methylbutoxy, neopentyloxy, hexyloxy, isohexyloxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy groups;

nitro groups;

alkoxycarbonyl groups, in which the alkoxy part has from 1 to 6 carbon atoms, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, 2-methylbutoxycarbonyl, neopentyloxycarbonyl, hexyloxycarbonyl, isohexyloxycarbonyl, 4-methylpentyloxycarbonyl, 3-methylpentyloxycarbonyl, 2-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl and 2,3-dimethylbutoxycarbonyl groups;

aryl groups having from 6 to 14 ring carbon atoms and being unsubstituted or having at least one substituent selected from the group consisting of substituents (b), defined and exemplified herein other than the aryl groups, such as those exemplified above in respect of substituents (a);

cyano groups;

alkylenedioxy groups having from 1 to 4 carbon atoms, such as the methylenedioxy, ethylenedioxy and propylenedioxy groups;

and divalent aliphatic hydrocarbon groups having from 1 to 4 carbon atoms such as the methylene, dimethylene, propylene and trimethylene groups;

groups of formula —$NR^dR^e$, where $R^d$ and $R^e$ are independently selected from the group consisting of hydrogen atoms and alkyl groups having from 1 to 6, preferably from 1 to 4, carbon atoms, such as the amino, methylamino, ethylamino, propylamino, isopropylamino, butylamino, isobutylamino, sec-butylamino, t-butylamino, pentylamino, hexylamino, dimethylamino, diethylamino, dipropylamino, diisopropylamino, dibutylamino, diisobutylamino, methylethylamino, methylpropylamino, methylisopropylamino, methyl butylamino, methylisobutylamino, methyl-sec-butylamino, methyl-t-butylamino, ethylpropylamino and ethylbutylamino groups;

haloalkoxycarbonyl groups, in which the alkoxy part has from 1 to 6 carbon atoms, such as the trifluoromethoxycarbonyl, trichloromethoxycarbonyl, difluoromethoxycarbonyl, dichloromethoxycarbonyl, dibromomethoxycarbonyl, fluoromethoxycarbonyl, 2,2,2-trichloroethoxycarbonyl, 2,2,2-trifluoroethoxycarbonyl, 2-bromoethoxycarbonyl, 2-chloroethoxycarbonyl, 2-fluoroethoxycarbonyl and 2,2-dibromoethoxycarbonyl groups;

aralkyloxycarbonyl groups, in which the aralkyl part comprises an alkyl group having from 1 to 6 carbon atoms which is substituted with from 1 to 3 aryl groups, said aryl groups being unsubstituted or having at least one substituent selected from the group consisting of substituents (b), defined below, such as those exemplified above in relation to hydroxy protecting groups;

groups of formula —CO—$NR^dR^e$, where $R^d$ and $R^e$ are as defined above, such as the carbamoyl, methylcarbamoyl, ethylcarbamoyl, propylcarbamoyl, isopropylcarbamoyl, butylcarbamoyl, isobutylcarbamoyl, sec-butylcarbamoyl, t-butylcarbamoyl, pentylcarbamoyl, hexylcarbamoyl, dimethylcarbamoyl, diethylcarbamoyl, dipropylcarbamoyl, diisopropylcarbamoyl, dibutylcarbamoyl, diisobutylcarbamoyl, methylethylcarbamoyl, methylpropylcarbamoyl, methylisopropylcarbamoyl methylbutylcarbamoyl, methylisobutylcarbamoyl, methyl-sec-butylcarbamoyl, methyl-t-butylcarbamoyl, ethylpropylcarbamoyl and ethylbutylcarbamoyl groups;

and aliphatic acyl groups having from 1 to 20 carbon atoms, such as those exemplified above in relation to the hydroxy-protecting groups.

Examples of the various groups and atoms which may be included within substituents (c) and (d) are as given in relation to the corresponding groups and atoms included within substituents (b).

Of the compounds of the present invention, we prefer those in which:

(A) one of $R^1$ and $R^4$ represents a hydroxy group, a protected hydroxy group as defined above, or a group of formula —OP(O)(OH)$_2$, and the other represents a group of formula —OP(O)(OH)$_2$;

one of $R^2$ and $R^3$ represents an aliphatic acyl group having from 6 to 20 carbon atoms, said group having 0 or at least one halogen substituent and 0 or 1 substituent selected from the group consisting of hydroxy groups, aliphatic carboxylic acyloxy groups having from 6 to 20 carbon atoms and halogen-substituted aliphatic carboxylic acyloxy groups having from 6 to 20 carbon atoms, and the other of $R^2$ and $R^3$ represents an aliphatic carboxylic acyl group having from 6 to 20 carbon atoms, said group (i) having at least one halogen substituent and 1 substituent selected from the group consisting of hydroxy groups and aliphatic carboxylic acyloxy groups having from 6 to 20 carbon atoms or (ii) having at least one halogen-substituted aliphatic carboxylic acyloxy group having from 6 to 20 carbon atoms and 0 or 1 substituent selected from the group consisting of halogen atoms, hydroxy groups and aliphatic carboxylic acyloxy groups having from 6 to 20 carbon atoms; and $R^5$ represents a hydroxy group or a protected hydroxy group, as defined above.

(B) one of $R^1$ and $R^5$ represents a hydroxy group or a protected hydroxy group, as defined above, and the other represents a fluorine atom;

$R^2$ and $R^3$ are independently selected from the group consisting of aliphatic carboxylic acyl groups having from 6 to 20 carbon atoms, said acyl groups being unsubstituted or having at least one substituent selected from the group consisting of substituents (a), as defined above; and $R^4$ represents a group of formula —OP(O)(OH)$_2$.

More preferred are:

(C) the compounds defined in (A) and (B) above in which the glucopyran moiety has the D configuration.

Still more preferred are those compounds in which:

(D) one of $R^1$ and $R^4$ represents a group of formula —OP(O)(OH)$_2$, and the other represents a hydroxy group or a group of formula —OP(O)(OH)$_2$.

(E) one of $R^2$ and $R^3$ represents an aliphatic acyl group having from 10 to 16 carbon atoms, said group having at least one halogen substituent and 0 or 1 substituent selected from the group consisting of hydroxy groups and aliphatic carboxylic acyloxy groups having from 10 to 16 carbon atoms, and the other of $R^2$ and $R^3$ represents an aliphatic carboxylic acyl group having from 10 to 16 carbon atoms, said group having at least one substituent selected from the group consisting of halogen atoms, hydroxy groups and aliphatic carboxylic acyloxy groups having from 10 to 16 carbon atoms.

(F) $R^2$ represents an aliphatic acyl group having from 10 to 16 carbon atoms, said group having at least one halogen substituent and 0 or 1 substituent selected from the group consisting of hydroxy groups and aliphatic carboxylic acyloxy groups having from 10 to 16 carbon atoms.

(G) $R^5$ represents a hydrogen atom or a carboxy-substituted aliphatic carboxylic acyloxy group in which the acyl part has from 1 to 6 carbon atoms and the carboxy substituent is at the terminal remote from the oxy group of the acyloxy.

(H) $R^1$ represents a hydroxy group or a protected hydroxy group, as defined above.

(I) one of $R^2$ and $R^3$ represents an aliphatic carboxylic acyl group having from 12 to 16 carbon atoms or a substituted aliphatic carboxylic acyl group having from 12 to 16 carbon atoms and having at least one substituent selected from the group consisting of halogen atoms, hydroxy groups, aliphatic carboxylic acyloxy groups having from 12 to 16 carbon atoms and halogen-substituted aliphatic carboxylic acyloxy groups having from 12 to 16 carbon atoms, provided that it is substituted by no more than one said hydroxy group and by no more than one said acyloxy group, and the other of $R^2$ and $R^3$ represents a substituted aliphatic carboxylic acyl group having from 12 to 16 carbon atoms and having at least one halogen substituent and 0 or 1 substituent selected from the group consisting of hydroxy groups and aliphatic carboxylic acyloxy groups having from 12 to 16 carbon atoms.

(J) it is as defined in (B) above, wherein $R^5$ represents a fluorine atom.

(K) it is as defined in (B) above, wherein:

$R^1$ represents a hydroxy group or a protected hydroxy group, as defined above;

one of $R^2$ and $R^3$ represents an aliphatic carboxylic acyl group having from 12 to 16 carbon atoms or a substituted aliphatic carboxylic acyl group having from 12 to 16 carbon atoms and having at least one substituent selected from the group consisting of halogen atoms, hydroxy groups and aliphatic carboxylic acyloxy groups having from 12 to 16 carbon atoms, provided that it is substituted by no more than one said hydroxy group and by no more than one said acyloxy group, and the other of $R^2$ and $R^3$ represents a substituted aliphatic carboxylic acyl group having from 12 to 16 carbon atoms and having at least one halogen substituent and 0 or 1 substituent selected from the group consisting of hydroxy groups and aliphatic carboxylic acyloxy groups having from 12 to 16 carbon atoms;

$R^4$ represents a group of formula —OP(O)(OH)$_2$; and $R^5$ represents a fluorine atom or a hydroxy group.

(L) it is as defined in (B) above, wherein $R^1$ represents a hydroxy group.

(M) one of $R^2$ and $R^3$ represents an aliphatic acyl group having from 10 to 16 carbon atoms said group having at least one halogen substituent and 0 or 1 substituent selected from the group consisting of hydroxy groups and aliphatic carboxylic acyloxy groups having from 10 to 16 carbon atoms, and the other of $R^2$ and $R^3$ represents an aliphatic carboxylic acyl group having from 10 to 16 carbon atoms, said group having at least one substituent selected from the group consisting of halogen atoms, hydroxy groups and aliphatic carboxylic acyloxy groups having from 10 to 16 carbon atoms.

(N) $R^1$ represents a hydroxy group;

one of $R^2$ and $R^3$ represents an aliphatic acyl group having from 10 to 16 carbon atoms, said group having at least one halogen substituent and 0 or 1 substituent selected from the group consisting of hydroxy groups and aliphatic carboxylic acyloxy groups having from 10 to 16 carbon atoms, and the other of $R^2$ and $R^3$ represents an aliphatic carboxylic acyl group having from 10 to 16 carbon atoms, said group having at least one substituent selected from the group consisting of halogen atoms, hydroxy groups and aliphatic carboxylic acyloxy groups having from 10 to 16 carbon atoms.

$R^4$ represents a group of formula —OP(O)(OH)$_2$; and $R^5$ represents a fluorine atom or a hydroxy group.

(O) $R^1$ represents a hydroxy group, a fluorine atom or a group of formula —OP(O)(OH)$_2$;

$R^2$ and $R^3$ are independently selected from the group consisting of aliphatic carboxylic acyl groups having from 6 to 20 carbon atoms, said acyl groups being unsubstituted or having at least one substituent selected from the group consisting of substituents (a') defined below;

$R^4$ represents a hydroxy group or a group of formula OP(O)(OH)$_2$, where at least one of $R^1$ and $R^4$ represents a group of formula —OP(O)(OH)$_2$;

$R^5$ represents a hydroxy group or a fluorine atom;

provided that, except where at least one of $R^1$ and $R^5$ represents a fluorine atom, at least one of $R^2$ and $R^3$ represents a substituted aliphatic carboxylic acyl group having from 6 to 20 carbon atoms and having (i) at least one halogen substituent and (ii) at least one substituent selected from the group consisting of halogen atoms, hydroxy groups and aliphatic carboxylic acyloxy groups having from 6 to 20 carbon atoms or at least one of $R^2$ and $R^3$ represents a substituted aliphatic acyl group having from 6 to 20 carbon atoms and which is substituted by at least one halogen-substituted aliphatic carboxylic acyloxy group having from 6 to 20 carbon atoms;

substituents (a')

halogen atoms; hydroxy groups; aliphatic carboxylic acyloxy groups having from 6 to 20 carbon atoms; and halogen-substituted aliphatic carboxylic acyloxy groups having from 6 to 20 carbon atoms.

(P) one of $R^1$ and $R^4$ represents a hydroxy group or a group of formula —OP(O)(OH)$_2$ and the other represents a group of formula —OP(O)(OH)$_2$;

one of $R^2$ and $R^3$ represents an aliphatic carboxylic acyl group having from 6 to 20 carbon atoms, said group having 0 or at least one halogen substituent and 0 or 1 substituent selected from the group consisting of hydroxy groups, aliphatic carboxylic acyloxy groups having from 6 to 20 carbon atoms and halogen-substituted aliphatic carboxylic acyloxy groups having from 6 to 20 carbon atoms, and the other of $R^2$ and $R^3$ represents an aliphatic carboxylic acyl group having from 6 to 20 carbon atoms, said group (i) having at least one halogen substituent and 1 substituent selected from the group consisting of hydroxy groups and aliphatic carboxylic acyloxy groups having from 6 to 20 carbon atoms or (ii) having at least one halogen-substituted aliphatic carboxylic acyloxy group having from 6 to 20 carbon atoms and 0 or 1 substituent selected from the group consisting of halogen atoms, hydroxy groups and aliphatic carboxylic acyloxy groups having from 6 to 20 carbon atoms;

$R^5$ represents a hydroxy group.

(Q) one of $R^1$ and $R^5$ represents a hydroxy group and the other represents a fluorine atom;

$R^2$ and $R^3$ are independently selected from the group consisting of aliphatic carboxylic acyl groups having from 6 to 20 carbon atoms, said acyl groups being unsubstituted or having at least one substituent selected from the group consisting of substituents (a'), defined in (P) above;

$R^4$ represents a group of formula —OP(O)(OH)$_2$.

Certain of the compounds of the present invention may contain a carboxy group and can, therefore, form esters, which also form part of the present invention. There is no limitation upon the nature of such esters, provided that, where the resulting compound is to be used for therapeutic purposes, it is pharmaceutically acceptable, which, as is well known in the art, means that the compound does not have reduced activity (or unacceptably reduced activity) or increased toxicity (or unacceptably increased toxicity) as compared with the corresponding compound of formula (I), i.e. the free acid. Where, however, the compound is to be used for non-therapeutic purposes, e.g. as an intermediate in the preparation of other compounds, even this limitation does not apply, and the nature of the ester group may be chosen having regard simply to process criteria. Examples of suitable ester groups which may replace the hydrogen atom of the carboxy group include:

$C_1$–$C_{20}$ alkyl groups, more preferably $C_1$–$C_6$ alkyl groups, such as those exemplified in relation to substituents (b) etc. and higher alkyl groups as are well known in the art, such as the heptyl, 1-methylhexyl, 2-methylhexyl, 5-methylhexyl, 3-ethylpentyl, octyl, 2-methylheptyl, 5-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl 4-ethylheptadecyl, icosyl, 18-methylnonadecyl and 3-ethyloctadecyl groups, but most preferably the methyl, ethyl and t-butyl groups;

$C_3$–$C_7$ cycloalkyl groups, for example the cyclopropyl, cyclobutyl, cyclopentyl, cyclohexyl or cycloheptyl group;

aralkyl groups in which the aromatic group is $C_6$–$C_{14}$, which may be substituted or unsubstituted, and, if substituted, may have at least one substituent selected from the group consisting of substituents (b), defined and exemplified above; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 2-nitrobenzyl, 4-methoxybenzyl and piperonyl groups;

alkenyl groups, having from 2 to 6 carbon atoms, which may be substituted or unsubstituted and, if substituted, have at least one substituent selected from the group consisting of halogen atoms; examples of the unsubstituted groups are given above in relation to substituents (b), and preferred groups include the allyl, 2-chloroallyl and 2-methylallyl groups;

halogenated $C_1$–$C_6$, preferably $C_1$–$C_4$, alkyl groups in which the alkyl part is as defined and exemplified in relation to the alkyl groups which may be represented by substituents (b) etc. and the halogen atom is chlorine fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl group;

substituted silylalkyl groups, in which the alkyl part is as defined and exemplified in relation to the alkyl groups which may be represented by substituents (b) etc. and the silyl group has up to 3 substituents selected from the group consisting of $C_1$–$C_6$ alkyl groups and phenyl groups which are unsubstituted or have at least one substituent selected from the group consisting of substituents (b) defined and exemplified above, for example a 2-trimethylsilylethyl group;

phenyl groups, in which the phenyl group is unsubstituted or substituted, preferably with at least one $C_1$–$C_4$ alkyl or acylamino group, for example the phenyl, tolyl and benzamidophenyl groups;

phenacyl groups, which may be unsubstituted or have at least one substituent selected from the group consisting of substituents (b) defined and exemplified above, for example the phenacyl group itself or the p-bromophenacyl group;

cyclic and acyclic terpenyl groups, for example the geranyl, neryl, linalyl, phytyl, menthyl (especially m- and p- menthyl), thujyl, caryl, pinanyl, bornyl, norcaryl, norpinanyl, norbornyl, menthenyl, camphenyl and norbornenyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

alkoxymethyl groups, in which the alkoxy part is $C_1$–$C_6$, preferably $C_1$–$C_4$, and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxymethyl groups, in which the acyl group is preferably an alkanoyl group and is more preferably a $C_2$–$C_6$ alkanoyl group, such as the acetoxymethyl, propionyloxymethyl, butyryloxymethyl, isobutyryloxymethyl and pivaloyloxymethyl groups;

higher aliphatic acyloxyalkyl groups in which the acyl group is preferably an alkanoyl group and is more preferably a $C_2$–$C_6$ alkanoyl group, and the alkyl part is $C_2$–$C_6$, and preferably $C_2$–$C_4$, such as the 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably a $C_2$–$C_6$ alkanoyl group, the cycloalkyl substituent is $C_3$–$C_7$, and the alkyl part is a $C_1$–$C_6$ alkyl group, preferably a $C_1$–$C_4$ alkyl group, such as the (cyclohexylacetoxy)methyl, 1-(cyclohexylacetoxy)ethyl, 1-(cyclohexylacetoxy) propyl, 2-methyl-1-(cyclohexylacetoxy)propyl, (cyclopentylacetoxy)methyl, 1-(cyclopentylacetoxy) ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy) ethyl groups, in which the alkoxy part is $C_1$–$C_{10}$, preferably $C_1$–$C_6$, and more preferably $C_1$–$C_4$, and the alkyl part is $C_1$–$C_6$, preferably $C_1$–$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups are $C_1$–$C_6$, preferably $C_1$–$C_4$, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group is $C_3$–$C_{10}$, preferably $C_3$–$C_7$, is mono- or poly-cyclic and is optionally substituted by at least one (and preferably only one) $C_1$–$C_4$ alkyl group (e.g. selected from those alkyl groups exemplified above) and the alkyl group is a $C_1$–$C_6$, more preferably $C_1$–$C_4$, alkyl group (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent being $C_3$–$C_{10}$, preferably $C_3$–$C_7$, and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

(5-alkyl- or 5-phenyl-2-oxo-1,3-dioxolen-4-yl)alkyl groups in which each alkyl group (which may be the same or different) is $C_1$–$C_6$, preferably $C_1$–$C_4$, and the phenyl group may be unsubstituted or substituted by at least one substituent selected from the group consisting of substituents (b), for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl) ethyl groups; and other groups, especially groups which are easily removed in vivo such as the phthalidyl, indanyl and 2-oxo-4,5,6,7-tetrahydro-1,3-benzodioxolen-4-yl groups.

Of the above groups, we especially prefer those groups which can be removed easily in vivo, and most preferably the aliphatic acyloxymethyl groups, higher aliphatic acyloxyalkyl groups, cycloalkyl-aliphatic acyloxyalkyl groups, alkoxycarbonyloxyalkyl groups, cycloalkylcarbonyloxyalkyl groups, and cycloalkylalkoxycarbonyloxyalkyl groups.

The compounds of formula (I) may also form salts with cations, examples of which include:

metal atoms, especially alkali metal atoms, such as the sodium and potassium atoms, alkaline earth metal atoms, such as the calcium atom, and other atoms, such as the iron, magnesium, aluminum and cobalt atoms;

the ammonium group;

cations derived from a trialkylamine, such as triethylamine or trimethylamine, or from another organic base, such as procaine, dibenzylamine, phenethylamine, 2-phenylethylbenzylamine, ethanolamine, diethanolamine, a polyhydroxyalkylamine or N-methylglucosamine; and basic amino acids, such as lysine, arginine, ornithine or histidine.

Of the above, we prefer salts of an alkaline metal or of a mineral acid.

The compounds of the present invention will contain at least one asymmetric carbon atom in their molecules and may contain several, and can thus form optical isomers having the (R)-configuration or the (S)-configuration. Although these are all represented herein by a single molecular formula, the present invention includes both the individual, isolated isomers and mixtures, including racemates thereof. Where stereospecific synthesis techniques are employed, individual isomers may be prepared directly; on the other hand, if a mixture of isomers is prepared, the individual isomers may be obtained by conventional resolution techniques.

Examples of specific compounds of the invention are given in the following formulae (I-1) to (I-3), in which the substituents are as defined in the corresponding one of Tables 1 to 3, respectively [i.e. Table 1 relates to formula (I-1), Table 2 relates to formula (I-2) and Table 3 relates to formula (I-3)].

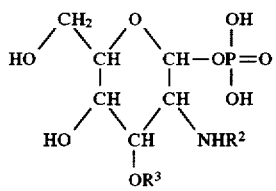
(I-1)

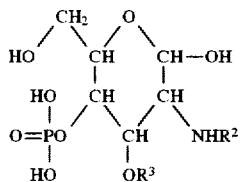
(I-2)

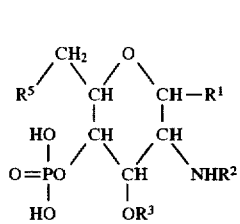
(I-3)

TABLE 1

| Cpd No. | $R^2$ | $R^3$ |
|---|---|---|
| 1-1 | —COCH$_2$CH(OH)C$_7$H$_{15}$ | —COCHFCH(OH)C$_{11}$H$_{23}$ |
| 1-2 | —COCH$_2$CH(OH)C$_9$H$_{19}$ | —COCHFCH(OH)C$_{11}$H$_{23}$ |
| 1-3 | —COCH$_2$CH(OH)C$_{11}$H$_{23}$ | —COCHFCH(OH)C$_{11}$H$_{23}$ |
| 1-4 | —COCH$_2$CH(OH)C$_{13}$H$_{27}$ | —COCHFCH(OH)C$_{11}$H$_{23}$ |
| 1-5 | —COCH$_2$CH(OH)C$_{15}$H$_{31}$ | —COCHFCH(OH)C$_{11}$H$_{23}$ |
| 1-6 | —COCH$_2$CH(OH)C$_{11}$H$_{23}$ | —COCHFCH(OH)C$_7$H$_{15}$ |
| 1-7 | —COCH$_2$CH(OH)C$_{11}$H$_{23}$ | —COCHFCH(OH)C$_9$H$_{19}$ |
| 1-8 | —COCH$_2$CH(OH)C$_{11}$H$_{23}$ | —COCHFCH(OH)C$_{11}$H$_{23}$ |
| 1-9 | —COCH$_2$CH(OH)C$_{11}$H$_{23}$ | —COCHFCH(OH)C$_{13}$H$_{27}$ |
| 1-10 | —COCH$_2$CH(OH)C$_{11}$H$_{23}$ | —COCHFCH(OH)C$_{15}$H$_{31}$ |
| 1-11 | —COCH$_2$CH(OH)C$_{11}$H$_{23}$ | —COCHClCH(OH)C$_{11}$H$_{23}$ |
| 1-12 | —COCH$_2$CH(OCOC$_{11}$H$_{23}$)—C$_9$H$_{19}$ | —COCHFCH(OH)C$_{11}$H$_{23}$ |
| 1-13 | —COCH$_2$CH(OCOC$_{11}$H$_{23}$)—C$_{11}$H$_{23}$ | —COCHFCH(OH)C$_{11}$H$_{23}$ |
| 1-14 | —COCH$_2$CH(OCOC$_{11}$H$_{23}$)—C$_{13}$H$_{27}$ | —COCHFCH(OH)C$_{11}$H$_{23}$ |
| 1-15 | —COCH$_2$CH(OCOC$_9$H$_{19}$)—C$_{11}$H$_{23}$ | —COCHFCH(OH)C$_{11}$H$_{23}$ |
| 1-16 | —COCH$_2$CH(OCOC$_{13}$H$_{27}$)—C$_{11}$H$_{23}$ | —COCHFCH(OH)C$_{11}$H$_{23}$ |
| 1-17 | —COCH$_2$CH(OCOC$_{11}$H$_{23}$)—C$_{11}$H$_{23}$ | —COCHClCH(OH)C$_{11}$H$_{23}$ |
| 1-18 | —COCH$_2$CH(OCOC$_{11}$H$_{23}$)—C$_{11}$H$_{23}$ | —COCH(OH)CHFC$_{11}$H$_{23}$ |
| 1-19 | —COCH$_2$CH(OH)C$_{11}$H$_{23}$ | —COCHFCH(OCOC$_{11}$H$_{23}$)—C$_{11}$H$_{23}$ |
| 1-20 | —COCH$_2$CH(OH)C$_{11}$H$_{23}$ | —COCHFCH(OCOC$_9$H$_{19}$)—C$_{11}$H$_{23}$ |
| 1-21 | —COCH$_2$CH(OH)C$_{11}$H$_{23}$ | —COCHFCH(OCOC$_{13}$H$_{27}$)—C$_{11}$H$_{23}$ |
| 1-22 | —COCH$_2$CH(OH)C$_{11}$H$_{23}$ | —COCHFCH(OCOC$_{11}$H$_{23}$)—C$_9$H$_{19}$ |
| 1-23 | —COCH$_2$CH(OH)C$_{11}$H$_{23}$ | —COCHFCH(OCOC$_{11}$H$_{23}$)—C$_{13}$H$_{27}$ |
| 1-24 | —COCH$_2$CH(OH)C$_9$H$_{19}$ | —COCHFCH(OCOC$_{11}$H$_{23}$)—C$_{11}$H$_{23}$ |
| 1-25 | —COCH$_2$CH(OH)C$_{13}$H$_{27}$ | —COCHFCH(OCOC$_{11}$H$_{23}$)—C$_{11}$H$_{23}$ |
| 1-26 | —COCH$_2$CH(OH)C$_{11}$H$_{23}$ | —COCHClCH(OCOC$_{11}$H$_{23}$)—C$_{11}$H$_{23}$ |
| 1-27 | —COCH$_2$CH(OCOC$_{11}$H$_{23}$)—C$_{11}$H$_{23}$ | —COCHFCH(OCOC$_{11}$H$_{23}$)—C$_{11}$H$_{23}$ |

TABLE 1-continued

| Cpd No. | $R^2$ | $R^3$ |
|---|---|---|
| 1-28 | —COCH$_2$CH(OCOC$_{11}$H$_{23}$)—C$_{11}$H$_{23}$ | —COCHFCH(OCOC$_9$H$_{19}$)—C$_{11}$H$_{23}$ |
| 1-29 | —COCH$_2$CH(OCOC$_{11}$H$_{23}$)—C$_{11}$H$_{23}$ | —COCHFCH(OCOC$_{13}$H$_{27}$)—C$_{11}$H$_{23}$ |
| 1-30 | —COCH$_2$CH(OCOC$_{11}$H$_{23}$)—C$_{11}$H$_{23}$ | —COCHFCH(OCOC$_{11}$H$_{23}$)—C$_9$H$_{19}$ |
| 1-31 | —COCH$_2$CH(OCOC$_{11}$H$_{23}$)—C$_{11}$H$_{23}$ | —COCHFCH(OCOC$_{11}$H$_{23}$)—C$_{13}$H$_{27}$ |
| 1-32 | —COCH$_2$CH(OCOC$_9$H$_{19}$)—C$_{11}$H$_{23}$ | —COCHFCH(OCOC$_{11}$H$_{23}$)—C$_{11}$H$_{23}$ |
| 1-33 | —COCH$_2$CH(OCOC$_{13}$H$_{27}$)—C$_{11}$H$_{23}$ | —COCHFCH(OCOC$_{11}$H$_{23}$)—C$_{11}$H$_{23}$ |
| 1-34 | —COCH$_2$CH(OCOC$_{11}$H$_{23}$)—C$_9$H$_{19}$ | —COCHFCH(OCOC$_{11}$H$_{23}$)—C$_{11}$H$_{23}$ |
| 1-35 | —COCH$_2$CH(OCOC$_{11}$H$_{23}$)—C$_{13}$H$_{27}$ | —COCHFCH(OCOC$_{11}$H$_{23}$)—C$_{11}$H$_{23}$ |
| 1-36 | —COCH$_2$CH(OCOC$_{11}$H$_{23}$)—C$_{11}$H$_{23}$ | —COCHClCH(OCOC$_{11}$H$_{23}$)—C$_{11}$H$_{23}$ |
| 1-37 | —COCH$_2$CH(OH)C$_{11}$H$_{23}$ | —COCHF.(CH$_2$)$_2$.CH(OH)—C$_9$H$_{19}$ |
| 1-38 | —COCH$_2$CH(OH)C$_{11}$H$_{23}$ | —COCHF.(CH$_2$)$_3$.CH(OH)—C$_8$H$_{17}$ |
| 1-39 | —COCH$_2$CH(OH)C$_{11}$H$_{23}$ | —COCHCl.(CH$_2$)$_4$.CH(OH)—C$_7$H$_{15}$ |
| 1-40 | —COCH$_2$CH(OH)C$_{11}$H$_{23}$ | —COCHBr.(CH$_2$)$_5$.CH(OH)—C$_6$H$_{13}$ |
| 1-41 | —COCH$_2$CH(OH)C$_{11}$H$_{23}$ | —COCHF.(CH$_2$)$_6$.CH(OH)—C$_5$H$_{11}$ |
| 1-42 | —COCH$_2$CH(OH)C$_{11}$H$_{23}$ | —COCHCl.(CH$_2$)$_7$.CH(OH)—C$_4$H$_9$ |
| 1-43 | —COCHF.CH(OH)C$_{11}$H$_{23}$ | —COCH$_2$CH(OH)C$_{11}$H$_{23}$ |
| 1-44 | —COCHF.CH(OH)C$_{11}$H$_{23}$ | —COCH$_2$CH(OH)C$_9$H$_{19}$ |
| 1-45 | —COCHF.CH(OH)C$_{11}$H$_{23}$ | —COCH$_2$CH(OH)C$_{13}$H$_{27}$ |
| 1-46 | —COCHCl.CH(OH)C$_9$H$_{19}$ | —COCH$_2$CH(OH)C$_{11}$H$_{23}$ |
| 1-47 | —COCHBr.CH(OH)C$_{13}$H$_{27}$ | —COCH$_2$CH(OH)C$_{11}$H$_{23}$ |
| 1-48 | —COCHF.CH(OH)C$_9$H$_{19}$ | —COCH$_2$CH(OH)C$_9$H$_{19}$ |
| 1-49 | —COCHCl.CH(OH)C$_{13}$H$_{27}$ | —COCH$_2$CH(OH)C$_{13}$H$_{27}$ |
| 1-50 | —COCHF.CH(OH)C$_9$H$_{19}$ | —COCH$_2$CH(OH)C$_{13}$H$_{27}$ |
| 1-51 | —COCHF.CH(OH)C$_{13}$H$_{27}$ | —COCH$_2$CH(OH)C$_9$H$_{19}$ |
| 1-52 | —COCHF.CH(OH)C$_{11}$H$_{23}$ | —COCH$_2$CH(OCOC$_{11}$H$_{23}$)—C$_{11}$H$_{23}$ |
| 1-53 | —COCHF.CH(OH)C$_{11}$H$_{23}$ | —COCH$_2$CH(OCOC$_9$H$_{19}$)—C$_{11}$H$_{23}$ |
| 1-54 | —COCHF.CH(OH)C$_{11}$H$_{23}$ | —COCH$_2$CH(OCOC$_{13}$H$_{27}$)—C$_{11}$H$_{23}$ |
| 1-55 | —COCHCl.CH(OH)C$_{11}$H$_{23}$ | —COCH$_2$CH(OCOC$_{11}$H$_{23}$)—C$_9$H$_{19}$ |
| 1-56 | —COCHBr.CH(OH)C$_{11}$H$_{23}$ | —COCH$_2$CH(OCOC$_{11}$H$_{23}$)—C$_{13}$H$_{27}$ |
| 1-57 | —COCHF.CH(OH)C$_9$H$_{19}$ | —COCH$_2$CH(OCOC$_{11}$H$_{23}$)—C$_{11}$H$_{23}$ |
| 1-58 | —COCHCl.CH(OH)C$_9$H$_{19}$ | —COCH$_2$CH(OCOC$_9$H$_{19}$)—C$_{11}$H$_{23}$ |
| 1-59 | —COCHF.CH(OH)C$_9$H$_{19}$ | —COCH$_2$CH(OCOC$_{13}$H$_{27}$)—C$_{11}$H$_{23}$ |
| 1-60 | —COCHF.CH(OH)C$_9$H$_{19}$ | —COCH$_2$CH(OCOC$_{11}$H$_{23}$)—C$_9$H$_{19}$ |
| 1-61 | —COCHF.CH(OH)C$_9$H$_{19}$ | —COCH$_2$CH(OCOC$_{11}$H$_{23}$)—C$_{13}$H$_{27}$ |
| 1-62 | —COCHCl.CH(OH)C$_{13}$H$_{27}$ | —COCH$_2$CH(OCOC$_{11}$H$_{23}$)—C$_{11}$H$_{23}$ |
| 1-63 | —COCHF.CH(OCOC$_{11}$H$_{23}$)—C$_{11}$H$_{23}$ | —COCH$_2$CH(OH)C$_{11}$H$_{23}$ |
| 1-64 | —COCHF.CH(OCOC$_9$H$_{19}$)—C$_{11}$H$_{23}$ | —COCH$_2$CH(OH)C$_{11}$H$_{23}$ |
| 1-65 | —COCHF.CH(OCOC$_{13}$H$_{27}$)—C$_{11}$H$_{23}$ | —COCH$_2$CH(OH)C$_{11}$H$_{23}$ |
| 1-66 | —COCHCl.CH(OCOC$_{11}$H$_{23}$)—C$_{13}$H$_{27}$ | —COCH$_2$CH(OH)C$_{11}$H$_{23}$ |
| 1-67 | —COCHBr.CH(OCOC$_{13}$H$_{27}$)—C$_9$H$_{19}$ | —COCH$_2$CH(OH)C$_{11}$H$_{23}$ |
| 1-68 | —COCHF.CH(OCOC$_{11}$H$_{23}$)—C$_{11}$H$_{23}$ | —COCH$_2$CH(OH)C$_9$H$_{19}$ |
| 1-69 | —COCHCl.CH(OCOC$_9$H$_{19}$)—C$_{11}$H$_{23}$ | —COCH$_2$CH(OH)C$_{13}$H$_{27}$ |
| 1-70 | —COCHF.CH(OCOC$_{11}$H$_{23}$)— | —COCH$_2$CH(OCOC$_{11}$H$_{23}$)— |

TABLE 1-continued

| Cpd No. | R² | R³ |
|---|---|---|
| | —C₁₁H₂₃ | —C₁₁H₂₃ |
| 1-71 | —COCHF.CH(OCOC₉H₁₉)— | —COCH₂CH(OCOC₉H₁₉)— |
| | —C₁₁H₂₃ | —C₁₁H₂₃ |
| 1-72 | —COCHF.CH(OCOC₁₃H₂₇)— | —COCH₂CH(OCOC₁₃H₂₇)— |
| | —C₁₁H₂₃ | —C₁₁H₂₃ |
| 1-73 | —COCHCl.CH(OCOC₁₁H₂₃)— | —COCH₂CH(OCOC₁₁H₂₃)— |
| | —C₁₃H₂₇ | —C₉H₁₉ |
| 1-74 | —COCHF.CH(OH)C₁₁H₂₃ | —COCH₂CH(OCOC₁₃H₂₇)— |
| | | —C₁₁H₂₃ |
| 1-75 | —COCH₂CH(OH)C₁₁H₂₃ | —COCH₂CH(OCOCF₂C₁₂H₂₅)— |
| | | —C₁₁H₂₃ |
| 1-76 | —COCH₂CH(OCOC₁₃H₂₇)— | —COCH₂CH(OCOCF₂C₁₂H₂₅)— |
| | —C₁₁H₂₃ | —C₁₁H₂₃ |
| 1-77 | —COCH₂CH(OCOC₁₁H₂₃)— | —COCH₂CH(OCOCF₂C₁₂H₂₅)— |
| | —C₁₁H₂₃ | —C₁₁H₂₃ |
| 1-78 | —COCH₂CH(OH)C₉H₁₉ | —COCH₂CH(OCOCF₂C₁₂H₂₅)— |
| | | —C₁₁H₂₃ |
| 1-79 | —COCH₂CH(OCOC₁₃H₂₇)— | —COCH₂CH(OCOCF₂C₁₂H₂₅)— |
| | —C₉H₁₉ | —C₁₁H₂₃ |
| 1-80 | —COCH₂CH(OCOC₁₁H₂₃)— | —COCH₂CH(OCOCF₂C₁₂H₂₅)— |
| | —C₉H₁₉ | —C₁₁H₂₃ |
| 1-81 | —COCH₂CH(OH)C₁₁H₂₃ | —COCH₂CH(OCOCF₂C₁₀H₂₁)— |
| | | —C₁₁H₂₃ |
| 1-82 | —COCH₂CH(OCOC₁₃H₂₇)— | —COCH₂CH(OCOCF₂C₁₀H₂₁)— |
| | —C₁₁H₂₃ | —C₁₁H₂₃ |
| 1-83 | —COCH₂CH(OCOC₁₁H₂₃)— | —COCH₂CH(OCOCF₂C₁₀H₂₁)— |
| | —C₁₁H₂₃ | —C₁₁H₂₃ |
| 1-84 | —COCH₂CH(OH)C₉H₁₉ | —COCH₂CH(OCOCF₂C₁₀H₂₁)— |
| | | —C₁₁H₂₃ |
| 1-85 | —COCH₂CH(OCOC₁₃H₂₇)— | —COCH₂CH(OCOCF₂C₁₀H₂₁)— |
| | —C₉H₁₉ | —C₁₁H₂₃ |
| 1-86 | —COCH₂CH(OCOC₁₁H₂₃)— | —COCH₂CH(OCOCF₂C₁₀H₂₁)— |
| | —C₉H₁₉ | —C₁₁H₂₃ |
| 1-87 | —COCH₂CH(OH)C₁₁H₂₃ | —COCF₂CH(OCOC₁₁H₂₃)— |
| | | —C₁₁H₂₃ |
| 1-88 | —COCH₂CH(OCOC₁₃H₂₇)— | —COCF₂CH(OCOC₁₁H₂₃)— |
| | —C₁₁H₂₃ | —C₁₁H₂₃ |
| 1-89 | —COCH₂CH(OCOC₁₁H₂₃)— | —COCF₂CH(OCOC₁₁H₂₃)— |
| | —C₁₁H₂₃ | —C₁₁H₂₃ |
| 1-90 | —COCH₂CH(OH)C₉H₁₉ | —COCF₂CH(OCOC₁₁H₂₃)— |
| | | —C₁₁H₂₃ |
| 1-91 | —COCH₂CH(OCOC₁₃H₂₇)— | —COCF₂CH(OCOC₁₁H₂₃)— |
| | —C₉H₁₉ | —C₁₁H₂₃ |
| 1-92 | —COCH₂CH(OCOC₁₁H₂₃)— | —COCF₂CH(OCOC₁₁H₂₃)— |
| | —C₉H₁₉ | —C₁₁H₂₃ |
| 1-93 | —COCH₂CH(OH)C₁₁H₂₃ | —COCF₂CH(OCOC₁₃H₂₇)— |
| | | —C₁₁H₂₃ |
| 1-94 | —COCH₂CH(OCOC₁₃H₂₇)— | —COCF₂CH(OCOC₁₃H₂₇)— |
| | —C₁₁H₂₃ | —C₁₁H₂₃ |
| 1-95 | —COCH₂CH(OCOC₁₁H₂₃)— | —COCF₂CH(OCOC₁₃H₂₇)— |
| | —C₁₁H₂₃ | —C₁₁H₂₃ |
| 1-96 | —COCH₂CH(OH)C₉H₁₉ | —COCF₂CH(OCOC₁₃H₂₇)— |
| | | —C₁₁H₂₃ |
| 1-97 | —COCH₂CH(OCOC₁₃H₂₇)— | —COCF₂CH(OCOC₁₃H₂₇)— |
| | —C₉H₁₉ | —C₁₁H₂₃ |
| 1-98 | —COCH₂CH(OCOC₁₁H₂₃)— | —COCF₂CH(OCOC₁₃H₂₇)— |
| | —C₉H₁₉ | —C₁₁H₂₃ |
| 1-99 | —COCH₂CH(OH)C₁₁H₂₃ | —COCF₂CH(OH)C₁₁H₂₃ |
| 1-100 | —COCH₂CH(OCOC₁₃H₂₇)— | —COCF₂CH(OH)C₁₁H₂₃ |
| | —C₁₁H₂₃ | |
| 1-101 | —COCH₂CH(OCOC₁₁H₂₃)— | —COCF₂CH(OH)C₁₁H₂₃ |
| | —C₁₁H₂₃ | |
| 1-102 | —COCH₂CH(OH)C₉H₁₉ | —COCF₂CH(OH)C₁₁H₂₃ |
| 1-103 | —COCH₂CH(OCOC₁₃H₂₇)— | —COCF₂CH(OH)C₁₁H₂₃ |
| | —C₉H₁₉ | |
| 1-104 | —COCH₂CH(OCOC₁₁H₂₃)— | —COCF₂CH(OH)C₁₁H₂₃ |
| | —C₉H₁₉ | |
| 1-105 | —COCF₂CH(OH)C₁₁H₂₃ | —COCH₂CH(OCOC₁₃H₂₇)— |
| | | —C₁₁H₂₃ |
| 1-106 | —COCF₂CH(OCOC₁₁H₂₃)— | —COCH₂CH(OCOC₁₃H₂₇)— |
| | —C₁₁H₂₃ | —C₁₁H₂₃ |
| 1-107 | —COCF₂CH(OCOC₁₃H₂₇)— | —COCH₂CH(OCOC₁₃H₂₇)— |
| | —C₁₁H₂₃ | —C₁₁H₂₃ |
| 1-108 | —COCH₂CH(OCOCF₂C₁₂H₂₅)— | —COCH₂CH(OCOC₁₃H₂₇)— |
| | —C₁₁H₂₃ | —C₁₁H₂₃ |
| 1-109 | —COCH₂CH(OCOCF₂C₁₀H₂₁)— | —COCH₂CH(OCOC₁₃H₂₇)— |

TABLE 1-continued

| Cpd No. | R² | R³ |
|---|---|---|
| | —$C_{11}H_{23}$ | |
| 1-110 | —$COCF_2CH(OH)C_{11}H_{23}$ | —$COCH_2CH(OCOC_{11}H_{23})$—$C_{11}H_{23}$ |
| 1-111 | —$COCF_2CH(OCOC_{11}H_{23})$—$C_{11}H_{23}$ | —$COCH_2CH(OCOC_{11}H_{23})$—$C_{11}H_{23}$ |
| 1-112 | —$COCF_2CH(OCOC_{13}H_{27})$—$C_{11}H_{23}$ | —$COCH_2CH(OCOC_{11}H_{23})$—$C_{11}H_{23}$ |
| 1-113 | —$COCH_2CH(OCOCF_2C_{12}H_{25})$—$C_{11}H_{23}$ | —$COCH_2CH(OCOC_{11}H_{23})$—$C_{11}H_{23}$ |
| 1-114 | —$COCH_2CH(OCOCF_2C_{10}H_{21})$—$C_{11}H_{23}$ | $COCH_2CH(OCOC_{11}H_{23})$—$C_{11}H_{23}$ |
| 1-115 | —$COCF_2CH(OH)C_{11}H_{23}$ | —$COCF_2CH(OCOC_{13}H_{27})$—$C_{11}H_{23}$ |
| 1-116 | —$COCF_2CH(OCOC_{11}H_{23})$—$C_{11}H_{23}$ | —$COCF_2CH(OCOC_{13}H_{27})$—$C_{11}H_{23}$ |
| 1-117 | —$COCF_2CH(OCOC_{13}H_{27})$—$C_{11}H_{23}$ | —$COCF_2CH(OCOC_{13}H_{27})$—$C_{11}H_{23}$ |
| 1-118 | —$COCH_2CH(OCOCF_2C_{12}H_{25})$—$C_{11}H_{23}$ | —$COCF_2CH(OCOC_{13}H_{27})$—$C_{11}H_{23}$ |
| 1-119 | —$COCH_2CH(OCOCF_2C_{10}H_{21})$—$C_{11}H_{23}$ | —$COCF_2CH(OCOC_{13}H_{27})$—$C_{11}H_{23}$ |
| 1-120 | —$COCF_2CH(OH)C_{11}H_{23}$ | —$COCF_2CH(OCOC_{11}H_{23})$—$C_{11}H_{23}$ |
| 1-121 | —$COCF_2CH(OCOC_{11}H_{23})$—$C_{11}H_{23}$ | —$COCF_2CH(OCOC_{11}H_{23})$—$C_{11}H_{23}$ |
| 1-122 | —$COCF_2CH(OCOC_{13}H_{27})$—$C_{11}H_{23}$ | —$COCF_2CH(OCOC_{11}H_{23})$—$C_{11}H_{23}$ |
| 1-123 | —$COCH_2CH(OCOCF_2C_{12}H_{25})$—$C_{11}H_{23}$ | —$COCF_2CH(OCOC_{11}H_{23})$—$C_{11}H_{23}$ |
| 1-124 | —$COCH_2CH(OCOCF_2C_{10}H_{21})$—$C_{11}H_{23}$ | —$COCF_2CH(OCOC_{11}H_{23})$—$C_{11}H_{23}$ |
| 1-125 | —$COCF_2C_{12}H_{25}$ | —$COCH_2CH(OCOC_{13}H_{27})$—$C_{11}H_{23}$ |
| 1-126 | —$COCF_2C_{12}H_{25}$ | —$COCH_2CH(OCOC_{11}H_{23})$—$C_{11}H_{23}$ |

TABLE 2

| Cpd No. | R² | R³ |
|---|---|---|
| 2-1 | —$COCH_2CH(OH)C_7H_{15}$ | —$COCHFCH(OH)C_{11}H_{23}$ |
| 2-2 | —$COCH_2CH(OH)C_9H_{19}$ | —$COCHFCH(OH)C_{11}H_{23}$ |
| 2-3 | —$COCH_2CH(OH)C_{11}H_{23}$ | —$COCHFCH(OH)C_{11}H_{23}$ |
| 2-4 | —$COCH_2CH(OH)C_{13}H_{27}$ | —$COCHFCH(OH)C_{11}H_{23}$ |
| 2-5 | —$COCH_2CH(OH)C_{15}H_{31}$ | —$COCHFCH(OH)C_{11}H_{23}$ |
| 2-6 | —$COCH_2CH(OH)C_{11}H_{23}$ | —$COCHFCH(OH)C_7H_{15}$ |
| 2-7 | —$COCH_2CH(OH)C_{11}H_{23}$ | —$COCHFCH(OH)C_{15}H_{31}$ |
| 2-8 | —$COCH_2CH(OH)C_{11}H_{23}$ | —$COCHClCH(OH)C_{11}H_{23}$ |
| 2-9 | —$COCH_2CH(OCOC_{11}H_{23})$—$C_9H_{19}$ | —$COCHFCH(OH)C_{11}H_{23}$ |
| 2-10 | —$COCH_2CH(OCOC_{11}H_{23})$—$C_{11}H_{23}$ | —$COCHFCH(OH)C_{11}H_{23}$ |
| 2-11 | —$COCH_2CH(OCOC_{11}H_{23})$—$C_{13}H_{27}$ | —$COCHFCH(OH)C_{11}H_{23}$ |
| 2-12 | —$COCH_2CH(OCOC_9H_{19})$—$C_{11}H_{23}$ | —$COCHFCH(OH)C_{11}H_{23}$ |
| 2-13 | —$COCH_2CH(OH)C_{11}H_{23}$ | —$COCHFCH(OCOC_9H_{19})$—$C_{11}H_{23}$ |
| 2-14 | —$COCH_2CH(OH)C_{11}H_{23}$ | —$COCHFCH(OCOC_{13}H_{27})$—$C_{11}H_{23}$ |
| 2-15 | —$COCH_2CH(OH)C_{11}H_{23}$ | —$COCHFCH(OCOC_{11}H_{23})$—$C_9H_{19}$ |
| 2-16 | —$COCH_2CH(OH)C_{11}H_{23}$ | —$COCHClCH(OCOC_{11}H_{23})$—$C_{11}H_{23}$ |
| 2-17 | —$COCH_2CH(OCOC_{11}H_{23})$—$C_{11}H_{23}$ | —$COCHFCH(OCOC_{11}H_{23})$—$C_{11}H_{23}$ |
| 2-18 | —$COCH_2CH(OCOC_{11}H_{23})$—$C_{11}H_{23}$ | —$COCHFCH(OCOC_9H_{19})$—$C_{11}H_{23}$ |
| 2-19 | —$COCH_2CH(OCOC_{11}H_{23})$—$C_{11}H_{23}$ | —$COCHFCH(OCOC_{13}H_{27})$—$C_{11}H_{23}$ |
| 2-20 | —$COCH_2CH(OCOC_{11}H_{23})$—$C_{11}H_{23}$ | —$COCHFCH(OCOC_{11}H_{23})$—$C_9H_{19}$ |
| 2-21 | —$COCH_2CH(OCOC_{11}H_{23})$—$C_{11}H_{23}$ | —$COCHFCH(OCOC_{11}H_{23})$—$C_{13}H_{27}$ |
| 2-22 | —$COCH_2CH(OH)C_{11}H_{23}$ | —$COCHF.(CH_2)_2.CH(OH)$—$C_9H_{19}$ |
| 2-23 | —$COCH_2CH(OH)C_{11}H_{23}$ | —$COCHF.(CH_2)_3.CH(OH)$—$C_8H_{17}$ |
| 2-24 | —$COCH_2CH(OH)C_{11}H_{23}$ | —$COCHCl.(CH_2)_4CH(OH)$—$C_7H_{15}$ |
| 2-25 | —$COCH_2CH(OH)C_{11}H_{23}$ | —$COCHBr.(CH_2)_5.CH(OH)$—$C_6H_{13}$ |
| 2-26 | —$COCH_2CH(OH)C_{11}H_{23}$ | —$COCHF.(CH_2)_6CH(OH)$—$C_5H_{11}$ |
| 2-27 | —$COCHFCH(OH)C_{11}H_{23}$ | —$COCH_2CH(OH)C_{11}H_{23}$ |
| 2-28 | —$COCHFCH(OH)C_{11}H_{23}$ | —$COCH_2CH(OH)C_9H_{19}$ |
| 2-29 | —$COCHFCH(OH)C_{11}H_{23}$ | —$COCH_2CH(OH)C_{13}H_{27}$ |
| 2-30 | —$COCHClCH(OH)C_9H_{19}$ | —$COCH_2CH(OH)C_{11}H_{23}$ |
| 2-31 | —$COCHBrCH(OH)C_{13}H_{27}$ | —$COCH_2CH(OH)C_{11}H_{23}$ |
| 2-32 | —$COCHFCH(OH)C_9H_{19}$ | —$COCH_2CH(OH)C_9H_{19}$ |

TABLE 2-continued

| Cpd No. | $R^2$ | $R^3$ |
|---|---|---|
| 2-33 | —COCHClCH(OH)$C_{13}H_{27}$ | —COCH$_2$CH(OH)$C_{13}H_{27}$ |
| 2-34 | —COCHFCH(OH)$C_9H_{19}$ | —COCH$_2C_9$H(OH)$C_{13}H_{27}$ |
| 2-35 | —COCHFCH(OH)$C_{13}H_{27}$ | —COCH$_2$CH(OH)$C_9H_{19}$ |
| 2-36 | —COCHFCH(OH)$C_{11}H_{23}$ | —COCH$_2$CH(OCOC$_{11}H_{23}$)—$C_{11}H_{23}$ |
| 2-37 | —COCHClCH(OH)$C_9H_{19}$ | —COCH$_2$CH(OCOC$_9H_{19}$)—$C_{11}H_{23}$ |
| 2-38 | —COCHFCH(OH)$C_{11}H_{23}$ | —COCH$_2$CH(OCOC$_{13}H_{27}$)—$C_{11}H_{23}$ |
| 2-39 | —COCHFCH(OH)$C_9H_{19}$ | —COCH$_2$CH(OCOC$_{11}H_{23}$)—$C_9H_{19}$ |
| 2-40 | —COCHFCH(OH)$C_9H_{19}$ | —COCH$_2$CH(OCOC$_{11}H_{23}$)—$C_{13}H_{27}$ |
| 2-41 | —COCHClCH(OH)$C_{13}H_{27}$ | —COCH$_2$CH(OCOC$_{11}H_{23}$)—$C_{11}H_{23}$ |
| 2-42 | —COCHFCH(OCOC$_{11}H_{23}$)—$C_{11}H_{23}$ | —COCH$_2$CH(OH)$C_{11}H_{23}$ |
| 2-43 | —COCHFCH(OCOC$_{11}H_{23}$)—$C_{11}H_{23}$ | —COCH$_2$CH(OCOC$_{11}H_{23}$)—$C_{11}H_{23}$ |
| 2-44 | —COCHFCH(OCOC$_9H_{19}$)—$C_{11}H_{23}$ | —COCH$_2$CH(OCOC$_9H_{19}$)—$C_{11}H_{23}$ |
| 2-45 | —COCHFCH(OCOC$_{13}H_{27}$)—$C_{11}H_{23}$ | —COCH$_2$CH(OCOC$_{13}H_{27}$)—$C_{11}H_{23}$ |
| 2-46 | —COCHClCH(OCOC$_{11}H_{23}$)—$C_{13}H_{27}$ | —COCH$_2$CH(OCOC$_{11}H_{23}$)—$C_9H_{19}$ |
| 2-47 | —COCH$_2$CH(OCOC$_{13}H_{27}$)—$C_{11}H_{23}$ | —COCHFCH(OH)$C_{11}H_{23}$ |
| 2-48 | —COCH$_2$CH(OCOC$_{13}H_{27}$)—$C_{11}H_{23}$ | —COCHFCH(OCOC$_{13}H_{27}$)—$C_{11}H_{23}$ |
| 2-49 | —COCHFCH(OCOC$_{13}H_{27}$)—$C_{11}H_{23}$ | —COCH$_2$CH(OH)$C_{11}H_{23}$ |
| 2-50 | —COCHFCH(OH)$C_{11}H_{23}$ | —COCH$_2$CH(OCOC$_{13}H_{27}$)—$C_{11}H_{23}$ |
| 2-51 | —COCH$_2$CH(OH)$C_{11}H_{23}$ | —COCHFCH(OH)$C_9H_{19}$ |
| 2-52 | —COCH$_2$CH(OH)$C_{11}H_{23}$ | —COCHFCH(OH)$C_{13}H_{27}$ |
| 2-53 | —COCH$_2$CH(OH)$C_{11}H_{23}$ | —COCHFCH(OCOC$_{15}H_{31}$)—$C_{11}H_{23}$ |
| 2-54 | —COCHFCH(OH)$C_9H_{19}$ | —COCH$_2$CH(OH)$C_{11}H_{23}$ |
| 2-55 | —COCHFCH(OCOC$_{11}H_{23}$)—$C_{11}H_{23}$ | —COCH$_2$CH(OCOC$_{13}H_{27}$)—$C_{11}H_{23}$ |
| 2-56 | —COCHFCH(OH)$C_9H_{19}$ | —COCH$_2$CH(OCOC$_{11}H_{23}$)—$C_{11}H_{23}$ |
| 2-57 | —COCHFCH(OH)$C_{11}H_{23}$ | —COCHFCH(OH)$C_{11}H_{23}$ |
| 2-58 | —COCHFCH(OH)$C_{11}H_{23}$ | —COCHFCH(OCOC$_{11}H_{23}$)—$C_{11}H_{23}$ |
| 2-59 | —COCHFCH(OH)$C_{11}H_{23}$ | —COCHFCH(OCOC$_{13}H_{27}$)—$C_{11}H_{23}$ |
| 2-60 | —COCHFCH(OCOC$_{11}H_{23}$)—$C_{11}H_{23}$ | —COCHFCH(OH)$C_{11}H_{23}$ |
| 2-61 | —COCHFCH(OCOC$_{11}H_{23}$)—$C_{11}H_{23}$ | —COCHFCH(OCOC$_{11}H_{23}$)—$C_{11}H_{23}$ |
| 2-62 | —COCHFCH(OCOC$_{11}H_{23}$)—$C_{11}H_{23}$ | —COCHFCH(OCOC$_{13}H_{27}$)—$C_{11}H_{23}$ |
| 2-63 | —COCHFCH(OCOC$_{13}H_{27}$)—$C_{11}H_{23}$ | —COCHFCH(OH)$C_{11}H_{23}$ |
| 2-64 | —COCHFCH(OCOC$_{13}H_{27}$)—$C_{11}H_{23}$ | —COCHFCH(OCOC$_{11}H_{23}$)—$C_{11}H_{23}$ |
| 2-65 | —COCHFCH(OCOC$_{13}H_{27}$)—$C_{11}H_{23}$ | —COCHFCH(OCOC$_{13}H_{27}$)—$C_{11}H_{23}$ |
| 2-66 | —COCH$_2$CH(OH)$C_{11}H_{23}$ | —COCH$_2$CH(OCOCF$_2C_{12}H_{25}$)—$C_{11}H_{23}$ |
| 2-67 | —COCH$_2$CH(OCOC$_{13}H_{27}$)—$C_{11}H_{23}$ | —COCH$_2$CH(OCOCF$_2C_{12}H_{25}$)—$C_{11}H_{23}$ |
| 2-68 | —COCH$_2$CH(OCOC$_{11}H_{23}$)—$C_{11}H_{23}$ | —COCH$_2$CH(OCOCF$_2C_{12}H_{25}$)—$C_{11}H_{23}$ |
| 2-69 | —COCH$_2$CH(OH)$C_9H_{19}$ | —COCH$_2$CH(OCOCF$_2C_{12}H_{25}$)—$C_{11}H_{23}$ |
| 2-70 | —COCH$_2$CH(OCOC$_{13}H_{27}$)—$C_9H_{19}$ | —COCH$_2$CH(OCOCF$_2C_{12}H_{25}$)—$C_{11}H_{23}$ |
| 2-71 | —COCH$_2$CH(OCOC$_{11}H_{23}$)—$C_9H_{19}$ | —COCH$_2$CH(OCOCF$_2C_{12}H_{25}$)—$C_{11}H_{23}$ |
| 2-72 | —COCH$_2$CH(OH)$C_{11}H_{23}$ | —COCH$_2$CH(OCOCF$_2C_{10}H_{21}$)—$C_{11}H_{23}$ |
| 2-73 | —COCH$_2$CH(OCOC$_{13}H_{27}$)—$C_{11}H_{23}$ | —COCH$_2$CH(OCOCF$_2C_{10}H_{21}$)—$C_{11}H_{23}$ |
| 2-74 | —COCH$_2$CH(OCOC$_{11}H_{23}$)—$C_{11}H_{23}$ | —COCH$_2$CH(OCOCF$_2C_{10}H_{21}$)—$C_{11}H_{23}$ |
| 2-75 | —COCH$_2$CH(OH)$C_9H_{19}$ | —COCH$_2$CH(OCOCF$_2C_{10}H_{21}$)—$C_{11}H_{23}$ |
| 2-76 | —COCH$_2$CH(OCOC$_{13}H_{27}$)—$C_9H_{19}$ | —COCH$_2$CH(OCOCF$_2C_{10}H_{21}$)—$C_{11}H_{23}$ |
| 2-77 | —COCH$_2$CH(OCOC$_{11}H_{23}$)—$C_9H_{19}$ | —COCH$_2$CH(OCOCF$_2C_{10}H_{21}$)—$C_{11}H_{23}$ |
| 2-78 | —COCH$_2$CH(OH)$C_{11}H_{23}$ | —COCF$_2$CH(OCOC$_{11}H_{23}$)—$C_{11}H_{23}$ |
| 2-79 | —COCH$_2$CH(OCOC$_{13}H_{27}$)—$C_{11}H_{23}$ | —COCF$_2$CH(OCOC$_{11}H_{23}$)—$C_{11}H_{23}$ |
| 2-80 | —COCH$_2$CH(OCOC$_{11}H_{23}$)—$C_{11}H_{23}$ | —COCF$_2$CH(OCOC$_{11}H_{23}$)—$C_{11}H_{23}$ |
| 2-81 | —COCH$_2$CH(OH)$C_9H_{19}$ | —COCF$_2$CH(OCOC$_{11}H_{23}$)—$C_{11}H_{23}$ |
| 2-82 | —COCH$_2$CH(OCOC$_{13}H_{27}$)—$C_9H_{19}$ | —COCF$_2$CH(OCOC$_{11}H_{23}$)—$C_{11}H_{23}$ |
| 2-83 | —COCH$_2$CH(OCOC$_{11}H_{23}$)—$C_9H_{19}$ | —COCF$_2$CH(OCOC$_{11}H_{23}$)—$C_{11}H_{23}$ |
| 2-84 | —COCH$_2$CH(OH)$C_{11}H_{23}$ | —COCF$_2$CH(OCOC$_{13}H_{27}$)—$C_{11}H_{23}$ |
| 2-85 | —COCH$_2$CH(OCOC$_{13}H_{27}$)—$C_{11}H_{23}$ | —COCF$_2$CH(OCOC$_{13}H_{27}$)—$C_{11}H_{23}$ |
| 2-86 | —COCH$_2$CH(OCOC$_{11}H_{23}$)—$C_{11}H_{23}$ | —COCF$_2$CH(OCOC$_{13}H_{27}$)—$C_{11}H_{23}$ |
| 2-87 | —COCH$_2$CH(OH)$C_9H_{19}$ | —COCF$_2$CH(OCOC$_{13}H_{27}$)—$C_{11}H_{23}$ |
| 2-88 | —COCH$_2$CH(OCOC$_{13}H_{27}$)—$C_9H_{19}$ | —COCF$_2$CH(OCOC$_{13}H_{27}$)—$C_{11}H_{23}$ |
| 2-89 | —COCH$_2$CH(OCOC$_{11}H_{23}$)—$C_9H_{19}$ | —COCF$_2$CH(OCOC$_{13}H_{27}$)—$C_{11}H_{23}$ |
| 2-90 | —COCH$_2$CH(OH)$C_{11}H_{23}$ | —COCF$_2$CH(OH)$C_{11}H_{23}$ |
| 2-91 | —COCH$_2$CH(OCOC$_{13}H_{27}$)—$C_{11}H_{23}$ | —COCF$_2$CH(OH)$C_{11}H_{23}$ |
| 2-92 | —COCH$_2$CH(OCOC$_{11}H_{23}$)—$C_{11}H_{23}$ | —COCF$_2$CH(OH)$C_{11}H_{23}$ |
| 2-93 | —COCH$_2$CH(OH)$C_9H_{19}$ | —COCF$_2$CH(OH)$C_{11}H_{23}$ |
| 2-94 | —COCH$_2$CH(OCOC$_{13}H_{27}$)—$C_9H_{19}$ | —COCF$_2$CH(OH)$C_{11}H_{23}$ |
| 2-95 | —COCH$_2$CH(OCOC$_{11}H_{23}$)—$C_9H_{19}$ | —COCF$_2$CH(OH)$C_{11}H_{23}$ |
| 2-96 | —COCF$_2$CH(OH)$C_{11}H_{23}$ | —COCH$_2$CH(OCOC$_{13}H_{27}$)—$C_{11}H_{23}$ |
| 2-97 | —COCF$_2$CH(OCOC$_{11}H_{23}$)—$C_{11}H_{23}$ | —COCH$_2$CH(OCOC$_{13}H_{27}$)—$C_{11}H_{23}$ |
| 2-98 | —COCF$_2$CH(OCOC$_{13}H_{27}$)—$C_{11}H_{23}$ | —COCH$_2$CH(OCOC$_{13}H_{27}$)—$C_{11}H_{23}$ |
| 2-99 | —COCH$_2$CH(OCOCF$_2C_{12}H_{24}$)—$C_{11}H_{23}$ | —COCH$_2$CH(OCOC$_{13}H_{27}$)—$C_{11}H_{23}$ |
| 2-100 | —COCH$_2$CH(OCOCF$_2C_{10}H_{21}$)—$C_{11}H_{23}$ | —COCH$_2$CH(OCOC$_{13}H_{27}$)—$C_{11}H_{23}$ |
| 2-101 | —COCF$_2$CH(OH)$C_{11}H_{23}$ | —COCH$_2$CH(OCOC$_{11}H_{23}$)—$C_{11}H_{23}$ |
| 2-102 | —COCF$_2$CH(OCOC$_{11}H_{23}$)—$C_{11}H_{23}$ | —COCH$_2$CH(OCOC$_{11}H_{23}$)—$C_{11}H_{23}$ |
| 2-103 | —COCF$_2$CH(OCOC$_{13}H_{27}$)—$C_{11}H_{23}$ | —COCH$_2$CH(OCOC$_{11}H_{23}$)—$C_{11}H_{23}$ |
| 2-104 | —COCH$_2$CH(OCOCF$_2C_{12}H_{25}$)—$C_{11}H_{23}$ | —COCH$_2$CH(OCOC$_{11}H_{23}$)—$C_{11}H_{23}$ |
| 2-105 | —COCH$_2$CH(OCOCF$_2C_{10}H_{21}$)—$C_{11}H_{23}$ | —COCH$_2$CH(OCOC$_{11}H_{23}$)—$C_{11}H_{23}$ |
| 2-106 | —COCF$_2$CH(OH)$C_{11}H_{23}$ | —COCF$_2$CH(OCOC$_{13}H_{27}$)—$C_{11}H_{23}$ |
| 2-107 | —COCF$_2$CH(OCOC$_{11}H_{23}$)—$C_{11}H_{23}$ | —COCF$_2$CH(OCOC$_{13}H_{27}$)—$C_{11}H_{23}$ |
| 2-108 | —COCF$_2$CH(OCOC$_{13}H_{27}$)—$C_{11}H_{23}$ | —COCF$_2$CH(OCOC$_{13}H_{27}$)—$C_{11}H_{23}$ |

TABLE 2-continued

| Cpd No. | $R^2$ | $R^3$ |
|---|---|---|
| 2-109 | $-COCH_2CH(OCOCF_2C_{12}H_{25})-C_{11}H_{23}$ | $-COCF_2CH(OCOC_{13}H_{27})-C_{11}H_{23}$ |
| 2-110 | $-COCH_2CH(OCOCF_2C_{10}H_{21})-C_{11}H_{23}$ | $-COCF_2CH(OCOC_{13}H_{27})-C_{11}H_{23}$ |
| 2-111 | $-COCF_2CH(OH)C_{11}H_{23}$ | $-COCF_2CH(OCOC_{11}H_{23})-C_{11}H_{23}$ |
| 2-112 | $-COCF_2CH(OCOC_{11}H_{23})-C_{11}H_{23}$ | $-COCF_2CH(OCOC_{11}H_{23})-C_{11}H_{23}$ |
| 2-113 | $-COCF_2CH(OCOC_{13}H_{27})-C_{11}H_{23}$ | $-COCF_2CH(OCOC_{11}H_{23})-C_{11}H_{23}$ |
| 2-114 | $-COCH_2CH(OCOCF_2C_{12}H_{25})-C_{11}H_{23}$ | $-COCF_2CH(OCOC_{11}H_{23})-C_{11}H_{23}$ |
| 2-115 | $-COCH_2CH(OCOCF_2C_{10}H_{21})-C_{11}H_{23}$ | $-COCF_2CH(OCOC_{11}H_{23})-C_{11}H_{23}$ |
| 2-116 | $-COCF_2C_{12}H_{25}$ | $-COCF_2CH(OCOC_{13}H_{27})-C_{11}H_{23}$ |
| 2-117 | $-COCF_2C_{12}H_{25}$ | $-COCF_2CH(OCOC_{11}H_{23})-C_{11}H_{23}$ |
| 2-118 | $-COCHFCH(OH)C_{11}H_{23}$ | $-COC_{13}H_{27}$ |
| 2-119 | $-COCHFCH(OCOC_{13}H_{27})-C_{11}H_{23}$ | $-COC_{13}H_{27}$ |

TABLE 3

| Cpd No. | $R^1$ | $R^5$ | $R^2$ | $R^3$ |
|---|---|---|---|---|
| 3-1 | F | OH | $-COCH_2CH(OH)C_{11}H_{23}$ | $-COCH_3CH(OCOC_{13}H_{27})-C_{11}H_{23}$ |
| 3-2 | OH | F | $-COCH_2CH(OH)C_{11}H_{23}$ | $-COCH_3CH(OCOC_{13}H_{27})-C_{11}H_{23}$ |
| 3-3 | F | OH | $-COCHFCH(OH)C_{11}H_{23}$ | $-COCH_3CH(OCOC_{13}H_{27})-C_{11}H_{23}$ |
| 3-4 | OH | F | $-COCHFCH(OH)C_{11}H_{23}$ | $-COCH_3CH(OCOC_{13}H_{27})-C_{11}H_{23}$ |
| 3-5 | F | OH | $-COCF_2CH(OH)C_{11}H_{23}$ | $-COCH_3CH(OCOC_{13}H_{27})-C_{11}H_{23}$ |
| 3-6 | OH | F | $-COCF_2CH(OH)C_{11}H_{23}$ | $-COCH_3CH(OCOC_{13}H_{27})-C_{11}H_{23}$ |
| 3-7 | F | OH | $-COCH_2CH(OCOC_{11}H_{23})-C_{11}H_{23}$ | $-COCH_3CH(OCOC_{13}H_{27})-C_{11}H_{23}$ |
| 3-8 | OH | F | $-COCH_2CH(OCOC_{11}H_{23})-C_{11}H_{23}$ | $-COCH_3CH(OCOC_{13}H_{27})-C_{11}H_{23}$ |
| 3-9 | F | OH | $-COCH_2CH(OCOC_{13}H_{27})-C_{11}H_{23}$ | $-COCH_3CH(OCOC_{13}H_{27})-C_{11}H_{23}$ |
| 3-10 | OH | F | $-COCH_2CH(OCOC_{13}H_{27})-C_{11}H_{23}$ | $-COCH_3CH(OCOC_{13}H_{27})-C_{11}H_{23}$ |
| 3-11 | F | OH | $-COCH_2CH(OH)C_{11}H_{23}$ | $-COCH_3CH(OCOC_{11}H_{23})-C_{11}H_{23}$ |
| 3-12 | OH | F | $-COCH_2CH(OH)C_{11}H_{23}$ | $-COCH_3CH(OCOC_{11}H_{23})-C_{11}H_{23}$ |
| 3-13 | F | OH | $-COCH_2CH(OH)C_{11}H_{23}$ | $-COCH_3CH(OCOC_{11}H_{23})-C_{11}H_{23}$ |
| 3-14 | OH | F | $-COCHFCH(OH)C_{11}H_{23}$ | $-COCH_3CH(OCOC_{11}H_{23})-C_{11}H_{23}$ |
| 3-15 | F | OH | $-COCF_2CH(OH)C_{11}H_{23}$ | $-COCH_3CH(OCOC_{11}H_{23})-C_{11}H_{23}$ |
| 3-16 | OH | F | $-COCF_2CH(OH)C_{11}H_{23}$ | $-COCH_3CH(OCOC_{11}H_{23})-C_{11}H_{23}$ |
| 3-17 | F | OH | $-COCH_2CH(OCOC_{11}H_{23})-C_{11}H_{23}$ | $-COCH_3CH(OCOC_{11}H_{23})-C_{11}H_{23}$ |
| 3-18 | OH | F | $-COCH_2CH(OCOC_{11}H_{23})-C_{11}H_{23}$ | $-COCH_3CH(OCOC_{11}H_{23})-C_{11}H_{23}$ |
| 3-19 | F | OH | $-COCH_2CH(OCOC_{13}H_{27})-C_{11}H_{23}$ | $-COCH_3CH(OCOC_{11}H_{23})-C_{11}H_{23}$ |
| 3-20 | OH | F | $-COCH_2CH(OCOC_{13}H_{27})-C_{11}H_{23}$ | $-COCH_3CH(OCOC_{11}H_{23})-C_{11}H_{23}$ |
| 3-21 | F | OH | $-COCH_2CH(OH)C_{11}H_{23}$ | $-COCH_2CH(OH)C_{11}H_{23}$ |
| 3-22 | OH | F | $-COCH_2CH(OH)C_{11}H_{23}$ | $-COCH_2CH(OH)C_{11}H_{23}$ |
| 3-23 | F | OH | $-COCHFCH(OH)C_{11}H_{23}$ | $-COCH_2CH(OH)C_{11}H_{23}$ |
| 3-24 | OH | F | $-COCHFCH(OH)C_{11}H_{23}$ | $-COCH_2CH(OH)C_{11}H_{23}$ |
| 3-25 | F | OH | $-COCF_2CH(OH)C_{11}H_{23}$ | $-COCH_2CH(OH)C_{11}H_{23}$ |
| 3-26 | OH | F | $-COCF_2CH(OH)C_{11}H_{23}$ | $-COCH_2CH(OH)C_{11}H_{23}$ |
| 3-27 | F | OH | $-COCH_2CH(OCOC_{11}H_{23})-C_{11}H_{23}$ | $-COCH_2CH(OH)C_{11}H_{23}$ |
| 3-28 | OH | F | $-COCH_2CH(OCOC_{11}H_{23})-C_{11}H_{23}$ | $-COCH_2CH(OH)C_{11}H_{23}$ |
| 3-29 | F | OH | $-COCH_2CH(OCOC_{13}H_{27})-C_{11}H_{23}$ | $-COCH_2CH(OH)C_{11}H_{23}$ |
| 3-30 | OH | F | $-COCH_2CH(OCOC_{13}H_{27})-C_{11}H_{23}$ | $-COCH_2CH(OH)C_{11}H_{23}$ |
| 3-31 | F | OH | $-COCH_2CH(OH)C_{11}H_{23}$ | $-COCHFCH(OH)C_{11}H_{23}$ |
| 3-32 | OH | F | $-COCH_2CH(OH)C_{11}H_{23}$ | $-COCHFCH(OH)C_{11}H_{23}$ |
| 3-33 | F | OH | $-COCHFCH(OH)C_{11}H_{23}$ | $-COCHFCH(OH)C_{11}H_{23}$ |
| 3-34 | OH | F | $-COCHFCH(OH)C_{11}H_{23}$ | $-COCHFCH(OH)C_{11}H_{23}$ |
| 3-35 | F | OH | $-COCF_2CH(OH)C_{11}H_{23}$ | $-COCHFCH(OH)C_{11}H_{23}$ |
| 3-36 | OH | F | $-COCF_2CH(OH)C_{11}H_{23}$ | $-COCHFCH(OH)C_{11}H_{23}$ |
| 3-37 | F | OH | $-COCH_2CH(OCOC_{11}H_{23})-C_{11}H_{23}$ | $-COCHFCH(OH)C_{11}H_{23}$ |
| 3-38 | OH | F | $-COCH_2CH(OCOC_{11}H_{23})-C_{11}H_{23}$ | $-COCHFCH(OH)C_{11}H_{23}$ |
| 3-39 | F | OH | $-COCH_2CH(OCOC_{13}H_{27})-C_{11}H_{23}$ | $-COCHFCH(OH)C_{11}H_{23}$ |
| 3-40 | OH | F | $-COCH_2CH(OCOC_{13}H_{27})-C_{11}H_{23}$ | $-COCHFCH(OH)C_{11}H_{23}$ |
| 3-41 | F | OH | $-COCH_2CH(OH)C_{11}H_{23}$ | $-COCHFCH(OCOC_{11}H_{23})-C_{11}H_{23}$ |
| 3-42 | OH | F | $-COCH_2CH(OH)C_{11}H_{23}$ | $-COCHFCH(OCOC_{11}H_{23})-C_{11}H_{23}$ |
| 3-43 | F | OH | $-COCHFCH(OH)C_{11}H_{23}$ | $-COCHFCH(OCOC_{11}H_{23})-C_{11}H_{23}$ |
| 3-44 | OH | F | $-COCHFCH(OH)C_{11}H_{23}$ | $-COCHFCH(OCOC_{11}H_{23})-C_{11}H_{23}$ |
| 3-45 | F | OH | $-COCF_2CH(OH)C_{11}H_{23}$ | $-COCHFCH(OCOC_{11}H_{23})-C_{11}H_{23}$ |
| 3-46 | OH | F | $-COCF_2CH(OH)C_{11}H_{23}$ | $-COCHFCH(OCOC_{11}H_{23})-C_{11}H_{23}$ |
| 3-47 | F | OH | $-COCH_2CH(OCOC_{11}H_{23})-C_{11}H_{23}$ | $-COCHFCH(OCOC_{11}H_{23})-C_{11}H_{23}$ |
| 3-48 | OH | F | $-COCH_2CH(OCOC_{11}H_{23})-C_{11}H_{23}$ | $-COCHFCH(OCOC_{11}H_{23})-C_{11}H_{23}$ |
| 3-49 | F | OH | $-COCH_2CH(OCOC_{13}H_{27})-C_{11}H_{23}$ | $-COCHFCH(OCOC_{11}H_{23})-C_{11}H_{23}$ |
| 3-50 | OH | F | $-COCH_2CH(OCOC_{13}H_{17})-C_{11}H_{23}$ | $-COCHFCH(OCOC_{11}H_{23})-C_{11}H_{23}$ |
| 3-51 | F | OH | $-COCH_2CH(OH)C_{11}H_{23}$ | $-COCHFCH(OCOC_{13}H_{27})-C_{11}H_{23}$ |
| 3-52 | OH | F | $-COCH_2CH(OH)C_{11}H_{23}$ | $-COCHFCH(OCOC_{13}H_{27})-C_{11}H_{23}$ |
| 3-53 | F | OH | $-COCHFCH(OH)C_{11}H_{23}$ | $-COCHFCH(OCOC_{13}H_{27})-C_{11}H_{23}$ |
| 3-54 | OH | F | $-COCHFCH(OH)C_{11}H_{23}$ | $-COCHFCH(OCOC_{13}H_{27})-C_{11}H_{23}$ |
| 3-55 | F | OH | $-COCF_2CH(OH)C_{11}H_{23}$ | $-COCHFCH(OCOC_{13}H_{27})-C_{11}H_{23}$ |
| 3-56 | OH | F | $-COCF_2CH(OH)C_{11}H_{23}$ | $-COCHFCH(OCOC_{13}H_{27})-C_{11}H_{23}$ |

TABLE 3-continued

| Cpd No. | $R^1$ | $R^5$ | $R^2$ | $R^3$ |
|---|---|---|---|---|
| 3-57 | F | OH | —COCH$_2$CH(OCOC$_{11}$H$_{23}$)—C$_{11}$H$_{23}$ | —COCHFCH(OCOC$_{13}$H$_{27}$)—C$_{11}$H$_{23}$ |
| 3-58 | OH | F | —COCH$_2$CH(OCOC$_{11}$H$_{23}$)—C$_{11}$H$_{23}$ | —COCHFCH(OCOC$_{13}$H$_{27}$)—C$_{11}$H$_{23}$ |
| 3-59 | F | OH | —COCH$_2$CH(OCOC$_{13}$H$_{27}$)—C$_{11}$H$_{23}$ | —COCHFCH(OCOC$_{13}$H$_{27}$)—C$_{11}$H$_{23}$ |
| 3-60 | OH | F | —COCH$_2$CH(OCOC$_{13}$H$_{27}$)—C$_{11}$H$_{23}$ | —COCHFCH(OCOC$_{13}$H$_{27}$)—C$_{11}$H$_{23}$ |
| 3-61 | F | OH | —COCH$_2$CH(OH)C$_{11}$H$_{23}$ | —COCF$_2$CH(OH)C$_{11}$H$_{23}$ |
| 3-62 | OH | F | —COCH$_2$CH(OH)C$_{11}$H$_{23}$ | —COCF$_2$CH(OH)C$_{11}$H$_{23}$ |
| 3-63 | F | OH | —COCHFCH(OH)C$_{11}$H$_{23}$ | —COCF$_2$CH(OH)C$_{11}$H$_{23}$ |
| 3-64 | OH | F | —COCHFCH(OH)C$_{11}$H$_{23}$ | —COCF$_2$CH(OH)C$_{11}$H$_{23}$ |
| 3-65 | F | OH | —COCF$_2$CH(OH)C$_{11}$H$_{23}$ | —COCF$_2$CH(OH)C$_{11}$H$_{23}$ |
| 3-66 | OH | F | —COCF$_2$CH(OH)C$_{11}$H$_{23}$ | —COCF$_2$CH(OH)C$_{11}$H$_{23}$ |
| 3-67 | F | OH | —COCH$_2$CH(OCOC$_{11}$H$_{23}$)—C$_{11}$H$_{23}$ | —COCF$_2$CH(OH)C$_{11}$H$_{23}$ |
| 3-68 | OH | F | —COCH$_2$CH(OCOC$_{11}$H$_{23}$)—C$_{11}$H$_{23}$ | —COCF$_2$CH(OH)C$_{11}$H$_{23}$ |
| 3-69 | F | OH | —COCH$_2$CH(OCOC$_{13}$H$_{27}$)—C$_{11}$H$_{23}$ | —COCF$_2$CH(OH)C$_{11}$H$_{23}$ |
| 3-70 | OH | F | —COCH$_2$CH(OCOC$_{13}$H$_{27}$)—C$_{11}$H$_{23}$ | —COCF$_2$CH(OH)C$_{11}$H$_{23}$ |
| 3-71 | F | OH | —COCH$_2$CH(OH)C$_{11}$H$_{23}$ | —COCH$_2$CH(OCOC$_{13}$H$_{27}$)—C$_{11}$H$_{23}$ |
| 3-72 | OH | F | —COCH$_2$CH(OH)C$_{11}$H$_{23}$ | —COCF$_2$CH(OCOC$_{13}$H$_{27}$)—C$_{11}$H$_{23}$ |
| 3-73 | F | OH | —COCHFCH(OH)C$_{11}$H$_{23}$ | —COCF$_2$CH(OCOC$_{13}$H$_{27}$)—C$_{11}$H$_{23}$ |
| 3-74 | OH | F | —COCHFCH(OH)C$_{11}$H$_{23}$ | —COCF$_2$CH(OCOC$_{13}$H$_{27}$)—C$_{11}$H$_{23}$ |
| 3-75 | F | OH | —COCF$_2$CH(OH)C$_{11}$H$_{23}$ | —COCF$_2$CH(OCOC$_{13}$H$_{27}$)—C$_{11}$H$_{23}$ |
| 3-76 | OH | F | —COCF$_2$CH(OH)C$_{11}$H$_{23}$ | —COCF$_2$CH(OCOC$_{13}$H$_{27}$)—C$_{11}$H$_{23}$ |
| 3-77 | F | OH | —COCH$_2$CH(OCOC$_{11}$H$_{23}$)—C$_{11}$H$_{23}$ | —COCF$_2$CH(OCOC$_{13}$H$_{27}$)—C$_{11}$H$_{23}$ |
| 3-78 | OH | F | —COCH$_2$CH(OCOC$_{11}$H$_{23}$)—C$_{11}$H$_{23}$ | —COCF$_2$CH(OCOC$_{13}$H$_{27}$)—C$_{11}$H$_{23}$ |
| 3-79 | F | OH | —COCH$_2$CH(OCOC$_{13}$H$_{27}$)—C$_{11}$H$_{23}$ | —COCF$_2$CH(OCOC$_{13}$H$_{27}$)—C$_{11}$H$_{23}$ |
| 3-80 | OH | F | —COCH$_2$CH(OCOC$_{13}$H$_{27}$)—C$_{11}$H$_{23}$ | —COCF$_2$CH(OCOC$_{13}$H$_{27}$)—C$_{11}$H$_{23}$ |
| 3-81 | OH | F | —COCH$_2$CH(OH)C$_{11}$H$_{23}$ | —COCH$_2$CH(OH)C$_{11}$H$_{23}$ |
| 3-82 | OH | F | —COCHFCH(OH)C$_{11}$H$_{23}$ | —COCH$_2$CH(OH)C$_{11}$H$_{23}$ |
| 3-83 | OH | F | —COCF$_2$CH(OH)C$_{11}$H$_{23}$ | —COCH$_2$CH(OH)C$_{11}$H$_{23}$ |
| 3-84 | OH | F | —COCH$_2$CH(OCOC$_{13}$H$_{27}$)—C$_{13}$H$_{27}$ | —COCH$_2$CH(OH)C$_{11}$H$_{23}$ |
| 3-85 | OH | F | —COCH$_2$CH(OCOC$_{11}$H$_{23}$)—C$_{13}$H$_{27}$ | —COCH$_2$CH(OH)C$_{11}$H$_{23}$ |
| 3-86 | OH | F | —COCHFCH(OCOC$_{13}$H$_{27}$)—C$_{11}$H$_{23}$ | —COCH$_2$CH(OH)C$_{11}$H$_{23}$ |
| 3-87 | OH | F | —COCHFCH(OCOC$_{11}$H$_{23}$)—C$_{11}$H$_{23}$ | —COCH$_2$CH(OH)C$_{11}$H$_{23}$ |
| 3-88 | OH | F | —COCF$_2$CH(OCOC$_{13}$H$_{27}$)—C$_{11}$H$_{23}$ | —COCH$_2$CH(OH)C$_{11}$H$_{23}$ |
| 3-89 | OH | F | —COCF$_2$CH(OCOC$_{11}$H$_{23}$)—C$_{11}$H$_{23}$ | —COCH$_2$CH(OH)C$_{11}$H$_{23}$ |
| 3-90 | OH | F | —COC$_{13}$H$_{27}$ | —COCH$_2$CH(OH)C$_{11}$H$_{23}$ |
| 3-91 | OH | F | —COCH$_2$CHFC$_{11}$H$_{23}$ | —COCH$_2$CH(OH)C$_{11}$H$_{23}$ |
| 3-92 | OH | F | —COCH$_2$CH(OH)C$_{11}$H$_{23}$ | —COCHFCH(OH)C$_{11}$H$_{23}$ |
| 3-93 | OH | F | —COCHFCH(OH)C$_{11}$H$_{23}$ | —COCHFCH(OH)C$_{11}$H$_{23}$ |
| 3-94 | OH | F | —COCF$_2$CH(OH)C$_{11}$H$_{23}$ | —COCHFCH(OH)C$_{11}$H$_{23}$ |
| 3-95 | OH | F | —COCH$_2$CH(OCOC$_{13}$H$_{27}$)—C$_{13}$H$_{27}$ | —COCHFCH(OH)C$_{11}$H$_{23}$ |
| 3-96 | OH | F | —COCH$_2$CH(OCOC$_{11}$H$_{23}$)—C$_{13}$H$_{27}$ | —COCHFCH(OH)C$_{11}$H$_{23}$ |
| 3-97 | OH | F | —COCHFCH(OCOC$_{13}$H$_{27}$)—C$_{11}$H$_{23}$ | —COCHFCH(OH)C$_{11}$H$_{23}$ |
| 3-98 | OH | F | —COCHFCH(OCOC$_{11}$H$_{23}$)—C$_{11}$H$_{23}$ | —COCHFCH(OH)C$_{11}$H$_{23}$ |
| 3-99 | OH | F | —COCF$_2$CH(OCOC$_{13}$H$_{27}$)—C$_{11}$H$_{23}$ | —COCHFCH(OH)C$_{11}$H$_{23}$ |
| 3-100 | OH | F | —COCF$_2$CH(OCOC$_{11}$H$_{23}$)—C$_{11}$H$_{23}$ | —COCHFCH(OH)C$_{11}$H$_{23}$ |
| 3-101 | OH | F | —COC$_{13}$H$_{27}$ | —COCHFCH(OH)C$_{11}$H$_{23}$ |
| 3-102 | OH | F | —COCH$_2$CHFC$_{11}$H$_{23}$ | —COCHFCH(OH)C$_{11}$H$_{23}$ |
| 3-103 | OH | F | —COCH$_2$CH(OH)C$_{11}$H$_{23}$ | —COCF$_2$CH(OH)C$_{11}$H$_{23}$ |
| 3-104 | OH | F | —COCHFCH(OH)C$_{11}$H$_{23}$ | —COCF$_2$CH(OH)C$_{11}$H$_{23}$ |
| 3-105 | OH | F | —COCF$_2$CH(OH)C$_{11}$H$_{23}$ | —COCF$_2$CH(OH)C$_{11}$H$_{23}$ |
| 3-106 | OH | F | —COCH$_2$CH(OCOC$_{13}$H$_{27}$)—C$_{13}$H$_{27}$ | —COCF$_2$CH(OH)C$_{11}$H$_{23}$ |
| 3-107 | OH | F | —COCH$_2$CH(OCOC$_{11}$H$_{23}$)—C$_{13}$H$_{27}$ | —COCF$_2$CH(OH)C$_{11}$H$_{23}$ |
| 3-108 | OH | F | —COCHFCH(OCOC$_{13}$H$_{27}$)—C$_{11}$H$_{23}$ | —COCF$_2$CH(OH)C$_{11}$H$_{23}$ |
| 3-109 | OH | F | —COCHFCH(OCOC$_{11}$H$_{23}$)—C$_{11}$H$_{23}$ | —COCF$_2$CH(OH)C$_{11}$H$_{23}$ |
| 3-110 | OH | F | —COCF$_2$CH(OCOC$_{13}$H$_{27}$)—C$_{11}$H$_{23}$ | —COCF$_2$CH(OH)C$_{11}$H$_{23}$ |
| 3-111 | OH | F | —COCF$_2$CH(OCOC$_{11}$H$_{23}$)—C$_{11}$H$_{23}$ | —COCF$_2$CH(OH)C$_{11}$H$_{23}$ |
| 3-112 | OH | F | —COC$_{13}$H$_{27}$ | —COCF$_2$CH(OH)C$_{11}$H$_{23}$ |
| 3-113 | OH | F | —COCH$_2$CHFC$_{11}$H$_{23}$ | —COCF$_2$CH(OH)C$_{11}$H$_{23}$ |
| 3-114 | OH | F | —COCH$_2$CH(OH)C$_{11}$H$_{23}$ | —COCH$_2$CH(OCOC$_{13}$H$_{27}$)—C$_{13}$H$_{27}$ |
| 3-115 | OH | F | —COCHFCH(OH)C$_{11}$H$_{23}$ | —COCH$_2$CH(OCOC$_{13}$H$_{27}$)—C$_{13}$H$_{27}$ |
| 3-116 | OH | F | —COCF$_2$CH(OH)C$_{11}$H$_{23}$ | —COCH$_2$CH(OCOC$_{13}$H$_{27}$)—C$_{13}$H$_{27}$ |
| 3-117 | OH | F | —COCH$_2$CH(OCOC$_{13}$H$_{27}$)—C$_{13}$H$_{27}$ | —COCH$_2$CH(OCOC$_{13}$H$_{27}$)—C$_{13}$H$_{27}$ |
| 3-118 | OH | F | —COCH$_2$CH(OCOC$_{11}$H$_{23}$)—C$_{13}$H$_{27}$ | —COCH$_2$CH(OCOC$_{13}$H$_{27}$)—C$_{13}$H$_{27}$ |
| 3-119 | OH | F | —COCHFCH(OCOC$_{13}$H$_{27}$)—C$_{11}$H$_{23}$ | —COCH$_2$CH(OCOC$_{13}$H$_{27}$)—C$_{13}$H$_{27}$ |
| 3-120 | OH | F | —COCHFCH(OCOC$_{11}$H$_{23}$)—C$_{11}$H$_{23}$ | —COCH$_2$CH(OCOC$_{13}$H$_{27}$)—C$_{13}$H$_{27}$ |
| 3-121 | OH | F | —COCF$_2$CH(OCOC$_{13}$H$_{27}$)—C$_{11}$H$_{23}$ | —COCH$_2$CH(OCOC$_{13}$H$_{27}$)—C$_{13}$H$_{27}$ |
| 3-122 | OH | F | —COCF$_2$CH(OCOC$_{11}$H$_{23}$)—C$_{11}$H$_{23}$ | —COCH$_2$CH(OCOC$_{13}$H$_{27}$)—C$_{13}$H$_{27}$ |
| 3-123 | OH | F | —COC$_{13}$H$_{27}$ | —COCH$_2$CH(OCOC$_{13}$H$_{27}$)—C$_{13}$H$_{27}$ |
| 3-124 | OH | F | —COCH$_2$CHFC$_{11}$H$_{23}$ | —COCH$_2$CH(OCOC$_{13}$H$_{27}$)—C$_{13}$H$_{27}$ |
| 3-125 | OH | F | —COCF$_2$CH(OH)C$_{11}$H$_{23}$ | —COCH$_2$CH(OCOC$_{13}$H$_{27}$)—C$_{11}$H$_{23}$ |
| 3-126 | OH | F | —COCHFCH(OH)C$_{11}$H$_{23}$ | —COCH$_2$CH(OCOC$_{11}$H$_{23}$)—C$_{13}$H$_{27}$ |
| 3-127 | OH | F | —COCF$_2$CH(OH)C$_{11}$H$_{23}$ | —COCH$_2$CH(OCOC$_{11}$H$_{23}$)—C$_{13}$H$_{27}$ |
| 3-128 | OH | F | —COCH$_2$CH(OCOC$_{13}$H$_{27}$)—C$_{13}$H$_{27}$ | —COCH$_2$CH(OCOC$_{11}$H$_{23}$)—C$_{13}$H$_{27}$ |
| 3-129 | OH | F | —COCH$_2$CH(OCOC$_{11}$H$_{23}$)—C$_{13}$H$_{27}$ | —COCH$_2$CH(OCOC$_{11}$H$_{23}$)—C$_{13}$H$_{27}$ |
| 3-130 | OH | F | —COCHFCH(OCOC$_{13}$H$_{27}$)—C$_{11}$H$_{23}$ | —COCH$_2$CH(OCOC$_{11}$H$_{23}$)—C$_{13}$H$_{27}$ |
| 3-131 | OH | F | —COCHFCH(OCOC$_{11}$H$_{23}$)—C$_{11}$H$_{23}$ | —COCH$_2$CH(OCOC$_{11}$H$_{23}$)—C$_{13}$H$_{27}$ |
| 3-132 | OH | F | —COCF$_2$CH(OCOC$_{13}$H$_{27}$)—C$_{11}$H$_{23}$ | —COCH$_2$CH(OCOC$_{11}$H$_{23}$)—C$_{13}$H$_{27}$ |

TABLE 3-continued

| Cpd No. | R¹ | R⁵ | R² | R³ |
|---|---|---|---|---|
| 3-133 | OH | F | —$COCF_2CH(OCOC_{11}H_{23})$—$C_{11}H_{23}$ | —$COCH_2CH(OCOC_{11}H_{23})$—$C_{13}H_{27}$ |
| 3-134 | OH | F | —$COC_{13}H_{27}$ | —$COCH_2CH(OCOC_{11}H_{23})$—$C_{13}H_{27}$ |
| 3-135 | OH | F | —$COCH_2CHFC_{11}H_{23}$ | —$COCH_2CH(OCOC_{11}H_{23})$—$C_{13}H_{27}$ |
| 3-136 | OH | F | —$COCH_2CH(OH)C_{11}H_{23}$ | —$COCHFCH(OCOC_{13}H_{27})$—$C_{11}H_{23}$ |
| 3-137 | OH | F | —$COCHFCH(OH)C_{11}H_{23}$ | —$COCHFCH(OCOC_{13}H_{27})$—$C_{11}H_{23}$ |
| 3-138 | OH | F | —$COCF_2CH(OH)C_{11}H_{23}$ | —$COCHFCH(OCOC_{13}H_{27})$—$C_{11}H_{23}$ |
| 3-139 | OH | F | —$COCH_2CH(OCOC_{13}H_{27})$—$C_{13}H_{27}$ | —$COCHFCH(OCOC_{13}H_{27})$—$C_{11}H_{23}$ |
| 3-140 | OH | F | —$COCH_2CH(OCOC_{11}H_{23})$—$C_{13}H_{27}$ | —$COCHFCH(OCOC_{13}H_{27})$—$C_{11}H_{23}$ |
| 3-141 | OH | F | —$COCHFCH(OCOC_{13}H_{27})$—$C_{11}H_{23}$ | —$COCHFCH(OCOC_{13}H_{27})$—$C_{11}H_{23}$ |
| 3-142 | OH | F | —$COCHFCH(OCOC_{11}H_{23})$—$C_{11}H_{23}$ | —$COCHFCH(OCOC_{13}H_{27})$—$C_{11}H_{23}$ |
| 3-143 | OH | F | —$COCF_2CH(OCOC_{13}H_{27})$—$C_{11}H_{23}$ | —$COCHFCH(OCOC_{13}H_{27})$—$C_{11}H_{23}$ |
| 3-144 | OH | F | —$COCF_2CH(OCOC_{11}H_{23})$—$C_{11}H_{23}$ | —$COCHFCH(OCOC_{13}H_{27})$—$C_{11}H_{23}$ |
| 3-145 | OH | F | —$COC_{13}H_{27}$ | —$COCHFCH(OCOC_{13}H_{27})$—$C_{11}H_{23}$ |
| 3-146 | OH | F | —$COCH_2CHFC_{11}H_{23}$ | —$COCHFCH(OCOC_{13}H_{27})$—$C_{11}H_{23}$ |
| 3-147 | OH | F | —$COCH_2CH(OH)C_{11}H_{23}$ | —$COCHFCH(OCOC_{11}H_{23})$—$C_{11}H_{23}$ |
| 3-148 | OH | F | —$COCHFCH(OH)C_{11}H_{23}$ | —$COCHFCH(OCOC_{11}H_{23})$—$C_{11}H_{23}$ |
| 3-149 | OH | F | —$COCF_2CH(OH)C_{11}H_{23}$ | —$COCHFCH(OCOC_{11}H_{23})$—$C_{11}H_{23}$ |
| 3-150 | OH | F | —$COCH_2CH(OCOC_{13}H_{27})$—$C_{13}H_{27}$ | —$COCHFCH(OCOC_{11}H_{23})$—$C_{11}H_{23}$ |
| 3-151 | OH | F | —$COCH_2CH(OCOC_{11}H_{23})$—$C_{13}H_{27}$ | —$COCHFCH(OCOC_{11}H_{23})$—$C_{11}H_{23}$ |
| 3-152 | OH | F | —$COCHFCH(OCOC_{13}H_{27})$—$C_{11}H_{23}$ | —$COCHFCH(OCOC_{11}H_{23})$—$C_{11}H_{23}$ |
| 3-153 | OH | F | —$COCHFCH(OCOC_{11}H_{23})$—$C_{11}H_{23}$ | —$COCHFCH(OCOC_{11}H_{23})$—$C_{11}H_{23}$ |
| 3-154 | OH | F | —$COCF_2CH(OCOC_{13}H_{27})$—$C_{11}H_{23}$ | —$COCHFCH(OCOC_{11}H_{23})$—$C_{11}H_{23}$ |
| 3-155 | OH | F | —$COCF_2CH(OCOC_{11}H_{23})$—$C_{11}H_{23}$ | —$COCHFCH(OCOC_{11}H_{23})$—$C_{11}H_{23}$ |
| 3-156 | OH | F | —$COC_{13}H_{27}$ | —$COCHFCH(OCOC_{11}H_{23})$—$C_{11}H_{23}$ |
| 3-157 | OH | F | —$COCH_2CHFC_{11}H_{23}$ | —$COCHFCH(OCOC_{11}H_{23})$—$C_{11}H_{23}$ |
| 3-158 | OH | F | —$COCH_2CH(OH)C_{11}H_{23}$ | —$COC_{13}H_{27}$ |
| 3-159 | OH | F | —$COCHFCH(OH)C_{11}H_{23}$ | —$COC_{13}H_{27}$ |
| 3-160 | OH | F | —$COCF_2CH(OH)C_{11}H_{23}$ | —$COC_{13}H_{27}$ |
| 3-161 | OH | F | —$COCH_2CH(OCOC_{13}H_{27})$—$C_{13}H_{27}$ | —$COC_{13}H_{27}$ |
| 3-162 | OH | F | —$COCH_2CH(OCOC_{11}H_{23})$—$C_{13}H_{27}$ | —$COC_{13}H_{27}$ |
| 3-163 | OH | F | —$COCHFCH(OCOC_{13}H_{27})$—$C_{11}H_{23}$ | —$COC_{13}H_{27}$ |
| 3-164 | OH | F | —$COCHFCH(OCOC_{11}H_{23})$—$C_{11}H_{23}$ | —$COC_{13}H_{27}$ |
| 3-165 | OH | F | —$COCF_2CH(OCOC_{13}H_{27})$—$C_{11}H_{23}$ | —$COC_{13}H_{27}$ |
| 3-166 | OH | F | —$COCF_2CH(OCOC_{11}H_{23})$—$C_{11}H_{23}$ | —$COC_{13}H_{27}$ |
| 3-167 | OH | F | —$COC_{13}H_{27}$ | —$COC_{13}H_{27}$ |
| 3-168 | OH | F | —$COCH_2CHFC_{11}H_{23}$ | —$COC_{13}H_{27}$ |
| 3-169 | OH | F | —$COCH_2CH(OH)C_{11}H_{23}$ | —$COCH_2CHFC_{11}H_{23}$ |
| 3-170 | OH | F | —$COCHFCH(OH)C_{11}H_{23}$ | —$COCH_2CHFC_{11}H_{23}$ |
| 3-171 | OH | F | —$COCF_2CH(OH)C_{11}H_{23}$ | —$COCH_2CHFC_{11}H_{23}$ |
| 3-172 | OH | F | —$COCH_2CH(OCOC_{13}H_{27})$—$C_{13}H_{27}$ | —$COCH_2CHFC_{11}H_{23}$ |
| 3-173 | OH | F | —$COCH_2CH(OCOC_{11}H_{23})$—$C_{13}H_{27}$ | —$COCH_2CHFC_{11}H_{23}$ |
| 3-174 | OH | F | —$COCHFCH(OCOC_{13}H_{27})$—$C_{11}H_{23}$ | —$COCH_2CHFC_{11}H_{23}$ |
| 3-175 | OH | F | —$COCHFCH(OCOC_{11}H_{23})$—$C_{11}H_{23}$ | —$COCH_2CHFC_{11}H_{23}$ |
| 3-176 | OH | F | —$COCF_2CH(OCOC_{13}H_{27})$—$C_{11}H_{23}$ | —$COCH_2CHFC_{11}H_{23}$ |
| 3-177 | OH | F | —$COCF_2CH(OCOC_{11}H_{23})$—$C_{11}H_{23}$ | —$COCH_2CHFC_{11}H_{23}$ |
| 3-178 | OH | F | —$COC_{13}H_{27}$ | —$COCH_2CHFC_{11}H_{23}$ |
| 3-179 | OH | F | —$COCH_2CHFC_{11}H_{23}$ | —$COCH_2CHFC_{11}H_{23}$ |
| 3-180 | F | OH | —$COCH_2CH(OH)C_{11}H_{23}$ | —$COCH_2CH(OH)C_{11}H_{23}$ |
| 3-181 | F | OH | —$COCHFCH(OH)C_{11}H_{23}$ | —$COCH_2CH(OH)C_{11}H_{23}$ |
| 3-182 | F | OH | —$COCF_2CH(OH)C_{11}H_{23}$ | —$COCH_2CH(OH)C_{11}H_{23}$ |
| 3-183 | F | OH | —$COCH_2CH(OCOC_{13}H_{27})$—$C_{13}H_{27}$ | —$COCH_2CH(OH)C_{11}H_{23}$ |
| 3-184 | F | OH | —$COCH_2CH(OCOC_{11}H_{23})$—$C_{13}H_{27}$ | —$COCH_2CH(OH)C_{11}H_{23}$ |
| 3-185 | F | OH | —$COCHFCH(OCOC_{13}H_{27})$—$C_{11}H_{23}$ | —$COCH_2CH(OH)C_{11}H_{23}$ |
| 3-186 | F | OH | —$COCHFCH(OCOC_{11}H_{23})$—$C_{11}H_{23}$ | —$COCH_2CH(OH)C_{11}H_{23}$ |
| 3-187 | F | OH | —$COCF_2CH(OCOC_{13}H_{27})$—$C_{11}H_{23}$ | —$COCH_2CH(OH)C_{11}H_{23}$ |
| 3-188 | F | OH | —$COCF_2CH(OCOC_{11}H_{23})$—$C_{11}H_{23}$ | —$COCH_2CH(OH)C_{11}H_{23}$ |
| 3-189 | F | OH | —$COC_{13}H_{27}$ | —$COCH_2CH(OH)C_{11}H_{23}$ |
| 3-190 | F | OH | —$COCH_2CHFC_{11}H_{23}$ | —$COCH_2CH(OH)C_{11}H_{23}$ |
| 3-191 | F | OH | —$COCH_2CH(OH)C_{11}H_{23}$ | —$COCHFCH(OH)C_{11}H_{23}$ |
| 3-192 | F | OH | —$COCHFCH(OH)C_{11}H_{23}$ | —$COCHFCH(OH)C_{11}H_{23}$ |
| 3-193 | F | OH | —$COCF_2CH(OH)C_{11}H_{23}$ | —$COCHFCH(OH)C_{11}H_{23}$ |
| 3-194 | F | OH | —$COCH_2CH(OCOC_{13}H_{27})$—$C_{13}H_{27}$ | —$COCHFCH(OH)C_{11}H_{23}$ |
| 3-195 | F | OH | —$COCH_2CH(OCOC_{11}H_{23})$—$C_{13}H_{27}$ | —$COCHFCH(OH)C_{11}H_{23}$ |
| 3-196 | F | OH | —$COCHFCH(OCOC_{13}H_{27})$—$C_{11}H_{23}$ | —$COCHFCH(OH)C_{11}H_{23}$ |
| 3-197 | F | OH | —$COCHFCH(OCOC_{11}H_{23})$—$C_{11}H_{23}$ | —$COCHFCH(OH)C_{11}H_{23}$ |
| 3-198 | F | OH | —$COCF_2CH(OCOC_{13}H_{27})$—$C_{11}H_{23}$ | —$COCHFCH(OH)C_{11}H_{23}$ |
| 3-199 | F | OH | —$COCF_2CH(OCOC_{11}H_{23})$—$C_{11}H_{23}$ | —$COCHFCH(OH)C_{11}H_{23}$ |
| 3-200 | F | OH | —$COC_{13}H_{27}$ | —$COCHFCH(OH)C_{11}H_{23}$ |
| 3-201 | F | OH | —$COCH_2CHFC_{11}H_{23}$ | —$COCHFCH(OH)C_{11}H_{23}$ |
| 3-202 | F | OH | —$COCH_2CH(OH)C_{11}H_{23}$ | —$COCF_2CH(OH)C_{11}H_{23}$ |
| 3-203 | F | OH | —$COCHFCH(OH)C_{11}H_{23}$ | —$COCF_2CH(OH)C_{11}H_{23}$ |
| 3-204 | F | OH | —$COCF_2CH(OH)C_{11}H_{23}$ | —$COCF_2CH(OH)C_{11}H_{23}$ |
| 3-205 | F | OH | —$COCH_2CH(OCOC_{13}H_{27})$—$C_{13}H_{27}$ | —$COCF_2CH(OH)C_{11}H_{23}$ |
| 3-206 | F | OH | —$COCH_2CH(OCOC_{11}H_{23})$—$C_{13}H_{27}$ | —$COCF_2CH(OH)C_{11}H_{23}$ |
| 3-207 | F | OH | —$COCHFCH(OCOC_{13}H_{27})$—$C_{11}H_{23}$ | —$COCF_2CH(OH)C_{11}H_{23}$ |
| 3-208 | F | OH | —$COCHFCH(OCOC_{11}H_{23})$—$C_{11}H_{23}$ | —$COCF_2CH(OH)C_{11}H_{23}$ |

TABLE 3-continued

| Cpd No. | $R^1$ | $R^5$ | $R^2$ | $R^3$ |
|---|---|---|---|---|
| 3-209 | F | OH | —$COCF_2CH(OCOC_{13}H_{27})$—$C_{11}H_{23}$ | —$COCF_2CH(OH)C_{11}H_{23}$ |
| 3-210 | F | OH | —$COCF_2CH(OCOC_{11}H_{23})$—$C_{11}H_{23}$ | —$COCF_2CH(OH)C_{11}H_{23}$ |
| 3-211 | F | OH | —$COC_{13}H_{27}$ | —$COCF_2CH(OH)C_{11}H_{23}$ |
| 3-212 | F | OH | —$COCH_2CHFC_{11}H_{23}$ | —$COCF_2CH(OH)C_{11}H_{23}$ |
| 3-213 | F | OH | —$COCH_2CH(OH)C_{11}H_{23}$ | —$COCH_2CH(OCOC_{13}H_{27})$—$C_{13}H_{27}$ |
| 3-214 | F | OH | —$COCHFCH(OH)C_{11}H_{23}$ | —$COCH_2CH(OCOC_{13}H_{27})$—$C_{13}H_{27}$ |
| 3-215 | F | OH | —$COCF_2CH(OH)C_{11}H_{23}$ | —$COCH_2CH(OCOC_{13}H_{27})$—$C_{13}H_{27}$ |
| 3-216 | F | OH | —$COCH_2CH(OCOC_{13}H_{27})$—$C_{13}H_{27}$ | —$COCH_2CH(OCOC_{13}H_{27})$—$C_{13}H_{27}$ |
| 3-217 | F | OH | —$COCH_2CH(OCOC_{11}H_{23})$—$C_{13}H_{27}$ | —$COCH_2CH(OCOC_{13}H_{27})$—$C_{13}H_{27}$ |
| 3-218 | F | OH | —$COCHFCH(OCOC_{13}H_{27})$—$C_{11}H_{23}$ | —$COCH_2CH(OCOC_{13}H_{27})$—$C_{13}H_{27}$ |
| 3-219 | F | OH | —$COCHFCH(OCOC_{11}H_{23})$—$C_{11}H_{23}$ | —$COCH_2CH(OCOC_{13}H_{27})$—$C_{13}H_{27}$ |
| 3-220 | F | OH | —$COCF_2CH(OCOC_{13}H_{27})$—$C_{11}H_{23}$ | —$COCH_2CH(OCOC_{13}H_{27})$—$C_{13}H_{27}$ |
| 3-221 | F | OH | —$COCF_2CH(OCOC_{11}H_{23})$—$C_{11}H_{23}$ | —$COCH_2CH(OCOC_{13}H_{27})$—$C_{13}H_{27}$ |
| 3-222 | F | OH | —$COC_{13}H_{27}$ | —$COCH_2CH(OCOC_{13}H_{27})$—$C_{13}H_{27}$ |
| 3-223 | F | OH | —$COCH_2CHFC_{11}H_{23}$ | —$COCH_2CH(OCOC_{13}H_{27})$—$C_{13}H_{27}$ |
| 3-224 | F | OH | —$COCH_2CH(OH)C_{11}H_{23}$ | —$COCH_2CH(OCOC_{11}H_{23})$—$C_{13}H_{27}$ |
| 3-225 | F | OH | —$COCHFCH(OH)C_{11}H_{23}$ | —$COCH_2CH(OCOC_{11}H_{23})$—$C_{13}H_{27}$ |
| 3-226 | F | OH | —$COCF_2CH(OH)C_{11}H_{23}$ | —$COCH_2CH(OCOC_{11}H_{23})$—$C_{13}H_{27}$ |
| 3-227 | F | OH | —$COCH_2CH(OCOC_{13}H_{27})$—$C_{13}H_{27}$ | —$COCH_2CH(OCOC_{11}H_{23})$—$C_{13}H_{27}$ |
| 3-228 | F | OH | —$COCH_2CH(OCOC_{11}H_{23})$—$C_{13}H_{27}$ | —$COCH_2CH(OCOC_{11}H_{23})$—$C_{13}H_{27}$ |
| 3-229 | F | OH | —$COCHFCH(OCOC_{13}H_{27})$—$C_{11}H_{23}$ | —$COCH_2CH(OCOC_{11}H_{23})$—$C_{13}H_{27}$ |
| 3-230 | F | OH | —$COCHFCH(OCOC_{11}H_{23})$—$C_{11}H_{23}$ | —$COCH_2CH(OCOC_{11}H_{23})$—$C_{13}H_{27}$ |
| 3-231 | F | OH | —$COCF_2CH(OCOC_{13}H_{27})$—$C_{11}H_{23}$ | —$COCH_2CH(OCOC_{11}H_{23})$—$C_{13}H_{27}$ |
| 3-232 | F | OH | —$COCF_2CH(OCOC_{11}H_{23})$—$C_{11}H_{23}$ | —$COCH_2CH(OCOC_{11}H_{23})$—$C_{13}H_{27}$ |
| 3-233 | F | OH | —$COC_{13}H_{27}$ | —$COCH_2CH(OCOC_{11}H_{23})$—$C_{13}H_{27}$ |
| 3-234 | F | OH | —$COCH_2CHFC_{11}H_{23}$ | —$COCH_2CH(OCOC_{11}H_{23})$—$C_{13}H_{27}$ |
| 3-235 | F | OH | —$COCH_2CH(OH)C_{11}H_{23}$ | —$COCHFCH(OCOC_{13}H_{27})$—$C_{11}H_{23}$ |
| 3-236 | F | OH | —$COCHFCH(OH)C_{11}H_{23}$ | —$COCHFCH(OCOC_{13}H_{27})$—$C_{11}H_{23}$ |
| 3-237 | F | OH | —$COCF_2CH(OH)C_{11}H_{23}$ | —$COCHFCH(OCOC_{13}H_{27})$—$C_{11}H_{23}$ |
| 3-238 | F | OH | —$COCH_2CH(OCOC_{13}H_{27})$—$C_{13}H_{27}$ | —$COCHFCH(OCOC_{13}H_{27})$—$C_{11}H_{23}$ |
| 3-239 | F | OH | —$COCH_2CH(OCOC_{11}H_{23})$—$C_{13}H_{27}$ | —$COCHFCH(OCOC_{13}H_{27})$—$C_{11}H_{23}$ |
| 3-240 | F | OH | —$COCHFCH(OCOC_{13}H_{27})$—$C_{11}H_{23}$ | —$COCHFCH(OCOC_{13}H_{27})$—$C_{11}H_{23}$ |
| 3-241 | F | OH | —$COCHFCH(OCOC_{11}H_{23})$—$C_{11}H_{23}$ | —$COCHFCH(OCOC_{13}H_{27})$—$C_{11}H_{23}$ |
| 3-242 | F | OH | —$COCF_2CH(OCOC_{13}H_{27})$—$C_{11}H_{23}$ | —$COCHFCH(OCOC_{13}H_{27})$—$C_{11}H_{23}$ |
| 3-243 | F | OH | —$COCF_2CH(OCOC_{11}H_{23})$—$C_{11}H_{23}$ | —$COCHFCH(OCOC_{13}H_{27})$—$C_{11}H_{23}$ |
| 3-244 | F | OH | —$COC_{13}H_{27}$ | —$COCHFCH(OCOC_{13}H_{27})$—$C_{11}H_{23}$ |
| 3-245 | F | OH | —$COCH_2CHFC_{11}H_{23}$ | —$COCHFCH(OCOC_{13}H_{27})$—$C_{11}H_{23}$ |
| 3-246 | F | OH | —$COCH_2CH(OH)C_{11}H_{23}$ | —$COCHFCH(OCOC_{11}H_{23})$—$C_{11}H_{23}$ |
| 3-247 | F | OH | —$COCHFCH(OH)C_{11}H_{23}$ | —$COCHFCH(OCOC_{11}H_{23})$—$C_{11}H_{23}$ |
| 3-248 | F | OH | —$COCF_2CH(OH)C_{11}H_{23}$ | —$COCHFCH(OCOC_{11}H_{23})$—$C_{11}H_{23}$ |
| 3-249 | F | OH | —$COCH_2CH(OCOC_{13}H_{27})$—$C_{13}H_{27}$ | —$COCHFCH(OCOC_{11}H_{23})$—$C_{11}H_{23}$ |
| 3-250 | F | OH | —$COCH_2CH(OCOC_{11}H_{23})$—$C_{13}H_{27}$ | —$COCHFCH(OCOC_{11}H_{23})$—$C_{11}H_{23}$ |
| 3-251 | F | OH | —$COCHFCH(OCOC_{13}H_{27})$—$C_{11}H_{23}$ | —$COCHFCH(OCOC_{11}H_{23})$—$C_{11}H_{23}$ |
| 3-252 | F | OH | —$COCHFCH(OCOC_{11}H_{23})$—$C_{11}H_{23}$ | —$COCHFCH(OCOC_{11}H_{23})$—$C_{11}H_{23}$ |
| 3-253 | F | OH | —$COCF_2CH(OCOC_{13}H_{27})$—$C_{11}H_{23}$ | —$COCHFCH(OCOC_{11}H_{23})$—$C_{11}H_{23}$ |
| 3-254 | F | OH | —$COCF_2CH(OCOC_{11}H_{23})$—$C_{11}H_{23}$ | —$COCHFCH(OCOC_{11}H_{23})$—$C_{11}H_{23}$ |
| 3-255 | F | OH | —$COC_{13}H_{27}$ | —$COCHFCH(OCOC_{11}H_{23})$—$C_{11}H_{23}$ |
| 3-256 | F | OH | —$COCH_2CHFC_{11}H_{23}$ | —$COCHFCH(OCOC_{11}H_{23})$—$C_{11}H_{23}$ |
| 3-257 | F | OH | —$COCH_2CH(OH)C_{11}H_{23}$ | —$COC_{13}H_{27}$ |
| 3-258 | F | OH | —$COCHFCH(OH)C_{11}H_{23}$ | —$COC_{13}H_{27}$ |
| 3-259 | F | OH | —$COCF_2CH(OH)C_{11}H_{23}$ | —$COC_{13}H_{27}$ |
| 3-260 | F | OH | —$COCH_2CH(OCOC_{13}H_{27})$—$C_{13}H_{27}$ | —$COC_{13}H_{27}$ |
| 3-261 | F | OH | —$COCH_2CH(OCOC_{11}H_{23})$—$C_{13}H_{27}$ | —$COC_{13}H_{27}$ |
| 3-262 | F | OH | —$COCHFCH(OCOC_{13}H_{27})$—$C_{11}H_{23}$ | —$COC_{13}H_{27}$ |
| 3-263 | F | OH | —$COCHFCH(OCOC_{11}H_{23})$—$C_{11}H_{23}$ | —$COC_{13}H_{27}$ |
| 3-264 | F | OH | —$COCF_2CH(OCOC_{13}H_{27})$—$C_{11}H_{23}$ | —$COC_{13}H_{27}$ |
| 3-265 | F | OH | —$COCF_2CH(OCOC_{11}H_{23})$—$C_{11}H_{23}$ | —$COC_{13}H_{27}$ |
| 3-266 | F | OH | —$COC_{13}H_{27}$ | —$COC_{13}H_{27}$ |
| 3-267 | F | OH | —$COCH_2CHFC_{11}H_{23}$ | —$COC_{13}H_{27}$ |
| 3-268 | F | OH | —$COCH_2CH(OH)C_{11}H_{23}$ | —$COCH_2CHFC_{11}H_{23}$ |
| 3-269 | F | OH | —$COCHFCH(OH)C_{11}H_{23}$ | —$COCH_2CHFC_{11}H_{23}$ |
| 3-270 | F | OH | —$COCF_2CH(OH)C_{11}H_{23}$ | —$COCH_2CHFC_{11}H_{23}$ |
| 3-271 | F | OH | —$COCH_2CH(OCOC_{13}H_{27})$—$C_{13}H_{27}$ | —$COCH_2CHFC_{11}H_{23}$ |
| 3-272 | F | OH | —$COCH_2CH(OCOC_{11}H_{23})$—$C_{13}H_{27}$ | —$COCH_2CHFC_{11}H_{23}$ |
| 3-273 | F | OH | —$COCHFCH(OCOC_{13}H_{27})$—$C_{11}H_{23}$ | —$COCH_2CHFC_{11}H_{23}$ |
| 3-274 | F | OH | —$COCHFCH(OCOC_{11}H_{23})$—$C_{11}H_{23}$ | —$COCH_2CHFC_{11}H_{23}$ |
| 3-275 | F | OH | —$COCF_2CH(OCOC_{13}H_{27})$—$C_{11}H_{23}$ | —$COCH_2CHFC_{11}H_{23}$ |
| 3-276 | F | OH | —$COCF_2CH(OCOC_{11}H_{23})$—$C_{11}H_{23}$ | —$COCH_2CHFC_{11}H_{23}$ |
| 3-277 | F | OH | —$COC_{13}H_{27}$ | —$COCH_2CHFC_{11}H_{23}$ |
| 3-278 | F | OH | —$COCH_2CHFC_{11}H_{23}$ | —$COCH_2CHFC_{11}H_{23}$ |

Of the compounds referred to above, the following compounds are preferred, that is to say Compounds No. 1-8, 1-16, 1-21, 1-22, 1-52, 1-54, 1-59, 1-65, 1-72, 1-74, 1-105, 1-106, 1-107, 1-110, 1-111, 1-112, 1-115, 1-116, 1-117, 1-120, 1-121, 1-122, 1-125, 1-126, 2-3, 2-4, 2-9, 2-14, 2-15, 2-19, 2-36, 2-38, 2-59, 2-66, 2-72, 2-78, 2-84, 2-87, 2-91, 2-93, 2-96, 2-97, 2-98, 2-99, 2-101, 2-102, 2-103, 2-104, 2-106, 2-107, 2-108, 2-111, 2-112, 2-113, 2-116, 2-117, 3-2, 3-4, 3-6, 3-8, 3-10, 3-12, 3-14, 3-16, 3-30, 3-32, 3-36, 3-42, 3-44, 3-46, 3-52, 3-54, 3-56, 3-62, 3-64, 3-66, 3-72, 3-74, 3-76, 3-85, 3-89, 3-92, 3-97, 3-103, 3-114, 3-122, 3-123, 3-124, 3-125, 3-133, 3-143, 3-144, 3-156, 3-157, 3-158, 3-163, 3-167 and 3-176. More preferred are Compounds No. 1-21, 1-54, 1-74, 1-105, 1-110, 1-115, 1-120, 1-125, 1-126, 2-14, 2-38, 2-59, 2-66, 2-72, 2-78, 2-84, 2-96, 2-101, 2-106, 2-111, 2-116, 2-117, 3-2, 3-4, 3-6, 3-42, 3-52, 3-56, 3-72, 3-74, 3-76, 3-114, 3-123, 3-156 and 3-158.

The most preferred compounds are Compounds No.:

2-38. 2-Deoxy-2-(2'-fluoro-3'-hydroxytetradecanoylamino)-3-O-[3"-(tetradecanoyloxy)tetradecanoyl]glucopyranosyl-4-phosphate;

2-66. 2-Deoxy-2-(3'-hydroxytetradecanoylamino)-3-O-[3"-(2,2-difluorotetradecanoyloxy)tetradecanoyl]glucopyranosyl-4-phosphate, especially its 2-deoxy-2-[(3'R)-3'-hydroxytetradecanoylamino]-3-O-[(3"R)-3"-(2,2-difluorotetradecanoyloxy)tetradecanoyl]-D-glucopyranosyl-4-phosphate isomer;

2-84. 2-Deoxy-2-(3'-hydroxytetradecanoylamino)-3-O-[2",2"-difluoro-3"-(tetradecanoyloxy)tetradecanoyl]glucopyranosyl-4-phosphate;

2-96. 2-Deoxy-2-(2',2'-difluoro-3'-hydroxytetradecanoylamino)-3-O-(3-tetradecanoyloxytetradecanoyl)glucopyranosyl-4-phosphate, especially its 2-deoxy-2-[(R)-2',2'-difluoro-3'-hydroxytetradecanoylamino]-3-O-[(R)-3-tetradecanoyloxytetradecanoyl]-D-glucopyranosyl-4-phosphate and 2-deoxy-2-[(S)-2',2'-difluoro-3'-hydroxytetradecanoylamino]-3-O-[(R)-3-tetradecanoyloxytetradecanoyl]-D-glucopyranosyl-4-phosphate isomers;

2-101. 2-Deoxy-2-(2',2'-difluoro-3'-hydroxytetradecanoylamino)-3-O-(3-tetradecanoyloxytetradecanoyl)glucopyranosyl-4-phosphate;

2-106. 2-Deoxy-2-(2',2'-difluoro-3'-hydroxytetradecanoylamino)-3-O-(2",2"-difluoro-3"-tetradecanoyloxytetradecanoyl)glucopyranosyl-4-phosphate;

2-111. 2-Deoxy-2-(2',2'-difluoro-3'-hydroxytetradecanoylamino)-3-O-(2",2"-difluoro-3"-dodecanoyloxytetradecanoyl]glucopyranosyl-4-phosphate;

3-2. 2,6-Dideoxy-6-fluoro-2-(3'-hydroxytetradecanoylamino)-3-O-(3"-tetradecanoyloxytetradecanoyl)glucopyranosyl-4-phosphate, especially its 2,6-dideoxy-6-fluoro-2-[(R)-3'-hydroxytetradecanoylamino]-3-O-[(R)-3"-tetradecanoyloxytetradecanoyl]-D-glucopyranosyl-4-phosphate isomer;

3-72. 2,6-Dideoxy-6-fluoro-2-(3'-hydroxytetradecanoylamino)-3-O-(2",2"-difluoro-3"-tetradecanoyloxytetradecanoyl)glucopyranosyl-4-phosphate; and 3-125. 2,6-Dideoxy-6-fluoro-2-(2',2'-difluoro-3'-hydroxytetradecanoylamino)-3-O-(3"-tetradecanoyloxytetradecanoyl)glucopyranosyl-4-phosphate.

In the case of all of the compounds listed above, including those referred to as preferred, more preferred and most preferred, we prefer the isomer having the D-configuration.

The compounds of the present invention may be prepared by a variety of processes well known to those skilled in the art for the preparation of compounds of this type, and any such known process may be used and forms a part of the present invention. However in general terms, the compounds may be prepared by:

(a) reacting a compound of formula (II):

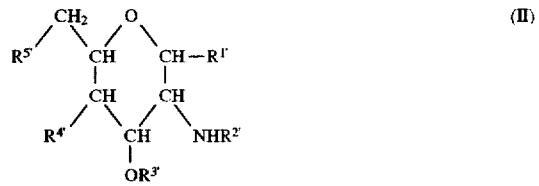

(in which one of $R^{1'}$ and $R^{4'}$ represents a hydroxy group and the other represents, in the case of $R^{1'}$, a protected hydroxy group or a fluorine atom, or, in the case of $R^{4'}$, a group of formula $-OP(=O)(OH)_2$ or a protected hydroxy group;

$R^{2'}$ and $R^{3'}$ are independently selected from the group consisting of the groups represented by $R^2$ and $R^3$, the groups represented by $R^2$ and $R^3$ in which any reactive group is protected, and hydroxy- or amino-protecting groups;

$R^{5'}$ represents a protected hydroxy group or a fluorine atom;)

with a compound of formula (III):

(in which each $R^{10}$ is independently selected from the group consisting of phosphoric acid protecting groups, and X represents a halogen atom), to prepare a compound of Formula (IV):

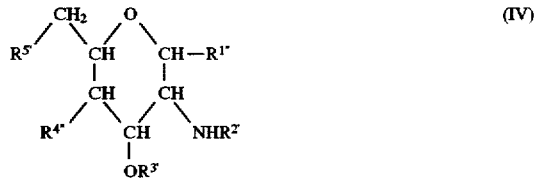

[in which: one or both of $R^{1''}$ and $R^{4''}$ represents a group of formula $-OP(=O)(OR^{10})_2$, in which $R^{10}$ is as defined above, and, where only one represents said group, the other represents, in the case of $R^{1''}$, a protected hydroxy group or a fluorine atom, or, in the case of $R^{4''}$, a protected hydroxy group; and $R^{2''}$, $R^{3''}$ and $R^{5'}$ are as defined above;]

and then, where desired, removing protecting groups and optionally replacing any one or more of the groups represented by any of $R^{1''}$, $R^{2'}$, $R^{3'}$, $R^{4''}$ and $R^{5'}$ by any of the groups represented by $R^1$, $R^2$, $R^3$, $R^4$ and $R^5$ in the definition of formula (I), above;

and optionally esterifying or salifying the product.

In more detail, the compounds of the present invention may be prepared by the reactions shown in the following Reaction Schemes A to E, depending on the exact compounds which it is desired to prepare.

Reaction Scheme A:
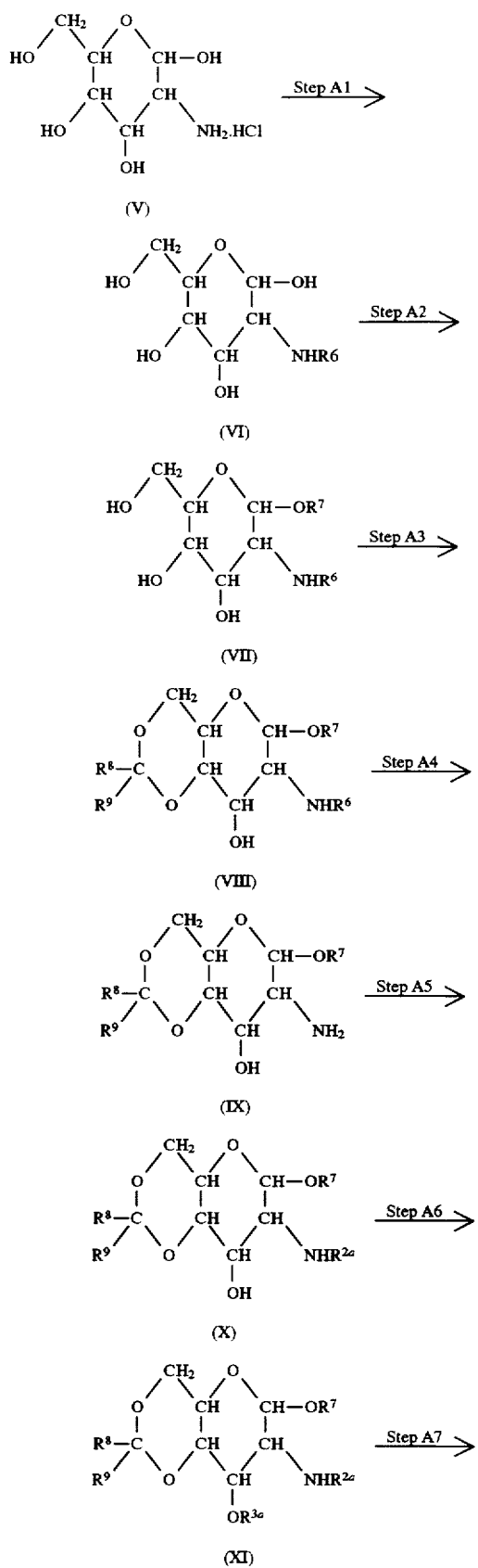
-continued
Reaction Scheme A:
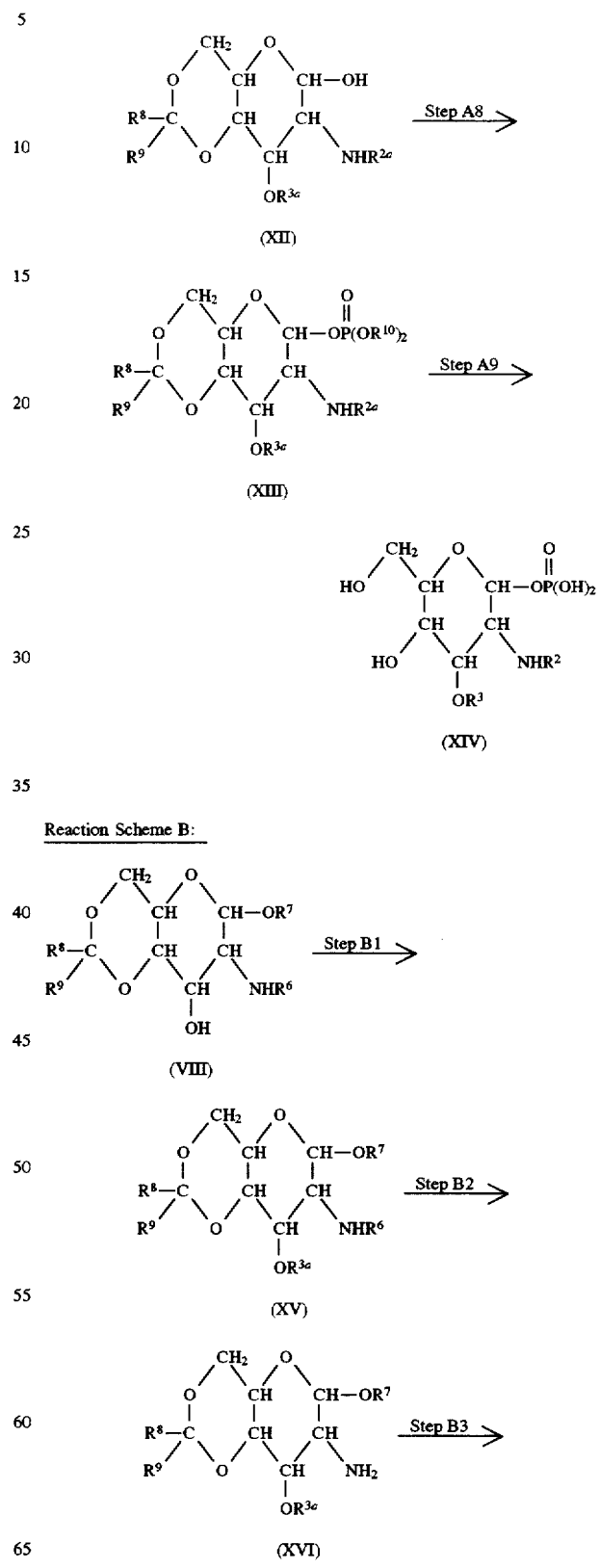

Reaction Scheme B:
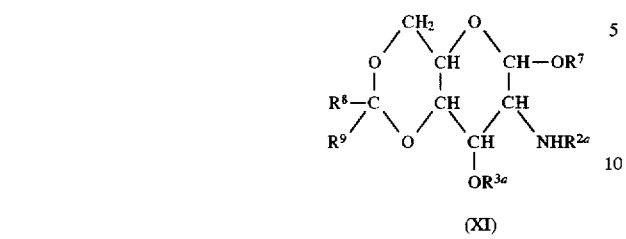
(XI)
Reaction Scheme C:
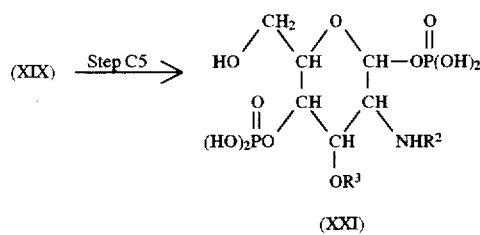
(XXI)
Reaction Scheme C:
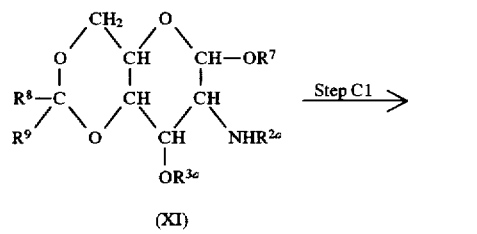
(XI) Step C1 →
Reaction Scheme D:
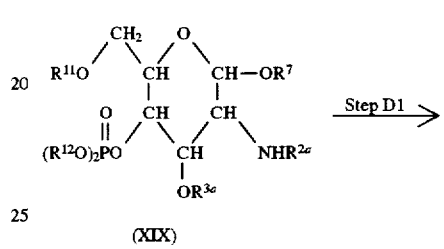
(XIX) Step D1 →
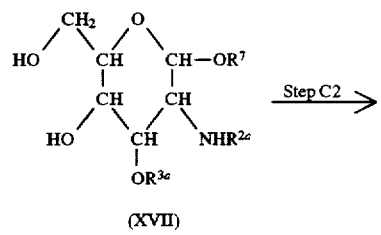
(XVII) Step C2 →
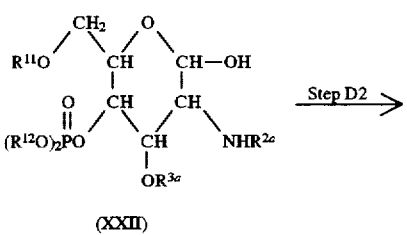
(XXII) Step D2 →
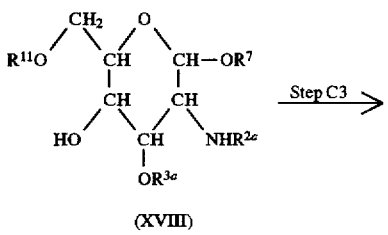
(XVIII) Step C3 →
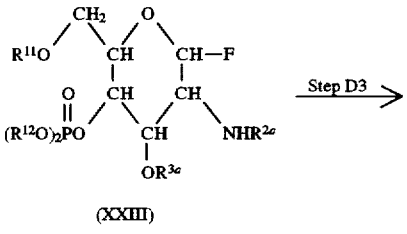
(XXIII) Step D3 →
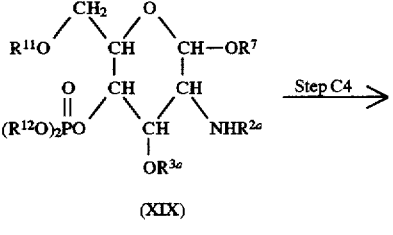
(XIX) Step C4 →
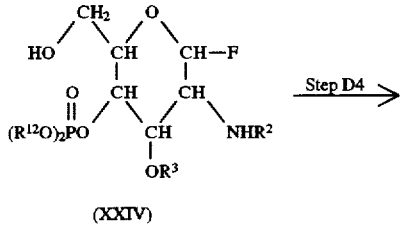
(XXIV) Step D4 →
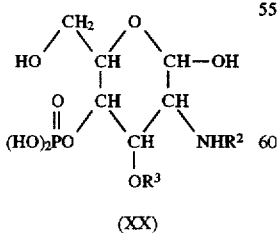
(XX)
OR
(XXV)

Reaction Scheme E:

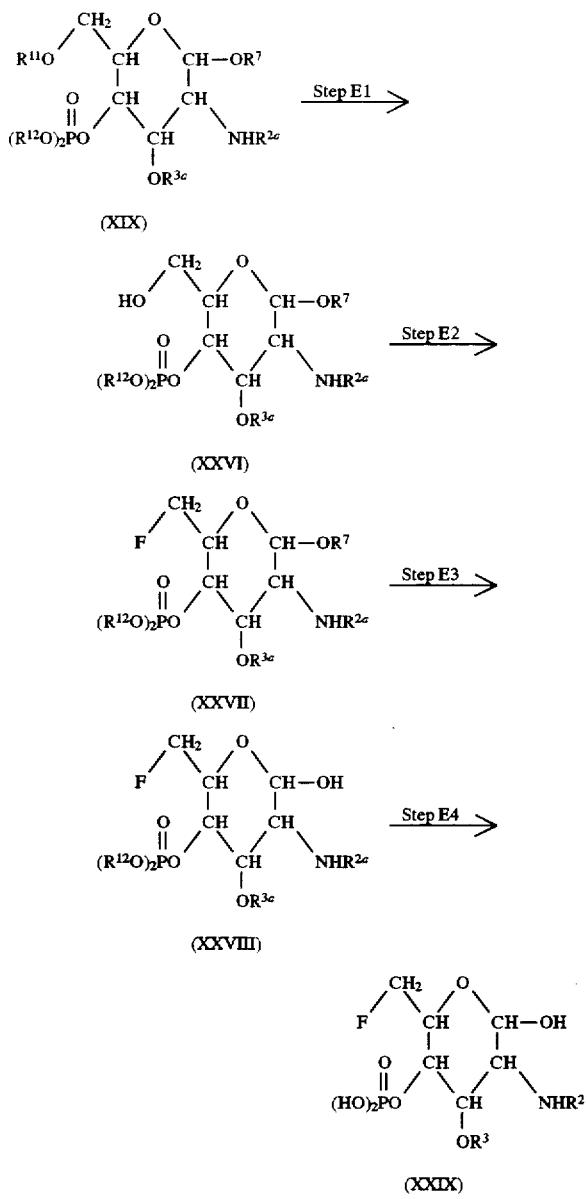

In the above formulae:

$R^2$ and $R^3$ are as defined above;

$R^{2a}$ and $R^{3a}$ are the same or different and each represents any of the groups defined above for $R^2$ and $R^3$ but in which any reactive group is optionally protected;

$R^6$ represents an amino-protecting group, such as the aliphatic acyl groups exemplified above, the aromatic acyl groups exemplified above, the alkoxycarbonyl groups exemplified above, the alkenyloxycarbonyl groups exemplified above, the aralkyloxycarbonyl groups exemplified above, the silyl groups exemplified above or the aralkyl groups exemplified above, and is preferably a trifluoroacetyl group;

$R^7$ and $R^{11}$ may be the same or different from each other and each represents a hydroxy-protecting group as defined above for $R^1$, $R^4$ and $R^5$;

$R^8$ and $R^9$ may be the same or different from each other and each represents: a straight or branched chain alkyl group having from 1 to 6 carbon atoms, such as a methyl, ethyl, propyl, isopropyl, butyl, isobutyl, sec-butyl, t-butyl, pentyl, isopentyl, 2-methylbutyl, neopentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl or 2,3-dimethylbutyl group; or an aryl group having from 5 to 12, preferably 6 to 10, carbon atoms, such as a phenyl or naphthyl group, which may be unsubstituted or may have from 1 to 4 substituents on the ring, said substituents being selected from the group consisting of amino groups, nitro groups, cyano groups, carboxy groups (which may be esterifed with the above lower alkyl groups, with the halogenated lower alkyl groups mentioned below or with the aralkyl groups exemplified above), carbamoyl groups, halogen atoms, lower alkyl groups, halogenated lower alkyl groups (such as the trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl and 2,2-dibromoethyl groups), and the aliphatic acyl groups exemplified above, and is preferably a halogen atom or a halogenated lower alkyl group; and $R^{10}$ and $R^{12}$ may be the same or different from each other and each represents a protecting group for a phosphoryl group or for a phosphono group, such as the aryl groups or the aralkyl groups exemplified above.

In Step A1 of Reaction Scheme A, glucosamine hydrochloride of formula (V) is reacted with the acid corresponding to the amino-protecting group $R^6$ or with a reactive derivative of that acid. The nature of the reagent chosen will, of course, depend on the nature of the group $R^6$ which it is wished to introduce; in the case of the preferred trifluoroacetyl group, the reagent will be trifluoroacetic acid or a reactive derivative thereof. Where the reagent is a free acid, such as trifluoroacetic acid, the reaction is preferably carried out in the presence of a condensation agent, such as dicyclohexylcarbodiimide (DCC). Where the reagent is an anhydride of the acid, such as trifluoroacetic anhydride, the reaction preferably takes place in the presence of an organic base, such as triethylamine, diisopropylethylamine, N-methylmorpholine, pyridine, 4-(N,N-dimethylamino) pyridine (DMAP), N,N-dimethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU). Alternatively, where the reagent is an active ester, e.g. a trifluoroacetate such as ethyl trifluoroacetate, the reaction preferably also takes place in the presence of one of the above organic bases. The reaction in this Step prepares an amide of formula (VI).

The reaction is normally and preferably effected in the presence of a solvent. There is no particular restriction on the nature of the solvent to be employed, provided that it has no adverse effect on the reaction or on the reagents involved and that it can dissolve the starting materials to a certain degree. Examples of suitable solvents include: halogenated hydrocarbons, especially halogenated aliphatic hydrocarbons, such as methylene chloride and chloroform; ethers, such as diethyl ether, tetrahydrofuran, dioxane and dimethoxyethane; alcohols, such as methanol, ethanol, propanol, isopropanol, butanol, isobutanol and isoamyl alcohol; amides, especially fatty acid amides, such as dimethylformamide, dimethylacetoamide and hexamethylphosphoric triamide; and sulfoxides, such as dimethyl sulfoxide.

The reaction can take place over a wide range of temperatures, and the precise reaction temperature is not critical to the invention. In general, we find it convenient to carry out the reaction at a temperature from 0° C. to 100° C., preferably at room temperature. The time required for the reaction may also vary widely, depending on many factors, notably the reaction temperature and the nature of the reagents and the solvent employed. However, provided that the reaction is effected under the preferred conditions outlined above, a period of from 0.1 to 24 hours will usually suffice.

In Step A2 of Reaction Scheme A, a glycoside bond is formed by reacting the amide of formula (VI) with an alcohol of formula $R^7OH$ (where $R^7$ is as defined above, e.g. methanol, ethanol, benzyl alcohol or allyl alcohol) in the presence of an acid catalyst to prepare the compound of formula (VII).

The alcohol of formula $R^7OH$ is preferably used in a large excess to serve as the reaction solvent.

There is no particular restriction on the acid to be used as the catalyst, provided that it functions as an acid and has no harmful effect on the reaction or on the reagents. Preferred acids include: mineral acids, such as hydrochloric acid or sulfuric acid; and organic acids, especially organic sulfonic acids, such as p-toluenesulfonic acid. These acids may be used in the hydrous state, if desired.

The reaction can take place over a wide range of temperatures, and the precise reaction temperature is not critical to the invention. In general, we find it convenient to carry out the reaction at a temperature from 0° C. to 200° C., preferably at the reflux temperature of the reaction medium. The time required for the reaction may also vary widely, depending on many factors, notably the reaction temperature and the nature of the reagents and the solvent employed. However, provided that the reaction is effected under the preferred conditions outlined above, a period of from 0.1 to 24 hours will usually suffice.

In Step A3 of the Reaction Scheme, the diol of formula (VII), prepared as described above, is protected by introducing a group of formula $R^8R^9C<$, for example an isopropylidene, benzylidene or ethylidene group at the 4-position and 6-position of the compound of formula (VII); this reaction takes place in a solvent and in the presence of a catalyst to prepare a compound of formula (VIII).

There is no restriction on the nature of the reagents employed in this Step for the protection of the diol, and any such reagent commonly used for diol protection may equally be used here. Preferred examples include: aldehyde derivatives, such as benzaldehyde; ketone derivatives, such as acetone; and dimethoxy compounds, such as 2,2-dimethoxypropane or benzaldehyde dimethyl acetal.

There is also no particular restriction on the nature of the solvent to be employed, provided that it has no adverse effect on the reaction or on the reagents involved. Examples of suitable solvents include: halogenated hydrocarbons, especially halogenated aliphatic hydrocarbons, such as methylene chloride or chloroform; ethers, such as dioxane or tetrahydrofuran; aliphatic hydrocarbons, such as hexane or pentane; aromatic hydrocarbons, such as benzene or toluene; esters, such as ethyl acetate; and polar solvents, e.g. amides, such as dimethylformamide, and ketones, such as acetone.

There is no particular restriction on the nature of the catalyst to be used, provided that it has no adverse effect on the reaction or the reagents, and any acid commonly used in reactions of this type may equally be used here. Examples include: organic acids, especially organic sulfonic acids, and their salts, such as p-toluenesulfonic acid, camphorsulfonic acid and pyridium p-toluenesulfonate; inorganic catalysts, such as hydrochloric acid; and Lewis acids, such as zinc chloride, aluminum chloride and stannic chloride.

The reaction can take place over a wide range of temperatures, and the precise reaction temperature is not critical to the invention. In general, we find it convenient to carry out the reaction at a temperature from 0° C. to 100° C. The time required for the reaction may also vary widely, depending on many factors, notably the reaction temperature and the nature of the reagents and solvent employed. However, provided that the reaction is effected under the preferred conditions outlined above, a period of from 0.1 to 24 hours will usually suffice.

In Step A4 of Reaction Scheme A, the $R^6$ group of the compound of formula (VIII) is eliminated to prepare a compound of formula (IX).

Many reactions can be used to remove this protecting group, the nature of the reaction depending on the nature of the protecting group, e.g. as illustrated below.

For example, when a silyl group is used as the $R^6$ group, it can generally be eliminated by treating the compound of formula (VIII) with a compound which generates a fluorine anion, such as tetrabutylammonium fluoride. The reaction is preferably effected in the presence of a solvent. There is no particular restriction on the nature of the solvent to be employed, provided that it has no adverse effect on the reaction or on the reagents involved. Examples of suitable solvents include ethers, such as tetrahydrofuran and dioxane.

The reaction can take place over a wide range of temperatures, and the precise reaction temperature is not critical to the invention. In general, we find it convenient to carry out the reaction at about room temperature. The time required for the reaction may also vary widely, depending on many factors, notably the reaction temperature and the nature of the reagents. However, provided that the reaction is effected under the preferred conditions outlined above, a period of from 10 minutes to 18 hours will usually suffice.

If the $R^{10}$ group is an aliphatic acyl group, an aromatic acyl group or an alkoxycarbonyl group, it can be eliminated by treating the compound of formula (VIII) with a base in the presence or an aqueous solvent or by reduction. There is no particular restriction on the nature of the base employed in this reaction, provided that it does not affect other parts of the molecule, and any base commonly used in reactions of this type may equally be used here. Examples of suitable bases include: alkali metal carbonates, such as sodium carbonate or potassium carbonate; alkali metal hydroxides, such as sodium hydroxide or potassium hydroxide; and concentrated methanolic ammonia. The reaction is preferably effected in the presence of a solvent. There is no particular restriction on the nature of the solvent to be employed, provided that it has no adverse effect on the reaction or on the reagents involved, and any solvent commonly used for hydrolytic reactions may be used. Examples of suitable solvents include: water; a mixture of water and an organic solvent, such as an alcohol (e.g. methanol, ethanol or propanol) or an ether (e.g. tetrahydrofuran or dioxane). The reaction can take place over a wide range of temperatures, and the precise reaction temperature is not critical to the invention. In general, we find it convenient to carry out the reaction at a temperature from 0° C. to 150° C. in order to prevent side reactions. The time required for the reaction may also vary widely, depending on many factors, notably the reaction temperature and the nature of the reagents. However, provided that the reaction is effected under the preferred conditions outlined above, a period of from 1 to 10 hours will usually suffice.

Elimination of the $R^6$ group through reduction may be carried out using a reducing agent such as sodium borohydride by a conventional method.

If the $R^6$ group is an aralkyl group or an aralkyloxycarbonyl group, elimination of the group is preferably carried out by catalytic reduction at ambient temperature using a catalyst, such as platinum or palladium-on-carbon. This reaction is preferably effected in the presence of a solvent. There is no particular restriction on the nature of the solvent to be employed, provided that it has no adverse effect on the reaction or on the reagents involved. Examples of suitable solvents include: alcohols, such as methanol, ethanol or isopropanol; ethers, such as diethyl ether, tetrahydrofuran or dioxane; aromatic hydrocarbons, such as toluene, benzene or xylene; aliphatic hydrocarbons, such as hexane or cyclohexane; esters, such as ethyl acetate or propyl acetate; fatty acids, such as acetic acid; and mixtures of any one or more of such organic solvents with water. Any catalyst commonly used in reduction reactions can be used for this one, and preferred examples include palladium-on-carbon, Raney nickel, platinum oxide, platinum black, rhodium-aluminum oxide, triphenylphosphine-rhodium chloride and palladium-barium sulfate.

The reaction pressure is not critical, but it is usually from 1 to 10 atmospheres.

The reaction can take place over a wide range of temperatures, and the precise reaction temperature is not critical to the invention. In general, we find it convenient to carry out the reaction at a temperature from 0° C. to 100° C. The time required for the reaction may also vary widely, depending on many factors, notably the reaction temperature, the type of catalyst and the nature of the reagents. However, provided that the reaction is effected under the preferred conditions outlined above, a period of from 5 minutes to 24 hours will usually suffice.

If the $R^6$ group is an alkenyloxycarbonyl group, it can usually be eliminated under the same elimination conditions as are used in the case when the $R^6$ group is an aliphatic acyl group, an aromatic acyl group or a lower alkoxycarbonyl group. It should be noted that, when the $R^6$ group is an allyloxycarbonyl group, elimination is particularly conveniently carried out by using palladium and triphenylphosphine or nickel tetracarbonyl, as this reaction may be carried out with the least side reactions.

In Step A5 of Reaction Scheme A, the amino moiety at the 2-position of the compound of formula (IX) is acylated, preferably with from 1.0 to 1.1 equivalents of one of the acylation agents described below, to prepare the compound of formula (X).

The acylation may be carried out by allowing this amino moiety to react with a carboxylic acid of formula $R^{2a}OH$ (wherein $R^{2a}$ is as defined above) in the presence of a condensation agent, such as dicyclohexylcarbodiimide (DCC) or carbonyldiimidazole, or with an activated acylation agent of formula $R^{2a}Y$ (wherein $R^{2a}$ is as defined above; and Y represents a leaving group, for example, a group of formula $OR^{2a}$, a halogen atom (such as a chlorine, bromine or iodine atom), an aliphatic acyloxy group [such as an alkylcarbonyloxy group, e.g. an acetoxy or propionyloxy group, a halogenated alkylcarbonyloxy group, e.g. a chloroacetoxy, dichloroacetoxy, trichloroacetoxy or trifluoroacetoxy group, a lower alkoxyalkylcarbonyloxy group, e.g. a methoxyacetoxy group, or an unsaturated alkylcarbonyloxy group, e.g. an (E)-2-methyl-2-butenoyloxy group]; an aromatic acyloxy group (such as an arylcarbonyloxy group, e.g. a benzoyloxy group, a halogenated arylcarbonyloxy group, e.g. a 2-bromobenzoyloxy or 4-chlorobenzoyloxy group, a lower alkylated arylcarbonyloxy group, e.g. a 2,4,6-trimethylbenzoyloxy or 4-toluoyloxy group, a lower alkoxylated arylcarbonyloxy group, e.g. a 4-anisoyloxy group, a nitrated arylcarbonyloxy group, e.g. a 4-nitrobenzoyloxy or 2-nitrobenzoyloxy group), a trihalomethoxy group (such as a trichloromethoxy group), a lower alkanesulfonyloxy group (such as a methanesulfonyloxy or ethanesulfonyloxy group), a halogenated lower alkanesulfonyloxy group (such as a trifluoromethanesulfonyloxy or pentafluoroethanesulfonyloxy group), an arylsulfonyloxy group (such as a benzenesulfonyloxy or p-toluenesulfonyloxy group). The reaction is preferably effected in a solvent in the presence of a base.

There is no particular restriction on the nature of the solvent to be employed, provided that it has no adverse effect on the reaction or on the reagents involved. Examples of suitable solvents include: halogenated hydrocarbons, especially halogenated aliphatic hydrocarbons, such as methylene chloride, chloroform or carbon tetrachloride; ethers, such as diethyl ether, dioxane or tetrahydrofuran; aliphatic hydrocarbons, such as hexane; aromatic hydrocarbons, such as benzene or toluene; esters, such as ethyl acetate; and polar solvents, including sulfoxides such as dimethyl sulfoxide and amides such as dimethylformamide.

There is also no particular restriction on the nature of the base employed, and any base commonly used in reactions of this type may equally be used here. Preferred examples include organic bases such as triethylamine, pyridine, DBU, DBN, N,N-dimethylaniline, N,N-diethylaniline and N,N-dimethylaminopyridine.

The reaction can take place over a wide range of temperatures, and the precise reaction temperature is not critical to the invention. In general, we find it convenient to carry out the reaction at a temperature from 0° C. to 100° C., and preferably at from 20° to 50° C. The time required for the reaction may also vary widely, depending on many factors, notably the reaction temperature and the nature of the reagents and solvent. However, provided that the reaction is effected under the preferred conditions outlined above, a period of from 0.1 to 24 hours will usually suffice.

In Step A6 of Reaction Scheme A, the hydroxy moiety at the 3-position of the compound of formula (X) is modified with an $R^{3a}$ group to give a compound of formula (XI). This reaction is essentially the same as and may be carried out under the same conditions and using the same reagents as the acylation of the amino moiety in Step A5.

In Step A7 of Reaction Scheme A, the protecting group $R^7$ at the 1-position of the compound of formula (XI) is eliminated to prepare a compound of formula (XII).

The nature of the reaction employed to remove this protecting group will, of course, depend on the nature of the protecting group itself, and any reaction known in the art for removing protecting groups in compounds of this type may equally be employed here.

For example, if the $R^7$ group is a silyl group, an aralkyloxycarbonyl group, an aralkyl group, an aliphatic acyl group, an aromatic acyl group, an alkoxycarbonyl group, an alkoxymethyl group or a substituted ethyl group, its elimination may be effected in the same manner as in the case when the group $R^6$ is to be eliminated in accordance with Step A4.

If the $R^7$ group is a tetrahydropyranyl group, a tetrahydrofuranyl group, a tetrahydrothiopyranyl group a tetrahydrothienyl group or a vinyl group, it can usually be eliminated by treating the compound of formula (XI) with an acid in a solvent. There is no particular restriction on the nature of the acid to be used here, and preferred examples include hydrochloric acid, sulfuric acid, β-toluenesulfonic acid and acetic acid.

The reaction is normally and preferably effected in the presence of a solvent. There is no particular restriction on the nature of the solvent to be employed, provided that it has no adverse effect on the reaction or on the reagents involved. Examples of suitable solvents include: organic solvents, such as alcohols (e.g. methanol or ethanol), ethers (e.g. tetrahydrofuran or dioxane) and mixtures of of any one or more of such organic solvents and water.

The reaction can take place over a wide range of temperatures, and the precise reaction temperature is not critical to the invention. In general, we find it convenient to carry out the reaction at a temperature from 0° C. to 50° C. The time required for the reaction may also vary widely, depending on many factors, notably the reaction temperature and the nature of the reagents. However, provided that the reaction is effected under the preferred conditions outlined above, a period of from 10 minutes to 18 hours will usually suffice.

If the $R^7$ group is an alkenyloxycarbonyl group, it can be eliminated by treatment with a base under the same conditions as are used for the elimination reaction in the case where the group $R^7$ is an aliphatic acyl group, an aromatic acyl group or an alkoxycarbonyl group. It should be noted that, when the $R^7$ group is an allyloxycarbonyl group, elimination is conveniently carried out using palladium and triphenylphosphine or nickel tetracarbonyl, as this reaction may be carried out with the least side reactions.

If the group $R^7$ is an allyl group, it can preferably be eliminated by reacting the compound of formula (XI) in a solvent in the presence of a catalyst to shift the double bond and convert the group into an enol ether type group, immediately followed by the addition of pyridine-iodine-water or of an inorganic acid, such as concentrated hydrochloric acid or sulfuric acid.

The reaction is normally and preferably effected in the presence of a solvent. There is no particular restriction on the nature of the solvent to be employed, provided that it has no adverse effect on the reaction or on the reagents involved. Examples of suitable solvents include: halogenated hydrocarbons, especially halogenated aliphatic hydrocarbons, such as methylene chloride, chloroform or carbon tetrachloride; ethers, such as diethyl ether, dioxane or tetrahydrofuran; aliphatic hydrocarbons, such as hexane; aromatic hydrocarbons, such as benzene or toluene; esters, such as ethyl acetate; and polar solvents, for example sulfoxides such as dimethyl sulfoxide and fatty acid amides such as dimethylformamide.

Examples of the catalyst which may be used here include catalysts known to be capable of moving a double bond, such as palladium catalysts, e.g. palladium chloride and palladium acetate, rhodium catalysts, e.g. 1,5-cyclooctadiene-bis[methyldiphenylphosphine]rhodium hexafluorophosphate and rhodium acetate, and iridium catalysts, e.g. 1,5-cyclooctadiene-bis [methyldiphenylphosphine]iridium hexafluorophosphate.

The reaction can take place over a wide range of temperatures, and the precise reaction temperature is not critical to the invention. In general, we find it convenient to carry out the reaction at a temperature from 0° to 100° C. The time required for the reaction may also vary widely, depending on many factors, notably the reaction temperature and the nature of the reagents, the catalyst and the solvent employed. However, provided that the reaction is effected under the preferred conditions outlined above, a period of from 1 to 5 hours will usually suffice.

In Step A8 of Reaction Scheme A, the hydroxy group at the 1-position of the compound of formula (XII) thus obtained is phosphorylated to prepare a compound of formula (XIII).

The phosphorylation can be effected by forming an anion with a base in a solvent, and then by reacting this anion with a phosphorylation agent.

There is no particular restriction on the nature of the solvent to be employed, provided that it has no adverse effect on the reaction or on the reagents involved. Examples of suitable solvents include: ethers, such as diethyl ether, dioxane or tetrahydrofuran; and halogenated aliphatic hydrocarbons, such as methylene chloride.

There is no particular restriction on the nature of the base to be used here, provided that it is capable of forming an anion, and any base commonly used for reactions of this type may equally be used here. Preferred examples include: lithium compounds, such as butyllithium and phenyllithium; and organic bases, such as DBU, DBN, DMAP, triethylamine and pyridine.

The phosphorylation agent used may be any reagent commonly employed for phosphorylation, such as dibenzyl chlorophosphate or diphenyl chlorophosphate.

The reaction can take place over a wide range of temperatures, and the precise reaction temperature is not critical to the invention. In general, we find it convenient to carry out the reaction at a temperature from −78° to 50° C., preferably from −78° C. to about room temperature. The time required for the reaction may also vary widely, depending on many factors, notably the reaction temperature and the nature of the reagents and the solvent. However, provided that the reaction is effected under the preferred conditions outlined above, a period of from 10 minutes to 24 hours will usually suffice. In Step A9 of Reaction Scheme A, the protecting groups for the compound of formula (XIII) are eliminated to prepare the compound of formula (XIV) and, if desired, any protecting group in or represented by for $R^{3a}$ is also eliminated.

The nature of the reactions employed to eliminate the protecting group for the phosphoric acid residue and the hydroxy-protecting group will depend principally on the nature of the protecting group, and the desired elimination reactions can be effected in any order; if desired, the protecting group for the phosphoric acid residue can be eliminated simultaneously with the elimination of the hydroxy-protecting group. However, we prefer that the protecting group for the phosphoric acid residue $R^{10}$ should be eliminated last, for ease of handling.

For example, when the $R^{10}$ group is an aralkyl group, such as a benzyl group, all of the protecting groups can be eliminated at one time by catalytic reduction in the presence of a palladium-on-carbon catalyst at −78° C. to 25° C., including the case where the hydroxy groups of $R^{2a}$ and/or $R^{3a}$ have a protecting group. Also, if the $R^{10}$ group is an aryl group, such as a phenyl group, elimination of the protecting group can be effected by catalytic reduction in the presence of a palladium-on-carbon catalyst, followed by catalytic reduction in the presence of a platinum oxide catalyst.

In the case of a protecting group containing the $R^8$ group or $R^9$ group, it can be optionally eliminated (for example, in the case of an acetonide) by purification through silica gel chromatography. However, the protecting group can usually more conveniently be eliminated in a solvent (such as aqueous acetic acid, an ether, e.g. tetrahydrofuran or dioxane, or an alcohol, e.g. ethanol or methanol) at 0° to 100° C. using a catalyst such as dilute hydrochloric acid, dilute sulfuric acid or p-toluenesulfonic acid.

When a water-soluble salt of phosphoric acid is to be obtained, the compound of formula (XIV) is first washed with an inorganic acid diluted with water (such as dilute hydrochloric acid) and is then dissolved in a solvent (such as chloroform), after which a base is added.

Reaction Schemes B to E illustrate variations for preparing different products or for preparing intermediate products via different routes.

In Step B1 of Reaction Scheme B, the hydroxy group at the 3-position of the compound of formula (VIII), prepared in Step A3, is acylated with the $R^{3a}$ group to prepare a compound of formula (XV). The acylation is essentially the same reaction as and may be carried out using the same reagents and reaction conditions as described in Step A5.

In Step B2 of Reaction Scheme B, the protecting group $R^6$ for the amino group at the 2-position of the compound of formula (XV) is eliminated to prepare a compound of formula (XVI) in the same manner as described in Step A4.

In Step B3 of Reaction Scheme B, the amino group at the 2-position of the compound of formula (XVI) is modified with the $R^{2a}$ group according to the procedure described in Step A5 to prepare a compound of formula (XI).

The compound of formula (XI) thus prepared may then be subjected to the procedures described in Steps A7 to A9 to prepare a compound corresponding to the compound of formula (XIV).

In Step C1 of Reaction Scheme C, the hydroxy groups at the 4- and 6-positions of the compound of formula (XI) are eliminated to prepare a compound of formula (XVII). This may be effected using procedures similar to those described in Step A9.

In Step C2 of Reaction Scheme C, the hydroxy group at the 6-position of the compound of formula (XVII) is protected with an $R^{11}$ group to prepare a compound of formula (XVIII).

The compound of formula (XVIII) can be prepared by allowing the primary hydroxy group at the 6-position of the compound of formula (XVII) to react with a compound of formula $R^{11}Y$ (wherein $R^{11}$ and Y are as defined above), such as chloromethyl methyl ether, benzyl chloromethyl ether, benzyl bromomethyl ether, benzyl chloroformate or 2,2,2-trichloroethyl chloroformate, at 50° to 50° C. in a solvent (e.g., halogenated hydrocarbon, such as methylene chloride, chloroform or carbon tetrachloride, an ether, such as diethyl ether, dioxane or tetrahydrofuran, an aliphatic hydrocarbon such as hexane, an aromatic hydrocarbon, such as benzene or toluene, an ester, such as ethyl acetate, or a polar solvent, such as dimethyl sulfoxide, dimethylformamide or acetone) using a base (e.g., DBU, DBN, DMAP, DABCO, pyridine, triethylamine, aniline, N,N-dimethylaniline or N,N-diethylaniline); or in a solvent (e.g. acetone, tetrahydrofuran or dioxane) using an aqueous solution of a base (e.g. sodium hydroxide, potassium hydroxide, potassium carbonate, sodium carbonate and sodium hydrogen carbonate).

In Step C3 of Reaction Scheme C, the hydroxy group at the 4-position of the compound of formula (XVIII) is phosphorylated to prepare a compound of formula (XIX). This reaction is essentially the same as and may be carried out under the same conditions and using the same reagents as that described in Step A8.

In Step C4 of Reaction Scheme C, the protecting groups of the compound of formula (XIX) are eliminated to prepare a compound of formula (XX). In this Step, the elimination of the protecting groups $R^7$ and $R^{11}$ for the hydroxy groups can be carried out according to the procedures described in Step A7. If a hydroxy-protecting group is present on $R^{2a}$ and/or $R^{3a}$, elimination of these protecting groups and the protecting group $R^{12}$ for the phosphoric acid residue may be carried out according to the procedures described in Step A9. However, the elimination is preferably carried out by contriving conditions such that the protecting group $R^{12}$ for the phosphoric acid residue may be eliminated after any other protecting groups have first been eliminated.

Alternatively, n Step C5 of Reaction Scheme C, the protecting group for the hydroxy group at the 1-position of the compound of formula (XIX) is selectively eliminated, which may be effected according to the procedures described in Step A7, and then the hydroxy group at the 1-position of the resulting compound is phosphorylated according to the procedures described in Step A8. The hydroxy-protecting group $R^{11}$ and/or the hydroxy-protecting group if present on $R^{3a}$ and/or $R^{2a}$, and the protecting group $R^{12}$ for the phosphoric acid residue may then be eliminated to prepare the compound of formula (XXI), following the procedures described in Step A9.

In Step D1 of Reaction Scheme D, the protecting group $R^7$ for the hydroxy group at the 1-position of the compound of formula (XIX) is selectively eliminated to prepare a compound of formula (XXII). This reaction is essentially the same as and may be carried out under the same conditions and using the same reagents as the removal reactions described in Step A7 of Reaction Scheme A.

In Step D2 of Reaction Scheme D, the hydroxy group at the 1-position of the compound of formula (XXII) is replaced by a fluorine atom, using a fluorination reagent, to prepare a compound of formula (XXIII).

The reaction is preferably effected in the presence of a solvent. There is no particular restriction on the nature of the solvent to be employed, provided that it has no adverse effect on the reaction or on the reagents involved and that it dissolves the starting materials at least to some degree. Examples of suitable solvents include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, the dichloroethanes, chlorobenzene or the dichlorobenzenes; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; and ketones, such as acetone, methyl ethyl ketone, methyl isobutyl ketone, isophorone or cyclohexanone.

The nature of the fluorination reagent used here is not particularly critical and any reagent which may conventionally be used for the fluorination of alcohols may also be used in this reaction. Preferred examples include compounds of formula: $(R^{13})(R^{14})NSF_3$ [wherein $R^{-}$ and $R^{14}$ are the same or different and each represents a lower alkyl group, e.g. as exemplified above (preferably methyl or ethyl group), or represent together a lower alkylene group which may optionally be interrupted by an oxygen atom. Examples of the lower alkylene group include alkylenes group having from 1 to 6 carbon atoms, such as the methylene, methylmethylene, ethylene, propylene, trimethylene, tetramethylene, 1-methyltrimethylene, 2-methyltrimethylene, 3-methyltrimethylene, 3-pentamethylene and hexamethylene groups, preferably a tetramethylene or pentamethylene groups]. The dialkylaminosulfur trifluoride compounds are preferred.

The reaction can take place over a wide range of temperatures, and the precise reaction temperature is not critical to the invention. In general, we find it convenient to carry out the reaction at a temperature from −20° to 120° C., preferably from 0° C. to 100° C. The time required for the reaction may also vary widely, depending on many factors, notably the reaction temperature and the nature of the reagents. However, provided that the reaction is effected under the preferred conditions outlined above, a period of from 0.1 hour to 5 days will usually suffice.

In Step D3 of Reaction Scheme D, the protecting group $R^{11}$ for the hydroxy group at the 6-position of the compound of formula (XXIII) is eliminated to prepare a compound of formula (XXIV) and, if desired, the protecting group for the hydroxy group in the $R^{2a}$ group and/or $R^{3a}$ group is also eliminated. This Step is essentially the same as and may be carried out using the same reagents and reaction conditions as described in Step A7.

In Step D4 of Reaction Scheme D, the protecting group for the phosphoric acid residue of the compound of formula (XXIV) is eliminated, to prepare a compound of formula (XXV). This reaction is essentially the same as and may be carried out under the same conditions and using the same reagents as are described in Step A9 of Reaction Scheme A.

In Step E1 of Reaction Scheme E, the protecting group $R^{11}$ for the hydroxy group at the 6-position of the compound of formula (XIX) is selectively eliminated to prepare a compound of formula (XXVI). This reaction is essentially the same as and may be carried out under the same conditions and using the same reagents as the removal reactions described in Step A7 of Reaction Scheme A.

In Step E2 of Reaction Scheme E, the hydroxy group at the 6-position of the compound of formula (XXVI) is converted to a fluorine atom to prepare a compound of formula (XXVII). This reaction is essentially the same as and may be carried out under the same conditions and using the same reagents as the fluorination reaction described in Step D2 of Reaction Scheme D.

In Step E3 of Reaction Scheme E, the protecting group $R^7$ for the hydroxy group at the 1-position of the compound of formula (XXVII) is selectively eliminated to prepare a compound of formula (XXVIII). This Step is essentially the same as and may be carried out using the same reagents and reaction conditions as described in Step A7.

In Step E4 of Reaction Scheme E, the protecting group for the phosphoric acid residue of the compound of formula (XXVIII) is eliminated to prepare a compound of formula (XXIX). If desired, this may be followed by elimination of any hydroxy-protecting group in the group $R^{2a}$ and/or the group $R^{3a}$, e.g. by the procedures described in Step A9 of Reaction Scheme A.

BIOLOGICAL ACTIVITY

The compounds of the present invention have been found to have activity of the Lipid A type, without (it is presently believed) the adverse toxicity of Lipid A and associated natural products or compounds derived from those natural products. This activity is illustrated by the following test.

Assay of [$^{14}$C]-Prostaglandin D2 released in cultured cells

The cells employed were a macrophage-like mouse cell line J774.1. They were seeded at approximately $5\times10^5$ cells per well in 12-well dishes each containing 1 ml of a culture medium comprising Ham F-12 supplemented with 10% newborn calf serum.

The cells were then cultured at 37° C. overnight, after which they were labelled with $^{14}$C by incubation with [$^{14}$C]-arachidonic acid at 37° C. for 18 hours. At the end of this time, each well was washed three times, each time with 0.5 ml of the culture medium kept at 37° C. 10 μmole of one of the compounds under test were then added to each well, and the cells were incubated for a further 12 hours at 37° C. The culture media were then collected and centrifuged for 5 minutes at 10,000×G. The medium was acidified by the addition of 0.1N aqueous hydrochloric acid to a pH value of 3.0, and the prostaglandin D2 released into the medium was then extracted with a 2:1 by volume mixture of chloroform and methanol. The resulting mixture was analysed by thin layer chromatography (TLC) using as the developing solvent a mixture of chloroform, ethyl acetate, methanol, acetic acid and water in a ratio of 70:30:8:1:0.5 by volume. The radiolabelled prostaglandin D2 was located by autoradiography. The regions showing radioactivity were scraped from the TLC plates and the radioactivity was counted by a scintillation counter, thus giving a reliable measure of the amount of prostaglandin D2 produced. The amount of stimulation of prostaglandin D2 production by the test compound is a reliable measure of the Lipid A-like activity of the compound [see, for example, Zoeller et al., J. Biol. Chem., 262, No. 35, pp 17212–17220 (1987)].

Several compounds of the present invention were and these are identified in the following Table 4 by reference to the number of the following Example in which that compound was produced. In addition, the known compound GLA-60, recognised to be the most active compound of this type publicly known at present, was tested. The results, in terms of the number of counts per minute, are shown in the following Table 4.

TABLE 4

| Compound of Example No. | Prostaglandin D2 content (counts per minute) |
|---|---|
| 8 | 123 |
| 9 | 16 |
| 12 (2R isomer) | 185 |
| 12 (2S isomer) | 185 |
| 13 | 20 |
| 14 | 13 |
| 15 | 76 |
| 16 | 26 |
| GLA-60 | 104 |

As can be seen from the results given above, the best of the compounds of the present invention has an activity which is very significantly better than that of GLA-60, whilst all of the compounds of the present invention tested to date, all of which are shown above, exhibit, even at worst, a significant level of activity.

It is, therefore, expected that the compounds of the present invention will be useful in the treatment, prophylaxis, support and diagnosis of a variety of diseases and disorders, including those involving deficiencies in the immune system and tumorous conditions.

The compounds of the present invention may be administered to human or other patients by any suitable route and may, if desired, be formulated with conventional additives, excipients, diluents or other such agents to facilitate administration, absorption, transport to the site or activity or patient or physician acceptance, as is well known in the art. For example, they may be administered orally in the form of tablets, capsules, granules, powders or syrups; or parenterally in the form of an injection or a suppository. These pharmaceutical preparations can be prepared according to known methods using additives such as excipients, binders, disintegrators, lubricants, stabilizers or corrigents. The dose to be administered will depend on many factors, including the condition, age, and body weight of the patient, as well as the nature and severity of the disease or disorder to be treated. However, it would normally be expected to be administered in an amount of from 0.01 to 50 mg/kg per day for an adult human patient, and this may be administered in single or divided doses.

The invention is further illustrated by the following non-limiting Examples, which show the preparation of various of the compounds of the present invention.

EXAMPLE 1

2-Deoxy-2-|(3'R)-3'-hydroxytetradecanoylamino|-3-O-|(2"RS,3"SR)-2"-fluoro-3"-hydroxytetradecanoyl| -α-D-glucopyranosyl-1-phosphate 1(a) N-Trifluoroacetylglucosamine 160 g (0.742 mole) of D-(+)-glucosamine hydrochloride were dissolved in 2200 ml of methanol (99.6% purity), and 187.9 g (1.86 mole) of triethylamine were added to the resulting solution. 115.9 g of ethyl trifluoroacetate were then added dropwise to the resulting mixture, whilst ice-cooling, after which the mixture was stirred overnight at room temperature. At the end of this time, the mixture was concentrated by evaporation under reduced pressure, and then benzene (250 ml twice) and ethyl acetate (250 ml) were repeatedly added to the residue, which was then concentrated by evaporation under reduced pressure and then finally dried sufficiently in vacuo. The whole of the resulting crude trifluoroacetyl compound was used in the subsequent step (b) without purification.

1(b) Allyl 2-deoxy-2-trifluoroacetylamino-D-glucopyranoside 1850 ml of a 2% w/w solution of hydrochloric acid in allyl alcohol were added to the crude trifluoroacetyl compound obtained as described in Example 1(a) above, and the mixture was heated under reflux for 30 minutes. At the end of this time, the mixture was cooled to about 50° C. with ice-water and filtered through a Celite (trade mark) filter aid. The filtrate was concentrated by evaporation under reduced pressure and then sufficiently dried in vacuo. The whole of the resulting crude allyl ether compound was used in the subsequent step 1(c) without purification.

1(c) Allyl 2-deoxy-2-trifluoroacetylamino-4,6-O-isopropylidene-D-glucopyranoside The whole of the crude allyl ether compound obtained as described in Example 1(b) above was dissolved in 740 ml of dimethylformamide, and 370 ml of 2,2-dimethoxypropane were added to the resulting solution. 7.5 g of pyridinium β-toluenesulfonate were then added, and the mixture was stirred at room temperature overnight. At the end of this time, the mixture was concentrated by evaporation under reduced pressure and diluted with ethyl acetate. Precipitates were removed by filtration, and the filtrate was washed with a saturated aqueous solution of sodium hydrogen carbonate, with water and with a saturated aqueous solution of sodium chloride, in that order; it was then dried over anhydrous magnesium sulfate. The dried material was then filtered using a Celite filter aid and activated carbon; the filtrate was then concentrated by evaporation under reduced pressure. The residue was applied to a silica gel chromatography column to carry out separation and purification, using a 3:2 by volume mixture of cyclohexane and ethyl acetate as the eluent, to obtain 80.5 g of the title compound having an α-ether bond at the 1-position and 77.3 g of the title compound having an β-ether bond at the 1-position. Either the α-compound or the β-compound can be used in the subsequent reaction of step 1(d).

α-Allyl compound

Mass spectrum, m/z: 356 (M⁺+1), 340, 298, 282, 256, 240, 222, 211, 193, 168, 126, 109, 101.

β-Allyl compound

Mass spectrum, m/z: 356 (M⁺+1), 340, 298, 280, 240, 222, 211, 193, 168, 155, 145, 126, 114, 101.

1(d) Allyl 2-deoxy-2-amino-4,6-O-isopropylidene-β-D-glucopyranoside 10 g of the trifluoroacetyl compound obtained as described in Example 1(c) above were dissolved in 200 ml of ethanol (99.5% purity), and 100 ml of a 1N aqueous solution of sodium hydroxide were added to the resulting solution, after which the mixture was heated under reflux for 4 hours. At the end of this time, the mixture was concentrated by evaporation under reduced pressure and diluted with ethyl acetate. The ethyl acetate layer was washed with water and with a saturated aqueous solution of sodium chloride, after which it was dried over anhydrous magnesium sulfate. It was then filtered, and the ethyl acetate was removed by evaporation under reduced pressure. The oily residue was applied to a silica gel chromatography column and purified using ethyl acetate as the eluent, to obtain 6.6 g (yield 90.5%) of the title compound.

Nuclear Magnetic Resonance Spectrum (CDCl$_3$, 60 MHz) δ ppm:

1.43 (3H, singlet);

1.52 (3H, singlet);

2.40 (3H, broad);

2.6–4.6 (9H, multiplet); 5.05–6.35 (3H, multiplet).

Elemental analysis: Calculated for C$_{12}$H$_{21}$NO$_5$ (molecular weight 259.3): C, 55.58%; H, 8.16%; N, 5.40%. Found: C, 55.37%; H, 8.05%; N, 5.40%.

1(e) Allyl 2-deoxy-2-|(3'R)-3'-benzyloxytetradecanoylamino|-4,6-O-isopropylidene-β-D-glucopyranoside 5 g (19.3 mmole) of the compound obtained as described in Example 1(d) above were dissolved in 150 ml of methylene chloride, and then 6.8 g of (R)-3-benzyloxytetradecanoic acid, followed by 4.79 g of N,N'-dicyclohexylcarbodiimide, were added to the resulting solution; the mixture was then stirred at room temperature for one hour. At the end of this time, the mixture was filtered, and the filtrate was concentrated by evaporation under reduced pressure and diluted with ethyl acetate. The ethyl acetate layer was washed with a saturated aqueous solution of sodium hydrogen carbonate and with a saturated aqueous solution of sodium chloride, in that order, after which it was dried over anhydrous magnesium sulfate. It was then filtered and the ethyl acetate was removed by evaporation under reduced pressure. The residue was applied to a silica gel chromatography column and purified using a 1:1 by volume mixture of cyclohexane and ethyl acetate as the eluent, to obtain 5.33 g (yield 48%) of the title compound.

Infrared Absorption Spectrum (KBr) $v_{max}$ cm$^{-1}$: 3510, 3280, 1643, 1550.

Nuclear Magnetic Resonance Spectrum (CDCl$_3$, 270 MHz) δ ppm:

0.88 (3H, triplet, J=6.9 Hz);

1.20–1.41 (18H, multiplet);

1.45 (3H, singlet);

1.52 (3H, singlet);

1.56–1.70 (2H, multiplet);

2.43 (1H, doublet of doublets, J=6.9 & 15.4 Hz);

2.56 (1H, doublet of doublets, J=3.7 & 15.0 Hz);

3.19–3.29 (1H, multiplet);

3.46–3.63 (2H, multiplet);

3.75–3.94 (5H, multiplet);

4.18–4.24 (1H, multiplet);

4.36 (1H, doublet, J=2.6 Hz);

4.45–4.62 (3H, multiplet);

5.12–5.26 (2H, multiplet);

5.70–5.88 (1H, multiplet);

6.72 (1H, doublet, J=5.9 Hz);
7.30–7.37 (5H, multiplet).

1(f) Allyl 2-deoxy-2-[(3'R)-3'-benzyloxytetradecanoylamino]-3-O-[(2"RS, 3"SR)-2"-fluoro-3"-(benzyloxycarbonyloxy)tetradecanoyl]-4,6-O-isopropylidene-β-D-glucopyranoside 1 g (1.74 mmole) of the N-acyl compound obtained as described in 1(e) was dissolved in 80 ml of methylene chloride, and 828 mg of (±)-syn-2-fluoro-3-benzyloxycarbonyloxytetradecanoic acid were added to the resulting solution. 359 mg of N,N'-dicyclohexylcarbodiimide and 255 mg of 4-dimethylaminopyridine were then added, in that order, to the resulting mixture, after which the mixture was stirred at room temperature for one hour. At the end of this time, the mixture was filtered, concentrated by evaporation under reduced pressure and diluted with ethyl acetate. The ethyl acetate layer was washed with a saturated aqueous solution of sodium hydrogen carbonate and with a saturated aqueous solution of sodium chloride, in that order, and was then dried over anhydrous magnesium sulfate. It was then filtered, and the ethyl acetate was removed by evaporation under reduced pressure. The residue was subjected to silica gel column chromatography, using a 5:1 by volume mixture of cyclohexane and ethyl acetate as the eluent, to give 1.22 g (yield 73.6%) of the title compound.

Elemental analysis: Calculated for $C_{55}H_{84}FNO_{11} \cdot H_2O$ (molecular weight, 972.3): C, 67.94%; H, 8.96%; N, 1.44%; F, 1.95%. Found: C, 67.79%; H, 8.98%; N, 1.40%; F, 1.96%.

Infrared Absorption Spectrum (liquid film) $v_{max}$, $cm^{-1}$: 3290, 1750, 1655.

Nuclear Magnetic Resonance Spectrum (CDCl$_3$, 60 MHz) δ ppm:

0.66–2.43 (57H, multiplet);

3.12–6.53 {17H, multiplet [including 4.98 (2H, singlet)]};

7.28 (10H, singlet).

1(g) 2-Deoxy-2-[(3'R)-3'-benzyloxytetradecanoylamino]-3-O-[(2"RS, 3"SR)-2"-fluoro-3"-(benzyloxycarbonyloxy)tetradecanoyl]-4,6-O-isopropylidene-D-glucopyranose 380 mg of the compound obtained as described in Example 1(f) above were dissolved in 20 ml of dry tetrahydrofuran, and 17 mg (5% mole) of 1,5-cyclooctadiene-bis(methyldiphenylphosphine)iridium hexafluorophosphate were added to the resulting solution. The reaction vessel was then purged first with nitrogen and subsequently with hydrogen. As soon as the color of the liquid changed from red to colorless, the atmosphere in the reaction vessel was replaced by nitrogen. The mixture was then stirred at room temperature for 3 hours, after which 2 ml of water, 200 mg of iodine and 0.2 ml of pyridine were added, and the mixture was stirred at room temperature for a further 30 minutes. At the end of this time, the mixture was concentrated by evaporation under reduced pressure and diluted with ethyl acetate. The reaction mixture was then washed with a 5% w/v aqueous solution of sodium thiosulfate, with a saturated aqueous solution of sodium hydrogen carbonate and with a saturated aqueous solution of sodium chloride, in that order, after which the mixture was dried over anhydrous magnesium sulfate, filtered and concentrated by evaporation under reduced pressure. The resulting residue was subjected to silica gel column chromatography; using a 3:1 by volume mixture of cyclohexane and ethyl acetate as the eluent, to obtain 280 mg (yield 76.9%) of the title compound.

Nuclear Magnetic Resonance Spectrum (CDCl$_3$, 60 MHz) δ ppm:

0.53–2.78 (58H, multiplet);

3.48–5.43 {11H, multiplet [including 5.12 (2H, singlet)]};

6.25 (1H, doublet, J=8 Hz);

7.28–7.48 (10H, multiplet).

Elemental analysis: Calculated for $C_{52}H_{80}FNO_{11}$ (molecular weight, 914.2): C, 68.32%; H, 8.82%; N, 1.53%; F, 2.08%. Found: C, 68.17%; H, 8.99%; N, 1.56%; F, 2.13%.

1(h) 2-Deoxy-2-[(3'R)-3'-hydroxytetradecanoylamino]-3-O-[(2"RS, 3"SR)-2"-fluoro-3"-hydroxytetradecanoyl]-α-D-glucopyranosyl-1-phosphate 550 mg of the compound obtained as described in Example 1(g) above were dissolved in 20 ml of dry tetrahydrofuran, and 0.4 ml of butyllithium (as a 1.6M solution in hexane) was added slowly at −78° C. under a stream of nitrogen to the resulting solution. After 2 minutes, 5 ml of a dry tetrahydrofuran solution containing 231 mg of dibenzyl phosphorochloridate were added dropwise to the mixture. After a further 5 minutes, 1 g of 10% w/w palladium-on-carbon was added at the same temperature to effect hydrogenation. After 15 minutes, the mixture was allowed to return to room temperature from −78° C. and stirred for 3 hours. At the end of this time, it was filtered and the tetrahydrofuran was removed by evaporation under reduced pressure. The residue was subjected to silica gel column chromatography using a 5:1 by volume mixture of chloroform and methanol as the eluent, to give 98 mg (yield 22.3%) of the title compound.

FAB mass spectrum, m/z: 728 [M−H]⁻.

("FAB/MS" is "fast atom bombardment mass spectrum").

EXAMPLE 2

2-Deoxy-2-[(2'R,3'S)-2'-fluoro-3'-hydroxytetradecanoylamido]-3-O-[(3"R)-3"-hydroxytetradecanoyl]-α-D-glucopyranosyl-1-phosphate 2(a) Allyl 2-deoxy-2-[(2'R,3'S) and (2'S,3'R)-2'-fluoro-3'-(benzyloxycarbonyloxy)tetradecanoylamino]-4,6-O-isopropylidene-β-D-glucopyranoside 10 g (38.56 mmole) of allyl 2-deoxy-2-amino-4,6-O-isopropylidene-β-D-glucopyranoside [prepared as described in Example 1(d)] were dissolved in 200 ml of methylene chloride, and 16.06 g of (±)-syn-2-fluoro-3-(benzyloxycarbonyloxy)tetradecanoic acid were added to the resulting solution. 9.55 g of N,N'-dicyclohexylcarbodiimide were then added to the resulting mixture, after which it was stirred at room temperature for one hour. At the end of this time, the mixture was filtered, concentrated by evaporation under reduced pressure, and then diluted with ethyl acetate. The ethyl acetate layer was washed with a saturated aqueous solution of sodium hydrogen carbonate and with a saturated aqueous solution of sodium chloride, in that order, after which it was dried over anhydrous magnesium sulfate. It was then filtered, and the ethyl acetate was removed by evaporation under reduced pressure. The residue was purified through a silica gel chromatography column, using a 2:1 by volume mixture of cyclohexane and ethyl acetate as the eluent, to obtain 9.60 g (yield 39.0%) of the (2'R, 3'S) isomer of the desired N-acyl compound and 9.67 g (yield 39.3% of the (2'S, 3'R) isomer of the desired N-acyl compound.

(2'R, 3'S) compound

Nuclear Magnetic Resonance Spectrum (CDCl$_3$, 270 MHz) δ ppm:

0.88 (3H, triplet, J=6.9 Hz);

1.18–1.43 (18H, multiplet);

1.47 (3H, singlet);

1.53 (3H, singlet);
1.67–1.98 (2H, multiplet);
3.15–3.24 (1H, multiplet);
3.57–3.84 (5H, multiplet);
3.91 (1H, doublet of doublets, J=5.5 & 10.6 Hz);
4.02 (1H, doublet of doublets, J=6.2 & 12.8 Hz);
4.23–4.30 (1H, multiplet);
4.39 (1H, doublet, J=8.06 Hz);
4.94 (1H, doublet of doublets, J=2.2 & 47.6 Hz);
5.14–5.28 (5H, multiplet);
6.45 (1H, triplet, J=5.4 Hz);
7.34–7.41 (5H, multiplet).

Infrared Absorption Spectrum (CHCl$_3$) $v_{max}$ cm$^{-1}$: 1750, 1685, 1535.

Elemental analysis: Calculated for C$_{34}$H$_{52}$FNO$_9$ (molecular weight, 637.8): C, 64.03%; H, 8.22%; N, 2.20%; F, 2.98%. Found: C, 63.96%; H, 8.44%; N, 2.59%; F, 2.97%.

(2'S, 3'R) compound

Nuclear Magnetic Resonance Spectrum (CDCl$_3$, 270 MHz) δ ppm:

0. 88 (3H, triplet, J=6.9 Hz);
1.18–1.43 (18H multiplet);
1.45 (3H, singlet);
1.53 (3H, singlet);
1.54–2.01 (2H, multiplet);
3.30–3.36 (3H, multiplet);
3.55 (1H, triplet, J=9.5 Hz);
3.80 (1H, triplet, J=10.3 Hz);
3.93 (1H, doublet of doublets, J=5.5 & 11.0 Hz);
4.01–4.14 (2H, multiplet);
4.27 (1H, doublet of doublets, J=5.5 & 18.3 Hz);
4.87 (1H, doublet, J=8.4 Hz);
4.91 (1H, doublet of doublets, J=2.2 & 48.0 Hz);
5.09–5.3 (5H, multiplet);
5.78–5.93 (1H, multiplet);
6.60 (1H, triplet, J=5.1 Hz);
7.26–7.38 (5H, multiplet).

Elemental analysis: Calculated for C$_{34}$H$_{52}$FNO$_9$ (molecular weight, 637.8): C, 64.03%; H, 8.22%; N, 2.20%; F, 2.98%. Found: C, 63.84%; H, 8.33%; N, 2.76%; F, 3.02%.

Infrared Absorption Spectrum (CHCl$_3$) $v_{max}$ cm$^{-1}$: 1750, 1685, 1535.

2(b) Allyl 2-deoxy-2-[(2'R,3'S)-2'-fluoro-3'-(benzyloxycarbonyloxy)tetradecanoylamino]-3-O-[(3"R)-3"-benzyloxytetradecanoyl]-4,6-O-isopropylidene-β-D-glucopyranoside 3.5 g (5.49 mmole) of the (2'R, 3'S) compound obtained as described in Example 2(a) were dissolved in 150 ml of methylene chloride, and 1.93 g of (R)-3-benzyloxytetradecanoic acid was added to the resulting solution. 0.7 g of 4-dimethylaminopyridine and 1.36 g of N,N'-dicyclohexylcarbodiimide were then added to the resulting mixture, which was then stirred at room temperature for one hour. At the end of this time, the mixture was filtered, concentrated by evaporation under reduced pressure and diluted with ethyl acetate. The ethyl acetate layer was washed with a saturated aqueous solution of sodium hydrogen carbonate and with a saturated aqueous solution of sodium chloride, in that order, after which it was dried over anhydrous magnesium sulfate. It was then filtered, and the ethyl acetate was removed by evaporation under reduced pressure. The residue was purified by column chromatography through silica gel, using a 5:1 by volume mixture of cyclohexane and ethyl acetate as the eluent, to yield 3.54 g (67.6%) of the title compound.

Nuclear Magnetic Resonance Spectrum (CDCl$_3$, 270 MHz) δ ppm:

0.88 (6H, triplet, J=6.6 Hz);
1.25–1.73 (46H, multiplet);
2.42–2.61 (2H, multiplet);
3.35–3.42 (1H, multiplet);
3.56–4.08 (6H, multiplet);
4.21–4.28 (1H, multiplet);
4.40–4.98 (4H, multiplet);
5.07–5.36 (6H, multiplet);
5.72–5.86 (1H, multiplet);
6.44–6.48 (1H, multiplet);
7.14–7.35 (10H, multiplet).

Infrared Absorption Spectrum (CHCl$_3$) $v_{max}$ cm$^{-1}$: 1743, 1695, 1530.

2(c) 2-Deoxy-2-[(2'R,3'S)-2'-fluoro-3'-(benzyloxycarbonyloxy)tetradecanoylamino]-3-O-[(3"R)-3"-benzyloxytetradecanoyl]-4,6-O-isopropylidene-D-glucopyranose The whole of the compound prepared as described in Example 2(b) above was treated in the same manner as described in Example 1(g) to obtain 2.69 g (yield 79.3%) of the title compound.

Nuclear Magnetic Resonance Spectrum (CDCl$_3$, 270 MHz) δ ppm:

0.88 (6H, triplet, J=6.2 Hz);
1.23–1.73 (46H, multiplet);
2.42–2.54 (3H, multiplet);
3.60–4.02 (6H, multiplet);
4.42–5.27 (9H, multiplet);
7.16–7.46 (10H, multiplet).

Infrared Absorption Spectrum (CHCl$_3$) $v_{max}$ cm$^{-1}$: 1745, 1685, 1535.

2(d) 2-Deoxy-2-[(2'R,3'S)-2'-fluoro-3'-hydroxytetradecanoylamino]-3-O-[(3'R)-3'-hydroxytetradecanoyl]-α-D-glucopyranosyl-1-phosphate 914 mg of the compound obtained as described in Example 2(c) was treated in the same manner as described in Example 1(h) to obtain 91 mg (yield 11%) of the title compound.

FAB mass spectrum, m/z: 728 [M–H]$^-$.

EXAMPLE 3

2-Deoxy-2-[(2'S,3'R)-2'-fluoro-3'-hydroxytetradecanoylamido]-3-O-[(3"R)-3"-hydroxytetradecanoyl]-α-D-glucopyranosyl-1-phosphate 3(a) Allyl 2-deoxy-2-[(2'S,3'R)-2'-fluoro-3'-(benzyloxycarbonyloxy)tetradecanoylamino]-3-O-[(3"R)-3"-(benzyloxycarbonyloxy)tetradecanoyl]-4,6-O-isopropylidene-β-D-glucopyranoside 3.5 g of allyl 2-deoxy-2-[(2'S,3'R)-2'-fluoro-3'-(benzyloxycarbonyloxy)tetradecanoylamino]-4,6-O-isopropylidene-β-D-glucopyranoside [prepared as described in Example 2(a)] were reacted with 2.0 g of (R)-3-benzyloxycarbonyloxytetradecanoic acid, 0.7 g of 4-dimethylaminopyridine and 1.36 g of N,N'-dicyclohexylcarbodiimide in 150 ml of methylene chloride, in the same manner as described in Example 2(b), to obtain 2.7 g (yield 49.3%) of the title compound.

3(b) 2-Deoxy-2-[(2'S,3'R)-2'-fluoro-3'-(benzyloxycarbonyloxy)tetradecanoylamino]-3-O-[(3"R)-3"-(benzyloxycarbonyloxy)tetradecanoyl]-4,6-O-isopropylidene-D-glucopyranose The whole of the compound obtained as described in Example 3(a) was treated in the same manner as described in Example 1(g), to obtain 1.75 g (yield 67.5%) of the title compound.

Nuclear Magnetic Resonance Spectrum (CDCl₃, 60 MHz) δ ppm:

0.81–2.34 (52H, multiplet);

2.47–2.78 (2H, multiplet);

3.00 (1H, broad);

3.45–5.51 {14H, multiplet [including [5.12 (4H, singlet)]};

6.65 (1H, broad);

7.35 (10H, singlet).

Infrared Absorption Spectrum (CHCl₃) ν$_{max}$ cm⁻¹: 1745, 1670, 1545.

3(c) 2-Deoxy-2-[(2'S,3'R)-2'-fluoro-3'-hydroxytetradecanoylamido]-3-O-[(3"R)-3-hydroxytetradecanoyl)-α-D-glucopyranosyl-1-phosphate The whole of the compound obtained as described in Example 3(b) was treated in the same manner as in Example 1(h), to obtain 190 mg (yield 29.3%) of the title compound.

EXAMPLE 4

2-Deoxy-2-[(2'R,3'S)-2'-fluoro-3'-hydroxytetradecanoylamido]-3-O-[(3"R)-3"-hydroxytetradecanoyl]-α-D-glucopyranosyl-4-phosphate 4(a) Allyl 2-deoxy-2-[(2'R,3'S)-2'-fluoro-3'-(benzyloxycarbonyloxy)tetradecanoylamino]-3-O-[(3"R)-3"-(benzyloxycarbonyloxy)tetradecanoyl]-4,6-O-isopropylidene-β-D-glucopyranoside 5.1 g of allyl 2-deoxy-2-[(2'R, 3'S)-2'-fluoro-3'-(benzyloxycarbonyloxy)tetradecanoylamino]-4,6-O-isopropylidene-α-D-glucopyranoside [prepared as described in Example 2(a)] was reacted with 2.9 g of (R)-3-(benzyloxycarbonyloxy)tetradecanoic acid, 1.0 g of 4-dimethylaminopyridine and 2.0 g of N,N'-dicyclohexylcarbodiimide in 200 ml of methylene chloride, in the same manner as described in Example 3(a), to obtain 6.1 g (yield 77.9%) of the title compound.

Nuclear Magnetic Resonance Spectrum (CDCl₃, 60 MHz) δ ppm:

0.86–2.23 (52H, multiplet);

2.45–2.84 (2H, multiplet);

3.17–6.30 {19H, multiplet [including 5.12 (4H, singlet)]};

6.58 (1H, broad);

7.33 (10H, singlet).

Infrared Absorption Spectrum (KBr) ν$_{max}$ cm⁻¹: 1745, 1671, 1545.

4(b) Ally 2-deoxy-2-[(2'R,3'S)-2'-fluoro-3'-(benzyloxycarbonyloxy)tetradecanoylamino]-3-O-[(3"R)-3"-(benzyloxycarbonyloxy)tetradecanoyl]-β-D-glucopyranoside 5 g (5.24 mmole) of the compound obtained as described in Example 4(a) were suspended in 50 ml of 80% v/v aqueous acetic acid, and the suspension was stirred at 50° C. for 30 minutes. At the end of this time, the acid was removed by evaporation under reduced pressure. The residue was purified by chromatography through a silica gel column, using a 1:1 by volume mixture of cyclohexane and ethyl acetate as the eluent, to obtain 4.55 g (yield 94.8%) of the title compound.

Nuclear Magnetic Resonance Spectrum (CDCl₃, 270 MHz) δ ppm:

0.88 (6H, triplet, J=6.9 Hz);

1.08–1.84 (40H, multiplet);

2.47 (1H, doublet of doublets, J=8.1 & 15.0 Hz);

2.58 (1H, doublet of doublets, J=3.7 & 15.0 Hz);

3.26 (1H, broad);

3.40–3.45 (1H, multiplet);

3.61 (1H, triplet, J=9.2 Hz);

3.75–3.94 (3H, multiplet);

4.00–4.31 (2H, multiplet);

4.63 (1H, doublet, J=8.4 Hz);

4.82–5.28 (11H, multiplet);

5.75–5.88 (1H, multiplet);

6.00 (1H, doublet of doublets, J=4.4 & 8.4 Hz);

7.33–7.38 (10H, multiplet).

Elemental analysis: Calculated for C₅₃H₈₀FNO₁₃ (molecular weight, 958.2): C, 66.43%; H, 8.42%; N, 1.46%; F, 1.98%. Found: C, 66.48%; H, 8.72%; N, 1.60%; F, 1.96%.

Infrared Absorption Spectrum (CHCl₃) ν$_{max}$ cm⁻¹: 1745, 1695, 1535.

4(c) Allyl 2-deoxy-2-[(2'R,3'S)-2'-fluoro-3'-(benzyloxycarbonyloxy)tetradecanoylamino]-3-O-[(3"R)-3"-(benzyloxycarbonyloxy)tetradecanoyl]-6-O-benzyloxycarbonyl-β-D-glucopyranoside 4.3 g (4.5 mmole) of the compound obtained as described in Example 4(b) were dissolved in 100 ml of methylene chloride, and 822 mg of 4-dimethylaminopyridine were added to the resulting solution. 916 mg of benzyl chloroformate were then added dropwise, and the mixture was stirred at room temperature for one hour. At the end of this time, the mixture was concentrated by evaporation under reduced pressure and diluted with ethyl acetate. The ethyl acetate layer was washed with a saturated aqueous solution of sodium hydrogen carbonate and with a saturated aqueous solution of sodium chloride, in that order, after which it was dried over anhydrous magnesium sulfate. It was then filtered, and the ethyl acetate was removed by evaporation under reduced pressure. The residue was purified by chromatography through a silica gel column, using a 5:1 by volume mixture of cyclohexane and ethyl acetate as the eluent, to obtain 2.43 g (yield 49.6%) of the title compound.

Nuclear Magnetic Resonance Spectrum (CDCl₃, 60 MHz) δ ppm:

0.64–1.89 (46H, multiplet);

2.37–2.64 (2H, multiplet);

3.09–6.20 {22H, multiplet [including 5.09 (4H, singlet), 5.13 (2H, singlet)]};

6.49 (1H, broad);

7.32 (15H, singlet).

Infrared Absorption Spectrum (CHCl₃) ν$_{max}$ cm⁻¹: 1745, 1695, 1533.

4(d) Allyl 2-deoxy-2-[(2'R,3'S)-2'-fluoro-3'-(benzyloxycarbonyloxy)tetradecanoylamino]-3-O-[(3"R)-3"-(benzyloxycarbonyloxy)tetradecanoyl]-4-O-diphenylphosphoryl-6-O-benzyloxycarbonyl-β-D-glucopyranoside 2.2 g (2.01 mmole) of the compound obtained as described in Example 4(c) were dissolved in 30 ml of methylene chloride, and 1.47 g of 4-dimethylaminopyridine was then added to the resulting solution. 1.62 g of diphenyl chlorophosphate was then added dropwise, after which the mixture was stirred at room temperature for one hour. At the end of this time, the mixture was concentrated by evaporation under reduced pressure and diluted with ethyl acetate. The ethyl acetate layer was washed with a saturated aqueous solution of sodium hydrogen carbonate and with a saturated aqueous solution of sodium chloride, in that order, after which it was dried over anhydrous magnesium sulfate. It was then filtered, and the ethyl acetate was removed by evaporation under reduced pressure. The residue was purified by chromatography through a silica gel column, using a 3:1 by volume mixture of cyclohexane and ethyl acetate as the eluent, to obtain 2.65 g (yield 99.3%) of the title compound.

Nuclear Magnetic Resonance Spectrum (CDCl$_3$, 60 MHz) δ ppm:

0.64–2.05 (46H, multiplet);

2.25–2.51 (2H, multiplet);

3.00–6.15 {21H, multiplet [including 5.08 (6H, singlet)]};

6.63 (1H, broad);

7.18–7.33 (25H, 2multiple).

Infrared Absorption Spectrum (CHCl$_3$) $v_{max}$ cm$^{-1}$: 1747, 1690, 1590, 1530.

4(e) 2-Deoxy-2-[(2'R,3'S)-2'-fluoro-3'-(benzyloxycarbonyloxy)tetradecanoylamino]-3-O-[(3"R)-3"-benzyloxycarbonyloxy)tetradecanoyl]-4-O-diphenylphosphoryl-6-O-benzyloxycarbonyl-D-glucopyranose 2.50 g of the compound obtained as described in Example 4(d) was treated in the same manner as described in Example 1(g) to obtain 1.68 g (yield 69.3%) of the title compound.

Nuclear Magnetic Resonance Spectrum (CDCl$_3$, 270 MHz) δ ppm:

0.88 (6H, triplet, J=6.2 Hz);

1.13–1.71 (40H, multiplet);

2.37 (1H, doublet of doublets, J=7.33 & 17.22 Hz);

2.55 (1H, doublet of doublets, J=5.13 & 17.22 Hz);

3.61 (1H, broad);

3.83–3.90 (1H, multiplet);

4.16–4.37 (3H, multiplet);

4.64–4.81 (2H, multiplet);

4.96–5.28 (9H, multiplet);

5.56 (1H, doublet of doublets, J=9.2 & 11.0 Hz);

6.84 (1H, doublet of doublets, J=3.3 & 7.7 Hz);

7.09–7.37 (25H, multiplet).

Infrared Absorption Spectrum (CHCl$_3$) $v_{max}$ cm$^{-1}$: 1743, 1685, 1590.

4(f) 2-Deoxy-2-[(2'R,3'S)-2'-fluoro-3'-hydroxytetradecanoylamino)-3-O-[(3"R)-3"-hydroxytetradecanoyl]-D-glucopyranosyl-4-phosphate 3 g (1.01 mmole) of the compound obtained as described in Example 4(e) was dissolved in 30 ml of tetrahydrofuran, and 1 g of 10% w/w palladium-on-carbon was added to the resulting solution. Catalytic reduction was then allowed to take place in an atmosphere of hydrogen at room temperature for 3 hours. At the end of this time, the reaction mixture was filtered, and 200 mg of platinum oxide were added to the filtrate to carry out further catalytic reduction at room temperature for 2 hours. The reaction mixture was then filtered, and the tetrahydrofuran was removed by evaporation under reduced pressure. The residue was purified by chromatography through a silica gel column, using first a 9:1 by volume mixture of chloroform and methanol and then a 5:1 by volume mixture of chloroform and methanol as the eluents, to obtain 490 mg (yield 66.3%) of the title compound.

Infrared Absorption Spectrum (KBr) $v_{max}$ cm$^{-1}$: 1710, 1660.

FAB mass spectrum, m/z: 728 |M–H|$^-$.

EXAMPLE 5

2-Deoxy-2-[(2'S,3'R)-2'-fluoro-3'-hydroxytetradecanoylamino|-3-O-|(3"R)-3"-hydroxytetradecanoyl]-D-glucopyranosyl-4-phosphate 5(a) Allyl 2-deoxy-2-[(2'S,3'R)-2'-fluoro-3'-(benzyloxycarbonyloxy)tetradecanoylamino]-3-O-[(3"R)-3"-benzyloxytetradecanoyl]-4,6-O-isopropylidene-β-D-glucopyranoside 4.5 g (7.06 mmole) of allyl 2-deoxy-2-[(2'S, 3'R)-2-fluoro-3'-(benzyloxycarbonyloxy)tetradecanoylamino|-4,6-O-isopropylidene-β-D-glucopyranoside [prepared as described in Example 2(a)] were dissolved in 100 ml of tetrahydrofuran, and 857 ml of triethylamine were added to the resulting solution. 2.86 g of 3-benzyloxytetradecanoyl chloride were then added dropwise to the resulting mixture, and the mixture was stirred at room temperature for one hour. At the end of this time, the mixture was concentrated by evaporation under reduced pressure, after which it was diluted with ethyl acetate. The ethyl acetate layer was then washed with a saturated aqueous solution of sodium hydrogen carbonate and with a saturated aqueous solution of sodium chloride, in that order, and was then dried over anhydrous magnesium sulfate. It was then filtered, and the ethyl acetate was removed by evaporation under reduced pressure. The residue was purified by chromatography through a silica gel column, using a 5:1 by volume mixture of cyclohexane and ethyl acetate as the eluent, to obtain 5.1 g (yield 75.7%) of the title compound.

Nuclear Magnetic Resonance Spectrum (CDCl$_3$, 60 MHz) δ ppm:

0.65–2.08 {52H, multiplet [including 1.43 (3H, singlet)]};

2.43–2.72 (2H, multiplet);

3.05–6.21 {19H, multiplet [including 4.48 (2H, singlet), 5.12 (2H, singlet)]};

6.31–6.67 (1H, multiplet);

7.28 (5H, singlet);

7.30 (5H, singlet).

Infrared Absorption Spectrum (KBr) $v_{max}$ cm$^{-1}$: 1745, 1670, 1545, 1268, 1089.

5(b) Allyl 2-deoxy-2-[(2'S,3'R)-2'-fluoro-3'-(benzyloxycarbonyloxy)tetradecanoylamino]-3-O-[(3"R)-3"-benzyloxytetradecanoyl]-β-D-glucopyranoside 4.50 g of the compound obtained as described in Example 5(a) was treated in the same manner as described in Example 4(b) to obtain 4.14 g (yield 96%) of the title compound.

Nuclear Magnetic Resonance Spectrum (CDCl$_3$, 60 MHz) δ ppm:

0.62–2.18 (46H, multiplet);

2.32–2.91 (4H, multiplet);

3.20–4.25 (8H, multiplet);

4.28–4.71 {3H, multiplet [including 4.48 (2H, singlet)]};

4.86–6.19 (8H, multiplet);

6.45–6.85 (1H, multiplet);

7.28 (5H, singlet);

7.31 (5H, singlet).

Infrared Absorption Spectrum (KBr) $v_{max}$ cm$^{-1}$: 1742, 1669, 1578, 1271.

5(c) Allyl 2-deoxy-2-|(2'S,3'R)-2'-fluoro-3'-(benzyloxycarbonyloxy)tetradecanoylamino|-3-O-|(3"R)-3"-benzyloxytetradecanoyl|-6-O-benzyloxycarbonyl-β-D-glucopyranoside 3.80 g of the compound obtained as described in Example 5(b) was treated in the same manner as described in Example 4(c) to obtain 2.85 g (yield 65.4%) of the title compound.

Nuclear Magnetic Resonance Spectrum (CDCl$_3$, 60 Hz) δ ppm:

0.85–2.08 (46H, multiplet);

2.41–2.64 (2H, multiplet);

3.00 (1H, broad);

3.48–6.08 {21H, multiplet |including 4.45 (2H, singlet), 5.15 (4H, singlet)|};

6.18–6.72 (1H, multiplet);

7.26–7.56 (15H, multiplet).

Infrared Absorption Spectrum (KBr) $v_{max}$ cm$^{-1}$: 1750, 1727, 1676, 1548.

5(d) Allyl 2-deoxy-2-[(2'S,3'R)-2'-fluoro-3'-benzyloxycarbonyloxytetradecanoylamino]-3-O-|(3"R)-3"-benzyloxytetradecanoyl)-4-O-diphenylphosphoryl-6-O-benzyloxycarbonyl-β-D-glucopyranoside 2.60 g of the compound obtained as described in Example 5(c) was treated in the same manner as described in Example 4(d) to obtain 3.16 g (yield 99.5%) of the title compound.

Nuclear Magnetic Resonance Spectrum (CDCl$_3$, 60 MHz) δ ppm:

0.72–1.87 (46H, multiplet);

2.26–2.49 (2H, multiplet);

3.45–6.05 {21H, multiplet [including 4.30 (2H, singlet), 5.05 (4H, singlet)|};

6.18–6.50 (1H, multiplet);

6.89–7.49 (25H, multiplet).

Infrared Absorption Spectrum (KBr) $v_{max}$ cm$^{-1}$: 1743, 1679, 1541, 1494.

5(e) 2-Deoxy-2-[(2'S,3'R)-2'-fluoro-3'-(benzyloxycarbonyloxy)tetradecanoylamino]-3-O-[(3"R)-3"-benzyloxytetradecanoyl -4-O-diphenylphosphoryl-6-O-benzyloxycarbonyl-D-glucopyranose 2.80 g of the compound obtained as described in Example 5(d) was treated in the same manner as described in Example 1(g) to obtain 1.8 g (yield 66.4%) of the title compound.

Nuclear Magnetic Resonance Spectrum (CDCl$_3$, 60 MHz) δ ppm:

0.66–2.01 (46H, multiplet);

2.16–2.56 (2H, multiplet);

2.89 (1H, doublet, J=5 Hz);

3.38–5.71 {16H, multiplet [including 4.32 (2H, singlet), 5.10 (4H, singlet)|};

6.45–6.81 (1H, multiplet);

7.08–7.45 (25H, multiplet).

Infrared Absorption Spectrum (KBr) $v_{max}$ cm$^{-1}$: 1747, 1685, 1590.

5(f) 2-Deoxy-2-[(2'S, 3'R)-2'-fluoro-3'-hydroxytetradecanoylamino]-3-O-[(3"R)-3"-hydroxytetradecanoyl]-4-O-diphenylphosphoryl-D-glucopyranose 880 mg (0.6 mmole) of the compound obtained as described in Example 5(e) were dissolved in 30 ml of tetrahydrofuran, and 1 g of 10% w/w palladium-on-carbon was added to the resulting solution. Catalytic reduction was then allowed to take place at room temperature for 2 hours under an atmosphere of hydrogen, after which the mixture was filtered. The tetrahydrofuran was removed from the filtrate by evaporation under reduced pressure. The residue was purified by chromatography through a silica gel column, using ethyl acetate as the eluent, to obtain 340 mg (yield 56.2%) of the title compound.

Elemental analysis: Calculated for C$_{46}$H$_{73}$FNO$_{12}$P (molecular weight, 882.1): C, 62.64%; H, 8.34%; N, 1.59%; F, 2.15%; P, 3.51%. Found: C, 62.89%; H, 8.24%; N, 1.47%; F, 2.15%; P, 3.41%.

5(g) 2-Deoxy-2-|(2'S,3'R)-2'-fluoro-3'-hydroxytetradecanoylamino]-3-O-|(3"R)-3"-hydroxytetradecanoyl]-D-glucopyranosyl-4-phosphate 490 mg (0.56 mmole) of the compound obtained as described in Example 5(f) were dissolved in 30 ml of tetrahydrofuran, and 80 g of platinum oxide were added to the resulting solution; catalytic reduction was then allowed to take place at room temperature for 3 hours, under an atmosphere of hydrogen. The reaction mixture was then filtered, and the tetrahydrofuran was removed by evaporation under reduced pressure to obtain 380 mg (yield 93.7%) of the title compound.

Elemental analysis: Calculated for C$_{34}$H$_{65}$FNO$_{12}$P (molecular weight, 729.9): C, 55.95%; H, 8.98%; N, 1.92%; F, 2.60%; P, 4.24%. Found: C, 55.84%; H, 9.22%; N, 1.94%; F, 2.51%; P, 4.09%.

FAB mass spectrum, m/z: 728[M–H]⁻502.

EXAMPLE 6

2-Deoxy-2-[(2'R,3'S)-2'-fluoro-3'-tetradecanoyloxytetradecanoylamino]-3-O-tetradecanoyl-D-glucopyranosyl-4-phosphate 6(a) Allyl 2-deoxy-2-[(2'R,3'S) and (2'S,3'R)-2'-fluoro-3'-(tetradecanoyloxy)tetradecanoylamino)-4,6-O-isopropylidene-β-D-glucopyranoside 5.18 g (20 mmole) of allyl 2-deoxy-2-amino-4,6-O-isopropylidene-β-D-glucopyranoside 5.18 g (20 mmole) of allyl 2-deoxy-2-amino-4,6-O-isopropylidene-β-D-glucopyranoside [prepared as described in Example 1(d)] were dissolved in 150 ml of methylene chloride, and 9.93 g of (±)-syn-2-fluoro-3-(tetradecanoyloxy)tetradecanoic acid were added to the resulting solution. 4.95 g of N,N'-dicyclohexylcarbodiimide were then added to the resulting mixture, and the mixture was stirred at room temperature for 1 hour. At the end of this time, the mixture was filtered, concentrated by evaporation under reduced pressure, and diluted with ethyl acetate. The ethyl acetate layer was washed with a saturated aqueous solution of sodium hydrogen carbonate and with a saturated aqueous solution of sodium chloride, in that order, and was then dried over anhydrous magnesium sulfate. The ethyl acetate was then removed by evaporation under reduced pressure, and the resulting residue was purified by chromatography through a silica gel column, using a 3:1 by volume mixture of cyclohexane and ethyl acetate as the eluent, to obtain first 5.65 g (yield 39.6%) of the (2'R, 3'S) isomer of the title compound and then 5.55 g (yield 38.9%) of the (2'S, 3'R) isomer of the title compound.

(3'R, 3'S) Compound

Nuclear Magnetic Resonance Spectrum (CDCl$_3$, 270 MHz) δ ppm:

0.88 (6H, triplet, J=6.9 Hz);

1.20–1.38 (38H, multiplet);

1.44 (3H, singlet);

1.52 (3H, singlet);

1.60–1.84 (5H, multiplet);

2.30 (2H, triplet);

3.23–3.33 (1H, multiplet);

3.58–3.85 (4H, multiplet);

3.93 (1H, doublet of doublets, J=5.5 & 10.6 Hz);

4.07 (1H, doublet of doublets, J=6.2 & 12.8 Hz);

4.30–4.37 (1H, multiplet);

4.76 (1H, doublet, J=7.7 Hz);

4.93 (1H, doublet of doublets, J=2.9 & 48.0 Hz);

5.20–5.36 (3H, multiplet);

5.79–5.94 (1H, multiplet);

6.44 (1H, triplet, J=5.5 Hz).

Infrared Absorption Spectrum (CHCl$_3$) $v_{max}$ cm$^{-1}$: 1735, 1680, 1535.

(2'S, 3'R) Compound

Nuclear Magnetic Resonance Spectrum (CDCl$_3$, 270 MHz) δ ppm:

0.88 (6H, triplet, J=6.9 Hz);

1.20–1.38 (38H, multiplet);

1.45 (3H, singlet);

1.52 (3H, singlet);

1.56–1.76 (5H, multiplet);

2.29 (2H, triplet);

3.30–3.41 (2H, multiplet);

3.57 (1H, triplet, J=9.2 Hz);

3.80 (1H, triplet, J=10.6 Hz);

3.93 (1H, doublet of doublets, J=5.5 & 11.0 Hz);

4.05–4.16 (2H, multiplet);

4.29–4.36 (1H, multiplet);

4.7 (1H, doublet, J=8.1 Hz);

4.89 (1H, doublet of doublets, J=2.2 & 48.0 Hz);

5.20–5.34 (3H, multiplet);

5.80–5.89 (1H, multiplet);

6.52 (1H, triplet, J=5.5 Hz).

Infrared Absorption Spectrum (CHCl$_3$) $v_{max}$ cm$^{-1}$: 1735, 1680, 1535.

6(b) Allyl 2-deoxy-2-[(2'R,3'S)-2'-fluoro-3'-(tetradecanoyloxy)tetradecanoylamino]-3-O-tetradecanoyl-4,6-O-isopropylidene-β-D-glucopyranoside 2 g (2.8 mmole) of the (2'R, 3'S) compound obtained as described in Example 6(a) were dissolved in 30 ml of methylene chloride, and 728 mg of tetradecanoyl chloride were added to the resulting solution. 313 mg of triethylamine were then added to the resulting mixture, and the mixture was stirred at room temperature for 1 hour. At the end of this time, the mixture was concentrated by evaporation under reduced pressure, and diluted with ethyl acetate. It was then washed with a saturated aqueous solution of sodium hydrogen carbonate and with a saturated aqueous solution of sodium chloride, in that order. The mixture was then dried over anhydrous magnesium sulfate, after which it was filtered, and the ethyl acetate was removed by evaporation under reduced pressure. The residue was purified by chromatography through a silica gel column, using a 5:1 by volume mixture of cyclohexane and ethyl acetate as the eluent, to obtain 1.35 g (52.1%) of the title compound.

Nuclear Magnetic Resonance Spectrum (CDCl$_3$, 270 MHz) δ ppm:

0.88 (9H, triplet, J=6.6 Hz);

1.13–1.67 {70H, multiplet [including 1.36 (3H, singlet), 1.46 (3H, singlet)]};

2.25–2.35 (4H, multiplet);

3.32–3.41 (1H, multiplet);

3.66–3.85 (3H, multiplet);

3.95 (1H, doublet of doublets, J=5.5 & 10.6 Hz);

4.05 (1H, doublet of doublets, J=6.2 & 12.8 Hz);

4.26–4.34 (1H, multiplet);

4.74–4.93 (2H, multiplet);

5.16–5.29 (4H, multiplet);

5.75–5.89 (1H, multiplet);

6.34 (1H, doublet of doublets, J=4.4 & 8.8 Hz).

Elemental analysis: Calculated for C$_{54}$H$_{98}$FNO$_9$ (molecular weight, 924.4): C, 70.17%; H, 10.69%; N, 1.52%; F, 2.06%. Found: C, 70.41%; H, 10.58%; N, 1.47%; F, 1.99%.

Infrared Absorption Spectrum (CHCl$_3$) $v_{max}$ cm$^{-1}$: 1740, 1695.

Mass spectrum, m/z: 924 (M$^+$+1), 909, 883, 867, 737, 724, 655, 638, 610, 526, 513, 452.

6(c) Allyl 2-deoxy-2-[(2'R,3'S)-2'-fluoro-3'-tetradecanoyloxytetradecanoylamino]-3-O-tetradecanoyl-β-D-glucopyranoside 2.6 g of the compound obtained as described in Example 6(b) was treated in the same manner as described in Example 4(b) to obtain 2 g (yield 80.4%) of the title compound.

Nuclear Magnetic Resonance Spectrum. (CDCl$_3$, 60 MHz) δ ppm:

0.66–1.91 (74H, multiplet);

2.09–2.55 (4H, multiplet);

2.87–6.16 (15H, multiplet);

6.54 (1H, multiplet).

Infrared Absorption Spectrum (KBr) $v_{max}$ cm$^{-1}$: 1739, 1668, 1553, 1458, 1175.

6(d) Allyl 2-deoxy-2-[(2'R,3'S)-2'-fluoro-3'-tetradecanoyloxytetradecanoylamino]-3-O-tetradecanoyl-6-O-benzyloxycarbonyl-β-D-glucopyranoside 1.9 g (2.15 mmole) of the compound obtained as described in Example 6(c) was dissolved in 20 ml of methylene chloride, and 550 mg of benzyl chloroformate were added to the resulting solution. 327 mg of triethylamine were then added to the resulting mixture, and the mixture was stirred at room temperature for 5 hours. At the end of this time, the mixture was concentrated by evaporation under reduced pressure, and diluted with ethyl acetate. The ethyl acetate layer was washed with a saturated aqueous solution of sodium hydrogen carbonate and with a saturated aqueous solution of sodium chloride, in that order, after which it was dried over anhydrous magnesium sulfate. It was then filtered, and the ethyl acetate was removed by evaporation under reduced pressure. The residue was purified by chromatography through a silica gel column, using a 3:1 by volume mixture of cyclohexane and ethyl acetate as the eluent, to obtain 660 mg (yield 30.2%) of the title compound.

Nuclear Magnetic Resonance Spectrum (CDCl$_3$, 270 MHz) δ ppm:

0.88 9H, triplet, J=6.9 Hz);

1.25–1.65 (66H, multiplet);

2.25–2.36 (4H, multiplet);

2.82 (1H, singlet);

3.59–3.66 (2H, multiplet);

4.03 (1H, doublet of doublets, J=6.2 & 12.8 Hz);

4.27 (1H, doublet of doublets, J=5.1 & 12.8 Hz);

4.42–4.52 (1H, multiplet);

4.81 (1H, doublet of doublets, J=3.7 & 47.6 Hz);

4.84 (1H, doublet, J=8.1 Hz);

5.14–5.27 (6H, multiplet);

5.76–5.89 (1H, multiplet);

6.37 (1H, doublet of doublets, J=4.4 & 8.1 Hz);

7.34–7.40 (50H, multiplet).

Infrared Absorption Spectrum (KBr) $v_{max}$ cm$^{-1}$: 1737, 1673, 1550, 1285.

6(e) Allyl 2-deoxy-2-[(2'R,3'S)-2'-fluoro-3'-tetradecanoyloxytetradecanoylamino]-3-O-tetradecanoyl-4-O-diphenylphosphoryl-6-O-benzyloxycarbonyl-β-D-glucopyranoside 600 mg (0.589 mmole) of the compound obtained as described in Example 6(d) were dissolved in 20 ml of methylene chloride, and 474.8 mg of diphenyl chlorophosphate were added to the resulting solution. 62.6 mg of triethylamine were then added to the resulting mixture, and the mixture was stirred at room temperature overnight. At the end of this time, the mixture was concentrated by evaporation under reduced pressure and the residue was diluted with ethyl acetate. The ethyl acetate layer was washed with a saturated aqueous solution of sodium hydrogen carbonate and with a saturated aqueous solution of sodium chloride, in that order, after which it was dried over anhydrous magnesium sulfate. It was then filtered, and the ethyl acetate was removed by evaporation under reduced pressure. The resulting residue was purified by chromatography through a silica gel column, using a 5:1 by volume mixture of cyclohexane and ethyl acetate as the eluent, to obtain 600 mg (yield 81.4%) of the title compound.

Nuclear Magnetic Resonance Spectrum (CDCl$_3$, 270 MHz) δ ppm:

0.88 (9H, triplet, J=6.9 Hz);

1.05–1.73 (64H, multiplet);

2.11–2.3 (4H, multiplet);

3.46–3.56 (1H, multiplet);

3.77–3.82 (1H, multiplet);

4.03 (1H, doublet of doublets, J=6.2 & 12.8 Hz);

4.19–4.38 (3H, multiplet);

4.63–4.89 (2H, multiplet);

5.01–5.26 (6H, multiplet);

5.64–5.87 (2H, multiplet);

6.37 (1H, doublet of doublets, J=4.4 & 7.7 Hz);

7.11–7.34 (15H, multiplet).

Elemental analysis: Calculated for $C_{71}H_{109}FNO_{14}P$ (molecular weight, 1250.6): C, 68.19%; H, 8.79%; N, 1.12%, F, 1.52%, P, 2.48%. Found: C, 67.97%; H, 8.56%; N, 1.21%; F, 1.47%; P, 2.47%.

Infrared Absorption Spectrum (CHCl$_3$) $v_{max}$ cm$^{-1}$: 1743, 1690.

6(f) 2-Deoxy-2-[(2'R,3'S)-2'-fluoro-3'-tetradecanoyloxytetradecanoylamino]-3-O-tetradecanoyl-4-O-diphenylphosphoryl-6-O-benzyloxycarbonyl-D-glucopyranose 600 mg of the compound obtained as described in Example 6(e) was treated in the same manner as described in Example 1(g) to obtain 490 mg (yield 84.3%) of the title compound.

Nuclear Magnetic Resonance Spectrum (CDCl$_3$, 270 MHz) δ ppm:

0.88 (9H, triplet; J=7.0 Hz);

1.11–1.66 (64H, multiplet);

2.11–2.29 (4H, multiplet);

3.36 (1H, singlet);

4.13–4.39 (4H, multiplet);

4.71–5.56 (7H, multiplet);

6.70 (1H, doublet of doublets, J=3.3 & 8.1 Hz);

7.11–7.35 (15H, multiplet).

Infrared Absorption Spectrum (CHCl$_3$) $v_{max}$ cm$^{-1}$: 1751, 1711, 1658.

6(g) 2-Deoxy-2-[(2'R,3'S)-2'-fluoro-3'-tetradecanoyloxytetradecanoylamino]-3-O-tetradecanoyl-4-O-diphenylphosphoryl-D-glucopyranose 490 mg of the compound obtained as described in Example 6(f) was treated in the same manner as described in Example 5(f) to obtain 270 mg (yield 75.9%) of the title compound.

Elemental analysis: Calculated for $C_{60}H_{99}FNO_{12}P$ (molecular weight, 1076.4): C, 66.95%; H, 9.27%; N, 1.30%; F, 1.76%; P, 2.88%. Found: C, 67.23%; H, 9.27%; N, 1.35%; F, 1.91%; P, 2.81%.

Infrared Absorption Spectrum (CHCl$_3$) $v_{max}$ cm$^{-1}$: 1735, 1685.

6(h) 2-Deoxy-2-[(2'R,3'S)-2'-fluoro-3'-tetradecanoyloxytetradecanoylamino]-3-O-tetradecanoyl-D-glucopyranosyl-4-phosphate 230 mg of the compound obtained as described in Example 6(g) was treated in the same manner as described in Example 5(g) to obtain 190 mg (yield 96.2%) of the title compound.

FAB mass spectrum m/z: 922 (M–H)$^-$.

EXAMPLE 7

2-Deoxy-2-[(2'S,3'R)-2'-fluoro-3'-tetradecanoyloxytetradecanoylamino]-3-O-tetradecanoyl-D-glucopyranosyl-4-phosphate 7(a) Allyl 2-deoxy-2-[(2'S,3'R)-2'-fluoro-3'-tetradecanoyloxytetradecanoylamino]-3-O-tetradecanoyl-4,6-O-isopropylidene-β-D-glucopyranoside 2.9 g (4.06 mmole) of allyl 2-deoxy-2-[(2'S, 3'R)-2'-fluoro-3'-(tetradecanoyloxy)tetradecanoylamino]-4,6-O-isopropylidene-β-D-glucopyranoside [prepared as described in Example 6(a)] were dissolved in 30 ml of methylene chloride, and 1.02 g of tetradecanoic acid was added to the resulting solution. 1 g of N,N'-dicyclohexylcarbodiimide was then added to the resulting mixture, and the mixture was stirred at room temperature for one hour. However, since the reaction did not proceed, 50 mg of 4-dimethylaminopyridine was then added, and the mixture was stirred at room temperature for a further 1 hour. At the end of this time, the mixture was concentrated by evaporation reduced pressure and diluted with ethyl acetate. The ethyl acetate layer was washed with a saturated aqueous solution of sodium hydrogen carbonate and with a saturated aqueous solution of sodium chloride, in that order, after which it was dried over anhydrous magnesium sulfate. It was then filtered, and the ethyl acetate was removed by evaporation under reduced pressure. The residue was purified by chromatography through a silica gel column, using a 5:1 by volume mixture of cyclohexane and ethyl acetate as the eluent, to obtain 3.8 g of the title compound quantitatively.

Nuclear Magnetic Resonance Spectrum (CDCl$_3$, 60 MHz) δ ppm:

0.66–2.01 (79H, multiplet);

2.05–2.61 (4H, multiplet);

3.30–6.23 (14H, multiplet);

6.85 (1H, multiplet).

Infrared Absorption Spectrum (KBr) $v_{max}$ cm$^{-1}$: 1741, 1666, 1544, 1468.

7(b) Allyl 2-deoxy-2-|(2'S,3'R)-2'-fluoro-3'-tetradecanoyloxytetradecanoylamino|-3-O-tetradecanoyl-β-D-glucopyranoside 3.8 g of the compound obtained as described in Example 7(a) was treated in the same manner as described in Example 4(b) to obtain 3.08 g (yield 84.7%) of the title compound.

Infrared Absorption Spectrum (KBr) $v_{max}$ cm$^{-1}$: 1736, 1671, 1553, 1467.

7(c) Allyl 2-deoxy-2-|(2'S, 3'R)-2'-fluoro-3'-tetradecanoyloxytetradecanoylamino|-3-O-tetradecanoyl-6-O-benzyloxymethyl-β-D-glucopyranoside 2.7 g (3.05 mmole) of the compound obtained as described in Example 7(b) were dissolved in 50 ml of methylene chloride, and 0.525 g of benzyl chloromethyl ether was added to the resulting solution. 0.355 g of tetramethylurea was then added to the resulting mixture, and the mixture was heated under reflux for 6 hours. At the end of this time, the methylene chloride was removed by evaporation under reduced pressure. The residue was purified by chromatography through a silica gel column, using a 3:1 by volume mixture of cyclohexane and ethyl acetate as the eluent, to obtain 2.08 g (yield 67.8%) of Nuclear Magnetic Resonance Spectrum (CDCl$_3$, 270 MHz) δ ppm:

0.88 (9H, triplet, J=6.9 Hz);

1.20–1.73 (65H, multiplet);

2.24–2.37 (4H, multiplet);

3.47–3.51 (1H, multiplet);

3.74 (1H, triplet, J=9.5 Hz);

3.89–4.11 (4H, multiplet);

4.26–4.33 (1H, multiplet);

4.59 (1H, doublet, J=8.4 Hz);

4.63 (2H, singlet);

4.79 (1H, doublet of doublets, J=4.3 & 48.4 Hz);

4.81 (2H, singlet);

5.03 (1H, doublet of doublets, J=9.2 & 10.6 Hz);

5.15–5.30 (3H, multiplet);

5.80–5.88 (1H, multiplet);

6.36 (1H, doublet of doublets, J=4.4 & 9.2 Hz);

7.29–7.36 (5H, multiplet).

Infrared Absorption Spectrum (CHCl$_3$) $v_{max}$ cm$^{-1}$: 3430, 1738, 1695.

Mass spectrum, m/z: 986, 928, 834, 175, 717, 596, 509, 456, 383, 354, 298, 285, 268.

7(d) Allyl 2-deoxy-2-[(2'S,3'R)-2'-fluoro-3'-tetradecanoyloxytetradecanoylamino]-3-O-tetradecanoyl-4-O-diphenylphosphoryl-6-O-benzyloxymethyl-β-D-glucopyranoside 2.0 g of the compound obtained as described in Example 7(c) was treated in the same manner as described in Example 6(e) to obtain 2.5 g of the title compound quantitatively.

Nuclear Magnetic Resonance Spectrum (CDCl$_3$, 270 MHz) δ ppm:

0.88 (9H, triplet, J=6.9 Hz);

1.10–1.68 (65H, multiplet);

2.08–2.31 (3H, multiplet);

3.65–3.69 (2H, multiplet);

3.78–3.84 (1H, multiplet);

4.03–4.11 (2H, multiplet);

4.25–4.32 (1H, multiplet);

4.50–4.85 (7H, multiplet);

5.15–5.39 (4H, multiplet);

5.76–5.83 (1H, multiplet);

6.38 (1H, doublet, J=4.8 & 9.2 Hz);

7.13–7.44 (15H, multiplet).

Infrared Absorption Spectrum (CHCl$_3$) $v_{max}$ cm$^{-1}$: 3430, 1740, 1695.

Mass spectrum, m/z: 1014, 994, 758, 670, 580, 440, 322, 268.

7(e) 2-Deoxy-2-|(2'S,3'R)-2'-fluoro-3'-tetradecanoyloxytetradecanoylamino|-3-O-tetradecanoyl-4-O-diphenylphosphoryl-6-O-benzyloxymethyl-D-glucopyranose 2.3 g of the compound obtained as described in Example 7(d) was treated in the same manner as described in Example 1(g) to obtain 1.58 g (yield 71%) of the title compound.

Nuclear Magnetic Resonance Spectrum (CDCl$_3$, 60 MHz) δ ppm:

0.63–2.42 (77H, multiplet);

3.55–5.78 {14H, multiplet |including 4.54 (2H, singlet), 4.66 (2H, singlet)|};

6.70 (1H, multiplet);

7.00–7.53 (15H, multiplet).

7(f) 2-Deoxy-2-|(2'S,3'R)-2'-fluoro-3'-tetradecanoyloxytetradecanoylamino]-3-O-tetradecanoyl-4-O-diphenylphosphoryl-D-glucopyranose 1.44 g (1.2 mmole) of the compound obtained as described in Example 7(e) was dissolved in 30 ml of methanol, and 1 g of 10% w/w palladium-on-carbon was added to the resulting solution. Catalytic reduction was then allowed to take place under an atmosphere of hydrogen at 40° to 45° C. for 3 hours. At the end of this time, the mixture was filtered, and the methanol was removed by evaporation under reduced pressure. The residue was purified by chromatography through a silica gel column, using a 1:1 by volume mixture of cyclohexane and ethyl acetate as the eluent, to obtain 715 mg (yield 55.2%) of the title compound.

Infrared Absorption Spectrum (CHCl$_3$) $v_{max}$ cm$^{-1}$: 3440, 1740, 1690.

Elemental analysis: Calculated for C$_{60}$H$_{99}$FNO$_{12}$P (molecular weight, 1076.4): C, 66.95%; H, 9.27%; N, 1.30%; F, 1.76%; P, 2.88%. Found: C, 66.96%; H, 9.30%; N, 1.17%; F, 1.74; P, 2.81%.

7(g) 2-Deoxy-2-[(2'S,3'R)-2'-fluoro-3'-tetradecanoyloxytetradecanoylamino]-3-O-tetradecanoyl-D-glucopyranosyl-4-phosphate 550 mg of the compound obtained as described in Example 7(f) was treated in the same manner as described in Example 5(g) to obtain 420 mg (yield 89%) of the title compound.

FAB mass spectrum, m/z: 922 [M−H]$^-$.

EXAMPLE 8

2-Deoxy-2-[(2'S,3'R)-2'-fluoro-3'-hydroxytetradecanoylamino]-3-O-[(3"R)-3"-(tetradecanoyloxy)tetradecanoyl)-D-glucopyranosyl-4-phosphate 8(a) Allyl 2-deoxy-2-[(2'S,3'R)-2'-fluoro-3'-(benzyloxycarbonyloxy)tetradecanoylamino|-3-O-[(3"R)-3"-(tetradecanoyloxy)tetradecanoyl|-4,6-O-isopropylidene-α-D-glucopyranoside 33.1 g of allyl 2-deoxy-2-[(2'S,3'R)-2'-fluoro-3'-(benzyloxycarbonyloxy)tetradecanoylamino|-4,6-O-isopropylidene-β-D-glucopyranoside [prepared as described in Example 2(a)] were dissolved in 700 ml of methylene chloride, and 25.9 g of 3-tetradecanoyloxytetradecanoic acid were added to the resulting solution. 7 g of 4-dimethylaminopyridine and 12.8 g of N,N'-dicyclohexylcarbodiimide were then added to the resulting mixture, and the mixture was stirred at room temperature for 2 hours. At the end of this time, the mixture was filtered, concentrated by evaporation under reduced pressure and diluted with ethyl acetate. The ethyl acetate layer was then washed with a saturated aqueous solution of sodium hydrogen carbonate and with a saturated aqueous solution of sodium chloride, in that order, after which it was dried over anhydrous magnesium sulfate. It was then filtered, and the ethyl acetate was removed by evaporation under reduced pressure. The residue was subjected to silica gel column chromatography, using a 5:1 by volume mixture of cyclohexane and ethyl acetate as the eluent, to obtain 47.7 g (yield 85.5%) of the title compound.

Nuclear Magnetic Resonance Spectrum (CDCl$_3$, 270 MHz) δ ppm:

0.86–0.90 (9H, multiplet);

1.25–1.77 {68H, multiplet [including 1.37 (3H, singlet), 1.48 (3H, singlet)]};

2.26 (2H, multiplet);

2.49 (1H, doublet of doublets, J=6.3 & 15.1 Hz);

2.62 (1H, doublet of doublets, J=6.3 & 15.1 Hz);

3.70–3.86 (5H, multiplet);

3.93–3.98 (1H, multiplet);

4.21–4.27 (1H, multiplet);

4.63 (1H, doublet, J=3.9 Hz);

4.90 (1H, doublet of doublets, J=2.4 & 47.4 Hz);

5.09–5.21 (7H, multiplet);

5.74–5.84 (1H, multiplet);

6.63 (1H, doublet of doublets, J=3.9 & 9.8 Hz);

7.26–7.36 (5H, multiplet).

Infrared Absorption Spectrum (CHCl$_3$) $v_{max}$ cm$^{-1}$: 3440, 1745, 1695, 1530.

Elemental analysis: Calculated for C$_{62}$H$_{104}$NFO$_{12}$: C: 69.30%; H: 9.76%; N: 1.30%; F: 1.77%. Found: C: 69.39%; H: 9.86%; N: 1.31%; F: 1.75%.

8(b) Allyl 2-deoxy-2-[(2'S,3'R)-2'-fluoro-3'-(benzyloxycarbonyloxy)tetradecanoylamino]-3-O-[(3"R)-3"-(tetradecanoyloxy)tetradecanoyl]-α-D-glucopyranoside 46 g of the compound obtained as described in Example 8(a) were treated in the same manner as described in Example 4(b) to obtain 42 g (yield 94.8%) of the title compound.

Nuclear Magnetic Resonance Spectrum (CDCl$_3$, 270 MHz) δ ppm:

0.85–0.90 (9H, multiplet);

1.04–1.78 (64H, multiplet);

2.26–2.31 (2H, multiplet);

2.47–2.59 (2H, multiplet);

3.63–3.88 (5H, multiplet);

3.96–4.02 (1H, multiplet);

4.16–4.23 (1H, multiplet);

4.66 (1H, doublet, J=3.7 Hz);

4.89 (1H, doublet of doublets, J=2.2 & 47.6 Hz);

5.09–5.21 (7H, multiplet);

5.73–5.87 (1H, multiplet);

6.66 (1H, doublet of doublets, J=3.7 & 9.5 Hz);

7.26–7.37 (5H, multiplet).

Infrared Absorption Spectrum (KBr) $v_{max}$ cm$^{-1}$: 1741, 1719, 1703, 1670, 1545, 1468.

Elemental analysis: Calculated for C$_{59}$H$_{100}$NFO$_{12}$: C: 68.51%; H: 9.74%; N: 1.35%; F: 1.84%. Found: C: 68.62%; H: 9.70%; N: 1.55%; F: 1.80%.

8(c) Allyl 2-deoxy-2-[(2'S,3'R)-2'-fluoro-3'-(benzyloxycarbonyloxy)tetradecanoylamino]-3-O-[(3"R)-3"-(tetradecanoyloxy)tetradecanoyl]-6-O-benzyloxycarbonyl-α-D-glucopyranoside 23.1 g of the compound obtained as described in Example 8(b) were treated in the same manner as described in Example 4(c) to obtain 10.6 g (yield 40.6%) of the title compound.

Nuclear Magnetic Resonance Spectrum (CDCl$_3$, 270 MHz) δ ppm:

0.85–0.90 (9H, multiplet);

1.02–1.77 (62H, multiplet);

2.25–2.31 (2H, multiplet);

2.46–2.59 (2H, multiplet);

3.31 (1H, doublet, J=4.2 Hz);

3.61 (1H, triplet of doublets, J=9.3 & 4.2 Hz);

3.76–3.86 (2H, multiplet);

3.93–4.00 (1H, multiplet);

4.16–4.24 (1H, multiplet);

4.38–4.48 (1H, multiplet);

4.88 (1H, doublet of doublets, J=2.2 & 47.6 Hz);

5.07–5.19 (9H, multiplet);

5.70–5.85 (1H, multiplet);

6.62 (1H, doublet of doublets, J=3.7 & 9.5 Hz);

7.26–7.40 (10H, multiplet).

Infrared Absorption Spectrum (KBr) $v_{max}$ cm$^{-1}$: 1747, 1738, 1724, 1712, 1678, 1547.

Elemental analysis: Calculated for C$_{67}$H$_{106}$NFO$_{14}$: C: 68.86%; H: 9.14%; N: 1.20%; F: 1.63%. Found: C: 68.77%; H: 9.18%; N: 1.42%; F: 1.64%.

8(d) Allyl 2-deoxy-2-[(2'S,3'R)-2'-fluoro-3'-(benzyloxycarbonyloxy)tetradecanoylamino]-3-O-[(3"R)-3"-(tetradecanoyloxy)tetradecanoyl]-4-O-diphenylphosphoryl-6-O-benzyloxycarbonyl-α-D-glucopyranoside 10.47 g of the compound obtained as described in Example 8(c) were treated in the same manner as described in Example 4(d) to obtain 11.46 g (yield 91.3%) of the title compound.

Nuclear Magnetic Resonance Spectrum (CDCl$_3$, 270 MHz) δ ppm:

0.85–0.90 (9H, multiplet);

1.03–1.80 (62H, multiplet);

2.13–2.19 (2H, multiplet);

2.33 (1H, doublet of doublets, J=7.3 & 15.8 Hz);

2.42 (1H, doublet of doublets, J=5.1 & 15.8 Hz);

3.75–3.82 (1H, multiplet);

3.89–4.02 (2H, multiplet);

4.17–4.36 (3H, multiplet);

4.64 (1H, doublet, J=3.7 Hz);

4.72 (1H, doublet of doublets, J=9.2 & 18.7 Hz);

4.85–5.22 (9H, multiplet);

5.42 (1H, doublet of doublets, J=9.2 & 11.0 Hz);

5.70–5.84 (1H, multiplet);

6.56 (1H, doublet of doublets, J=3.7 & 9.5 Hz);

7.12–7.65 (20H, multiplet).

Infrared Absorption Spectrum (liquid film) $v_{max}$ cm$^{-1}$: 1750, 1690, 1590.

Elemental analysis: Calculated for $C_{79}H_{115}NFO_{17}P$: C, 67.74%; H, 8.28%; N, 1.00%; F, 1.36%; P, 2.21%. Found: C, 68.77%; H, 9.18%; N, 1.42%; F, 1.64%; P, 2.14%.

8(e) 2-Deoxy-2-[(2'S,3'R)-2'-fluoro-3'-(benzyloxycarbonyloxy)tetradecanoylamino]-3-O-[(3"R)-3"-(tetradecanoyloxy)tetradecanoyl]4-O-diphenylphosphoryl-6-O-benzyloxycarbonyl-D-glucopyranose 1.4 g of the compound obtained as described in Example 8(d) was treated in the same manner as described in Example 1(g) to obtain 0.77 g (yield 56.6%) of the title compound.

Nuclear Magnetic Resonance Spectrum ($CDCl_3$, 270 MHz) δ ppm:

0.85–0.90 (9H, multiplet);
1.18–1.82 (62H, multiplet);
2.12–2.18 (2H, multiplet);
2.32 (1H, doublet of doublets, J=7.3 & 15.8 Hz);
2.41 (1H, doublet of doublets, J=5.5 & 15.8 Hz);
2.70 (1H, doublet of doublets, J=1.5 & 4.8 Hz);
4.09–4.18 (3H, multiplet);
4.29–4.34 (1H, multiplet);
4.67 (1H, doublet of doublets, J=9.2 & 18.7 Hz);
4.87 (1H, multiplet);
4.89 (1H, doublet of doublets, J=1.8 & 47.3 Hz);
5.61–5.25 (6H, multiplet);
5.46 (1H, doublet of doublets, J=9.2 & 11.0 Hz );
6. 63 (1H, doublet of doublets, J=3.3 & 8.8 Hz );
7.12–7.38 (20H, multiplet).

Infrared Absorption Spectrum (KBr) $v_{max}$ $cm^{-1}$: 1739, 1660, 1290, 1266, 1250, 1195.

Elemental analysis: Calculated for $C_{76}H_{111}FNO_{17}P$: C, 67.09%; H, 8.22%; N, 1.03%; F, 1.40%; P, 2.28%. Found: C, 67.04%; H, 7.97%; N, 1.64%; F, 1.35%; P, 2.15%.

8(f) 2-Deoxy-2-[(2'S,3'R)-2'-fluoro-3'-hydroxytetradecanoylamino]-3-O-[(3"R)-3"-(tetradecanoyloxy)tetradecanoyl]-4-O-diphenylphosphoryl-D-glucopyranose 6.5 g of the compound obtained as described in Example 8(e) were treated in the same manner as described in Example 5(f) to obtain 4.89 g (yield 93.7%) of the title compound.

Nuclear Magnetic Resonance Spectrum ($CDCl_3$, 60 MHz) δ ppm:

0.85–0.90 (9H, multiplet);
1.18–1.80 (62H, multiplet);
2.13–2.21 (2H, multiplet);
2.37–2.39 (2H, multiplet);
3.50–3.61 (4H, multiplet);
3.97–4.06 (2H, multiplet);
4.21–4.28 (1H, multiplet);
4.65–4.83 (2H, multiplet);
5.04–5.13 (1H, multiplet);
5.24–5.28 (2H, multiplet);
5.49–5.57 (1H, multiplet);
6.80–6.85 (1H, multiplet);
7.14–7.38 (10H, multiplet).

Infrared Absorption Spectrum (KBr) $v_{max}$ $cm^{-1}$: 1735, 1671, 1289, 1202, 1060.

Elemental analysis: Calculated for $C_{60}H_{99}FNO_{13}P$: C, 65.97%; H, 9.13%; N, 1.28%; F, 1.74%; P, 2.84%. Found: C, 65.93%; H, 9.25%; N, 1.48%; F, 1.63%; P, 2.84%.

8(g) 2-Deoxy-2-[(2'S, 3'R)-2'-fluoro-3'-hydroxytetradecanoylamino]-3-O-[(3"R)-3"-(tetradecanoyloxy)tetradecanoyl]-D-glucopyranosyl-4-phosphate 4.59 g of the compound obtained as described in Example 8(f) were treated in the same manner as described in Example 5(g) to obtain 3.9 g (yield 98.7%) of the title compound.

Nuclear Magnetic Resonance Spectrum (deuteropyridine, 270 MHz) δ ppm:

0.85–0.90 (9H, multiplet);
1.03–2.15 (62H, multiplet);
2.43–2.49 (2H, multiplet);
3.08–3.25 (2H, multiplet);
4.09–4.13 (1H, multiplet);
4.52–4.56 (2H, multiplet);
4.62–4.65 (1H, multiplet);
4.99–5.08 (1H, multiplet);
5.21–5.49 (2H, multiplet);
5.63–5.74 (2H, multiplet);
6.24–6.31 (1H, multiplet);
8.03–8.72 (6H, multiplet).

Infrared Absorption Spectrum (KBr) $v_{max}$ $cm^{-1}$: 1734, 1661, 1550, 1465, 1224, 1182, 1171, 1063.

Elemental analysis: Calculated for $C_{48}H_{91}FNO_{13}P$: C, 61.32%; H, 9.76%; N, 1.49%; F, 2.02%; P, 3.29%. Found: C, 60.66%; H, 9.87%; N, 1.68%; F, 1.91%; P, 3.10%.

EXAMPLE 9

2-Deoxy-2-[(2'R,3'S)-2'-fluoro-3'-hydroxytetradecanoylamido]-3-O-[(3"R)-3"-(tetradecanoyloxy)tetradecanoyl]-D-glucopyranosyl-4-phosphate 9(a) Allyl 2-deoxy-2-[(2'R,3'S)-2'-fluoro-3'-(benzyloxycarbonyloxy)tetradecanoylamino]-3-O-[(3"R)-3"-(tetradecanoyloxy)tetradecanoyl]-4,6-O-isopropylidene-α-D-glucopyranoside 1.1 g of allyl 2-deoxy-2-[(2'R,3'S)-2'-fluoro-3'-(benzyloxycarbonyloxy)tetradecanoylamino]-4,6-O-isopropylidene-α-D-glucopyranoside [prepared as described in Example 2(a)] was treated in the same manner as described in Example 8(a) to obtain 1.36 g (yield 73.8%) of the title compound.

Infrared Absorption Spectrum (liquid film) $v_{max}$ $cm^{-1}$: 1740, 1685, 1530, 1460.

Elemental analysis: Calculated for $C_{62}H_{104}FNO_{12}$: C, 69.30%; H, 9.76%; N, 1.30%; F, 1.77%. Found: C, 68.94%; H, 9.58%; N, 1.26%; F, 1.76%.

9(b) Allyl 2-deoxy-2-[(2'R,3'S)-2'-fluoro-3'-(benzyloxycarbonyloxy)tetradecanoylamino]-3-O-[(3"R)-3"-(tetradecanoyloxy)tetradecanoyl]-α-D-glucopyranoside 57.6 g of the compound obtained as described in Example 9(a) were treated in the same manner as described in Example 4(b) to obtain 42.6 g (yield 76.8%) of the title compound.

Nuclear Magnetic Resonance Spectrum ($CDCl_3$, 270 MHz) δ ppm:

0.86–0.90 (9H, multiplet);
1.25–1.76 (64H, multiplet);
2.25–2.45 (4H, multiplet);
3.64–3.76 (3H, multiplet);
3.85–3.90 (2H, multiplet);
3.95–4.00 (1H, multiplet);
4.14–4.21 (2H, multiplet);
4.84–5.32 (8H, multiplet);
5.83–5.87 (1H, multiplet);

7.07–7.10 (1H, multiplet);

7.26–7.38 (5H, multiplet).

Elemental analysis: Calculated for $C_{59}H_{100}O_{12}NF$: C, 68.51%; H, 9.74%; N, 1.35%; F, 1.84%. Found: C, 68.27%; H, 9.97%; N, 1.48%; F, 1.92%.

9(c) Allyl 2-deoxy-2-[(2'R,3'S)-2'-fluoro-3'-(benzyloxycarbonyloxy)tetradecanoylamino]-3-O-[(3"R)-3"-(tetradecanoyloxy)tetradecanoyl]-6-O-benzyloxycarbonyl-α-D-glucopyranoside 0.83 g of the compound obtained as described in Example 9(b) was treated in the same manner as described in Example 4(c) to obtain 0.6 g (yield 63.6%) of the title compound.

Nuclear Magnetic Resonance Spectrum (CDCl$_3$, 270 MHz) δ ppm:

0.86–0.90 (9H, multiplet);

1.25–1.76 (63H, multiplet);

2.23–2.45 (4H, multiplet);

3.63–3.65 (2H, multiplet);

3.85–3.98 (2H, multiplet);

4.11–4.19 (2H, multiplet);

4.43–4.93 (2H, multiplet);

4.89 (1H, doublet of doublets, J=2.6 & 47.3 Hz);

4.93 (1H, doublet, J=3.3 Hz);

5.01–5.30 (8H, multiplet);

5.76–5.92 (1H, multiplet);

7.03–7.07 (1H, multiplet);

7.26–7.41 (10H, multiplet).

Infrared Absorption Spectrum (liquid film) $v_{max}$ cm$^{-1}$: 1750, 1690.

Elemental analysis: Calculated for $C_{67}H_{106}O_{14}NF$: C, 68.86%; H, 9.14%; N, 1.20%; F, 1.63%. Found: C, 68.69%; H, 9.21%; N, 1.40%; F, 1.63%.

9(d) Allyl 2-deoxy-2-[(2'R,3'S)-2'-fluoro-3'-(benzyloxycarbonyloxy)tetradecanoylamino]-3-O-[(3"R)-3"-(tetradecanoyloxy)tetradecanoyl]-4-O-diphenylphosphoryl-6-O-benzyloxycarbonyl-α-D-glucopyranoside 30.5 g of the compound obtained as described in Example 9(c) were treated in the same manner as described in Example 4(d) to obtain 31 g (yield 96%) of the title compound.

Nuclear Magnetic Resonance Spectrum (CDCl$_3$, 270 MHz) δ ppm:

0.85–0.90 (9H, multiplet);

1.1–1.72 (62H, multiplet);

2.06–1.12 (2H, multiplet);

2.35 (1H, doublet of doublets, J=7.7 & 17.6 Hz);

2.52 (1H, doublet of doublets, J=5.5 & 17.6 Hz);

3.90–4.35 (6H, multiplet);

4.73 (1H, doublet of doublets, J=9.2 & 18.7 Hz);

4.89 (1H, doublet of doublets, J=2.6 & 47.6 Hz);

4.95 (1H, doublet, J=3.7 Hz);

5.04–5.29 (8H, multiplet);

5.47 (1H, doublet of doublets, J=9.2 & 11.0 Hz);

5.77–5.84 (1H, multiplet);

6.81 (1H, doublet of doublets, J=3.3 & 8.1 Hz);

7.11–7.37 (20H, multiplet).

Infrared Absorption Spectrum (liquid film) $v_{max}$ cm$^{-1}$: 1745, 1690, 1590, 1530.

Elemental analysis: Calculated for $C_{79}H_{115}O_{17}NFP$: C, 67.74%; H, 8.28%; N, 1.00%; F, 1.36%; P, 2.21%. Found: C, 67.37; H, 8.25%; N, 0.87%; F, 1.31%; P, 2.27%.

9(e) 2-Deoxy-2-[(2'R,3'S)-2'-fluoro-3'-(benzyloxycarbonyloxy)tetradecanoylamino]-3-O-[(3"R)-3"-(tetradecanoyloxy)tetradecanoyl]-4-O-diphenylphosphoryl-6-O-benzyloxycarbonyl-D-glucopyranose 15 g of the compound obtained as described in Example 9(d) were treated in the same manner as described in Example 1 (g) to obtain 11.6 g (yield 79.6%) of the title compound.

Nuclear Magnetic Resonance Spectrum (CDCl$_3$, 270 MHz) δ ppm:

0.85–0.90 (9H, multiplet);

1.14–1.75 (62H, multiplet);

2.08–2.13 (2H, multiplet);

2.33 (1H, doublet of doublets, J=7.7 & 16.9 Hz);

2.51 (1H, doublet of doublets, J=4.8 & 16.9 Hz);

3.63 (1H, doublet of doublets, J=1.1 & 4.03 Hz);

3.97 (1H, multiplet);

4.14–4.36 (3H, multiplet);

4.66–4.77 (1H, multiplet);

4.89 (1H, doublet of doublets, J=2.7 & 47.6 Hz);

5.02–5.20 (6H, multiplet);

5.30 (1H, triplet, J=3.7 Hz);

5.53 (1H, doublet of doublets, J=9.2 & 11.0 Hz);

6.92 (1H, doublet of doublets, J=2.9 & 7.7 Hz);

7.12–7.34 (20H, multiplet).

Infrared Absorption Spectrum (CHCl$_3$) $v_{max}$ cm$^{-1}$: 3420, 1750, 1690, 1590, 1530, 1490, 960.

Elemental analysis: Calculated for $C_{76}H_{111}NO_{17}FP$: C, 67.09%; H, 8.22%; N, 1.03%; F, 1.40%; P, 2.28%. Found: C, 67.20%; H, 8.29%; N, 0.97%; F, 1.28%; P, 2.21%.

9(f) 2-Deoxy-2-[(2'R,3'S)-2'-fluoro-3'-hydroxytetradecanoylamino]-3-O-[(3"R)-3"-(tetradecanoyloxy)tetradecanoyl]-4-O-diphenylphosphoryl-D-glucopyranose 11.6 g of the compound obtained as described in Example 9(e) were treated in the same manner as described in Example 5(f) to obtain 8.14 g (yield 87.4%) of the title compound.

Nuclear Magnetic Resonance Spectrum (CDCl$_3$, 270 MHz) δ ppm:

0.85–0.90 (9H, multiplet);

1.19–1.63 (62H, multiplet);

2.15–2.20 (2H, multiplet);

2.37 (1H, doublet of doublets, J=8.4 & 17.2 Hz);

2.68 (1H, doublet, J=8.8 Hz);

3.38 (1H, multiplet);

3.59–3.62 (2H, multiplet);

4.02–4.05 (3H, multiplet);

4.33–4.40 (1H, multiplet);

4.74 (1H, doublet of doublets, J=1.1 & 48.0 Hz);

4.77 (1H, doublet of doublets, J=9.5 & 19.1 Hz);

5.11–5.15 (1H, multiplet);

5.30 (1H, triplet, J=3.7 Hz);

5.54 (1H, doublet of doublets, J=9.5 & 10.3 Hz);

6.83 (1H, doublet of doublets, J=3.3 & 9.2 Hz);

7.15–7.39 (10H, multiplet).

Infrared Absorption Spectrum (KBr) $v_{max}$ cm$^{-1}$: 1736, 1661, 1585, 1560, 1492.

9(g) 2-Deoxy-2-[(2'R,3'S)-2'-fluoro-3'-hydroxytetradecanoylamino]-3-O-[(3"R)-3"-(tetradecanoyloxy)tetradecanoyl]-D-glucopyranosyl-4-phosphate 7.72 g of the compound obtained as described in Example 9(f) were treated in the same manner as described in Example 5(g) to obtain 6.7 g of the title compound quantitatively.

Nuclear Magnetic Resonance Spectrum (CDCl$_3$, 270 MHz) δppm:

0.85–0.91 (9H, multiplet);

1.25–2.01 (62H, multiplet);

2.38–2.44 (2H, multiple);

3.19 (2H, doublet, J=5.86 Hz);

4.43–4.59 (3H, multiplet);

4.99–5.07 (1H, multiplet);

5.15–5.33 {(2H, multiplet) |including 5.24 (1H, doublet of doublets, J=2.0 & 48.8 Hz);

5.74–5.81 (2H, multiplet);

6.28 (1H, triplet, J=9.8 Hz);

8.02 (1H, doublet of doublets, J=2.7 & 9.8 Hz);

8.61 (5H, broad singlet).

Infrared Absorption Spectrum (KBr) $v_{max}$ cm$^{-1}$: 1753, 1716, 1657, 1184, 1138, 1117, 1068.

Elemental analysis: Calculated for $C_{48}H_{91}FNO_{13}P$: C, 61.32%; H, 9.76%; N, 1.49%; F, 2.02%; P, 3.29%. Found: C, 61.04%; H, 9.92%; N, 1.60%; F, 1.92%; P, 3.27%.

EXAMPLE 10

2-Deoxy-2-[(2'S,3'R)-2'-fluoro-3'-tetradecanoyloxytetradecanoylamino]-3-O-[(3"R)-3"-hydroxytetradecanoyl]-D-glucopyranosyl-4-phosphate 10(a) Allyl 2-deoxy-2-[(2'S,3'R)-2'-fluoro-3'-tetradecanoyloxytetradecanoyl]-3-O-[(3"R)-3"-benzyloxytetradecanoyl]-4,6-O-isopropylidene-β-D-glucopyranoside 3.2 g of allyl 2-deoxy-2-[(2'S, 3'R)-2'-fluoro-3'-(tetradecanoyloxy)tetradecanoylamino]-4,6-O-isopropylidene-β-D-glucopyranoside [prepared as described in Example 6(a)] were treated in the same manner as described in Example 2(b) to obtain 4.12 g (yield 89.2%) of the title compound.

10(b) Allyl 2-deoxy-2-[(2'S,3'R)-2'-fluoro-3'-tetradecanoyloxytetradecanoylamino]-3-O-[(3"R)-3"-benzyloxytetradecanoyl)-β-D-glucopyranoside 4 g of the compound obtained as described in Example 10(a) were treated in the same manner as described in Example 4(b) to obtain 2.94 g (yield 75.4%) of the title compound.

Nuclear Magnetic Resonance Spectrum (CDCl$_3$, 60 MHz) δ ppm:

0.5–2.0 (71H, multiplet);

2.1–2.8 (4H, multiplet);

3.0–5.9 (18H, multiplet);

6.3–6.6 (2H, multiplet);

7.1–7.3 (5H, multiplet).

10(c) Allyl 2-deoxy-2-[(2'S,3'R)-2'-fluoro-3'-tetradecanoyloxytetradecanoylamino]-3-O-[(3"R)-3"-benzyloxytetradecanoyl|-6-O-benzyloxymethyl-β-D-glucopyranoside 2.73 g of the compound obtained as described in Example 10(b) were treated in the same manner as described in Example 7(c) to obtain 1.7 g (yield 55.5%) of the title compound.

Nuclear Magnetic Resonance Spectrum (CDCl$_3$, 60 MHz) δ ppm:

0.7–2.0 (71H, multiplet);

9.1–2.7 (4H, multiplet);

2.90 (1H, broad singlet);

3.4–5.5 (20H, multiplet);

6.2–6.6 (2H, multiplet);

7.1–7.4 (10H, multiplet).

10(d) Allyl 2-deoxy-2-[(2'S,3'R)-2'-fluoro-3'-tetradecanoyloxytetradecanoylamino|-3-O-|(3"R)-3"-benzyloxytetradecanoyl]-4-O-diphenylphosphoryl-6-O-benzyloxymethyl-β-D-glucopyranoside 1.65 g of the compound obtained as described in Example 10(c) was treated in the same manner as described in Example 4(d) to obtain 2.0 g of the title compound quantitatively.

Nuclear Magnetic Resonance Spectrum (CDCl$_3$, 60 MHz) δ ppm:

0.5–2.0 (71H, multiplet);

2.1–2.7 (4H, multiplet);

3.5–5.6 (20H, multiplet);

6.2–6.7 (2H, multiplet);

7.1–7.5 (20H, multiplet).

10(e) 2-Deoxy-2-[(2'S,3'R)-2'-fluoro-3'-tetradecanoyloxytetradecanoylamino|-3-O-[(3"R)-3"-benzyloxytetradecanoyl]-4-O-diphenylphosphoryl-6-O-benzyloxymethyl-D-β-glucopyranose 1.9 g of the compound obtained as described in Example 10(d) was treated in the same manner as described in Example 1(g) to obtain 0.88 g (yield 47.5% ) of the title compound.

Nuclear Magnetic Resonance Spectrum (CDCl$_3$, 270 MHz) δ ppm:

0.88 (9H, triplet, J=6.2–7.0 Hz);

1.15–1.70 (62H, multiplet);

2.20–2.45 (4H, multiplet);

3.07 (1H, multiplet);

3.60–3.82 (3H, multiplet);

4.20–4.90 (10H, multiplet);

5.17 (1H, multiplet);

5.30 (1H, triplet, J=3.3–3.7 Hz);

5.57 (1H, doublet of doublets, J=9.4 & 10.8 Hz);

6.68 (1H, doublet of doublets, J=3.5 & 8.6 Hz);

7.1–7.35 (20H, multiplet).

Infrared Absorption Spectrum (liquid film) $v_{max}$ cm$^{-1}$: 3450, 3300, 2920, 2860, 1740, 1680.

10(f) 2-Deoxy-2-[(2'S,3'R)-2'-fluoro-3'-tetradecanoyloxytetradecanoylamino]-3-O-[(3"R)-3"-hydroxytetradecanoyl]-4-O-diphenylphosphoryl-D-glucopyranose 0.78 g of the compound obtained as described in Example 10(e) was treated in the same manner as described in Example 7(f) to obtain 0.37 g (yield 51.4%) of the title compound.

Nuclear Magnetic Resonance Spectrum (CDCl$_3$, 270 MHz) δ ppm:

0.88 (9H, triplet, J=6.2–7.0 Hz);

1.10–1.30 (58H, multiplet);

1.40–1.75 (4H, multiplet);

2.10–2.33 (4H, multiplet);

3.50–4.10 (7H, multiplet);

4.70–4.98 (3H, multiplet);

5.13–5.40 (2H, multiplet);

5.56 (1H, triplet, J=9.5–10.3 Hz );

6.77 (1H, doublet of doublets, J=3.7 & 9.2 Hz);

7.15–7.38 (1H, multiplet).

10(g)  2-Deoxy-2-[(2'S,3'R)-2'-fluoro-3'-tetradecanoyloxytetradecanoylamino]-3-O-[(3"R)-3"-hydroxytetradecanoyl)-D-glucopyranosyl-4-phosphate 0.29 g of the compound obtained as described in Example 10(f) was treated in the same manner as described in Example 5(g) to obtain 0.25 g of the title compound quantitatively.

Nuclear Magnetic Resonance Spectrum (CF$_3$COOD, 270 MHz) δ ppm:

0.87–0.98 (9H, multiplet);

1.20–1.55 (58H, multiplet);

1.55–2.00 (4H, multiplet);

2.43–2.64 (2H, multiplet);

2.73–2.94 (2H, multiplet);

4.14–4.65 (5H, multiplet);

4.79 (1H, doublet of doublets, J=9.3 & 18.5 Hz);

5.15 (1H, doublet of doublets, J=1.0 & 46.9 Hz);

5.40–5.78 (3H, multiplet).

FAB mass spectrum, m/z: 938 [M−H]$^-$.

EXAMPLE 11

2-Deoxy-2-[(2'R, 3'S)-2'-fluoro-3'-tetradecanoyloxytetradecanoylamino]-3-O-[(3"R)-3"-hydroxytetradecanoyl]-D-glucopyranosyl-4-phosphate 11(a) Allyl 2-deoxy-2-[(2'R,3'S)-2'-fluoro-3'-tetradecanoyloxytetradecanoylamino]-3-O-[(3"R)-3"-benzyloxytetradecanoyl]-4,6-O-isopropylidene-β-D-glucopyranoside 3.4 g of allyl 2-deoxy-2-[(2'R,3'S)-2'-fluoro-3'-tetradecanoyloxytetradecanoylamino]-4,6-O-isopropylidene-β-D-glucopyranoside [prepared as described in Example 6(a)] were treated in the same manner as described in Example 2(b), to obtain 3.8 g (yield 77.4%) of the title compound.

Nuclear Magnetic Resonance Spectrum (CDCl$_3$, 60 MHz) δ ppm:

0.5–2.0 (77H, multiplet);

2.0–2.8 (4H, multiplet);

3.2–5.6 (16H, multiplet);

6.1–6.4 (2H, multiplet);

7.1–7.4 (5H, multiplet).

11(b) Allyl 2-deoxy-2-[(2'R,3'S)-2'-fluoro-3'-tetradecanoyloxytetradecanoylamino]-3-O-[(3"R)-3"-benzyloxytetradecanoyl]-β-D-glucopyranoside 3.68 g of the compound obtained as described in Example 11(a) were treated in the same manner as described in Example 4(b), to obtain 2.97 g (yield 84%) of the title compound.

11(c) Allyl 2-deoxy-2-[(2'R,3'S)-2'-fluoro-3'-tetradecanoyloxytetradecanoylamino]-3-O-[(3"R)-3'-benzyloxytetradecanoyl]-6-O-benzyloxymethyl-β-D-glucopyranoside 2.77 g of the compound obtained as described in Example 11(b) were treated in the same manner as described in Example 7(c) to obtain 2.36 g (yield 76%) of the title compound.

Nuclear Magnetic Resonance Spectrum (CDCl$_3$, 60 MHz) δ ppm:

0.6–2.0 (71H, multiplet);

2.0–2.7 (4H, multiplet);

3.4–6.2 (21H, multiplet);

6.2–6.6 (2H, multiplet);

7.1–7.5 (10H, multiplet).

11(d) Allyl 2-deoxy-2-[(2'R,3'S)-2'-fluoro-3'-tetradecanoyloxytetradecanoylamino]-3-O-[(3"R)-3"-benzyloxytetradecanoyl]-4-O-diphenylphosphoryl-6-O-benzyloxymethyl-β-D-glucopyranoside 2.25 g of the compound obtained as described in Example 11(c) were treated in the same manner as described in Example 4(d) to obtain 2.36 g (yield 86.4%) of the title compound.

Nuclear Magnetic Resonance Spectrum (CDCl$_3$, 60 MHz) δ ppm:

0.6–2.0 (71H, multiplet);

2.1–2.4 (4H, multiplet);

3.5–6.1 (20H, multiplet);

6.1–6.6 (2H, multiplet);

7.1–7.5 (20H, multiplet).

11(e)  2-Deoxy-2-[(2'R,3'S)-2'-fluoro-3'-tetradecanoyloxytetradecanoylamino]-3-O-[(3"R)-3"-benzyloxytetradecanoyl]-4-O-diphenylphosphoryl-6-O-benzyloxymethyl-D-glucopyranose 2.2 g of the compound obtained as described in Example 11(d) were treated in the same manner as described in Example 1(g) to obtain 1.83 g (yield 85.7%) of the title compound.

Nuclear Magnetic Resonance Spectrum (CDCl$_3$, 60 MHz) δ ppm:

0.5–2.0 (71H, multiplet);

2.1–2.6 (4H, multiplet);

3.6–5.9 (17H, multiplet);

6.75 (1H, broad singlet);

7.1–7.4 (20H, multiplet).

11 (f)  2-Deoxy-2-[(2'R,3'S)-2'-fluoro-3'-tetradecanoyloxytetradecanoylamino]-3-O-[(3"R)-3"-hydroxytetradecanoyl]-4-O-diphenylphosphoryl-β-D-glucopyranose 1.7 g of the compound obtained as described in Example 11(e) was treated in the same manner as described in Example 7(f) to obtain 0.6 g (yield 42.1%) of the title compound.

11(g)  2-Deoxy-2-[(2'R,3'S)-2'-fluoro-3'-tetradecanoyloxytetradecanoylamino]-3-O-[(3"R)-3"-hydroxytetradecanoyl]-D-glucopyranosyl-4-phosphate 0.54 g of the compound obtained as described in Example 11(f) was treated in the same manner as described in Example 5(g) to obtain 0.45 g (yield 96.8%) of the title compound.

Nuclear Magnetic Resonance Spectrum (CF$_3$COOD, 270 MHz) δ ppm:

0.87–0.98 (9H, multiplet);

1.27–1.60 (58H, multiplet);

1.65–1.93 (4H, multiplet);

2.50–2.60 (2H, multiplet);

2.80–2.90 (2H, multiplet);

4.12–4.62 (5H, multiplet);

4.80 (1H, doublet of doubles J=9.5 & 18.3 Hz);

5.18 (1H, doublet of doublets, J=2.7 & 48.6 Hz);

5.40–5.93 (3H, multiplet).

FAB mass spectrum, m/z: 938 [M−H]$^-$.

EXAMPLE 12

2-Deoxy-2-[(R and S)-2',2'-difluoro-3'-hydroxytetradecanoylamino]-3-O-[(R)-3-tetradecanoyloxytetradecanoyl]-D-glucopyranosyl-4-phosphate 12(a) Ally 2-deoxy-2-[(RS)-2',2'-difluoro-3'-(benzyloxycarbonyloxy)tetradecanoylamino]-4,6-O-isopropylidene-β-D-glucopyranoside 2.2 g of (R,S)-3-benzyloxycarbonyloxy-2,2-difluorotetradecanoic acid were dissolved in 20 ml of dry methylene chloride, and 2 ml of oxalic chloride were added to the resulting solution. One droplet of dimethylformamide was then added, and the mixture was stirred at room temperature for one hour. At the end of this time, the methylene chloride was removed by evaporation under reduced pressure to obtain an acid chloride.

Meanwhile, 1.51 g of allyl 2-deoxy-2-amino-4,6-O-isopropylidene-β-D-glucopyranoside [prepared as described in Example 1(d)] was dissolved in 20 ml of dry methylene chloride, and 700 mg of triethylamine were added to the resulting solution; the whole of the acid chloride prepared as described above was then added, whilst ice-cooling. The mixture was then stirred at room temperature for 1 hour, after which the methylene chloride was removed by evaporation under reduced pressure. The residue was diluted with ethyl acetate, and washed with a saturated aqueous solution of sodium hydrogen carbonate and with a saturated aqueous solution of sodium chloride, in that order, after which it was dried over anhydrous magnesium sulfate. The ethyl acetate was then removed by evaporation under reduced pressure and the residue was subjected to silica gel column chromatography, using a 2:1 by volume mixture of cyclohexane and ethyl acetate as the eluent, to obtain 2.64 g (yield 75.8%) of the title compound.

Nuclear Magnetic Resonance Spectrum (CDCl$_3$, 270 MHz) δ ppm:

0.88 (3H, triplet, J=6.2–7.0 Hz);

1.25–1.61 {24H, multiplet [including 1.45 (3H, singlet), 1.52 (3H, singlet)]};

1.72–1.79 (2H, multiplet);

2.95 (0.5H, doublet, J=3.3 Hz);

3.11 (0.5H, doublet, J=3.3 Hz);

3.21–3.60 (3H, multiplet);

3.76–4.13 (4H, multiplet);

4.23–4.33 (1H, multiplet);

4.70 (0.5H, doublet, J=8.4 Hz);

4.81 (0.5H, doublet, J=8.4 Hz);

5.14–5.31 (5H, multiplet);

5.75–5.91 (1H, multiplet);

6.47–6.54 (1H, multiplet);

7.30–7.40 (5H, multiplet).

Infrared Absorption Spectrum (CHCl$_3$) $v_{max}$ cm$^{-1}$: 3430, 2925, 2850, 1755, 1705, 1535, 1380, 1263.

Mass spectrum m/z: 655 (M$^+$), 640, 597, 532, 468, 385, 360, 242, 227, 184, 143, 108, 101, 91, 69, 43.

Elemental analysis: Calculated for C$_{34}$H$_{51}$F$_2$NO$_9$: C, 62.27%; H, 7.84%; N, 2.14%; F, 5.79%. Found: C, 62.20%; H, 7.76%; N, 2.06%; F, 5.74%.

12(b) Allyl 2-deoxy-2-[(RS)-2',2'-difluoro-3'-(benzyloxycarbonyloxy)tetradecanoylamino]-4,6-O-isopropylidene-3-O-[(R)-3"-tetradecanoyloxytetradecanoyl]-β-D-glucopyranoside 230 mg (0.5 mmole) of (R)-3-tetradecanoyloxytetradecanoic acid were dissolved in 4 ml of methylene chloride, and the resulting solution was then treated with 0.5 ml of oxalyl chloride for 2 hours to prepare the corresponding acid chloride. The excess oxalyl chloride and the solvent were then removed by evaporation under reduced pressure and the residue was dried over anhydrous magnesium sulfate.

Meanwhile, 262 mg (0.4 mmole) of the compound obtained as described in Example 12(a) and 50 mg of triethylamine were dissolved in 5 ml of methylene chloride, and the solution was ice-cooled thoroughly. The whole of the acid chloride prepared as described above was then dissolved in methylene chloride to give 5 ml of a solution; this solution was then added to the above ice-cooled solution. The starting material disappeared after 3 hours, and then the solvent was removed by evaporation under reduced pressure. The residue was diluted with ethyl acetate, and then the mixture was treated with a 5% w/v aqueous solution of sodium hydrogen carbonate and with a saturated aqueous solution of sodium chloride, in that order. The resulting mixture was then purified by column chromatography through 20 g of silica gel, using a 5:1 by volume mixture of cyclohexane and ethyl acetate as the eluent, to obtain 325.8 mg (yield 74.3%) of the title compound.

Nuclear Magnetic Resonance Spectrum (CDCl$_3$, 270 MHz) δ ppm:

0.85–0.90 (9H, multiplet);

1.20–1.80 (68H, multiplet);

2.20–2.31 (2H, multiplet);

2.43–2.66 (2H, multiplet);

3.35 (1H, multiplet);

3.68–4.07 (5H, multiplet);

4.26 (1H, multiplet);

4.58 (1H, multiplet);

5.11–5.41 (7H, multiplet);

5.74 (1H, multiplet);

6.58 (1H, multiplet);

7.29–7.38 (5H, multiplet).

Infrared Absorption Spectrum (liquid film) $v_{max}$ cm$^{-1}$: 3350, 2925, 2850, 1780, 1710.

12(c) Allyl 2-deoxy-2-[(RS)-2',2'-difluoro-3'-(benzyloxycarbonyloxy)tetradecanoylamino]-3-O-[(R)-3"-tetradecanoyloxytetradecanoyl]-β-D-glucopyranoside 50 ml of 85% acetic acid were added to 0.2 g of the compound obtained as described in Example 12(b), and the mixture was stirred at 60° C. for 50 minutes. The acetic acid was then removed by evaporation under reduced pressure and the residue was dried by means of a vacuum pump, after which the mixture was purified by column chromatography through 15 g of silica gel, using a 2:1 by volume mixture of cyclohexane and ethyl acetate as the eluent, to obtain 0.11 g (yield 57.9%) of the title compound.

Nuclear Magnetic Resonance Spectrum (CDCl$_3$, 270 MHz) δ ppm:

0.85–0.90 (9H, triplet, J=6.4–6.8 Hz);

1.18–1.42 (47H, multiplet);

1.43–1.80 (14H, multiple);

1.90–2.00 (1H, multiple);

2.09(1H, triplet, J=5.9–6.4 Hz);

2.25–2.32 (2H multiplet);

2.41–2.50 (2H, multiplet);

3.37–3.53 (1H, multiplet);

3.63–3.70 (2H, multiplet);

3.78–4.08 (4H, multiplet);

4.21–4.34 (1H, multiplet);

4.53 (0.4H, doublet, J=8.3 Hz);

4.59 (0.6H, doublet, J=8.3 Hz);

4.92–5.36 (7H, multiplet);

5.74–5.88 (1H, multiplet);

6.59 (0.6H, doublet, J=8.8 Hz);

6.69 (0.4H, doublet, J=8.8 Hz);

7.35–7.39 (5H, multiplet).

Infrared Absorption Spectrum (Nujol-trade mark) $v_{max}$ cm$^{-1}$: 3350, 3450, 3300, 2950, 1760, 1690, 1620, 1550.

Elemental analysis: Calculated for $C_{59}H_{99}F_2NO_{12}$: C, 67.33%; H, 9.48%; N, 1.33%; F, 3.61%. Found: C, 67.24%; H, 9.04%; N, 1.68%; F, 3.41%.

12(d) Allyl 6-O-benzyloxycarbonyl-2-deoxy-2-|(RS)-2',2'-difluoro-3'-(benzyloxycarbonyloxy)tetradecanoylamino|-3-O-|(R)-3"-tetradecanoyloxytetradecanoyl|-β-D-glucopyranoside 120 mg (0.11 mmole) of the compound obtained as described in Example 12(c) and 25.4 mg (1.3 equivalent) of benzyloxycarbonyl chloride were dissolved in 20 ml of methylene chloride, and the mixture was ice-cooled. 17.2 mg (1.5 equivalent) of 4-dimethylaminopyridine were then added to the solution and the mixture was stirred for 30 minutes. At the end of this time, the temperature of the mixture was allowed to return to room temperature, after which the mixture was stirred for 2 hours. It was then purified by column chromatography through 100 g of silica gel, using a 2:1 by volume mixture of cyclohexane and ethyl acetate as the eluent, to obtain 80 mg (yield 59.2%) of the title compound and 36 mg (yield 26.7%) of a substance protected at both the 4- and 6-positions.

Nuclear Magnetic Resonance Spectrum (CDCl$_3$, 270 MHz) δ ppm:

0.88 (9H, triplet, J=6.35–6.83 Hz);
1.25–1.73 (62H, multiplet);
2.24–2.31 (2H, multiplet);
2.41–2.48 (2H, multiplet);
3.52–3.69 (4H, multiplet);
3.90–4.02 (3H, multiplet);
4.18–4.30 (1H, multiplet);
4.42–4.57 (3H, multiplet);
5.02–5.25 (7H, multiplet);
5.68–5.85 (1H, multiplet);
6.48–6.65 (1H, doublet);
7.32–7.40 (10H, multiplet).

Infrared Absorption Spectrum (Nujol) $v_{max}$ cm$^{-1}$: 3500, 3300, 2900, 2850, 1720, 1690, 1540.

Elemental analysis: Calculated for $C_{67}H_{105}F_2NO_{14}$: C, 67.82%; H, 8.92%; N, 1.18%; F, 3.20%. Found: C, 67.19%; H, 8.75%; N, 0.89%; F, 2.99%.

12(e) Allyl 6-O-benzyloxycarbonyl-2-|(RS)-2',2'-difluoro-3'-(benzyloxycarbonyloxy)tetradecanoylamino|-4-O-diphenylphosphoryl-2-deoxy-3-O-[(R)-3-tetradecanoyloxytetradecanoyl]-β-D-glucopyranoside 0.5 g of the compound obtained as described in Example 12(d) was dissolved in 50 ml of tetrahydrofuran solvent, and 1 g of each of diphenyl phosphoryl chloride and 4-dimethylaminopyridine (representing an excess of each) were added to the resulting solution. The mixture was then heated under reflux for 3 hours. At the end of this time, the solvent was removed by evaporation under reduced pressure, and the residue was diluted with ethyl acetate. The mixture was then washed with a 5% aqueous solution of sodium hydrogen carbonate and with a saturated aqueous solution of sodium chloride, in that order. The resulting mixture was purified by column chromatography through 30 g of silica gel, using a 3:1 by volume mixture of cyclohexane and ethyl acetate as the eluent, to obtain 0.62 g (yield 97.5%) of the title compound Nuclear Magnetic Resonance Spectrum (CDCl$_3$, 270 MHz) δ ppm:

0.90 (9H, triplet, J=6.8 Hz);
1.14–1.75 (62H, multiplet);
2.12–2.41 (3H, multiplet);
3.61–3.83 (3H, multiplet);
3.91–4.04 (1H, multiplet);
4.13–4.23 (2H, multiplet);
4.30–4.38 (1H, multiplet);
4.69 (1H, doubled doublet of doublets, J=9.0, 9.0 & 18.0 Hz);
4.85 (1H, doublet, J=7.0 Hz);
4.99–5.39 (7H, multiplet);
5.47–5.6 (2H, multiplet);
5.67–5.85 (1H, multiplet);
6.80 (0.5H, doublet, J=7.0 Hz);
6.95 (0.5H, doublet, J=7.0 Hz);
7.10–7.36 (20H, multiplet).

Infrared Absorption Spectrum (liquid film) $v_{max}$ cm$^{-1}$: 3300, 2900, 2850, 1750, 1700, 1590, 1540.

Elemental analysis: Calculated for $C_{79}H_{114}F_2NO_{17}P$: C, 66.88%; H, 8.10%; N, 0.99%; F, 2.68%; P, 2.15%. Found: C, 66.15%; H, 7.92%; N, 1.03%; F, 2.45%; P, 2.13%.

12(f) 6-O-Benzyloxycarbonyl-4-O-diphenylphosphoryl-2-deoxy-2-[(RS)-2',2'-difluoro-3'-(benzyloxycarbonyloxy)tetradecanoylamino]-3-O-[(R)-3-tetradecanoyloxytetradecanoyl]-D-glucopyranoside 50 mg of the compound obtained as described in Example 12(e) and 30 mg (5% mole) of 1,5-cyclooctadiene-bis|methyldiphenylphosphine|iridium hexafluorophosphate were dissolved in 5 ml of tetrahydrofuran. The reaction vessel was first purged with nitrogen and then with hydrogen. As soon as the solution changed color, the atmosphere in the reaction vessel was replaced by nitrogen. The mixture was then stirred at room temperature for 3 hours, after which 1 ml of concentrated aqueous hydrochloric acid was added. The mixture was then stirred at 50° C. for 2 hours. At the end of this time, the mixture was purified by preparative thin layer chromatography (1 mm), using a 3:1 by volume mixture of cyclohexane and ethyl acetate as the developing solvent, to obtain 40 mg (yield 82.1%) of the title compound (as a mixture of the R and S isomers).

Nuclear Magnetic Resonance Spectrum (CDCl$_3$, 270 MHz) δ ppm:

0.83–0.90 (9H, triplet, J=6.5–6.8 Hz);
1.16–1.74 (62H, multiplet);
2.09–2.18 (2H, multiplet);
2.32–2.49 (2H, multiplet);
2.73–2.74 (0.5H, doublet, J=3.9 Hz);
3.28–3.29 (0.5H, doublet, J=3.9 Hz);
4.01–4.38 (4H, multiplet);
4.63–4.74 (1H, multiplet);
4.89–5.23 (7H, multiplet);
5.33–5.47 (1H, multiplet);
6.72–6.73 (1H, multiplet);
7.12–7.37 (20H, multiplet).

Infrared Absorption Spectrum (liquid film) $v_{max}$ cm$^{-1}$: 3350, 2925, 2850, 1750, 1710, 1590, 1540, 1490, 1460.

Elemental analysis: Calculated for $C_{76}H_{110}F_2NO_{17}P$: C, 66.21%; H, 8.04%; N, 1.01%; F, 2.75%; P, 2.24%. Found: C, 66.73%; H, 7.37%; N, 0.71%; F, 2.43%; P, 2.05%.

12(g) 4-O-Diphenylphosphoryl-2-deoxy-2-|(RS)-2',2'-difluoro-3'-hydroxytetradecanoylamino]-3-O-[(R)-3-tetradecanoyloxytetradecanoyl)-D-glucopyranoside 30 mg of the compound obtained as described in Example 12(f) were dissolved in 2 ml of tetrahydrofuran, and 20 mg of 10% w/w palladium-on-carbon were added. The atmosphere in the reaction vessel was then replaced by hydrogen using an aspirator. The reaction mixture was stirred at room temperature for 6 hours and then left to stand overnight. At the end of this time, the mixture was developed by preparative thin layer chromatography (1 mm), using a 1:1 by volume mixture of cyclohexane and ethyl acetate as the developing solvent, to obtain 10 mg (yield 41.2%) of each of the two title compounds (which have the 2-position substituent in the R or the S configurations).

2R compound (having low Rf value)

Nuclear Magnetic Resonance Spectrum ($CDCl_3$, 270 MHz) δ ppm:

0.85–0.90 (9H, triplet, J=6.34–6.36 Hz);
1.20–1.68 (62H, multiplet);
2.17–2.23 (2H, multiplet);
2.34–2.47 (2H, multiplet);
3.10 (1H, doublet, J=4.5 Hz);
3.18–3.27 (2H, multiplet);
3.54–3.61 (1H, multiplet);
3.92–4.03 (3H, multiplet);
4.27–4.36 (1H, multiplet);
4.78 (1H, quartet, J=9.2 Hz);
5.02–5.11 (1H, multiplet);
5.36 (1H, triplet, J=3.4 Hz);
5.53 (1H, triplet, J=9.3 Hz);
6.87–6.91 (1H, multiplet);
7.14–7.39 (10H, multiplet).

Infrared Absorption Spectrum (Nujol) $v_{max}$ $cm^{-1}$: 3500, 3450, 3375, 2900, 2850, 1730, 1680, 1600.

2S compound (having high Rf value)

Nuclear Magnetic Resonance Spectrum ($CDCl_3$, 270 MHz) δ ppm:

0.85–0.90 (9H, triplet, J=6.3–6.41 Hz);
1.21–1.68 (62H, multiplet);
2.17–2.23 (2H, multiplet);
2.34–2.50 (2H, multiplet);
3.08 (1H, doublet J=44 Hz );
3.18–3.29 (2H, multiplet);
3.54–3.61 (1H, multiplet);
3.94–4.00 (3H, multiplet);
4.27–4.36 (1H, multiplet);
4.79 (1H, quartet, J=9.4 Hz);
5.02–5.12 (1H, multiplet);
5.36 (1H, triplet, J=3.4 Hz);
5.53 (1H, triplet, J=9.7 Hz);
6.92–7.01 (1H, multiplet);
7.14–7.39 (10H, multiplet).

Infrared Absorption Spectrum (Nujol) $v_{max}$ $cm^{-1}$: 3500, 3450, 3375, 2900, 2850, 1730, 1680, 1600.

12(h) 2-Deoxy-2-[(R or S)-2',2'-difluoro-3'-hydroxytetradecanoylamino]-3-O-[(R)-3-tetradecanoyloxytetradecanoyl]-D-glucopyranosyl-4-phosphate 60 mg of each separately of the compounds obtained as described in Example 12(g) were dissolved in 2 ml of tetrahydrofuran, and 5 mg of platinum oxide were added. The atmosphere in the reaction vessel was then replaced by hydrogen, using an aspirator, after which the mixture was stirred at room temperature for 3 hours. At the end of this time, the platinum oxide was removed by filtration, and the tetrahydrofuran was removed by evaporation under reduced pressure to obtain the title compounds with 2-position substituents in either the R or the S configuration. The compound having a higher Rf value was obtained in an amount of 50 mg (yield 95%) from the starting compound having the higher Rf value, and the compound having a lower Rf value was obtained in an amount of 52 mg (yield 97%) from the starting compound having the lower Rf value. The developing solvent used was a 8:5:2:1 by volume mixture of chloroform, ethanol, acetic acid and water.

2R compound (having low Rf value)

Nuclear Magnetic Resonance Spectrum (deuteropyridine+$D_2O$, 270 MHz) δ ppm:

0.85–0.90 (9H, multiplet);
1.14–2.04 (62H, multiplet);
2.39–2.48 (2H, multiplet);
3.05–3.14 (1H, multiplet);
3.28–3.37 (1H, multiplet);
4.07–4.11 (1H, multiplet);
4.49–4.66 (3H, multiplet);
4.88–4.98 (1H, multiplet);
5.18–5.29 (1H, multiplet);
5.71–5.81 (2H, multiplet);
6.17–6.32 (1H, multiplet).

Infrared Absorption Spectrum (Nujol) $v_{max}$ $cm^{-1}$: 3500, 3350, 2900, 2850, 1720, 1680, 1590, 1540, 1490, 1460.

2S compound (having high Rf value)

Nuclear Magnetic Resonance Spectrum (deuteropyridine+$D_2O$, 270 MHz) δ ppm:

0.88–0.97 (9H, multiplet);
1.24–2.02 (62H, multiplet);
2.33–2.48 (2H, multiplet);
2.92–3.01 (1H, multiplet);
3.36–3.59 (1H, multiplet);
4.11–4.22 (1H, multiplet);
4.53–4.69 (3H, multiplet);
4.93–5.04 (1H, multiplet);
5.49–5.56 (1H, multiplet);
5.68–5.74 (1H, multiplet);
5.82–5.83 (1H, multiplet);
6.26–6.38 (1H, multiplet).

Infrared Absorption Spectrum (Nujol) $v_{max}$ $cm^{-1}$: 3500, 3350; 2900, 2850, 1720, 1680, 1590, 1540, 1490, 1460.

EXAMPLE 13

1,2-Dideoxy-1-fluoro-2-[(R)-3'-hydroxytetradecanoylamino]-3-O-[(R)-3"-tetradecanoyloxytetradecanoyl]-α-D-glucopyranosyl-4-phosphate 13(a) Allyl 2-deoxy-2-amino-4,6-O-isopropylidene-α-D-glucopyranoside 10 g of allyl 2-deoxy-2-trifluoroacetylamino-4,6-O-isopropylidene-α-D-glucopyranoside [prepared as described in Example 1 (c)] were dissolved in 200 ml of ethanol (99.5%), and 100 ml of a 1N aqueous solution of sodium hydroxide were added to the resulting solution; the mixture was then heated under reflux for 4 hours. At the end of this time, the mixture was concentrated by evaporation under reduced pressure, and the residue was diluted with ethyl acetate. The ethyl acetate layer was washed with water and with a saturated aqueous solution of sodium chloride, in that order, after which it was dried over anhydrous magnesium sulfate. It was then filtered, and the ethyl acetate was removed from the filtrate by evaporation under reduced pressure. The resulting oily residue was purified by chromatography through a silica gel column, using ethyl acetate as the eluent, to obtain 6.6 g (yield 90.5%) of the title compound. Nuclear Magnetic Resonance Spectrum (CDCl$_3$, 60 MHz) δ ppm:

1.42 (3H, singlet);
1.50 (3H, singlet);
2.98 (2H, broad);
3.5–4.4 (5H, multiplet);
4.6–6.3 (7H, multiplet).

Elemental analysis: Calculated for $C_{12}H_{21}NO_5$ (molecular weight, 259.3): C, 55.58%; H, 8.16%; N, 5.40%. Found: C, 55.37%; H, 8.05%; N, 5.40%.

13(b) Allyl 2-deoxy-2-[(3'R)-3'-benzyloxytetradecanoylamino]-4,6-O-isopropylidene-α-D-glucopyranoside and allyl 2-deoxy-2-[(3'S)-3'-benzyloxytetradecanoylamino]-4,6-O-isopropylidene-α-D-glucopyranoside 5 g (19.3 mmole) of the compound obtained as described in Example 13(a) were dissolved in 100 ml of methylene chloride. 6.8 g of (±)-3-benzyloxytetradecanoic acid, followed by 4.78 g of N,N'-dicyclohexylcarbodiimide were then added to the resulting solution, after which the mixture was stirred at room temperature for one hour. At the end of this time, the mixture was filtered, the filtrate was concentrated by evaporation under reduced pressure and the residue was diluted with ethyl acetate. The ethyl acetate layer was washed with a saturated aqueous solution of sodium hydrogen carbonate and with a saturated aqueous solution of sodium chloride, in that order; it was then dried over anhydrous magnesium sulfate, after which it was filtered and the ethyl acetate was removed from the filtrate by evaporation under reduced pressure. The residue was purified by chromatography through a silica gel column, using a 9:11 by volume mixture of cyclohexane and ethyl acetate as the eluent, to obtain 4.1 g of the 3'-R isomer of the title compound (Rf=0.289) and 4.2 g of the 3'-S isomer of the title compound (Rf=0.196), respectively.

3'R compound

Infrared Absorption Spectrum (KBr) $v_{max}$ cm$^{-1}$: 3510, 3280, 1643.

Nuclear Magnetic Resonance Spectrum (CDCl$_3$, 270 MHz) δ ppm:

0.88 (3H, triplet, J=6.9 Hz);
1.20–1.41 (18H, multiplet);
1.45 (3H, singlet);
1.52 (3H, singlet);
1.56–1.70 (2H, multiplet);
2.43 (1H, doublet of doublets, J=6.9 & 15.4 Hz);
2.56 (1H, doublet of doublets, J=3.7 & 15.0 Hz);
3.19–3.29 (1H, multiplet);
3.46–3.63 (2H, multiplet);
3.75–3.94 (5H, multiplet);
4.18–4.24 (1H, multiplet);
4.36 (1H, doublet, J=2.6 Hz);
4.45–4.62 (3H, multiplet);
5.12–5.26 (2H, multiplet);
5.70–5.88 (1H, multiplet);
6.72 (1H, doublet, J=5.9 Hz);
7.30–7.37 (5H, multiplet).

3'S compound

Infrared Absorption Spectrum (KBr) $v_{max}$ cm$^{-1}$: 3510, 3280, 1643.

Nuclear Magnetic Resonance Spectrum (CDCl$_3$, 270 MHz) δ ppm:

0.88 (3H, triplet, J=6.6 Hz);
1.15–1.73 (20H, multiplet );
1.45 (3H, singlet);
1.53 (3H, singlet);
2.35–2.62 (2H, multiplet);
3.02 (1H, doublet, J=2.6 Hz);
3.55–4.25 (9H, multiplet);
4.54, 4.59 (2H, AB quartet, J=11.4 Hz);
4.78 (1H, doublet, J=3.7 Hz);
5.10–5.28 (2H, multiplet);
5.66–5.84 (1H, multiplet);
6.77 (1H, doublet, J=8.8 Hz);
7.25–7.37 (5H, multiplet).

13(c) Allyl 2-[(R)-3'-benzyloxytetradecanoylamino]-2-deoxy-3-O-[(R)-3"-tetradecanoyloxytetradecanoyl]-4,6-O-isopropylidene-α-D-glucopyranoside and allyl 2-[(S)-3'-benzyloxytetradecanoylamino]-2-deoxy-3-O-[(R)-3"-tetradecanoyloxytetradecanoyl]-4,6-O-isopropylidene-α-D-glucopyranoside 1 g of the compound (either the 3'R compound or the 3'S compound) obtained as described in Example 13(b) was dissolved in 20 ml of tetrahydrofuran, and 0.869 g of 3(R)-tetradecanoyloxytetradecanoic acid was added to the solution. 0.466 g of N,N'-dimethylcyclohexylcarbodiimide and 0.233 g of 4-dimethylaminopyridine were then added to the mixture, after which the mixture was stirred at room temperature for 4 hours. The mixture was then filtered, the filtrate was concentrated by evaporation under reduced pressure and the residue was diluted with ethyl acetate, after which the mixture was washed with a saturated aqueous solution of sodium hydrogen carbonate and with a saturated aqueous solution of sodium chloride, in that order; it was then dried over anhydrous magnesium sulfate. The solution was then filtered, and the ethyl acetate was removed from the filtrate by evaporation under reduced pressure. The residue was purified by silica gel column chromatography, using a 85:15 by volume mixture of cyclohexane and ethyl acetate as the eluent, to obtain 1. 23 g (yield 70%) of the 3'R isomer of the title compound and 1.27 g (yield 73%) of the 3'S isomer of the title compound, respectively.

3'R compound

Infrared Absorption Spectrum (liquid film) $v_{max}$ cm$^{-1}$: 3350, 1730, 1650, 1530, 1470, 1370.

Nuclear Magnetic Resonance Spectrum (CDCl$_3$, 270 MHz) δ ppm:

0.80–1.00 (9H, multiplet);
1.00–1.80 (68H, multiplet);
2.10–2.70 (6H, multiplet);
3.60–4.40 (8H, multiplet);
4.49, 4.54 (2H, doublet, J=11.7 Hz);
4.65–4.90 (1H, multiplet);
5.03–5.35 (4H, multiplet);
5.60–5.95 (1H, multiplet);
6.25 (1H, doublet, J=9.5 Hz);
7.25–7.65 (5H, multiplet).

3'S compound

Infrared Absorption Spectrum (liquid film) $v_{max}$ cm$^{-1}$: 3400, 1730, 1670, 1650.

Nuclear Magnetic Resonance Spectrum (CDCl$_3$, 270 MHz) δ ppm:

0.80–0.97 (9H, multiplet);

1.10–1.70 (68H, multiplet);
2.12–2.64 (6H, multiplet);
3.63–3.90 (6H, multiplet);
3.95–4.05 (1H, multiplet);
4.22–4.34 (1H, multiplet);
4.49, 4.60 (2H, doublet, J=11.4 Hz);
4.78 (1H, doublet, J=3.7 Hz);
5.05–5.23 (4H, multiplet);
5.60–5.77 (1H, multiplet);
6.85 (1H, doublet, J=9.2 Hz);
7.25–7.40 (5H, multiplet).

13(d) Allyl 2-|(R)-3'-benzyloxytetradecanoylamino)-2-deoxy-3-O-|(R)-3"-tetradecanoyloxytetradecanoyl|-α-D-glucopyranoside and allyl 2-|(S)-3'-benzyloxytetradecanoylamino|-2-deoxy-3-O-|(R)-3"-tetradecanoyloxytetradecanoyl|-α-D-glucopyranoside 1 g of each separately of the 3'R isomer and the 3'S isomer of the compound obtained as described in Example 13(c) was dissolved in 20 ml of 90% acetic acid, and the solution was stirred at 55° to 60° C. for 1 hour. The acetic acid was then removed by evaporation under reduced pressure, and the residue was diluted with ethyl acetate. The diluted mixture was washed with a saturated aqueous solution of sodium hydrogen carbonate and with a saturated aqueous solution of sodium chloride, in that order, after which it was purified by silica gel column chromatography, using a 3:2 by volume mixture of cyclohexane and ethyl acetate as the eluent, to obtain 0.6 g (yield 57%) of the 3'R isomer of the title compound and 0.66 g (yield 69%) of the 3'S isomer of the title compound, respectively.

3'R compound

Infrared Absorption Spectrum (Nujol) $v_{max}$ cm$^{-1}$: 3480, 3400, 3300, 1735, 1720, 1700, 1650, 1550, 1465, 1380, 1310.

Nuclear Magnetic Resonance Spectrum (CDCl$_3$, 270 MHz) δ ppm:

0.82–0.95 (9H, multiplet);
1.15–1.70 (64H, multiplet);
2.24–2.58 (6H, multiplet);
3.62–3.92 (6H, multiplet);
4.00–4.10 (1H, multiplet);
4.20–4.30 (1H, multiplet);
4.50, 4.55 (2H, doublet, J=11.5 Hz);
4.79 (1H, doublet, J=3.3 Hz);
5.03–5.24 (4H, multiplet);
5.65–5.82 (1H, multiplet);
6.33 (1H, doublet, J=9.5 Hz);
7.22–7.36 (5H, multiplet).

3'S compound

Infrared Absorption Spectrum (Nujol) $v_{max}$ cm$^{-1}$: 3280, 1737, 1722, 1643, 1550, 1466, 1177, 1103, 1053.

Nuclear Magnetic Resonance Spectrum (CDCl$_3$, 270 MHz) δ ppm:

0.80–0.95 (9H, multiplet);
1.15–1.72 (62H, multiplet);
2.24–2.50 (6H, multiplet);
3.62–3.92 (6H, multiplet);
4.00–4.10 (1H, multiplet);
4.18–4.30 (1H, multiplet);
4.50, 4.57 (2H, doublet, J=11.4 Hz);
4.86 (1H, doublet, J=3.3 Hz);
5.02–5.27 (4H, multiplet);
5.64–5.81 (1H, multiplet);
6.80 (1H, doublet, J=8.8 Hz);
7.25–7.40 (5H, multiplet).

13(e) Allyl 6-O-benzyloxycarbonyl-2-|(R)-3'-benzyloxytetradecanoylamino|-2-deoxy-3-O-|(R)-3"-tetradecanoyloxytetradecanoyl|-α-D-glucopyranoside and ally 6-O-benzyloxycarbonyl-2-|(S)-3'-benzyloxytetradecanoylamino|-2-deoxy-3-O-|(R)-3"-tetradecanoyloxytetradecanoyl|-α-D-glucopyranoside 0.645 g of each separately of the 3'R isomer and the 3'S isomer of the compound obtained as described in Example 13(d) was dissolved in 10 ml of methylene chloride. 0.136 g of benzyloxycarbonyl chloride and 0.122 g of 4-dimethylaminopyridine were then added to the solution, whilst ice-cooling, after which the mixture was stirred at room temperature for 2 hours. At the end of this time, the methylene chloride was removed by evaporation under reduced pressure, and the residue was diluted with ethyl acetate. The diluted mixture was washed with a saturated aqueous solution of sodium hydrogen carbonate and with a saturated aqueous solution of sodium chloride, in that order, after which it was dried over anhydrous magnesium sulfate. It was then filtered and the ethyl acetate was removed from the filtrate by evaporation under reduced pressure. The residue was purified by silica gel column chromatography, using a 4:1 by volume mixture of cyclohexane and ethyl acetate as the eluent, to obtain 0.46 g (yield 63%) of each of the 3'R isomer of the title compound and of the 3'S isomer of the title compound, respectively.

3'R compound

Infrared Absorption Spectrum (Nujol) $v_{max}$ cm$^{-1}$: 3500, 3310, 1730, 1650, 1545, 1465, 1380, 1305, 1280.

Nuclear Magnetic Resonance Spectrum (CDCl$_3$, 270 MHz) δ ppm:

0.80–0.96 (9H, multiplet);
1.10–1.70 (62H, multiplet);
2.22–2.60 (6H, multiplet);
3.34 (1H, doublet, J=4.0 Hz);
3.53–3.66 (1H, multiplet);
3.72–3.90 (3H, multiplet);
3.95–4.05 (1H, multiplet);
4.20–4.32 (1H, multiplet);
4.35–4.52 (2H, multiplet);
4.49, 4.56 (2H, doublet, J=11.7 Hz);
4.77 (1H, doublet, J=3.7 Hz);
5.00–5.25 (6H, multiplet);
5.62–5.78 (1H, multiplet);
6.29 (1H, multiplet);
7.22–7.43 (10H, multiplet).

3'S compound

Infrared Absorption Spectrum (Nujol) $v_{max}$ cm$^{-1}$: 3500, 3290, 1737, 1720, 1647, 1546, 1466, 1282.

Nuclear Magnetic Resonance Spectrum (CDCl$_3$, 270 MHz) δ ppm:

0.82–0.93 (9H, multiplet);
1.15–1.65 (62H, multiplet);
2.22–2.50 (6H, multiplet);
3.33 (1H, doublet, J=4.0 Hz);
3.55–3.67 (1H, multiplet);
3.67–3.90 (3H, multiplet);
3.96–4.05 (1H, multiplet);

4.18–4.30 (1H, multiplet);
4.37–4.52 (2H, multiplet);
4.49, 4.57 (2H, doublet, J=11.4 Hz);
4.83 (1H, doublet, J=3.3 Hz);
5.00–5.22 (6H, multiplet);
5.60–5.77 (1H, multiplet);
6.76 (1H, doublet, J=8.8 Hz);
7.25–7.42 (10H, multiplet).

13(f) Allyl 2-deoxy-6-O-benzyloxycarbonyl-2-[(R)-3'-benzyloxytetradecanoylamino]-4-O-diphenylphosphoryl-3-O-[(R)-3"-tetradecanoyloxytetradecanoyl]-α-D-glucopyranoside and ally 2-deoxy-6-O-benzyloxycarbonyl-2-[(S)-3'-benzyloxytetradecanoylamino]-4-O-diphenylphosphoryl-3-O-[(R)-3"-tetradecanoyloxytetradecanoyl]-α-D-glucopyranoside 11.3 g of each separately of the 3'R isomer and the 3'S isomer of the compound obtained as described in Example 13(e) were dissolved in 230 ml of methylene chloride, and 8.22 g of diphenyl chlorophosphate and 7.48 g of 4-dimethylaminopyridine were added to the solution. The resulting mixture was then stirred at room temperature for 1 hour. At the end of this time, the methylene chloride was removed by evaporation under reduced pressure, and the residue was diluted with ethyl acetate. The diluted mixture was washed with a saturated aqueous solution of sodium hydrogen carbonate and with a saturated aqueous solution of sodium chloride, in that order, after which it was dried over anhydrous magnesium sulfate. It was then filtered, and the ethyl acetate was removed from the filtrate by evaporation under reduced pressure. The residue was purified by silica gel column chromatography, using a 7:3 by volume mixture of cyclohexane and ethyl acetate as the eluent, to obtain 6.12 g (yield 45%) of the 3'R isomer of the title compound and 11.34 g (yield 83%) of the 3'S isomer of the title compound, respectively.

3'R compound

Infrared Absorption Spectrum (Nujol) $v_{max}$ cm$^{-1}$: 1735, 1720, 1665, 1590, 1485, 1255, 1066, 965.

Nuclear Magnetic Resonance Spectrum (CDCl$_3$, 270 MHz) δ ppm:

0.82–0.94 (9H, multiplet);
1.10–1.60 (62H, multiplet);
2.10–2.20 (2H, multiplet);
2.30–2.46 (4H, multiplet);
3.67–3.78 (1H, multiplet);
3.78–3.90 (1H, multiplet);
3.90–4.03 (1H, multiplet);
4.15–4.37 (3H, multiplet);
4.48–4.54 (2H, AB quartet, J=11.4 Hz);
4.72 (1H, doublet of doublets, J=9.2 & 19.1 Hz);
4.80 (1H, doublet, J=3.3 Hz);
5.00–5.20 (5H, multiplet);
5.40 (1H, doublet of doublets, J=9.2 & 10.6 Hz);
5.62–5.77 (1H, multiplet);
6.22 (1H, doublet, J=8.8 Hz);
7.10–7.38 (20H, multiplet).

3'S compound

Infrared Absorption Spectrum (Nujol) $v_{max}$ cm$^{-1}$: 3350, 1745, 1650, 1590, 1490, 960.

Nuclear Magnetic Resonance Spectrum (CDCl$_3$, 270 MHz) δ ppm:

0.80–0.93 (9H, multiplet);
1.10–1.65 (62H, multiplet);
2.08–2.20 (2H, multiplet);
2.30–2.52 (4H, multiplet);
3.65–3.87 (2H, multiplet);
3.93–4.05 (2H, multiplet);
4.16–4.35 (3H, multiplet);
4.49, 4.61 (2H, doublet, J=11.4 Hz);
4.72 (1H, doublet of doublets, J=9.2 & 4.7 Hz);
4.85 (1H, doublet, J=3.3 Hz);
5.01–5.20 (5H, multiplet);
5.39 (1H, doublet of doublets, J=9.2 & 10.6 Hz);
5.59–5.74 (1H, multiplet);
6.86 (1H, doublet, J=8.8 Hz);
7.10–7.20 (20H, multiplet).

13(g) 2-deoxy-6-O-benzyloxycarbonyl-2-[(R)-3'-benzyloxytetradecanoylamino]-4-O-diphenylphosphoryl-3-O-[(R)-3"-tetradecanoyloxytetradecanoyl]-D-glucopyranoside and 2-deoxy-6-O-benzyloxycarbonyl-2-[(S)-3'-benzyloxytetradecanoylamino]-4-O-diphenylphosphoryl-3-O-[(R)-3"-tetradecanoyloxytetradecanoyl]-D-glucopyranoside 0.28 g of each separately of the 3'R isomer and the 3'S isomer of the compound obtained as described in Example 13(f) was dissolved in 5 ml of tetrahydrofuran, and 8.9 mg of 1,5-cyclooctadienebis(methyldiphenylphosphine)-iridium hexafluorophosphate were added to the resulting solution. The reaction vessel was then purged with nitrogen followed by hydrogen to activate the iridium complex, after which the atmosphere in the reaction vessel was replaced by nitrogen. The mixture was then stirred at room temperature for 3 hours, after which 0.5 ml of water, 0.1 g of iodine and 0.066 g of pyridine were added thereto. The mixture was then stirred at room temperature for a further 30 minutes. At the end of this time, the tetrahydrofuran was removed by evaporation under reduced pressure, and the residue was diluted with ethyl acetate. The ethyl acetate layer was washed with a saturated aqueous solution of sodium hydrogen carbonate and with a saturated aqueous solution of sodium chloride, in that order, after which the ethyl acetate was removed by evaporation under reduced pressure. The residue was purified by silica gel column chromatography, using a 7:3 by volume mixture of cyclohexane and ethyl acetate as the eluent, to obtain 0.23 g (yield 84%) of the 3'R isomer of the title compound and 0.24 g (yield 88%) of the 3'S isomer of the title compound, respectively.

3'R compound

Infrared Absorption Spectrum (Nujol) $v_{max}$ cm$^{-1}$: 3320, 1735, 1650, 1590, 1535, 1490, 1455.

Nuclear Magnetic Resonance Spectrum (CDCl$_3$, 270 MHz) δ ppm:

0.82–0.93 (9H, multiplet);
1.08–1.70 (62H, multiplet);
2.10–2.22 (2H, multiplet);
2.27–2.35 (2H, multiplet);
2.38–2.44 (2H, multiplet);
2.50 (1H, doublet of doublets, J=1.1 & 4.4 Hz);
3.82–3.93 (1H, multiplet);
4.10–4.39 (4H, multiplet);
4.39, 4.60 (2H, AB quartet, J=11.0 Hz);
4.68 (1H, doublet of doublets, J=9.2 & 18.3 Hz);
5.00–5.13 (4H, multiplet);
5.39 (1H, doublet of doublets, J=9.2 & 11.6 Hz);
6.22 (1H, doublet, J=8.8 Hz);

7.09–7.39 (20H, multiplet).

3'S compound

Infrared Absorption Spectrum (liquid film) $v_{max}$ cm$^{-1}$: 3600–3200, 1748, 1640, 1540, 1490, 961.

Nuclear Magnetic Resonance Spectrum (CDCl$_3$, 270 MHz) δ ppm:

0.82–0.96 (9H, multiplet);

1.07–1.65 (62H, multiplet);

2.12–2.22 (2H, multiplet);

2.32–2.46 (4H, multiplet);

2.99 (1H, doublet of doublets, J=1.5, 4.0 Hz);

3.70–3.82 (1H, multiplet);

4.13–4.38 (4H, multiplet);

4.52, 4.57 (2H, doublet, J=11.0 Hz);

4.71 (1H, doublet of doublets, J=9.2 & 18.7 Hz);

4.97–5.25 (4H, multiplet);

5.46 (1H, doublet of doublets, J=9.2 & 10.6 Hz);

6.86 (1H, doublet, J=8.4 Hz);

7.08–7.40 (20H, multiplet).

13(h) 6-O-Benzyloxycarbonyl-2-|(R)-3'-benzyloxytetradecanoylamino|-1,2-dideoxy-4-O-diphenylphosphoryl-1- fluoro-3-O-|(R)-3"-tetradecanoyloxytetradecanoyl|-α-D-glucopyranoside 1.36 g (8.44 mmole) of diethylaminosulfur trifluoride (DAST) was dissolved in 30 ml of dry methylene chloride, and 25 ml of a solution of 2.74 g (2.11 mmole) of 2-deoxy-6-O-benzyloxycarbonyl- 2-|(R)-3'-benzyloxytetradecanoylamino|-4-O-diphenylphosphoryl-3-O-|(R)-3"-tetradecanoyloxytetradecanoyl|-D-glucopyranoside [obtained as described in Example 13(g)] in dry methylene chloride was gradually added to the solution. The mixture was then stirred for 1 hour, whilst ice-cooling. At the end of this time, the reaction mixture was poured into 130 ml of ice-water to collect the methylene chloride layer. The aqueous layer was extracted with methylene chloride and washed with a saturated aqueous solution of sodium chloride; it was then dried over anhydrous magnesium sulfate and concentrated by evaporation under reduced pressure. The residue was purified by silica gel flash chromatography, using a 8:2 by volume mixture of cyclohexane and ethyl acetate as the eluent, to obtain 1.10 g (yield 40%) of the α-fluoro isomer of the title compound and 1.14 g (yield 42%) of the β-fluoro isomer of the title compound, respectively, both as white solids.

α-fluoro compound

Infrared Absorption Spectrum (Nujol) $v_{max}$ cm$^{-1}$: 3380, 1740, 1660, 1590.

Elemental analysis: Calculated for C$_{75}$H$_{111}$NO$_{14}$FP: C, 69.26%; H, 8.60%; N, 1.08%; F, 1.46%; P, 2.38%. Found: C, 69.11%; H, 8.62%; N, 1.02%; F, 1.42%; P, 2.35%.

β-fluoro compound

Infrared Absorption Spectrum (Nujol) $v_{max}$ cm$^{-1}$: 3320, 1745, 1725, 1662, 1590.

Elemental analysis: Calculated for C$_{75}$H$_{111}$NO$_{14}$FP: C, 69.26%; H, 8.60%; N, 1.08%; F, 1.46%; P, 2.38%. Found: C, 69.25%; H, 8.53%; N, 1.07%; F, 1.44%; P, 2.51%.

13(i) 1,2-Dideoxy-4-O-diphenylphosphoryl-1-fluoro- 2-[(R)-3'-hydroxytetradecanoylamino]-3-O-[(R)-3"-tetradecanoyloxytetradecanoyl|-α-D-glucopyranoside 0.4 g of the glycopyranosyl fluoride obtained as described in Example 13(h) was dissolved in 6 ml of tetrahydrofuran, and 0.4 g of 10% w/w palladium-on-carbon was added to the resulting solution. 24 ml of methanol and 50 mg of formic acid were then added to the mixture, after which the mixture was stirred at room temperature for 4 hours under a stream of hydrogen. At the end of this time, the palladium-on-carbon was removed from the reaction mixture by filtration using a Celite filter aid, and the filtrate was dried by evaporation under reduced pressure. The residue was purified by silica gel flash chromatography, using a 6:4 by volume mixture of cyclohexane and ethyl acetate as the eluent, to obtain 0.1 g (yield 30%) of the title compound as a powder.

Infrared Absorption Spectrum (Nujol) $v_{max}$ cm$^{-1}$: 3550, 342 0, 1732, 1646, 1590.

13(j) 1,2-Dideoxy-1-fluoro-2-|(R)-3'-hydroxytetradecanoylamino|-3-O-|(R)-3"-tetradecanoyloxytetradecanoyl|-α-D-glucopyranosyl-4-phosphate 85 mg of the compound obtained as described in Example 13(i) were dissolved in 5 ml of dry tetrahydrofuran, and 17 mg of platinum oxide were added to the resulting solution, after which the mixture was stirred at room temperature for 4 hours under a stream of hydrogen. The reaction mixture was then heated to 45° C. to dissolve insolubles, after which it was filtered using a Celite filter aid. The solvent was then removed by evaporation under reduced pressure to obtain 72 mg (yield 97%) of the title compound as a powder.

Nuclear Magnetic Resonance Spectrum (deuteropyridine, 270 MHz) δ ppm:

0.82–0.95 (9H, multiplet);

1.15–1.90 (62H, multiplet);

2.48 (2H, triplet, J=7.3 Hz);

2.80–2.90 (2H, multiplet);

3.06–3.30 (2H, multiplet);

4.01–4.60 (7H, multiplet);

5.00–5.50 (2H, multiplet);

5.71 (1H, triplet, J=5.9 Hz);

5.97 (1H, doublet of doublets, J=2.4 & 52.5 Hz);

6.06 (1H, triplet, J=10.3 Hz);

9.56 (1H, doublet, J=9.3Hz).

Infrared Absorption Spectrum (Nujol) $v_{max}$ cm$^{-1}$: 3250, 1722, 1645, 1550.

EXAMPLE 14

1,2-Dideoxy-1-fluoro-2-[(S)-3'-hydroxytetradecanoylamino]-3-O-[(R)-3"-tetradecanoyloxytetradecanoyl]-α-D-glucopyranosyl-4-phosphate 14(a) 6-O-Benzyloxycarbonyl-2-|(S)-3'-benzyloxytetradecanoylamino|-1,2-dideoxy-4-O-diphenylphosphoryl-1-fluoro-3-O-|(R)-3"-tetradecanoyloxytetradecanoyl|-α-D-glucopyranoside 1.49 g of diethylaminosulfur trifluoride was dissolved in 30 ml of dry methylene chloride, and 30 ml of a solution of 3.0 g (2.31 mmole) of 2-deoxy-6-O-benzyloxycarbonyl-2-[(S)-3'-benzyloxytetradecanoylamino)-4-O-diphenylphosphoryl-3-O-|(R)-3"-tetradecanoyloxytetradecanoyl]-D-glucopyranoside [obtained as described in Example 13(g)] in dry methylene chloride were gradually added, whilst ice-cooling, to the resulting solution. After completion of the addition, the mixture was stirred, whilst ice-cooling, for 1 hour and then at room temperature for a further 30 minutes. At the end of this time, the reaction mixture was poured into 150 ml of ice-water and the methylene chloride layer was collected. The aqueous layer was extracted with methylene chloride, washed with a saturated aqueous solution of sodium chloride, and dried over anhydrous magnesium sulfate, after which the mixture was concentrated by evaporation under reduced pressure. 5 g of silica gel (No. 9385, available from Merck) and 100 ml of methylene chloride were added to the residue, and the mixture was stirred overnight to convert the α, β-fluoro compound into the α-fluoro compound. The silica gel was then removed by filtration, and the methylene chloride was removed from the filtrate by evaporation under reduced pressure. The residue was then purified by silica gel flash chromatography, using a 85:15 by volume mixture of cyclohexane and ethyl acetate as the eluent, to obtain 2.4 g (yield 80%) of the title compound.

Infrared Absorption Spectrum (Nujol) $v_{max}$ cm$^{-1}$: 3390, 1740, 1650, 1590.

14(b) 1,2-Dideoxy-4-O-diphenylphosphoryl-1-fluoro-2-[(S)-3'-hydroxytetradecanoylamino]-3-O-[(R)-3"-tetradecanoyloxytetradecanoyl]-α-D-glucopyranoside 1.82 g of the compound obtained as described in Example 14(a) was dissolved in 12 ml of tetrahydrofuran, and 1.8 g of 10% w/w palladium-on-carbon was added to the resulting solution. 45 ml of methanol and 70 mg of formic acid were then added to the mixture, after which the mixture was stirred at room temperature for 5 hours under a stream of hydrogen. The palladium-on-carbon was then removed from the reaction mixture by filtration using a Celite filter aid, and the filtrate was dried by evaporation under reduced pressure. The residue was purified by silica gel flash chromatography, using a 6:4 by volume mixture of cyclohexane and ethyl acetate as the eluent, to obtain 0.38 g (yield 25%) of the title compound as a solid.

Infrared Absorption Spectrum (Nujol) $v_{max}$ cm$^{-1}$: 3600–3100, 1740, 1720, 1645, 1590.

Elemental analysis: Calculated for $C_{60}H_{99}NO_{12}FP$: C, 66.95%; H, 9.27%; N, 1.30%; F, 1.76%; P, 2.88%. Found: C, 67.04%.; H, 8.98%; N, 1.37%; F, 1.59%; P, 3.06%.

14(c) 1,2-Dideoxy-1-fluoro-2-[(S)-3'-hydroxytetradecanoylamino]-3-O-[(R)-3"-tetradecanoyloxytetradecanoyl]-α-D-glucopyranosyl-4-phosphate 80 mg of the compound obtained as described in Example 14(b) were dissolved in 3 ml of dry tetrahydrofuran, and 16 mg of platinum oxide were added to the resulting solution, after which the mixture was stirred at room temperature for 4 hours under a stream of hydrogen. The reaction mixture was then heated to 45° C. to dissolve insolubles, after which it was filtered using a Celite filter aid. The solvent was then removed from the filtrate by evaporation under reduced pressure to obtain 60 mg (yield 87%) of the title compound as a solid.

Nuclear Magnetic Resonance Spectrum (deuteropyridine, 270 MHz) δ ppm:

0.80–0.97 (9H, multiplet);
1.10–1.90 (62H, multiplet);
2.46 (2H, triplet, J=7.3 Hz);
2.82 (2H, doublet, J=5.9 Hz);
3.04–3.25 (2H, multiplet);
3.60–3.70 (1H, multiplet);
3.80–4.55 (6H, multiplet);
5.65–7.77 (1H, multiplet);
6.00–6.10 (1H, multiplet);
6.10 (1H, doublet of doublets, J=2.9 & 53.7 Hz);
9.47 (1H, doublet, J=9.3 Hz).

Infrared Absorption Spectrum (Nujol) $v_{max}$ cm$^{-1}$: 3550, 3300, 1730, 1650.

EXAMPLE 15

2,6-Dideoxy-6-fluoro-2-[(R)-3'-hydroxytetradecanoylamino]-3-O-[(R)-3"-tetradecanoyloxytetradecanoyl]-D-glucopyranosyl-4-phosphate 15(a) Allyl 2-[(R)-3'-benzyloxytetradecanoylamino]-2-deoxy-6-O-t-butyldimethylsilyl-3-O-[(R)-3"-tetradecanoyloxytetradecanoyl]-α-D-glucopyranoside 0.49 g (0.5 mmole) of allyl 2-[(R)-2'-benzyloxytetradecanoylamino]-2-deoxy-3-O-[(R)-3'-tetradecanoyloxytetradecanoyl]-α-D-glucopyranoside [prepared as described in Example 13(d)] was dissolved in 10 ml of dry methylene chloride, and 0.15 g (1.25 mmole) of 4-dimethylaminopyridine and 0.11 g (0.75 mmole) of t-butyldimethylsilyl chloride were added to the resulting solution. The mixture was then stirred at room temperature for 4 hours, after which the methylene chloride was removed by evaporation under reduced pressure. The residue was diluted with ethyl acetate and washed with a saturated aqueous solution of sodium hydrogen carbonate and with a saturated aqueous solution of sodium chloride, in that order, after which it was dried over anhydrous magnesium chloride. The mixture was then concentrated by evaporation under reduced pressure. The residue was purified by silica gel flash chromatography, using a 85:15 by volume mixture of cyclohexane and ethyl acetate as the eluent, to obtain 0.53 g (yield 97%) of the title compound as a colorless oil.

Nuclear Magnetic Resonance Spectrum (CDCl$_3$, 270 MHz) δ ppm:

0.08 (6H, singlet);
0.82–0.94 (18H, multiplet);
1.16–1.67 (62H, multiplet);
2.28 (2H, triplet, J=7.6 Hz);
2.35 (2H, doublet, J=5.9 Hz);
2.42–2.63 (2H, multiplet);
3.30 (1H, broad singlet);
3.60–4.10 (7H, multiplet);
4.18–4.30 (1H, multiplet);
4.49, 4.54 (2H, AB quartet, J=12.0 Hz);
4.77 (1H, doublet, J=3.9 Hz);
5.04–5.22 (4H, multiplet);
5.65–5.82 (1H, multiplet);
6.27 (1H, doublet, J=9.3 Hz);
7.22–7.35 (5H, multiplet).

Infrared Absorption Spectrum (Nujol) $v_{max}$ cm$^{-1}$: 3550–3150, 1730, 1650.

15(b) Allyl 2-[(R)-3'-benzyloxytetradecanoylamino]-2-deoxy-4-O-diphenylphosphoryl-6-O-t-butyldimethylsilyl-3-O-[(R)-3"-tetradecanoyloxytetradecanoyl]-α-D-glucopyranoside 100 mg (0.09 mmole) of the compound obtained as described in Example 15(a) and 34 mg (0.27 mmole) of 4-dimethylaminopyridine were dissolved in 2 ml of dry methylene chloride, and 1 ml of a solution of 70 mg (0.27 mmole) of diphenyl chlorophosphate in dry methylene chloride was gradually added to the resulting solution. The mixture was then stirred at room temperature for 1 hour, after which the methylene chloride was removed by evaporation under reduced pressure; the residue was diluted with ethyl acetate and was washed with a saturated aqueous solution of sodium hydrogen carbonate and with a saturated aqueous solution of sodium chloride, in that order, after which the mixture was dried over anhydrous magnesium sulfate and concentrated by evaporation under reduced pressure. The residue was purified by silica gel flash chromatography, using a 9:1 by volume mixture of cyclohexane and ethyl acetate as the eluent, to obtain 110 mg (yield 94%) of the title compound as a colorless oil.

Nuclear Magnetic Resonance Spectrum (CDCl$_3$, 270 MHz) δ ppm:

0.013 (6H, singlet);
0.82–0.95 (18H, multiplet);

1.10–2.66 (62H, multiplet);
2.14 (2H, triplet, J=6.3–8.3 Hz);
2.35 (2H, doublet, J=5.9 Hz);
2.44 (2H, doublet, J=6.8 Hz);
3.65–4.12 (7H, multiplet);
4.23–4.35 (1H, multiplet);
4.53, 4.57 (2H, AB quartet, J=11.5 Hz);
4.67 (1H, doublet of doublets, J=9.3 & 18.6 Hz);
4.80 (1H, doublet, J=3.4 Hz);
5.05–5.25 (3H, multiplet);
5.43 (1H, doublet of doublets, J=9.3 & 10.7 Hz);
5.67–5.85 (1H, multiplet);
6.23 (1H, doublet, J=9.3 Hz);
7.12–7.40 (15H, multiplet).

Infrared Absorption Spectrum (liquid film) $v_{max}$ cm$^{-1}$: 3350, 1740, 1675, 1590.

15(c) Allyl 2-[(R)-3'-benzyloxytetradecanoylamino]-2-deoxy-4-O-diphenylphosphoryl-3-O-[(R)-3"-tetradecanoyloxytetradecanoyl]-α-D-glucopyranoside 100 mg of the compound obtained as described in Example 15(b) were dissolved in 2 ml of tetrahydrofuran, and 0.4 ml of 3N aqueous hydrochloric acid was added to the resulting solution, after which the mixture was stirred at room temperature for 3 hours. At the end of this time, the tetrahydrofuran was removed by evaporation under reduced pressure. The residue was dissolved in ethyl acetate and washed with a saturated aqueous solution of sodium hydrogen carbonate and with a saturated aqueous solution of sodium chloride, in that order, after which the mixture was dried over anhydrous magnesium sulfate and concentrated by evaporation under reduced pressure. The residue was purified by silica gel flash chromatography, using a 7:3 by volume mixture of cyclohexane and ethyl acetate as the eluent, to obtain 90 mg (yield 95%) of the title compound as a solid.

Infrared Absorption Spectrum (Nujol) $v_{max}$ cm$^{-1}$: 3470, 3330, 1735, 1720, 1650, 1590.

Elemental analysis: Calculated for $C_{70}H_{110}O_{13}NP$: C, 69.80%; H, 9.20%; N, 1.16%; P, 2.57%. Found: C, 70.07%; H, 9.20%; N, 1.21%; P, 2.30%.

15(d) Allyl 2-[(R)-3'-benzyloxytetradecanoylamino]-2,6-dideoxy-4-O-diphenylphosphoryl-6-fluoro-3-O-[(R)-3'-tetradecanoyloxytetradecanoyl]-α-D-glucopyranoside 0.7 ml of a solution of 70 mg (0.06 mmole) of the compound obtained as described in Example 15(c) in dry methylene chloride was gradually added to 0.8 ml of a solution of 40 mg (0.23 mmole) of diethylaminosulfur trifluoride in dry methylene chloride, whilst ice-cooling, and the mixture was stirred, whilst ice-cooling, for 3 hours. At the end of this time, the mixture was stirred at room temperature for a further 30 minutes. The reaction mixture was then poured into 40 ml of ice-water, and the methylene chloride layer was collected. The aqueous layer was extracted with methylene chloride, washed with a saturated aqueous solution of sodium chloride, and dried over anhydrous magnesium sulfate, after which the mixture was concentrated by evaporation under reduced pressure. The residue was purified by silica gel flash chromatography, using a 8:2 by volume mixture of cyclohexane and ethyl acetate as the eluent, to obtain 60 mg (yield 87%) of the title compound as a solid.

Nuclear Magnetic Resonance Spectrum (CDCl$_3$, 270 MHz) δ ppm:
0.88 (9H, triplet, J=7.3–7.8 Hz);
1.10–1.65 (62H, multiplet);
2.15 (2H, triplet, J=7.6 Hz);
2.34 (2H, doublet, J=5.9 Hz);
2.42 (2H, doublet, J=6.3 Hz);
3.70–4.07 (4H, multiplet);
4.27–4.55 (3H, multiplet);
4.69 (1H, doublet of doublets, J=9.3 & 19.0 Hz);
4.84 (1H, doublet, J=3.9 Hz);
5.03–5.24 (3H, multiplet);
5.43 (1H, doublet of doublets, J=9.3 & 10.7 Hz);
5.63–5.80 (1H, multiplet);
6.25 (1H, doublet, J=8.8 Hz);
7.12–7.38 (15H, multiplet).

Infrared Absorption Spectrum (Nujol) $v_{max}$ cm$^{-1}$: 3330, 1740, 1730, 1660, 1600.

15(e) 2-[(R)-3'-Benzyloxytetradecanoylamino]-2,6-dideoxy-4-O-diphenylphosphoryl-6-fluoro-3-O-[(R)-3"-tetradecanoyloxytetradecanoyl]-D-glucopyranose 16 mg (0.019 mmole) of bis(methyldiphenylphosphine) cyclooctadiene iridium (I) hexafluorophosphate were added to 10 ml of a solution of 460 mg (0.37 mmole) of the compound obtained as described in Example 15(d) in dry tetrahydrofuran, and the iridium complex was activated with hydrogen, after which the mixture was stirred under a stream of nitrogen for 3 hours. At the end of this time, 0.19 g (0.74 mmole) of iodine, 1 ml of water and 0.12 g (1.48 mmole) of pyridine were added to the reaction mixture and the resulting mixture was stirred at room temperature for 30 minutes, after which the mixture was concentrated by evaporation under reduced pressure. The residue was dissolved in 80 ml of ethyl acetate and washed with a 5% w/v aqueous solution of sodium thiosulfate, with a saturated aqueous solution of sodium hydrogen carbonate and with a saturated aqueous solution of sodium chloride, in that order, after which the mixture was dried over anhydrous magnesium sulfate. The solvent was then removed by evaporation under reduced pressure, and the resulting residue was purified by silica gel flash chromatography, using a 75:25 by volume mixture of cyclohexane and ethyl acetate as the eluent, to obtain 370 mg (yield 85%) of the title compound as a pale yellow solid.

Nuclear Magnetic Resonance Spectrum (CDCl$_3$, 270 MHz) δ ppm:
1.07–1.72 (62H, multiplet);
2.15 (2H, triplet, J=7.6 Hz);
2.25–2.45 (5H, multiplet);
3.82–4.25 (3H, multiplet);
4.39, 4.62 (2H, AB quartet, J=11.2 Hz);
4.42 (2H, doublet of doublets, J=2.4 & 46.9 Hz);
4.67 (1H, doublet of doublets, J=9.3 & 19.1 Hz);
5.04 (1H, doublet, J=3.4 Hz);
5.04–5.15 (1H, multiplet);
5.41 (1H, doublet of doublets, J=9.3 & 10.7 Hz);
6.22 (1H, doublet, J=8.8 Hz);
7.12–7.40 (15H, multiplet).

Infrared Absorption Spectrum (Nujol) $v_{max}$ cm$^{-1}$: 3400, 1740, 1720, 1665, 1590.

15(f) 2,6-Dideoxy-4-O-diphenylphosphoryl-6-fluoro-2-[(R)-3'-hydroxytetradecanoylamino]-3-O-[(R)-3"-tetradecanoyloxytetradecanoyl-D-glucopyranose 370 mg of the compound obtained as described in Example 15(e) were dissolved in 4 ml of tetrahydrofuran, and 0.37 g of 10% w/w palladium-on-carbon was added to the resulting solution. 24 ml of methanol and 2 droplets of formic acid were then added to the mixture, after which the mixture was stirred for 3 hours under a stream of hydrogen while heating to 35° C. The reaction mixture was then diluted with tetrahydrofuran and the palladium-on-carbon was removed therefrom by filtration using a Celite filter aid. The filtrate was then dried by evaporation under reduced pressure. The residue was purified by silica gel flash chromatography, using a 65:35 by volume mixture of cyclohexane and ethyl acetate as the eluent, to obtain 220 mg (yield 65%) of the title compound as a solid.

Infrared Absorption Spectrum (Nujol) $v_{max}$ cm$^{-1}$: 3450–3200, 1740, 1642, 1595.

Elemental analysis: Calculated for $C_{60}H_{99}NO_{12}FP$: C, 66.95%; H, 9.27%; N, 1.30%; F, 1.76%; P, 2.88%. Found: C, 67.00%; H, 9.01%; N, 1.39%; F, 1.73%; P, 2.88%.

15(g) 2,6-Dideoxy-6-fluoro-2-[(R)-3'-hydroxytetradecanoylamino]-3-O-[(R)-3"-tetradecanoyloxytetradecanoyl]-D-glucopyranosyl-4-phosphate 0.135 g of the compound obtained as described in Example 15(f) was dissolved in 8 ml of dry tetrahydrofuran, and 27 mg of platinum oxide were added to the resulting solution, after which the mixture was stirred at room temperature for 1 hour under a stream of hydrogen. The reaction mixture was then diluted with tetrahydrofuran to dissolve insolubles and the platinum was removed by filtration. The filtrate was dried by evaporation under reduced pressure to obtain 107 mg (yield 92% ) of the title compound as a powder.

Nuclear Magnetic Resonance Spectrum (deuteropyridine, 270 MHz) δ ppm:

0.80–0.98 (9H, multiplet);

1.12–1.95 (62H, multiplet);

2.47 (2H, triplet, J=7.3 Hz);

2.77–2.92 (2H, multiplet);

2.97–3.36 (2H, multiplet);

3.62–3.70 (1H, multiplet);

4.45–5.80 (7H, multiplet);

6.24 (1H, doublet of doublets, J=8.8 & 10.7 Hz);

8.88 (1H, doublet, J=9.8Hz).

Infrared Absorption Spectrum (Nujol) $v_{max}$ cm$^{-1}$: 3600–3200, 1730, 1640, 1380.

Elemental analysis: Calculated for $C_{48}H_{91}NO_{12}FP$: C, 62.38%; H, 9.92%; N, 1.52%; F, 2.06%; P, 3.35%. Found: C, 61.56%; H, 9.75%; N, 1.50%; F, 1.91%; P, 3.09%.

EXAMPLE 16

2,6-Dideoxy-6-fluoro-2-[(S)-3'-hydroxytetradecanoylamino]-3-O-[(R)-3"-tetradecanoyloxytetradecanoyl]-D-glucopyranosyl-4-phosphate 16(a) Allyl 2-[(S)-3'-benzyloxytetradecanoylamino]-2-deoxy-6-O-t-butyldimethylsilyl-3-O-[(R)-3"-tetradecanoyloxytetradecanoyl]-α-D-glucopyranoside 0.5 g (0.51 mmole) of allyl 2-[(S)-3'-benzyloxytetradecanoylamino]-2-deoxy-3-O-[(R)-3"-tetradecanoyloxytetradecanoyl]-α-D-glucopyranoside [prepared as described in . Example 13(d)] was dissolved in 10 ml of dry methylene chloride, and 0.16 g (1.29 mmole) of 4-dimethylaminopyridine (DMAP) and 0.12 g (0.78 mmole) of t-butyldimethylsilyl chloride were added to the resulting solution, after which the mixture was stirred at room temperature for 4 hours. At the end of this time, the methylene chloride was removed by evaporation under reduced pressure, and the residue was diluted with ethyl acetate. The mixture was then washed with a saturated aqueous solution of sodium hydrogen carbonate and with a saturated aqueous solution of sodium chloride, in that order. It was then dried over anhydrous magnesium sulfate, and the solvent was removed by evaporation under reduced pressure. The residue was purified by silica gel flash chromatography, using a 9:1 by volume mixture of cyclohexane and ethyl acetate as the eluent, to obtain 0.56 g (yield 99%) of the title compound as a colorless oil.

Infrared Absorption Spectrum (liquid film) $v_{max}$ cm$^{-1}$: 3600–3150, 1730, 1650.

Elemental analysis:

Calculated for $C_{64}H_{115}NO_{10}Si$: C, 70.74%; H, 10.67%; N, 1.29%. Found: C, 70.93%; H, 10.40%; N, 1.24%.

16(b) Allyl 2-[(S)-3'-benzyloxytetradecanoylamino]-2-deoxy-4-O-diphenylphosphoryl-6-O-t-butyldimethylsilyl-3-O-[(R)-3"-tetradecanoyloxytetradecanoyl]-α-D-glucopyranoside 0.56 g (0.51 mmole) of the compound obtained as described in Example 16(a) and 0.19 g (1.54 mmole) of 4-dimethylaminopyridine were dissolved in 12 ml of dry methylene chloride, and 4 ml of a solution of diphenyl chlorophosphate in dry methylene were gradually added to the solution, after which the mixture was stirred at room temperature for 4 hours. At the end of this time, the methylene chloride was removed by evaporation under reduced pressure and the residue was diluted with ethyl acetate. The mixture was then washed with a saturated aqueous solution of sodium hydrogen carbonate and with a saturated aqueous solution of sodium chloride, in that order, after which it was dried over anhydrous magnesium sulfate. The solvent was then removed by evaporation under reduced pressure, and the resulting residue was purified by silica gel flash chromatography, using a 9:1 by volume mixture of cyclohexane and ethyl acetate as the eluent, to obtain 0.63 g (yield 93%) of the title compound as a colorless oil.

Infrared Absorption Spectrum (liquid film) $v_{max}$ cm$^{-1}$: 3350, 1735, 1670, 1590.

Elemental analysis: Calculated for $C_{76}H_{124}NO_{13}PSi$: C, 69.21%; H, 9.48%; N, 1.06%; P, 2.35%. Found: C, 69.37%; H, 9.22%; N, 1.05%; P, 2.29%.

16(c) Allyl 2-[(S)-3'-benzyloxytetradecanoylamino]-2-deoxy-4-O-diphenylphosphoryl-3-O-[(R)-3"-tetradecanoyloxytetradecanoyl]-α-D-glucopyranoside 0.56 g (0.42 mmole) of the compound obtained as described in Example 16(b) was dissolved in 10 ml of tetrahydrofuran, and 2 ml of 3N aqueous hydrochloric acid were added to the resulting solution, after which the mixture was stirred at room temperature for 4 hours. At the end of this time, the tetrahydrofuran was removed by evaporation under reduced pressure, and the residue was dissolved in ethyl acetate. The mixture was then washed with a saturated aqueous solution of sodium hydrogen carbonate and with a saturated aqueous solution of sodium chloride, in that order, after which it was dried over anhydrous magnesium sulfate. The solvent was then removed by evaporation under reduced pressure, and the residue was purified by silica gel flash chromatography, using a 7:3 by volume mixture of cyclohexane and ethyl acetate as the eluent, to obtain 0.45 g (yield 89%) of the title compound as a powder.

Infrared Absorption Spectrum (Nujol) $v_{max}$ cm$^{-1}$: 3450, 3320, 1730, 1650, 1585.

Elemental analysis: Calculated for $C_{70}H_{110}NO_{13}P$: C, 69.80%; H, 9.20%; N, 1.16%; P, 2.57%. Found: C, 70.07%; H, 9.13%; N, 1.16%; P, 2.53%.

16(d) Ally 2-[(S)-3'-benzyloxytetradecanoylamino]-2,6-dideoxy-4-O-diphenylphosphoryl-6-fluoro-3-O-[(R)-3"-tetradecanoyloxytetradecanoyl]-α-D-glucopyranoside 4 ml of a solution of 0.39 g (0.32 mmole) of the compound obtained as described in Example 1.6(c) in dry methylene chloride were gradually added to 4 ml of a solution of 0.21 g (1.3 mmole) of diethylaminosulfur trifluoride in dry methylene chloride, whilst ice-cooling, and the mixture was stirred for 3 hours, whilst ice-cooling; the mixture was then stirred at room temperature for a further 30 minutes. At the end of this time, the reaction mixture was poured into 40 ml of ice-water and the methylene chloride layer was collected. The aqueous layer was extracted with methylene chloride, washed with a saturated aqueous solution of sodium chlorine and dried over anhydrous magnesium sulfate, after which the mixture was concentrated by evaporation under reduced pressure. The residue was purified by silica gel flash chromatography, using a 8:2 by volume mixture of cyclohexane and ethyl acetate as the eluent, to obtain 0.36 g (yield 91%) of the title compound as a powder.

Infrared Absorption Spectrum (liquid film) $v_{max}$ cm$^{-1}$: 3350, 1740, 1675, 1590.

Elemental analysis: Calculated for $C_{70}H_{109}O_{12}NPF$: C, 69.68%; H, 9.11%; N, 1.16%; P, 1.57%; F, 2.57%. Found: C, 69.88%; H, 9.09%; N, 1.19%; P, 1.60%; F, 2.58%.

16(e) 2-[(S)-3'-Benzyloxytetradecanoylamino]-2,6-dideoxy-4-O-diphenylphosphoryl-6-fluoro-3-O-[(R)-3"-tetradecanoyloxytetradecanoyl]-D-glucopyranose 3.6 mg (0.004 mmole) of bis(methyldiphenylphosphine) cyclooctadiene iridium (I) hexafluorophosphate were added to 2 ml of a solution of 100 mg (0.08 mmole) of the compound obtained as described in Example 16(d) in dry tetrahydrofuran, and the iridium complex was activated with hydrogen, after which the mixture was stirred at room temperature for 3 hours under a stream of nitrogen. 40 mg (0.17 mmole) of iodine, 0.2 ml of water and 30 mg (0.33 mmole) of pyridine were then added to the reaction mixture, and the resulting mixture was stirred at room temperature for 30 minutes, after which the mixture was concentrated by evaporation under reduced pressure. The residue was dissolved in 20 ml of ethyl acetate, and the resulting solution was washed with a 5% aqueous solution of sodium thiosulfate, with a saturated aqueous solution of sodium hydrogen carbonate and with a saturated aqueous solution of sodium chloride, in that order; it was then dried over anhydrous magnesium sulfate. The solvent was then removed by evaporation under reduced pressure, and the resulting residue was purified by silica gel flash chromatography, using a 3:1 by volume mixture of cyclohexane and ethyl acetate as the eluent, to obtain 90 mg (yield 90%) of the title compound as a pale yellow powder.

Infrared Absorption Spectrum (Nujol) $v_{max}$ cm$^{-1}$: 3400, 1735, 1720, 1665, 1590.

Elemental analysis: Calculated for $C_{67}H_{105}NO_{12}PF$: C, 68.98%; H, 9.07%; N, 1.20%; F, 1.63%; P, 2.66%. Found: C, 69.04%; H, 9.16%; N, 1.12%; F, 1.60%; P, 2.53%.

16(f) 2,6-Dideoxy-4-O-diphenylphosphoryl-6-fluoro-2-[(S)-3'-hydroxytetradecanoylamino]-3-O-[(R)-3"-tetradecanoyloxytetradecanoyl)-D-glucopyranose 0.20 g of the compound obtained as described in Example 16(e) was dissolved in 2 ml of tetrahydrofuran, and 0.2 g of 10% w/w palladium-on-carbon was added to the resulting solution. 12 ml of methanol and one droplet of formic acid were then added to the mixture, after which the mixture was stirred for 5 hours under a stream of hydrogen whilst being heated to 35° C. At the end of this time, the reaction mixture was diluted with tetrahydrofuran and the palladium-on-carbon was removed by filtration using a Celite filter aid. The filtrate was dried by evaporation under reduced pressure, and the residue was purified by silica gel flash chromatography, using a 7:3 by volume mixture of cyclohexane and ethyl acetate as the eluent, to obtain 0.15 g (yield 81%) of the title compound as a solid.

Infrared Absorption Spectrum (Nujol) $v_{max}$ cm$^{-1}$: 3600–3100, 1730, 1660, 1590.

Elemental analysis:
Calculated for $C_{60}H_{99}NO_{12}PF$: C, 66.95%; H, 9.27%; N, 1.30%; F, 1.76%; P, 2.88%. Found: C, 67.03%; H, 9.22%; N, 1.38%; F, 1.71%; P, 2.70%.

16(g) 2,6-Dideoxy-6-fluoro-2-[(S)-3'-hydroxytetradecanoylamino]-3-O-[(R)-3"-tetradecanoyloxytetradecanoyl]-D-glucopyranosyl-4-phosphate 72 mg of the compound obtained as described in Example 16(f) were dissolved in 4 ml of dry tetrahydrofuran, and 15 mg of platinum oxide were added to the resulting solution, after which the mixture was stirred at room temperature for 30 minutes under a stream of hydrogen. The reaction mixture was then diluted with tetrahydrofuran, and the mixture was heated to 45° C. to dissolve a substance resembling agar-agar. Subsequently, the platinum was removed by filtration, and the filtrate was dried by evaporation under reduced pressure to obtain 62 mg of the title compound quantitatively.

Nuclear Magnetic Resonance Spectrum (deuteropyridine, 270 MHz) δ ppm:

0.80–0.97 (9H, multiplet);
1.10–1.90 (62H, multiplet);
2.45 (2H, triplet, J=7.3 Hz);
2.84 (2H, doublet, J=5.9 Hz).;
3.11 (1H, doublet of doublets, J=6.4 & 16.3 Hz);
3.27 (1H, doublet of doublets, J=6.4 & 16.3 Hz);
3.62–3.70 (1H, multiplet);
4.38–5.50 (7H, multiplet);
6.25 (1H, doublet of doublets, J=9.3 & 10.9 Hz).

Infrared Absorption Spectrum (Nujol) $v_{max}$ cm$^{-1}$: 3600–3200, 1730, 1700, 1650.

EXAMPLE 17

2-deoxy-2-[(3'R)-3'-hydroxytetradecanoylamino]-3-O-[(3"R)-3"-(2,2-difluorotetradecanoyloxy) tetradecanoyl]-D-glucopyranosyl-4-phosphate 17(a) Allyl 2-deoxy-2-[(3'R)-3'-benzyloxytetradecanoylamino]-3-O-[(3"R)-3"-(2,2-difluorotetradecanoyloxy) tetradecanoyl]-4,6-O-isopropylidene-β-D-glucopyranoside 4.1 g (7.12 mmole) of allyl 2-deoxy-2-[(3'R)-3'-benzyloxytetradecanoylamino]-4,6-O-isopropylidene-β-D-glucopyranoside [prepared as described in Example 1(e)] were dissolved in 100 ml of diethyl ether. 4.54 g (9.26 mmole) of (3R)-3-(2',2'-difluorotetradecanoyloxy) tetradecanoic acid, followed by 1.9 g (9.26 mmole) of N,N'-dicyclohexylcarbodiimide and 0.087 g (0.712 mmole) of 4-dimethylaminopyridine were then added to the resulting solution. The resulting mixture was then stirred for 1 hour at room temperature, after which the solvent was removed by evaporation under reduced pressure, and ethyl acetate was added to the mixture. The resulting precipitate was filtered off, and the ethyl acetate layer was washed with a saturated aqueous solution of sodium bicarbonate and with a saturated aqueous solution of sodium chloride, in that order; it was then dried over anhydrous magnesium sulfate. The ethyl acetate was then removed by evaporation under reduced pressure, and the resulting residue was purified by silica gel column chromatography using a 5:1 by volume mixture of cyclohexane and ethyl acetate as the eluent, to give 5.5 g (yield 74%) of the title compound.

Nuclear Magnetic Resonance Spectrum (CDCl₃, 270 MHz), δ ppm:

0.88 (9H, triplet, J=6.6 Hz);
1.16–1.72 {66H, multiplet [including 1.36(3H, singlet), 1.45(3H, singlet)]};
1.93–2.08 (2H, multiplet);
2.32–2.45 (2H, multiplet);
2.55 (1H, doublet of doublets, J=5.9 & 16.1 Hz);
2.69 (1H, doublet of doublets, J=7.3 & 16.1 Hz);
3.18–3.28 (1H, multiplet);
3.64–3.82 (4H, multiplet);
3.85–3.99 (3H, multiplet);
4.18–4.17 (1H, multiplet);
4.34 (1H, doublet, J=8.1 Hz);
4.47 (1H, doublet, J=11.7 Hz),
4.59 (1H, doublet, J=11.7 Hz);
5.05–5.36 (3H, multiplet);
5.71–5.83 (1H, multiplet);
6.33 (1H, doublet, J=9.5 Hz);
7.23–7.41 (5H, multiplet).

Infrared Absorption Spectrum (CHCl₃), $v_{max}$ cm⁻¹: 1765, 1675.

Mass spectrum (m/z): 1048 (M⁺+1), 1032, 1006, 941, 822, 806, 780, 742, 715, 677, 657, 634, 596, 558, 516, 502, 472, 388, 361, 334, 318, 276, 250, 209, 151, 101, 91, 55, 41.

Elemental analysis: Calculated for $C_{61}H_{103}F_2NO_{10}$ (molecular weight, 1048.5): C, 69.88%; H, 9.90%; N, 1.34%; F, 3.62%. Found: C, 70.04%; H, 9.74%; N, 1.45%; F, 3.55%

17(b) Allyl 2-deoxy-2-[(3'R)-3'-benzyloxytetradecanoylamino]-3-O-[(3"R)-3"-(2,2-difluorotetradecanoyloxy)tetradecanoyl]-β-D-glucopyranoside 4.8 g (4.58 mmole) of the compound obtained as described in Example 17(a) above were suspended in 200 ml of 90% aqueous acetic acid. The resulting suspension was then stirred for 2 hours at 50° C. At the end of this time, the acetic acid was removed by evaporation under reduced pressure, and the residue was purified by silica gel column chromatography, using a 1:1 by volume mixture of cyclohexane and ethyl acetate as the eluent, to give 3.1 g (yield 67%) of the title compound.

Nuclear Magnetic Resonance Spectrum (CDCl₃, 270 MHz), δ ppm:

0.82–0.95 (9H, multiplet);
1.15–1.77 (60H, multiplet);
1.91–2.12 (3H, multiplet);
2.31–2.48 (2H, multiplet);
2.55 (1H, doublet of doublets, J=4.4 & 16.1 Hz);
2.68 (1H, doublet of doublets, J=8.3 & 16.1 Hz);
2.73 (1H, doublet, J=4.4 Hz);
3.29–3.38 (1H, multiplet);
3.66 (1H, doubled doublet of doublets, J=4.4, 9.3 & 9.3 Hz);
3.70–4.00 (5H, multiplet);
4.18–4.28 (1H, multiplet);
4.35 (1H, doublet, J=8.3 Hz);
4.47 (1H, doublet, J=11.7 Hz);
4.60 (1H, doublet, J=11.7 Hz);
4.97–5.33 (4H, multiplet);
5.71–5.88 (1H, multiplet);
6.34 (1H, doublet, J=8.8 Hz);
7.28–7.41 (5H, multiplet).

Infrared Absorption Spectrum (CHCl₃), $v_{max}$ cm⁻¹: 1760, 1673.

Elemental analysis: Calculated for $C_{58}H_{99}F_2NO_{10}$ (molecular weight, 1008.4): C, 69.08%; H, 9.90%; N, 1.39%; F, 3.77%. Found: C, 69.17%; H, 9.85%; N, 1.38%; F, 3.62%.

17(c) Allyl 2-deoxy-2-[(3'R)-3'-benzyloxytetradecanoylamino]-3-O-[(3"R)-3"-(2,2-difluorotetradecanoyloxy)tetradecanoyl]-6-O-benzyloxymethyl-β-D-glucopyranoside 2.5 g (2.48 mmole) of the compound obtained as described in Example 17(b) above were dissolved in 50 ml of methylene chloride. 500 mg (3.22 mmole) of benzyl chloromethyl ether were added to this solution, and then 374 mg (3.22 mmole) of tetramethylurea. The mixture was stirred overnight at room temperature. The solvent was removed by evaporation under reduced pressure, and the resulting residue was dissolved in ethyl acetate. The ethyl acetate layer was washed with a saturated aqueous solution of sodium bicarbonate and with a saturated aqueous solution of sodium chloride, in that order; it was then dried over an anhydrous magnesium sulfate. The ethyl acetate was then removed by evaporation under reduced pressure, and the residue was purified by silica gel column chromatography, using a 3:1 by volume mixture of cyclohexane and ethyl acetate as the eluent, to give 1.65 g (yield 59%) of the title compound and 0.95 g of the starting material.

Nuclear Magnetic Resonance Spectrum (CDCl₃, 270 MHz), δ ppm:

0.84–0.94 (9H, multiplet);
16–1.75 (60H, multiplet);
1.91–2.11 (2H, multiplet);
2.32–2.46 (2H, multiplet);
2.51–2.73 (3H, multiplet);
3.35–3.46 (1H, multiplet);
3.60–3.99 (6H, multiplet);
4.18–4.30 (1H, multiplet);
4.34 (1H, doublet, J=8.3 Hz);
4.44–4.66 (4H, multiplet);
4.79 (2H, singlet);
4.98–5.38 (4H, multiplet);
5.69–5 87 (1H, multiplet);
6.89 (1H, doublet, J=8.8 Hz);
7.23–7.43 (10H, multiplet).

Infrared Absorption Spectrum (CHCl₃), $v_{max}$ cm⁻¹: 1760, 1675.

Elemental analysis: Calculated for $C_{66}H_{107}F_2NO_{11}$ (molecular weight, 1128.6): C, 70.24%; H, 9.56%; N, 1.24%; F, 3.37%. Found: C, 70.03%; H, 9.49%; N, 1.29%; F, 3.38%.

17(d) Allyl 2-deoxy-2-[(3'R)-3'-benzyloxytetradecanoylamino]-3-O-[(3"R)-3"-(2,2-difluorotetradecanoyloxy)tetradecanoyl]-4-O-diphenylphosphoryl-6-O-benzyloxymethyl-β-D-glucopyranoside 610 mg (0.54 mmole) of the compound obtained as described in Example 17(c) were dissolved in 20 ml of methylene chloride. 100 mg (0.59 mmole) of diphenyl chlorophosphate, followed by 33 mg (0.27 mmole) of 4-dimethylaminopyridine were then added to this solution. The mixture was then stirred for 3 hours at room temperature. Whilst confirming the progress of the reaction, a total of 640 mg (2.38 mmole) of diphenyl chlorophosphate and 198 mg (1.62 mmole) of 4-dimethylaminopyridine were added to the reaction mixture in 4 separate portions. The reaction mixture was then washed with 1N aqueous hydrochloric acid, with a saturated aqueous solution of sodium bicarbonate and with a saturated aqueous solution of sodium chloride, in that order; it was then dried over an anhydrous sodium sulfate. The methylene chloride was then removed by evaporation under reduced pressure, and the residue was purified by silica gel column chromatography, using a 4:1 by volume mixture of cyclohexane and ethyl acetate as the eluent, to give 530 mg (yield 72%) of title compound.

Nuclear Magnetic Resonance Spectrum (CDCl$_3$, 270 MHz), δ ppm:

0.83–0.94 (9H, multiplet);
1.08–1.75 (60H, multiplet);
1.87–2.09 (2H, multiplet);
2.29–2.55 (4H, multiplet);
3.56–3.87 (4H, multiplet);
3.94 (1H, doublet of doublets, J=6.4 & 12.7 Hz);
4.24 (1H, doublet of doublets, J=5.4 & 12.7 Hz);
4.43–4.81 (8H, multiplet);
5.03–5.29 (4H, multiplet);
5.50 (1H, doublet of doublets, J=9.3 & 9.8 Hz);
5.69–5.87 (1H, multiplet);
6.34 (1H, doublet, J=8.3 Hz);
7.18–7.39 (20H, multiplet).

Infrared Absorption Spectrum (CHCl$_3$), $\nu_{max}$ cm$^{-1}$: 1760, 1678, 1597, 1496, 960.

Elemental analysis: Calculated for C$_{78}$H$_{116}$NO$_{14}$F$_2$P (molecular weight, 1360.7): C, 68.85%; H, 8.59%; N, 1.03%; F, 2.79%; P, 2.28%. Found: C, 68.15%; H, 8.32%; N, 0.92%; F, 2.60%; P, 2.72%.

17(e) 2-deoxy-2-[(3'R)-3'-benzyloxytetradecanoylamino]-3-O-[(3"R)-3"-(2,2-difluorotetradecanoyloxy)tetradecanoyl]-4-O-diphenylphosphoryl-D-glucopyranose 530 mg (0.39 mmole) of the compound obtained as described in Example 17(d) were dissolved in 5 ml of tetrahydrofuran. 33 mg (10% mmole) of 1,5-cyclooctadiene-bis(methyldiphenylphosphine)iridium hexafluorophosphate were then added to this solution, and the atmosphere in the reaction vessel was replaced first by nitrogen, and then by hydrogen. It was confirmed that the catalyst was activated and that its color had turned from red to colorless, and then the atmosphere in the vessel was again replaced by nitrogen. The reaction mixture was stirred for 3 hours at room temperature, after which 2 ml of concentrated hydrochloric acid were added. The mixture was stirred overnight at room temperature and then the solvent was removed by evaporation under reduced pressure. Ethyl acetate was added to the residue, and the mixture was washed with water, with a saturated aqueous solution of sodium bicarbonate and with a saturated aqueous solution of sodium chloride, in that order; it was then dried over anhydrous magnesium sulfate. The ethyl acetate was removed by evaporation under reduced pressure, and the residue was purified by silica gel column chromatography, using a 1:2 by volume mixture of cyclohexane and ethyl acetate as the eluent, to give 258 mg (yield 55%) of the title compound.

Nuclear Magnetic Resonance Spectrum (CDCl$_3$, 270 MHz), δ ppm:

0.82–0.98 (9H, multiplet);
1.07–1.77 (60H, multiplet);
1.84–2.09 (2H, multiplet);
2.21–2.50 (5H, multiplet);
3.26 (1H, triplet, J=7.3 Hz);
3.52–3.62 (2H, multiplet);
3.81–3.91 (2H, multiplet);
4.19–4.30 (1H, multiplet);
4.39 (1H, doublet, J=11.2 Hz);
4.61 (1H, doublet, J=11.2 Hz);
4.67–4.78 (1H, multiplet);
4.98 (1H, triplet, J=3.9 Hz);
5.19–5.29 (1H, multiplet);
5.41 (1H, doublet of doublets, J=9.3 & 10.7 Hz);
6.23 (1H, doublet, J=9.3 Hz);
7.13–7.38 (15H, multiplet).

Infrared Absorption Spectrum (CHCl$_3$), $\nu_{max}$ cm$^{-1}$: 1750, 1660.

Elemental analysis: Calculated for C$_{67}$H$_{104}$NO$_{13}$FP (molecular weight, 1200.5): C, 67.03%; H, 8.73%; N, 1.17%; F, 3.16%; P, 2.58%. Found: C, 66.91%; H, 8.61%; N, 1.13%; F, 3.04%; P, 2.46%.

17(f) 2-Deoxy-2-[(3'R)-3'-hydroxytetradecanoylamino]-3-O-[(3"R)-3"-(2,2-difluorotetradecanoyloxy)tetradecanoyl]-4-O-diphenylphosphoryl-D-glucopyranose 250 mg (0.21 mmole) of the compound obtained as described in Example 17(e) were dissolved in 10 ml of methanol. 100 mg of 10% w/w palladium-on-carbon were then added to the resulting solution. The reaction mixture was then subjected to catalytic reduction under an atmosphere of hydrogen for 3 hours at room temperature. At the end of this time, the methanol was removed by evaporation under reduced pressure, and the residue was purified by silica gel column chromatography, using ethyl acetate as the eluent, to give 122 mg (yield 53%) of the title compound.

Infrared Absorption Spectrum (CHCl$_3$), $\nu_{max}$ cm$^{-1}$: 3425, 2925, 2855, 1760, 1660, 1590, 1490, 1180, 1157, 965.

Nuclear Magnetic Resonance Spectrum (CDCl$_3$, 270 MHz), δ ppm:

0.82–0.95 (9H, multiplet);
1.07–1.63 (60H, multiplet);
1.80–2.11 (2H, multiplet);
2.17–2.53 (4H, multiplet);
3.20–3.39 (2H, multiplet);
3.55–3.66 (2H, multiplet);
3.70 (1H, doublet, J=3.4 Hz);
3.38–4.04 (2H, multiplet);
4.21–4.33 (1H, multiplet);
4.76 (1H, doublet of doublets, J=9.3 & 9.8 Hz);
5.18–5.28 (1H, multiplet);
5.31 (1H, doublet of doublets, J=3.4 & 3.9 Hz);
5.48 (1H, doublet of doublets, J=9.8 & 10.3 Hz);
6.25 (1H, doublet, J=8.8 Hz);
7.13–7.42 (10H, multiplet).

17(g) 2-Deoxy-2-[(3'R )-3'-hydroxytetradecanoylamino]-3-O-[(3"R)-3"-(2,2-difluorotetradecanoyloxy)tetradecanoyl]-D-glucopyranosyl-4-phosphate 85 mg (0.08 mmole) of the compound obtained as described in Example 17(f) were dissolved in 10 ml of tetrahydrofuran. 15 mg of platinum oxide were then added to this solution, and the reaction mixture was subjected to catalytic reduction under an atmosphere of hydrogen for 5 hours at room temperature. At the end of this time, the tetrahydrofuran was removed by evaporation under reduced pressure, to give 72 mg (yield 98%) of the title compound.

Infrared Absorption Spectrum (KBr), $v_{max}$ cm$^{-1}$: 2956, 2923, 2853, 1761, 1644, 1549, 1467, 1188, 1128, 1058, 972.

EXAMPLE 18

Triethylamine salts of phosphorylated compounds

If it is necessary to obtain a water-soluble triethylamine salt of the phosphorylated compound obtained in any of the foregoing Examples, the following treatment may be carried out.

30 mg of the phosphorylated compound were suspended 8 ml of 0.1N aqueous hydrochloric acid, and 30 ml of a 1:2 by volume mixture of chloroform and methanol were then added thereto, after which the suspended material was dissolved with the aid of ultrasound. 10 ml of chloroform and 10 ml of 0.1N aqueous hydrochloric acid were then added to the solution, which caused the mixture to separate into two layers. The chloroform layer was collected, and the chloroform was removed by evaporation under reduced pressure. The residue was dissolved in 0.1% aqueous triethylamine to obtain an aqueous solution, which could be used as a sample for activity determination.

We claim:

1. A compound of formula (I) having a glucopyran moiety:

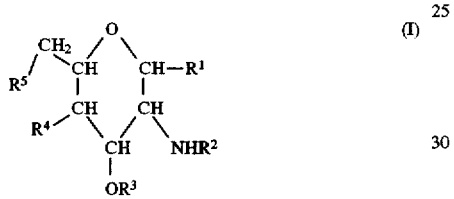

in which:

R$^1$ represents a hydroxy group, a protected hydroxy group as defined below, a fluorine atom, or a group of formula —OP(O)(OH)$_2$;

R$^2$ and R$^3$ are independently selected from the group consisting of aliphatic carboxylic acyl groups having from 6 to 20 carbon atoms, said acyl groups being unsubstituted or having one to three substituents selected from the group consisting of substituents (a), defined below; at least one of R$^2$ and R$^3$ being a fluorine substituted aliphatic carboxylic acyl group;

R$^4$ represents a hydroxy group, a protected hydroxy group as defined below, or a group of formula —OP(O)(OH)$_2$, where at least one of R$^1$ and R$^4$ represents a group of formula —OP(O)(OH)$_2$;

R$^5$ represents a hydroxy group, a protected hydroxy group as defined below, or a fluorine atom;

provided that, except where at least one of R$^1$ and R$^5$ represents a fluorine atom, either:

both or one of R$^2$ and R$^3$ represents an aliphatic carboxylic acyl group having from 6 to 20 carbon atoms and having one to three substituents selected from the group consisting of halogen atoms, hydroxy groups and aliphatic carboxylic acyloxy groups having from 6 to 20 carbon atoms or both or one of R$^2$ and R$^3$ represents a substituted aliphatic acyl group having from 6 to 20 carbon atoms and which is substituted by one to three halogen-substituted aliphatic carboxylic acyloxy group having from 6 to 20 carbon atoms, provided that one of R$^2$ and R$^3$ is a fluorine substituted aliphatic carboxylic acyl group;

said protected hydroxy groups are selected from the group consisting of: aliphatic carboxylic acyloxy groups having from 1 to 20 carbon atoms; halogenated carboxylic acyloxy groups having from 2 to 6 carbon atoms;

alkoxy-substituted carboxylic acyloxy groups in which the alkoxy part has from 1 to 6 carbon atoms and the acyl part has from 2 to 6 carbon atoms;

aromatic carboxylic acyloxy groups in which the aromatic part has from 6 to 14 ring carbon atoms and is unsubstituted or has one to three substituents selected from the group consisting of substituents (b), defined below; groups of formula Het-O- where Het represents a heterocyclic group having 5 or 6 ring atoms of which from 1 to 3 are hetero-atoms selected from the group consisting of nitrogen, oxygen and sulfur atoms, said heterocyclic group being unsubstituted or having one to three substituents selected from the group consisting of substituents (c), defined below; groups of formula R$^a$R$^b$R$^c$Si—O—, where R$^a$, R$^b$ and R$^c$ are independently selected from the group consisting of alkyl groups having from 1 to 6 carbon atoms and carbocyclic aryl groups having from 6 to 10 carbon atoms, said aryl groups being unsubstituted or having one to three substituents selected from the group consisting of substituents (b), defined below; alkoxyalkoxy groups, in which the two alkoxy parts are the same or different and each has from 1 to 6 carbon atoms; aralkyloxy groups in which an alkyl group having from 1 to 6 carbon atoms is substituted with from 1 to 3 aryl groups, said aryl groups being unsubstituted or having one to three substituents selected from the group consisting of substituents (b), defined below; alkoxycarbonyloxy groups, in which the alkoxy part has from 1 to 6 carbon atoms; substituted alkoxycarbonyloxy groups, in which the alkoxy part has 1 to 6 carbon atoms and which is substituted by substituents (d), defined below; alkenyloxycarbonyloxy groups, in which the alkenyl part has from 2 to 6 carbon atoms; alkenyloxy groups having from 2 to 6 carbon atoms; carboxy-substituted aliphatic carboxylic acyloxy groups in which the acyl part has from 1 to 6 carbon atoms, and in which the acyl part is unsubstituted or has one to three hydroxy substituents;

acyloxymethoxycarbonyloxy groups in which the acyl group is a carboxylic acyl group having from 1 to 6 carbon atoms; (arylselenyl)ethoxy groups in which the aryl part has from 6 to 14 ring carbon atoms and is unsubstituted or has one to three substituents selected from the group consisting of substituents (b), defined below;

alkoxyalkoxymethoxy groups, in which each alkoxy part has from 1 to 6 carbon atoms; methoxy groups substituted by one, two or three haloalkoxy substituents, in which the alkoxy part has from 1 to 6 carbon atoms and is substituted by one to three halogen atoms;

haloethoxy groups in which the ethyl part is substituted by one to three halogen atoms; and aralkyloxycarbonyloxy groups, in which the aralkyl part comprises an alkyl group having from 1 to 6 carbon atoms which is substituted with from 1 to 3 aryl groups, said aryl groups being unsubstituted or having one to three substituents selected from the group consisting of substituents (b), defined below;

substituent (a):

halogen atoms; aryl group having from 6 to 14 carbon atoms and being unsubstituted or having one to three substituents selected from the group consisting of substituents (b), defined below; aralkyl groups, in which an alkyl group having from 1 to 6 carbon atoms is substituted with from 1 to 3 aryl groups, said aryl groups being unsubstituted or having one to three substituents selected from the group consisting of substituents (b), defined below; hydroxy groups; aliphatic carboxylic acyloxy groups having from 6 to 20 carbon atoms; and halogen-substituted aliphatic carboxylic acyloxy groups having from 6 to 20 carbon atoms;

substituents (b):

halogen atoms; alkyl groups having from 1 to 6 carbon atoms; halogen-substituted alkyl groups having from 1 to 6 carbon atoms; alkoxy groups having from 1 to 6 carbon atoms; nitro groups; alkoxycarbonyl groups, in which the alkoxy part has from 1 to 6 carbon atoms; aryl groups having from 6 to 14 ring carbon atoms and being unsubstituted or having one to three substituents selected from the group consisting of substituents (b') defined below; cyano groups; alkylenedioxy groups having from 1 to 4 carbon atoms; divalent aliphatic hydrocarbon groups having from 1 to 4 carbon atoms; groups of formula —$NR^dR^e$, where $R^d$ and $R^e$ are independently selected from the group consisting of hydrogen atoms and alkyl groups having from 1 to 6 carbon atoms; haloalkoxycarbonyl groups, in which the alkoxy part has from 1 to 6 carbon atoms;

aralkyloxycarbonyl groups, in which the aralkyl part comprises an alkyl group having from 1 to 6 carbon atoms which is substituted with from 1 to 3 aryl groups, said aryl groups being unsubstituted or having one to three substituents selected from the group consisting of substituents (b'), defined below; groups of formula —CO—$NR^dR^e$, where $R^d$ and $R^e$ are as defined above;

and aliphatic acyl groups having from 1 to 20 carbon atoms;

substituents (c):

halogen atoms; alkyl groups having from 1 to 6 carbon atoms; halogen-substituted alkyl groups having from 1 to 6 carbon atoms; alkoxy groups having from 1 to 6 carbon atoms; aryl groups having from 6 to 14 ring carbon atoms and being unsubstituted or having one to three substituents selected from the group consisting of substituents (b') defined below; and oxygen atoms;

substituents (d):

halogen atoms; groups of formula $R^aR^bR^c$Si—O—, where $R^a$, $R^b$ and $R^c$ are as defined above; and alkanoyloxy groups, where the alkanoyl group thereof has from 1 to 6 carbon atoms;

substituents (b'):

halogen atoms; alkyl groups having from 1 to 6 carbon atoms; halogen-substituted alkyl groups having from 1 to 6 carbon atoms; alkoxy groups having from 1 to 6 carbon atoms; nitro groups; alkoxycarbonyl groups, in which the alkoxy part has from 1 to 6 carbon atoms; cyano groups; alkylenedioxy groups having from 1 to 4 carbon atoms; divalent aliphatic hydrocarbon groups having from 1 to 4 carbon atoms; groups of formula —$NR^dR^e$, where $R^d$ and $R^e$ are independently selected from the group consisting of hydrogen atoms and alkyl groups having from 1 to 6 carbon atoms; haloalkoxycarbonyl groups, in which the alkoxy part has from 1 to 6 carbon atoms;

groups of formula —CO—$NR^dR^e$, where $R^d$ and $R^e$ are as defined above; and aliphatic acyl groups having from 1 to 20 carbon atoms;

and salts thereof and, where the compound of formula (I) includes a carboxy group, esters thereof.

2. The compound of claim 1, wherein:

one of $R^1$ and $R^4$ represents a hydroxy group, a protected hydroxy group as defined in claim 1, or a group of formula —OP(O)(OH)$_2$, and the other represents a group of formula —OP(O)(OH)$_2$;

one of $R^2$ and $R^3$ represents an aliphatic carboxylic acyl group having from 6 to 20 carbon atoms, said aliphatic carboxylic acyl group being unsubstituted or substituted by at least one halogen substituent or a substituent selected from the group consisting of hydroxy groups, aliphatic carboxylic acyloxy groups having from 6 to 20 carbon atoms and halogen-substituted aliphatic carboxylic acyloxy groups having from 6 to 20 carbon atoms, and the other of $R^2$ and $R^3$ represents an aliphatic carboxylic acyl group having from 6 to 20 carbon atoms and substituted by one to three halogen substituents and 1 substituent selected from the group consisting of hydroxy groups and an aliphatic carboxylic acyloxy group having 6 to 20 carbon atoms or substituted by one to three halogen-substituted aliphatic carboxylic acyloxy groups having from 6 to 20 carbon atoms and being unsubstituted or substituted by a substituent selected from the group consisting of halogen atoms, hydroxy groups and aliphatic carboxylic acyloxy groups having from 6 to 20 carbon atoms;

provided that one of $R^2$ and $R^3$ is a fluorine substituted aliphatic carboxylic acyl group;

$R^5$ represents a hydroxy group or a protected hydroxy group, as defined in claim 1.

3. The compound of claim 2, wherein the glucopyran moiety has the D configuration.

4. The compound of claim 2, wherein one of $R^1$ and $R^4$ represents a group of formula —OP(O)(OH)$_2$, and the other represents a hydroxy group or a group of formula —OP(O)(OH)$_2$.

5. The compound of claim 2, wherein one of $R^2$ and $R^3$ represents aliphatic carboxylic acyl group having from 10 to 16 carbon atoms, said an aliphatic carboxylic acyl group having one to three halogen substituents and 0 or 1 substituent selected from the group consisting of hydroxy groups and aliphatic carboxylic acyloxy groups having from 10 to 16 carbon atoms, and the other of $R^2$ and $R^3$ represents an aliphatic carboxylic acyl group having from 10 to 16 carbon atoms, said group having one to three substituents selected from the group consisting of halogen atoms, hydroxy groups and aliphatic carboxylic acyloxy groups having from 10 to 16 carbon atoms, provided that one of $R^2$ and $R^3$ is a fluorine substituted aliphatic carboxylic acyl group.

6. The compound of claim 5, wherein $R^2$ represents an aliphatic carboxylic acyl group having from 10 to 16 carbon atoms, said aliphatic carboxylic acyl group having one to three halogen substituents and 0 or 1 substituent selected from the group consisting of hydroxy groups and aliphatic carboxylic acyloxy groups having from 10 to 16 carbon atoms.

7. The compound of claim 2, wherein $R^5$ represents a hydrogen atom or a carboxy-substituted aliphatic carboxylic acyloxy group in which the acyl part has from 1 to 6 carbon atoms and the carboxy substituent is at the terminal remote from the oxy group of the acyloxy.

117

8. The compound of claim 1, wherein:

one of $R^1$ and $R^5$ represents a hydroxy group or a protected hydroxy group, as defined in claim 1, and the other represents a fluorine atom;

$R^2$ and $R^3$ are independently selected from the group consisting of aliphatic carboxylic acyl groups having from 6 to 20 carbon atoms, said acyl groups being unsubstituted or having one to three substituents selected from the group consisting of substituent (a) as defined in claim 1, provided that one of $R^2$ and $R^3$ is a fluorine substituted aliphatic carboxylic acyl group;

$R^4$ represents a group of formula —OP(O)(OH)$_2$.

9. The compound of claim 8, wherein the glucopyran moiety has the D configuration.

10. The compound of claim 8, wherein $R^1$ represents a hydroxy group or a protected hydroxy group, as defined in claim 3.

11. The compound of claim 8, wherein one of $R^2$ and $R^3$ represents an aliphatic carboxylic acyl group having from 12 to 16 carbon atoms which is unsubstituted or is substituted by one to three substituents selected from the group consisting of halogen atoms, hydroxy groups, unsubstituted aliphatic carboxylic acyloxy groups having from 12 to 16 carbon atoms and halogen-substituted aliphatic carboxylic acyloxy groups having from 12 to 16 carbon atoms, provided that said aliphatic carboxylic acyl group is substituted by no more than one of said hydroxy groups and by no more than one said acyloxy group, and the other of $R^2$ and $R^3$ represents a substituted aliphatic carboxylic acyl group having from 12 to 16 carbon atoms and which is substituted by one to three halogen substituents and 0 or 1 substituent selected from the group consisting of hydroxy groups and aliphatic carboxylic acyloxy groups having from 2 to 16 carbon atoms and provided that one of $R^2$ and $R^3$ is a fluorine substituted aliphatic carboxylic acyl group.

12. The compound of claim 8, wherein $R^5$ represents a fluorine atom.

13. The compound of claim 8, wherein:

$R^1$ represents a hydroxy group or a protected hydroxy group, as defined in claim 8;

one of $R^2$ and $R^3$ represents an aliphatic carboxylic acyl group having from 12 to 16 carbon atoms or a substituted aliphatic carboxylic acyl group having from 12 to 16 carbon atoms and which is substituted by one to three substituents selected from the group consisting of halogen atoms, hydroxy groups and aliphatic carboxylic acyloxy groups having from 12 to 16 carbon atoms, provided that it is substituted by no more than one of said hydroxy groups and by no more than one of said acyloxy groups, and the other of $R^2$ and $R^3$ represents a substituted aliphatic carboxylic acyl group having from 12 to 16 carbon atoms which is substituted by one to three halogen substituents and 0 or 1 substituent selected from the group consisting of hydroxy groups and aliphatic carboxylic acyloxy groups having from 12 to 16 carbon atoms and provided that one of $R^2$ and $R^3$ is a fluorine substituted aliphatic carboxylic acyl group;

$R^4$ represents a group of formula —OP(O)(OH)$_2$; and $R^5$ represents a fluorine atom.

14. The compound of claim 13, wherein the glucopyran moiety has the D configuration.

15. The compound of claim 8, wherein $R^1$ represents a hydroxy group.

16. The compound of claim 8, wherein one of $R^2$ and $R^3$ represents an aliphatic carboxylic acyl group having from 10 to 16 carbon atoms, said aliphatic carboxylic acyl group having one to three halogen substituents and 0 to 1 substituent selected from the group consisting of hydroxy groups and aliphatic carboxylic acyloxy groups having from 10 to 16 carbon atoms, and the other of $R^2$ and $R^3$ represents an aliphatic carboxylic acyl group having from 10 to 16 carbon atoms, said aliphatic carboxylic acyl group having one to three substituents selected from the group consisting of halogen atoms, hydroxy groups and aliphatic carboxylic acyloxy groups having from 10 to 16 carbon atoms, provided that one of $R^2$ and $R^3$ is a fluorine substituted aliphatic carboxylic acid group.

17. The compound of claim 8, wherein:

$R^1$ represents a hydroxy group;

one of $R^2$ and $R^3$ represents an aliphatic carboxylic acyl group having from 10 to 16 carbon atoms, said aliphatic carboxylic acyl group having one to three halogen substituents and 0 to 1 substituent selected from the group consisting of hydroxy groups and aliphatic carboxylic acyloxy groups having from 10 to 16 carbon atoms, and the other of $R^2$ and $R^3$ represents an aliphatic carboxylic acyl group having from 10 to 16 carbon atoms, said aliphatic carboxylic acyl group having one to three substituents selected from the group consisting of halogen atoms, hydroxy groups and aliphatic carboxylic acyloxy groups having from 10 to 16 carbon atoms, provided that one of $R^2$ and $R^3$ is a fluorine substituted aliphatic carboxylic acid group, $R^4$ represents a group of formula —OP(O)(OH)$_2$; and $R^5$ represents a fluorine atom.

18. The compound of claim 1, wherein the glucopyran moiety has the D configuration.

19. The compound of claim 1, wherein:

$R^1$ represents a hydroxy group, a fluorine atom or a group of formula —OP(O)(OH)$_2$;

$R^2$ and $R^3$ are independently selected from the group consisting of aliphatic carboxylic acyl groups having from 6 to 20 carbon atoms, said aliphatic carboxylic acyl groups being unsubstituted or having one to three substituents selected from the group consisting of substituent (a') defined below, provided that one of $R^2$ and $R^3$ is a fluorine substituted aliphatic carboxylic acyl group;

$R^4$ represents a hydroxy group or a group of formula —OP(O)(OH)$_2$, where at least one of $R^1$ and $R^4$ represents a group of formula —OP(O)(OH)$_2$;

$R^5$ represents a hydroxy group or a fluorine atom;

provided that, except where both or one of $R^1$ and $R^5$ represents a fluorine atom, both or one of $R^2$ and $R^3$ represents a substituted aliphatic carboxylic acyl group having from 6 to 20 carbon atoms and which is substituted by (i) one to three halogen substituents and (ii) one to three substituents selected from the group consisting of halogen atoms, hydroxy groups and aliphatic carboxylic acyloxy groups having from 6 to 20 carbon atoms or both or one of $R^2$ and $R^3$ represents a substituted aliphatic acyl group having from 6 to 20 carbon atoms and which is substituted by one to three halogen-substituted aliphatic carboxylic acyloxy groups having from 6 to 20 carbon atoms;

substituents (a'):

halogen atoms; hydroxy groups; aliphatic carboxylic acyloxy groups having from 6 to 20 carbon atoms; and halogen-substituted aliphatic carboxylic acyloxy groups having from 6 to 20 carbon atoms.

20. The compound of claim 19, wherein:
one of $R^1$ and $R^4$ represents a hydroxy group or a group of formula —OP(O)(OH)$_2$ and the other represents a group of formula —OP(O)(OH)$_2$;
one of $R^2$ and $R^3$ represents an aliphatic carboxylic acyl group having from 6 to 20 carbon atoms, said aliphatic carboxylic acryl group having 0 or one to three halogen substituents and 0 or 1 substituent selected from the group consisting of hydroxy groups, aliphatic carboxylic acyloxy groups having from 6 to 20 carbon atoms and halogen-substituted aliphatic carboxylic acyloxy groups having from 6 to 20 carbon atoms, and the other of $R^2$ and $R^3$ represents an aliphatic carboxylic acyl group having from 6 to 20 carbon atoms having one to three halogen substituents and 1 substituent selected from the group consisting of hydroxy groups and aliphatic carboxylic acyloxy groups having from 6 to 20 carbon atoms or having one to three halogen-substituted aliphatic carboxylic acyloxy group having from 6 to 20 carbon atoms and 0 or 1 substituent selected from the group consisting of halogen atoms, hydroxy groups and aliphatic carboxylic acyloxy groups having from 6 to 20 carbon atoms, provided that one of $R^2$ and $R^3$ is a fluorine substituted aliphatic carboxylic acyl group;
$R^5$ represents a hydroxy group.

21. The compound of claim 20, wherein the glucopyran moiety has the D configuration.

22. The compound of claim 19, wherein:
one of $R^1$ and $R^5$ represents a hydroxy group and the other represents a fluorine atom;
$R^2$ and $R^3$ are independently selected from the group consisting of aliphatic carboxylic acyl groups having from 6 to 20 carbon atoms, said aliphatic carboxylic acyl groups being unsubstituted or having one to three substituents selected from the group consisting of substituent (a'), defined below, provided that one of $R^2$ and $R^3$ is a fluorine substitued aliphatic carboxylic acyl group;
$R^4$ represents a group of formula —OP(O)(OH)$_2$;
substituents (a'):
halogen atoms; hydroxy groups; aliphatic carboxylic acyloxy groups having from 6 to 20 carbon atoms; and halogen-substituted aliphatic carboxylic acyloxy groups having from 6 to 20 carbon atoms.

23. The compound of claim 22, wherein the glucopyran moiety has the D configuration.

24. The compound of claim 1, which is 2-deoxy-2-(2'-fluoro-3'-hydroxytetradecanoylamino)-3-O-[3"-(tetradecanoyloxy)tetradecanoyl]glucopyranosyl-4-phosphate.

25. The compound of claim 1, which is 2-deoxy-2-(3'-hydroxytetradecanoylamino)-3-O-[3"-(2,2-difluorotetradecanoyloxy)tetradecanoyl]glucopyranosyl-4-phosphate.

26. The compound of claim 1, which is 2-deoxy-2-[(3'R)-3'-hydroxytetradecanoylamino]-3-O-|(3"R)-3"-(2,2-difluorotetradecanoyloxy)tetradecanoyl]-D-glucopyranosyl-4-phosphate.

27. The compound of claim 1, which is 2-deoxy-2-(3'-hydroxytetradecanoylamino)-3-O-[2",2"-difluoro-3"-(tetradecanoyloxy)tetradecanoyl]glucopyranosyl-4-phosphate.

28. The compound of claim 1, which is 2-deoxy-2-(2',2'-difluoro-3'-hydroxytetradecanoylamino)-3-O-(3"-tetradecanoyloxytetradecanoyl)glucopyranosyl-4-phosphate.

29. The compound of claim 1, which is 2-deoxy-2-|(R)-2',2'-difluoro-3'-hydroxytetradecanoylamino|-3-O-|(R)-3"-tetradecanoyloxytetradecanoyl|-D-glucopyranosyl-4-phosphate.

30. The compound of claim 1, which is 2-deoxy-2-|(S)-2',2'-difluoro-3'-hydroxytetradecanoylamino|-3-O-|(R)-3"-tetradecanoyloxytetradecanoyl|-D-glucopyranosyl-4-phosphate.

31. The compound of claim 1, which is 2-deoxy-2-(2',2'-difluoro-3'-hydroxytetradecanoylamino)-3-O-(3"-dodecanoyloxytetradecanoyl)glucopyranosyl-4-phosphate.

32. The compound of claim 1, which is 2-deoxy-2-(2',2'-difluoro-3'-hydroxytetradecanoylamino)-3-O-(2",2"-difluoro-3"-tetradecanoyloxytetradecanoyl)glucopyranosyl-4-phosphate.

33. The compound of claim 1, which is 2-deoxy-2-(2',2'-difluoro-3'-hydroxytetradecanoylamino)-3-O-(2",2"-difluoro-3"-dodecanoyloxytetradecanoyl|glucopyranosyl-4-phosphate.

34. The compound of claim 1, which is 2,6-dideoxy-6-fluoro-2-(3'-hydroxytetradecanoylamino)-3-O-(3"-tetradecanoyloxytetradecanoyl)glucopyranosyl-4-phosphate.

35. The compound of claim 1, which is 2,6-dideoxy-6-fluoro-2-|(R)-3'-hydroxytetradecanoylamino|-3-O-|(R)-3"-tetradecanoyloxytetradecanoyl|-D-glucopyranosyl-4-phosphate.

36. The compound of claim 1, which is 2,6-dideoxy-6-fluoro-2-(3'-hydroxytetradecanoylamino)-3-O-(2",2"-difluoro-3"-tetradecanoyloxytetradecanoyl)glucopyranosyl-4-phosphate.

37. The compound of claim 1, which is 2,6-dideoxy-6-fluoro-2-(2',2'-difluoro-3'-hydroxytetradecanoylamino)-3-O-(3"-tetradecanoyloxytetradecanoyl)glucopyranosyl-4-phosphate.

38. The compound of claim 1, wherein $R^2$ and $R^3$ are both a fluorine substituted carboxylic acyl group.

39. A composition for the treatment, prophylaxis and diagnosis of patients suffering from diseases and disorders arising from deficiencies in the immune system, said composition comprising an effective amount of at least one compound of formula (I) or a pharmaceutically acceptable salt thereof, as claimed in claim 1, in admixture with a pharmaceutically acceptable carrier, diluent or exicipient.

40. The composition of claim 39, wherein
$R^1$ represents a hydroxy group or a protected hydroxy group;
one of $R^2$ and $R^3$ represents an unsubstituted aliphatic carboxylic acyl group having from 12 to 16 carbon atoms or a substitued aliphatic carboxylic acyl group having from 12 to 16 carbon atoms and having at least one substituent selected from the group consisting of halogen atoms, hydroxy groups and aliphatic carboxylic acyloxy groups having from 12 to 16 carbon atoms, provided that it is substituted by no more than one said hydroxy group and by no more than one said acyloxy group, and the other of $R^2$ and $R^3$ represents a substituted aliphatic carboxylic acyl group having from 12 to 16 carbon atoms and having at least one halogen substituent and 0 or 1 substituent selected from the group consisting of hydroxy groups and aliphatic carboxylic acyloxy groups having from 12 to 16 carbon atoms;
$R^4$ represents a group of formula —OP(O)(OH)$_2$; and
$R^5$ represents a fluorine atom or a hydroxy group.

41. The composition of claim 40, wherein the glucopyran moiety has a D configuration.

42. The composition of claim 39, wherein:

$R^1$ represents a hydroxy group;

one of $R^2$ and $R^3$ represents an aliphatic acyl group having from 10 to 16 carbon atoms, said aliphatic acyl group having at least one halogen substituent and 0 or 1 substituent selected from the group consisting of hydroxy groups and aliphatic carboxylic acyloxy groups having from 10 to 16 carbon atoms, and the other of $R^2$ and $R^3$ represents an aliphatic carboxylic acyl group having from 10 to 16 carbon atoms, said aliphatic carboxylic acyl group having at least one substituent selected from the group consisting of halogen atoms, hydroxy groups and aliphatic carboxylic acyloxy groups having from 10 to 16 carbon atoms;

$R^4$ represents a group of formula —OP(O)(OH)$_2$; and $R^5$ represents a fluorine atom or a hydroxy group.

43. The composition of claim 39, wherein:

$R^1$ represents a hydroxy group, a fluorine atom or a group of formula —OP(O)(OH)$_2$;

$R^2$ and $R^3$ are independently selected from the group consisting of aliphatic carboxylic acyl groups having from 6 to 20 carbon atoms, said acyl groups being unsubstituted or having at least one substituent selected from the group consisting of substituents (a'), defined below;

$R^4$ represents a hydroxy group or a group of formula —OP(O)(OH)$_2$, where at least one of $R^1$ and $R^4$ represents a group of formula —OP(O)(OH)$_2$;

$R^5$ represents a hydroxy group or a fluorine atom;

provided that, except where at least one of $R^1$ and $R^5$ represents a fluorine atom, at least one of $R^2$ and $R^3$ represents a substituted aliphatic carboxylic acyl group having from 6 to 20 carbon atoms and having (i) at least one halogen substituent and (ii) at least one substituent selected from the group consisting of halogen atoms, hydroxy groups and aliphatic carboxylic acyloxy groups having from 6 to 20 carbon atoms or at least one of $R^2$ and $R^3$ represents a substituted aliphatic acyl group having from 6 to 20 carbon atoms and which is substituted by at least one halogen-substituted aliphatic carboxylic acyloxy group having from 6 to 20 carbon atoms;

substituents (a'):
halogen atoms; hydroxy groups; aliphatic carboxylic acyloxy groups having from 6 to 20 carbon atoms; and halogen-substituted aliphatic carboxylic acyloxy groups having from 6 to 20 carbon atoms.

44. The composition of claim 43, wherein:

one of $R^1$ and $R^4$ represents a hydroxy group or a group of formula —OP(O)(OH)$_2$ and the other represents a group of formula —OP(O)(OH)$_2$;

one of $R^2$ and $R^3$ represents an aliphatic carboxylic acyl group having from 6 to 20 carbon atoms, said aliphatic carboxylic acyl group having 0 or at least one halogen substituent and 0 or 1 substituent selected from the group consisting of hydroxy groups, aliphatic carboxylic acyloxy groups having from 6 to 20 carbon atoms and halogen-substituted aliphatic carboxylic acyloxy groups having from 6 to 20 carbon atoms, and the other of $R^2$ and $R^3$ represents an aliphatic carboxylic acyl group having from 6 to 20 carbon atoms, said aliphatic carboxylic acyl group (i) having at least one halogen substituent and 1 substituent selected from the group consisting of hydroxy groups and aliphatic carboxylic acyloxy groups having from 6 to 20 carbon atoms or (ii) having at least one halogen-substituted aliphatic carboxylic acyloxy group having from 6 to 20 carbon atoms and 0 or 1 substituent selected from the group consisting of halogen atoms, hydroxy groups and aliphatic carboxylic acyloxy groups having from 6 to 20 carbon atoms;

$R^5$ represents a hydroxy group.

45. The composition of claim 43, wherein the glucopyran moiety has the D configuration.

46. The composition of claim 43, wherein one of $R^1$ and $R^5$ represents a hydroxy group and the other represents a fluorine atom;

$R^2$ and $R^3$ are independently selected from the group consisting of aliphatic carboxylic acyl groups having from 6 to 20 carbon atoms, said acyl groups being unsubstituted or having at least one substituent selected from the group consisting of substituents (a'), defined below;

$R^4$ represents a group of formula —OP(O)(OH)$_2$;

substituents (a'):
halogen atoms; hydroxy groups; aliphatic carboxylic acyloxy groups having from 6 to 20 carbon atoms; and halogen-substituted aliphatic carboxylic acyloxy groups having from 6 to 20 carbon atoms.

47. The composition of claim 46, wherein the glucopyran moiety has a D configuration.

48. The composition of claim 39, wherein said compound is selected from the group consisting of:

2-deoxy-2-(2'-fluoro-3'-hydroxytetradecanoylamino)-3-O-[3"-(tetradecanoyloxy)tetradecanoyl]glucopyranosyl-4-phosphate;

2-deoxy-2-(3'-hydroxytetradecanoylamino)-3-O-[3"-(2,2-difluorotetradecanoyloxy)tetradecanoyl]glucopyranosyl-4-phosphate;

2-deoxy-2-(3'-hydroxytetradecanoylamino)-3-O-[-2",2"-difluoro-3"-(tetradecanoyloxy)tetradecanoyl] glucopyranosyl -4-phosphate;

2-deoxy-2-(2',2'-difluoro-3'-hydroxytetradecanoylamino)-3-O-(3-tetradecanoyloxytetradecanoyl)glucopyranosyl-4-phosphate;

2-deoxy-2-(2',2'-difluoro-3'-hydroxytetradecanoylamino)-3-O-(3-dodecanoyloxytetradecanoyl)glucopyranosyl-4-phosphate;

2-deoxy-2-(2',2'-difluoro-3'-hydroxytetradecanoylamino)-3-O-(2",2"-difluoro-3"-tetradecanoyloxytetradecanoyl) glucopyranosyl-4-phosphate;

2-deoxy-2-(2',2'-difluoro-3'-hydroxytetradecanoylamino)-3-O-(2",2"-difluoro-3"-dodecanoyloxytetradecanoyl] glucopyranosyl-4-phosphate;

2,6-dideoxy-6-fluoro-2-(3'-hydroxytetradecanoylamino)-3-O-(3"-tetradecanoyloxytetradecanoyl)glucopyranosyl-4-phosphate;

2,6-dideoxy-6-fluoro-2-(3'-hydroxytetradecanoylamino)-3-O-(2",2"-difluoro-3"-tetradecanoyloxytetradecanoyl) glucopyranosyl-4-phosphate;

2,6-dideoxy-6-fluoro-2-(2",2"-difluoro-3'-hydroxytetradecanoylamino)-3-O-(3"-tetradecanoyloxytetradecanoyl)glucopyranosyl-4-phosphate;

and pharmaceutically acceptable salts thereof.

49. The composition of claim 39, wherein said compound is selected from the group consisting of:

2-deoxy-2-[(3'R)-3'-hydroxytetradecanoylamino]-3-O-[(3"R)-3"-(2,2-difluorotetradecanoyloxy)tetradecanoyl]-D-glucopyranosyl-4-phosphate;

2-deoxy-2-[(R)-2',2'-difluoro-3'-hydroxytetradecanoylamino]-3-O-[(R)-3-tetradecanoyloxytetradecanoyl]-D-glucopyranosyl-4-phosphate;

2-deoxy-2-|(S)-2',2'-difluoro-3'-hydroxytetradecanoylamino|-3-O-|(R)-3-tetradecanoyloxytetradecanoyl|-D-glucopyranosyl-4-phosphate;

2,6-dideoxy-6-fluoro-2-|(R)-3'-hydroxytetradecanoylamino|-3-O-|(R)-3"-tetradecanoyloxytetradecanoyl|-D-glucopyranosyl-4-phosphate;

and pharmaceutically acceptable salts thereof.

50. A method for the treatment or prophylaxis of a disease or disorder arising from a deficiency in the immune system or from a tumor in an animal, said method comprising administering to said animal an effective amount of at least one compound of formula (I) or a pharmaceutically acceptable salt thereof, as claimed in claim 1.

51. The method of claim 50, wherein $R^1$ represents a hydroxy group or a protected hydroxy group;

one of $R^2$ and $R^3$ represents an unsubstituted aliphatic carboxylic acyl group having from 12 to 16 carbon atoms or a substituted aliphatic carboxylic acyl group having from 12 to 16 carbon atoms and having at least one substituent selected from the group consisting of halogen atoms, hydroxy groups and aliphatic carboxylic acyloxy groups having from 12 to 16 carbon atoms, provided that it is substituted by no more than one said hydroxy group and by no more than one said acyloxy group, and the other of $R^2$ and $R^3$ represents a substituted aliphatic carboxylic acyl group having from 12 to 16 carbon atoms and having at least one halogen substituent and 0 or 1 substituent selected from the group consisting of hydroxy groups and aliphatic carboxylic acyloxy groups having from 12 to 16 carbon atoms;

$R^4$ represents a group of formula —OP(O)(OH)$_2$; and $R^5$ represents a fluorine atom or a hydroxy group.

52. The method of claim 51, wherein the glucopyran moiety has a D configuration.

53. The method of claim 50, wherein $R^1$ represents a hydroxy group;

one of $R^2$ and $R^3$ represents an aliphatic acyl group having from 10 to 16 carbon atoms, said aliphatic acyl group having at least one halogen substituent and 0 or 1 substituent selected from the group consisting of hydroxy groups and aliphatic carboxylic acyloxy groups having from 10 to 16 carbon atoms, and the other of $R^2$ and $R^3$ represents an aliphatic carboxylic acyl group having from 10 to 16 carbon atoms, said aliphatic carboxylic acyl group having at least one substituent selected from the group consisting of halogen atoms, hydroxy groups and aliphatic carboxylic acyloxy groups having from 10 to 16 carbon atoms;

$R^4$ represents a group of formula —OP(O)(OH)$_2$; and $R^5$ represents a fluorine atom or a hydroxy group.

54. The method of claim 50, wherein:

$R^1$ represents a hydroxy group, a fluorine atom or a group of formula —OP(O)(OH)$_2$;

$R^2$ and $R^3$ are independently selected from the group consisting of aliphatic carboxylic acyl groups having from 6 to 20 carbon atoms, said acyl groups being unsubstituted or having at least one substituent selected from the group consisting of substituents (a'), defined below;

$R^4$ represents a hydroxy group or a group of formula —OP(O)(OH)$_2$, where at least one of $R^1$ and $R^4$ represents a group of formula —OP(O)(OH)$_2$;

$R^5$ represents a hydroxy group or a fluorine atom;

provided that, except where at least one of $R^1$ and $R^5$ represents a fluorine atom, at least one of $R^2$ and $R^3$ represents a substituted aliphatic carboxylic acyl group having from 6 to 20 carbon atoms and having (i) at least one halogen substituent and (ii) at least one substituent selected from the group consisting of halogen atoms, hydroxy groups and aliphatic carboxylic acyloxy groups having from 6 to 20 carbon atoms or at least one of $R^2$ and $R^3$ represents a substituted aliphatic acyl group having from 6 to 20 carbon atoms and which is substituted by at least one halogen-substituted aliphatic carboxylic acyloxy group having from 6 to 20 carbon atoms;

substituents (a'):

halogen atoms; hydroxy groups; aliphatic carboxylic acyloxy groups having from 6 to 20 carbon atoms; and halogen-substituted aliphatic carboxylic acyloxy groups having from 6 to 20 carbon atoms.

55. The method of claim 50, wherein:

one of $R^1$ and $R^4$ represents a hydroxy group or a group of formula —OP(O)(OH)$_2$ and the other represents a group of formula —OP(O)(OH)$_2$;

one of $R^2$ and $R^3$ represents an aliphatic carboxylic acyl group having from 6 to 20 carbon atoms, said aliphatic carboxylic acyl group having 0 or at least one halogen substituent and 0 or 1 substituent selected from the group consisting of hydroxy groups, aliphatic carboxylic acyloxy groups having from 6 to 20 carbon atoms and halogen-substituted aliphatic carboxylic acyloxy groups having from 6 to 20 carbon atoms, and the other of $R^2$ and $R^3$ represents an aliphatic carboxylic acyl group having from 6 to 20 carbon atoms, said aliphatic carboxylic acyl group (i) having at least one halogen substituent and 1 substituent selected from the group consisting of hydroxy groups and aliphatic carboxylic acyloxy groups having from 6 to 20 carbon atoms or (ii) having at least one halogen-substituted aliphatic carboxylic acyloxy group having from 6 to 20 carbon atoms and 0 or 1 substituent selected from the group consisting of halogen atoms, hydroxy groups and aliphatic carboxylic acyloxy groups having from 6 to 20 carbon atoms;

$R^5$ represents a hydroxy group.

56. The method of claim 55, wherein the glucopyran moiety has a D configuration.

57. The method of claim 50, wherein:

one of $R^1$ and $R^5$ represents a hydroxy group and the other represents a fluorine atom;

$R^2$ and $R^3$ are independently selected from the group consisting of aliphatic carboxylic acyl groups having from 6 to 20 carbon atoms, said acyl groups being unsubstituted or having at least one substituent selected from the group consisting of substituents (a'), defined below;

$R^4$ represents a group of formula —OP(O)(OH)$_2$;

substituents (a'):

halogen atoms; hydroxy groups; aliphatic carboxylic acyloxy groups having from 6 to 20 carbon atoms; and halogen-substituted aliphatic carboxylic acyloxy groups having from 6 to 20 carbon atoms.

58. The method of claim 57, wherein the glucopyran moiety has a D configuration.

59. The method of claim 50, wherein said compound is selected from the group consisting of:

2-deoxy-2-(2'-fluoro-3'-hydroxytetradecanoylamino)-3-O-[3"-(tetradecanoyloxy)tetradecanoyl]glucopyranosyl-4-phosphate;

2-deoxy-2-(3'-hydroxytetradecanoylamino)-3-O-[3"-(2,2-difluorotetradecanoyloxy)tetradecanoyl]glucopyranosyl-4-phosphate;

2-deoxy-2-(3'-hydroxytetradecanoylamino)-3-O-[2",2"-difluoro-3"-(tetradecanoyloxy)tetradecanoyl]glucopyranosyl-4-phosphate;

2-deoxy-2-(2',2'-difluoro-3'-hydroxytetradecanoylamino)-3-O-(3-tetradecanoyloxytetradecanoyl)glucopyranosyl-4-phosphate;

2-deoxy-2-(2',2'-difluoro-3'-hydroxytetradecanoylamino)-3-O-(3-dodecanoyloxytetradecanoyl)glucopyranosyl-4-phosphate;

2-deoxy-2-(2',2'-difluoro-3'-hydroxytetradecanoylamino)-3-O-(2",2"-difluoro-3"-tetradecanoyloxytetradecanoyl)glucopyranosyl-4-phosphate;

2-deoxy-2-(2',2'-difluoro-3'-hydroxytetradecanoylamino)-3-O-(2",2"-difluoro-3"-dodecanoyloxytetradecanoyl]glucopyranosyl-4-phosphate;

2,6-dideoxy-6-fluoro-2-(3'-hydroxytetradecanoylamino)-3-O-(3"-tetradecanoyloxytetradecanoyl)glucopyranosyl-4-phosphate;

2,6-dideoxy-6-fluoro-2-(3'-hydroxytetradecanoylamino)-3-O-(2",2"-difluoro-3"-tetradecanoyloxytetradecanoyl)glucopyranosyl-4-phosphate;

2,6-dideoxy-6-fluoro-2-(2",2"-difluoro-3"-hydroxytetradecanoylamino)-3-O-(3"-tetradecanoyloxytetradecanoyl)glucopyranosyl-4-phosphate;

and pharmaceutically acceptable salts thereof.

60. The method of claim 50, wherein said compound is selected from the group consisting of:

2-deoxy-2-[(3'R)-3'-hydroxytetradecanoylamino]-3-O-[(3"R)-3"-(2,2-difluorotetradecanoyloxy)tetradecanoyl]-D-glucopyranosyl-4-phosphate;

2-deoxy-2-[(R)-2',2'-difluoro-3'-hydroxytetradecanoylamino]-3-O-[(R)-3-tetradecanoyloxytetradecanoyl]-D-glucopyranosyl-4-phosphate;

2-deoxy-2-[(S)-2',2'-difluoro-3'-hydroxytetradecanoylamino]-3-O-[(R)-3"-tetradecanoyloxytetradecanoyl]-D-glucopyranosyl-4-phosphate;

2,6-dideoxy-6-fluoro-2-[(R)-3'-hydroxytetradecanoylamino]-3-O-[(R)-3"-tetradecanoyloxytetradecanoyl]-D-glucopyranosyl-4-phosphate;

and pharmaceutically acceptable salts thereof.

\* \* \* \* \*

UNITED STATES PATENT AND TRADEMARK OFFICE
CERTIFICATE OF CORRECTION

PATENT NO. : 5,792,840
DATED : August 11, 1998
INVENTOR(S) : Shiozaki et al

It is certified that error appears in the above-identified patent and that said Letters Patent is hereby corrected as shown below:

Column 10, line 58: Replace "Is" with --is--.

Column 55, line 37: replace "50°" (first occurrence) with -- -50 --.

Column 56, line 3: delete "n" and insert --in--.

Column 70, lines 36-37: delete all of the subject matter on these two lines.

Column 117, line 17 (Claim 10): delete "3" and insert --8--.

Column 122, line 8 (Claim 45): delete "43" and insert --44--.

Signed and Sealed this

Nineteenth Day of October, 1999

Attest:

Attesting Officer

Q. TODD DICKINSON

Acting Commissioner of Patents and Trademarks